United States Patent
O'Donnell et al.

(10) Patent No.: US 11,931,365 B2
(45) Date of Patent: Mar. 19, 2024

(54) USE OF PPAR-DELTA AGONISTS IN THE TREATMENT OF DISEASE

(71) Applicant: Reneo Pharmaceuticals, Inc., Irvine, CA (US)

(72) Inventors: Niall O'Donnell, San Diego, CA (US); Lynn Purkins, San Diego, CA (US); Alejandro Dorenbaum, San Diego, CA (US)

(73) Assignee: RENEO PHARMACEUTICALS, INC., Irvine, CA (US)

( * ) Notice: Subject to any disclaimer, the term of this patent is extended or adjusted under 35 U.S.C. 154(b) by 0 days.

(21) Appl. No.: 18/101,527

(22) Filed: Jan. 25, 2023

(65) Prior Publication Data

US 2023/0233570 A1    Jul. 27, 2023

Related U.S. Application Data

(60) Provisional application No. 63/391,429, filed on Jul. 22, 2022, provisional application No. 63/302,894, filed on Jan. 25, 2022.

(51) Int. Cl.
| | | |
|---|---|---|
| *A61K 31/5375* | (2006.01) | |
| *A61K 45/06* | (2006.01) | |
| *A61P 21/00* | (2006.01) | |

(52) U.S. Cl.
CPC .......... *A61K 31/5375* (2013.01); *A61K 45/06* (2013.01); *A61P 21/00* (2018.01)

(58) Field of Classification Search
CPC ...... A61K 31/5375; A61K 45/06; A61P 21/00
See application file for complete search history.

(56) References Cited

U.S. PATENT DOCUMENTS

| | | | |
|---|---|---|---|
| 4,148,915 | A | 4/1979 | Thuillier et al. |
| 4,920,132 | A | 4/1990 | Huang et al. |
| 5,324,743 | A | 6/1994 | Dillard et al. |
| 5,773,469 | A | 6/1998 | Kanojia et al. |
| 5,919,793 | A | 7/1999 | Brown et al. |
| 6,448,293 | B1 | 9/2002 | Andrews et al. |
| 6,525,094 | B1 | 2/2003 | Zhang et al. |
| 6,555,577 | B1 | 4/2003 | Mogensen et al. |
| 6,569,901 | B2 | 5/2003 | Mogensen et al. |
| 6,630,504 | B2 | 10/2003 | Andrews et al. |

(Continued)

FOREIGN PATENT DOCUMENTS

| | | |
|---|---|---|
| WO | WO-9727847 A1 | 8/1997 |
| WO | WO-9727857 A1 | 8/1997 |

(Continued)

OTHER PUBLICATIONS

Caso et al., Effect of Coenzyme Q10 on Myopathic Symptoms in Patients Treated With Statins, 2007, Preventive Cardiology, 99(10), pp. 1409-1412 (Year: 2007).*

(Continued)

*Primary Examiner* — Savitha M Rao
*Assistant Examiner* — Andrew P Lee
(74) *Attorney, Agent, or Firm* — WILSON SONSINI GOODRICH & ROSATI

(57) ABSTRACT

Described herein is the use sodium (E)-2-(4-((3-(4-fluorophenyl)-3-(4-(3-morpholinoprop-1-yn-1-yl)phenyl)allyl)oxy)-2-methylphenoxy)acetate in the preparation of pharmaceutical compositions for the treatment of diseases or conditions that would benefit by administration with a PPARδ agonist compound.

14 Claims, 30 Drawing Sheets

(56) References Cited

U.S. PATENT DOCUMENTS

| | | | |
|---|---|---|---|
| 6,867,218 B2 | 3/2005 | Mogensen et al. |
| 6,869,967 B2 | 3/2005 | Jeppesen et al. |
| 6,869,975 B2 | 3/2005 | Abe et al. |
| 6,875,780 B2 | 4/2005 | Auerbach et al. |
| 6,972,294 B1 | 12/2005 | Murray et al. |
| 7,067,530 B2 | 6/2006 | Jeppesen et al. |
| 7,091,245 B2 | 8/2006 | Jeppesen et al. |
| 7,129,268 B2 | 10/2006 | Jeppesen et al. |
| 7,202,213 B2 | 4/2007 | Mogensen et al. |
| 7,220,877 B2 | 5/2007 | Sauerberg et al. |
| 7,709,528 B2 | 5/2010 | Jeppesen et al. |
| 7,943,613 B2 | 5/2011 | Sauerberg et al. |
| 7,943,669 B2 | 5/2011 | Ebdrup |
| 8,008,348 B2 | 8/2011 | Steiner et al. |
| 8,217,086 B2 | 7/2012 | Ebdrup |
| 8,362,016 B2 | 1/2013 | Sauerberg et al. |
| 8,388,968 B2 | 3/2013 | Berger et al. |
| 8,426,473 B2 | 4/2013 | Ebdrup |
| 8,551,993 B2 | 10/2013 | Sauerberg et al. |
| 9,487,493 B2 | 11/2016 | Valcarce Lopez et al. |
| 9,663,481 B2 | 5/2017 | Sauerberg et al. |
| 9,669,288 B2 | 6/2017 | Pertgen |
| 9,855,274 B2 | 1/2018 | Sauerberg et al. |
| 9,968,613 B2 | 5/2018 | Valcarce Lopez et al. |
| 10,456,406 B2 | 10/2019 | Valcarce Lopez et al. |
| 10,471,066 B2 | 11/2019 | Sauerberg et al. |
| 10,947,180 B2 | 3/2021 | Sauerberg et al. |
| 11,096,946 B2 | 8/2021 | Valcarce Lopez et al. |
| 11,267,795 B2 | 3/2022 | Del Rio Gancedo et al. |
| 2004/0024034 A1 | 2/2004 | Brooks et al. |
| 2005/0080115 A1 | 4/2005 | Jeppesen et al. |
| 2008/0114036 A1 | 5/2008 | Havranek et al. |
| 2008/0187928 A1 | 8/2008 | Evans et al. |
| 2009/0012171 A1 | 1/2009 | Polivka |
| 2009/0048257 A1 | 2/2009 | Sauerberg |
| 2009/0192162 A1 | 7/2009 | Ebdrup |
| 2010/0197950 A1 | 8/2010 | Rasmussen et al. |
| 2010/0210653 A1 | 8/2010 | Havranek et al. |
| 2011/0092517 A1 | 4/2011 | Barbaras et al. |
| 2011/0245244 A1 | 10/2011 | Sauerberg et al. |
| 2013/0203712 A1 | 8/2013 | Adams et al. |
| 2014/0024645 A1 | 1/2014 | Sauerberg et al. |
| 2015/0072985 A1 | 3/2015 | Valcarce Lopez et al. |
| 2015/0246059 A1 | 9/2015 | Freeman et al. |
| 2016/0023991 A1 | 1/2016 | Evans et al. |
| 2017/0027950 A1 | 2/2017 | Valcarce Lopez et al. |
| 2017/0226154 A1 | 8/2017 | Evans et al. |
| 2017/0304255 A1 | 10/2017 | Baiga et al. |
| 2017/0305894 A1 | 10/2017 | Baiga et al. |
| 2018/0071304 A1* | 3/2018 | Sauerberg ............... A61K 31/40 |
| 2018/0296562 A1 | 10/2018 | Valcarce Lopez et al. |
| 2020/0046717 A1 | 2/2020 | Valcarce Lopez et al. |
| 2022/0023306 A1 | 1/2022 | O'Carroll et al. |
| 2022/0072005 A1 | 3/2022 | Valcarce Lopez et al. |
| 2022/0117972 A1 | 4/2022 | O'Carroll et al. |
| 2022/0135532 A1 | 5/2022 | Del Rio Gancedo et al. |

FOREIGN PATENT DOCUMENTS

| | | | |
|---|---|---|---|
| WO | WO-9728115 A1 | 8/1997 | |
| WO | WO-9728137 A1 | 8/1997 | |
| WO | WO-9728149 A1 | 8/1997 | |
| WO | WO-9827974 A1 | 7/1998 | |
| WO | WO-9904815 A1 | 2/1999 | |
| WO | WO-0063153 A1 | 10/2000 | |
| WO | WO-0100603 A1 | 1/2001 | |
| WO | WO-0125181 A1 | 4/2001 | |
| WO | WO-0125226 A1 | 4/2001 | |
| WO | WO-0134200 A1 | 5/2001 | |
| WO | WO-0155085 A1 | 8/2001 | |
| WO | WO-0155086 A1 | 8/2001 | |
| WO | WO-0160807 A1 | 8/2001 | |
| WO | WO-0179150 A1 | 10/2001 | |
| WO | WO-0179197 A1 | 10/2001 | |
| WO | WO-0214291 A1 | 2/2002 | |
| WO | WO-0228434 A2 | 4/2002 | |
| WO | WO-0246154 A1 | 6/2002 | |
| WO | WO-0250048 A1 | 6/2002 | |
| WO | WO-02059098 A1 | 8/2002 | |
| WO | WO-02062774 A1 | 8/2002 | |
| WO | WO-02070011 A2 | 9/2002 | |
| WO | WO-02076957 A1 | 10/2002 | |
| WO | WO-03011807 A1 | 2/2003 | |
| WO | WO-03011814 A1 | 2/2003 | |
| WO | WO-03016291 A1 | 2/2003 | |
| WO | WO-03024395 A2 | 3/2003 | |
| WO | WO-03033453 A1 | 4/2003 | |
| WO | WO-03033493 A1 | 4/2003 | |
| WO | WO-03035603 A1 | 5/2003 | |
| WO | WO-03072100 A1 | 9/2003 | |
| WO | WO-03074050 A1 | 9/2003 | |
| WO | WO-03074051 A1 | 9/2003 | |
| WO | WO-03074052 A1 | 9/2003 | |
| WO | WO-03074495 A1 | 9/2003 | |
| WO | WO-03084916 A2 | 10/2003 | |
| WO | WO-03097607 A1 | 11/2003 | |
| WO | WO-2004000315 A1 | 12/2003 | |
| WO | WO-2004000762 A2 | 12/2003 | |
| WO | WO-2004005253 A1 | 1/2004 | |
| WO | WO-2004022533 A1 | 3/2004 | |
| WO | WO-2004037775 A1 | 5/2004 | |
| WO | WO-2004037776 A2 | 5/2004 | |
| WO | WO-2004060871 A1 | 7/2004 | |
| WO | WO-2004063165 A1 | 7/2004 | |
| WO | WO-2004063166 A1 | 7/2004 | |
| WO | WO-2004073606 A2 | 9/2004 | |
| WO | WO-2004080943 A1 | 9/2004 | |
| WO | WO-2004080947 A1 | 9/2004 | |
| WO | WO-2004092117 A1 | 10/2004 | |
| WO | WO-2004092130 A2 | 10/2004 | |
| WO | WO-2004093879 A1 | 11/2004 | |
| WO | WO-2005060958 A1 | 7/2005 | |
| WO | WO-2005097098 A2 | 10/2005 | |
| WO | WO-2005097762 A2 | 10/2005 | |
| WO | WO-2005097763 A2 | 10/2005 | |
| WO | WO-2005105725 A1 | 11/2005 | |
| WO | WO-2005105735 A1 | 11/2005 | |
| WO | WO-2005105736 A1 | 11/2005 | |
| WO | WO-2005115383 A2 | 12/2005 | |
| WO | WO-2006055187 A1 | 5/2006 | |
| WO | WO-2007003581 A1 | 1/2007 | |
| WO | WO-2007071766 A2 | 6/2007 | |
| WO | WO-2007101864 A2 | 9/2007 | |
| WO | WO-2007141295 A1 | 12/2007 | |
| WO | WO-2009086526 A2 | 7/2009 | |
| WO | WO-2014165827 A1 | 10/2014 | |
| WO | WO-2015035171 A1 | 3/2015 | |
| WO | WO-2016057322 A1 | 4/2016 | |
| WO | WO-2016057656 A1 * | 4/2016 | ............ A61K 31/00 |
| WO | WO-2016057658 A1 | 4/2016 | |
| WO | WO-2016057660 A1 | 4/2016 | |
| WO | WO-2017062468 A1 | 4/2017 | |
| WO | WO-2017180818 A1 | 10/2017 | |
| WO | WO-2017184583 A1 | 10/2017 | |
| WO | WO-2018067860 A1 | 4/2018 | |
| WO | WO-2018093839 A1 | 5/2018 | |
| WO | WO-2020163240 A1 | 8/2020 | |
| WO | WO-2020172421 A1 | 8/2020 | |
| WO | WO-2021055725 A1 | 3/2021 | |
| WO | WO-2022020376 A1 | 1/2022 | |
| WO | WO-2022115326 A1 | 6/2022 | |

OTHER PUBLICATIONS

Abadi et al. Limb immobilization induces a coordinate down-regulation of mitochondrial and other metabolic pathways in men and women. PLoS ONE 4(8):e6518 (2009).

Barbaras et al. CAS 154:276074 (2 pgs.) (2011).

Bastin. Regulation of mitochondrial fatty acid [beta]-oxidation in human: What can we learn from inborn fatty acid [beta]-oxidation deficiencies? Biochimie 96:113-120 (2014).

(56) References Cited

OTHER PUBLICATIONS

Bell et al. PPAR[delta] modulation rescues mitochondrial fatty acid oxidation defects in themdxmodel of muscular dystrophy. Mitochondrion 46:51-58 (2018).
Bennett. Assays of fatty acid beta-oxidation activity. Methods Cell Biol 80:179-197 (2007).
Berge et al. Pharmaceutical Salts. Journal of Pharmaceutical Sciences 66(1):1-19 (Jan. 1977).
Berger et al. Novel Peroxisome Proliferator-activated Receptor (PPAR) gamma and PPAR delta Ligands Produce Distinct Biological Effects. J Biol Chem 274(1):6718-6725 (1999).
Berger et al. Physiological and Therapeutic Roles of Peroxisome Proliferator-Activated Receptors. Diabetes Technology & Therapeutics 4(2):163-174 (2002).
Bernardo et al. Postnatal PPAR-delta Activation and Myostatin Inhibition Exert Distinct yet Complimentary Effects on the Metabolic Profile of Obese Insulin-Resistant Mice. PLOS One 5(6):1-11 (2010).
Bonnefont et al. Long-Term Follow-Up of Bezafibrate Treatment in Patients With the Myopathic Form of Carnitine Palmitoyltransferase 2 Deficiency. Clin Pharmacol Ther 88:101-108 (2010).
Byrn et al. Chapter II: Hydrates and Solvates. Solid-State Chemistry of Drugs, 2nd edition pp. 233-248 (1999).
Caira. Crystalline Polymorphism of Organic Compounds. Topics in Current Chemistry. 198:163-208 (Jan. 1998).
Castillero et al. PPAR-beta/delta Regulates Glucocorticoid- and Sepsis-Induced FOXO1 Activation and Muscle Wasting. PLOS One 8(3)(e59726):1-16 (2013).
Coll et al., Activation of peroxisome proliferator-activated receptor-{delta} by GW501516 prevents fatty acid-induced nuclear factor-{kappa}B activation and insulin resistance in skeletal muscle cells. Endocrinology 151(4):1560-1569 (2010).
De Boer et al. The temporal responses of protein synthesis, gene expression and cell signalling in human quadriceps muscle and patellar tendon to disuse. J Physiol 585:241-251 (2007).
De Grey. Foreseeable pharmaceutical repair of age-related extracellular damage. Curr Drug Targets 7:1469-1477 (2006).
Demmelmair et al., Comparison of the effects of rapeseed oil, olive oil and hydrogenated plant oil on postprandial lipids and fatty acid oxidation. https://www.semanticscholar.org/paper/Comparison-of-the-effects-of-rapeseed-oil-%2C-olive-Demmelmair-Broekaert/6139d1dc0b29935494a24ccf9783b9c5c90f53d0 Published at Semantic Scholar [1-25] (2005).
Djouadi et al. Correction of fatty acid oxidation in carnitine palmitoyl transferase 2-deficient cultured skin fibroblasts by bezafibrate. Pediatr. Res. 54:446-451 (2003).
Djouadi et al. Peroxisome proliferator activated receptor delta (PPARdelta) agonist but not PPARalpha corrects carnitine palmitoyl transferase 2 deficiency in human muscle cells. J. Clin. Endocrinol. Metab. 90:1791-1797 (2005).
Djouadi et al., PPARs as therapeutic targets for correction of inborn mitochondrial fatty acid oxidation disorders. Journal of Inherited Metabolic Disease 31(2):217-225 (2008).
Ehrenborg et al. Regulation of Skeletal Muscle Physiology and Metabolism by Peroxisome Proliferator-Activated Receptor delta. Pharmacological Reviews 61(3):373-393 (2009).
Fan et al. PPARγ Promotes Running Endurance by Preserving Glucose. Cell Metab. 25:1186-1193.e4 (2017).
Fedorova et al. Peroxisome Proliferator-Activated Receptor delta Agonist, HPP593, Prevents Renal Necrosis under Chronic Ischemia. PLOS One 8(5):1-13 (2013).
Ferrando et al. Prolonged bed rest decreases skeletal muscle and whole body protein synthesis. Am J Physiol 270:E627-633 (1996).
Fritz et al. Low-intensity exercise increases skeletal muscle protein expression of PPARdelta and UCP3 in type 2 diabetic patients. Diabetes Metab Res Rev 2:492-498 (2006).
Gaudel et al. Pharmacological activation of PPARbeta promotes rapid and calcineurin-dependent fiber remodeling and angiogenesis in mouse skeletal muscle. American Journal of Physiology 295(2):E297-E304 (2008).
Gibson et al. Decrease in human quadriceps muscle protein turnover consequent upon leg immobilization. Clin Sci (Lond) 72:503-509 (1987).
Gillingham et al. Triheptanoin versus trioctanoin for long-chain fatty acid oxidation disorders: a double blinded, randomized controlled trial. J Inherit Metab Dis 40(6):831-843 (2017).
Giron. Applications of Thermal Analysis and Coupled Techniques in Pharmaceutical Industry. J Therm Anal Calorim 68:335-357 (2002).
Giron. Investigations of Polymorphism and Pseudo-polymorphism in Pharmaceuticals by Combined Thermoanalytical Techniques. J Therm Anal Calorim 64:37-60 (2001).
Goddeeris et al., A Novel Small-Molecule PPARo Modulator for the Treatment of Fatty Acid Oxidation Disorders. Poster Session presented at INFORM: International Network for Fatty Acid Oxidation Research and Management; Rio de Janeiro, Brazil, Sep. 4, 2017.
Goetzman. Advances in the Understanding and Treatment of Mitochondrial Fatty Acid Oxidation Disorders. Curr Genet Med Rep. 5(3):132-142 (2017).
Goetzman et al. Expression and characterization of mutations in human very long-chain acyl-CoA dehydrogenase using a prokaryotic system. Mol. Genet. Metab. 91:138-147 (2007).
Guillory. Chapter 5: Generation of Polymorphs, Hydrates, Solvates, and Amorphous Solids. Polymorphism in Pharmaceutical Solids pp. 183-226 (Brittain, H.G., ed., 1999).
Handschin et al. Skeletal Muscle Fiber-type Switching, Exercise Intolerance, and Myopathy in PGC-1-alpha Muscle-specific Knockout Animals. The Journal of Biological Chemistry 282(41):30014-30021 (2007).
Herridge et al. Functional Disability 5 Years after Acute Respiratory Distress Syndrome. The New England Journal of Medicine, 364(14):1293-1304 (2011).
Hough et al. The role of future longitudinal studies in ICU survivors: understanding determinants and pathophysiology of weakness and neuromuscular dysfunction. Curr Opin Crit Care 13:489-496 (2007).
Hough. Improving physical function during and after critical care. Curr Opin Crit Care 19(5):488-495 (2013).
Houten et al. The Biochemistry and Physiology of Mitochondrial Fatty Acid (β-Oxidation and Its Genetic Disorders. Annual Review of Physiology 78(1):23-44 (2016).
Jahnke et al. Metabolic remodeling agents show beneficial effects in the dystrophin-deficient mdx mouse model. Skeletal Muscle 2(16):1-11 (2012).
Johri et al. Pharmacologic activation of mitochondrial biogenesis exerts widespread beneficial effects in a transgenic mouse model of Huntington's disease. Human Molecular Genetics 21(5):1124-1137 (2012) Advance Access published on Nov. 17, 2011.
Kadayat et al. Targeting Peroxisome Proliferator-Activated Receptor Delta (PPARσ): A Medicinal Chemistry Perspective. J. Med. Chem. 63(18):10109-10134 (2020).
Keraliya et al. Effect of Solvent on Crystal Habit and Dissolution Behavior of Tolbutamide by Initial Solvent Screening. Dissolution Technologies 17(1):16e21 (2010).
Kersten et al. Roles of PPARs in health and disease. Nature 405:421-424 (2000).
Knottnerus et al. Disorders of mitochondrial long-chain fatty acid oxidation and the carnitine shuttle. Rev Endocr Metab Disord 19(1):93-106 (2018).
Konttinen et al. PPAR[beta]/[delta]-agonist GW0742 ameliorates dysfunction in fatty acid oxidation in PSEN1[Delta]E9 astrocytes. Glia 67(1):146-159 (2019).
Lagu et al. Selective PPAR[delta] Modulators Improve Mitochondrial Function: Potential Treatment for Duchenne Muscular Dystrophy (DMD). ACS Med Chem Lett 9(9):935-940 (2018).
Lee et al., Multiple mitochondrial DNA deletions associated with age in skeletal muscle of rhesus monkeys. J. Gerontol. 48:B201-B205 (1993).
Levey et al. A more accurate method to estimate glomerular filtration rate from serum creatinine: a new prediction equation. Modification of Diet in Renal Disease Study Group. Ann Intern Med 130:461-470 (1999).

(56) References Cited

OTHER PUBLICATIONS

Liu et al. Identification of a Series of PPAR gamme/delta Dual Agonists via Solid-Phase Parallel Synthesis. Bioorg. Med. Chem. Lett. 11:2959-2962 (2001).
Lund et al. Bezafibrate activation of PPAR drives disturbances in mitochondrial redox bioenergetics and decreases the viability of cells from patients with VLCAD deficiency. Biochim Biophys Acta Mol Basis Dis. 1867(6):166100 (2021).
Luquet et al. Peroxisome proliferator-activated receptor delta controls muscle development and oxydative capability. FASEB J 17(13): 209-226 (2003).
Mahoney et al. Analysis of global mRNA expression in human skeletal muscle during recovery from endurance exercise. FASEB J 19:1498-1500 (2005).
Mancuso et al. International Workshop: Outcome measures and clinical trial readiness in primary mitochondrial myopathies in children and adults. Consensus recommendations. Nov. 10-18, 2016, Rome, Italy. Neuromuscul Disord., 12:1126-1137 (2017).
Michalik et al. Peroxisone proliferator-activated receptors: three isotypes for a multitude of functions. Curr Opin Biotechnology 10:564-570 (1999).
Migliavacca et al. Mitochondrial oxidative capacity and NAD+ biosynthesis are reduced in human sarcopenia across ethnicities. Nat Commun 10:5808 (2019).
Miura et al. Pharmacological activiation of PPAR-beta/delta stimulates utrophin A expression in skeletal muscle fibers and restores sarcolemmal integrity in mature mdx mice. Human Molecular Genetics 18(23):4640-4649 (2009) Advance Access published on Sep. 10, 2009.
Narkar et al. AMPK and PPAR-sigma agonists are exercise mimetics. Cell 134(3):405-415 (2008).
Niyazov et al. Primary Mitochondrial Disease and Secondary Mitochondrial Dysfunction: Importance of Distinction for Diagnosis and Treatment. Mol Syndromol 7:122-137 (2016).
Nsihia-Sefaa et al. Combined defects in oxidative phosphorylation and fatty acid β-oxidation in mitochondrial disease. Biosci. Rep. 36:e00313 (2016).
Parikh et al. Diagnosis and management of mitochondrial disease: a consensus statement from the Mitochondrial Medicine Society. Genet Med. 17(9):689-701 (2015).
PCT/US2020/016430 International Search Report and Written Opinion dated Apr. 28, 2020.
PCT/US/2020/019059 International Search Report and Written Opinion dated May 15, 2020.
PCT/US2021/042412 International Search Report and Written Opinion dated Nov. 10, 2021.
Reilly et al. PPARσ as a therapeutic target in metabolic disease. FEBS Letters 582(1):26-31 (2008).
Riserus et al. Activation of peroxisome proliferator-activated receptor (PPAR)delta promotes reversal of multiple metabolic abnormalities, reduces oxidative stress, and increases fatty acid oxidation in moderately obese men. Diabetes 57(2):332-339 (2008).
Rodriguez-Spong et al. General principles of pharmaceutical solid polymorphism: a supramolecular perspective. Adv Drug Deliv Rev 56:241-274 (2004).
Russell et al. Endurance training in humans leads to fiber type-specific increases in levels of peroxisome proliferator-activated receptor-gamma coactivator-1 and peroxisome proliferator-activated receptor-alpha in skeletal muscle. Diabetes 52:2874-2881 (2003).
Sacheck et al. Rapid disuse and denervation atrophy involve transcriptional changes similar to those of muscle wasting during systemic diseases. The FASEB Journal 21:140-155 (2007).
Sadowski et al. GAL4 fusion vectors for expression in yeast or mammalian cells. Gene 118:137 (1992).
Sandri et al. PGC-1-alpha protects skeletal muscle from atrophy by suppressing Fox03 action and atrophy-specific gene transcription. PNAS 103(44):16260-16265 (2006).
Sauerberg et al. Identification and Synthesis of a Novel Selective Partial PPAR-delta Agonist with Full Efficacy on Lipid Metabolism In Vitro and In Vivo. J Med Chem 50:1495-1503 (2007).
Shangraw et al. Insulin responsiveness of protein metabolism in vivo following bedrest in humans. Am J Physiol 255:E548-558 (1988).
Souillac et al. Characterization of Delivery Systems, Differential Scanning Calorimetry. Encyclopedia of Controlled Drug Delivery pp. 212-227 (John Wiley & Sons 1999).
Tanaka et al. Activation of peroxisome proliferator-activated receptor delta induces fatty acid beta-oxidation in skeletal muscle and attenuates metabolic syndrome. PNAS USA 100:15924-15929 (2003).
Tesch et al. Skeletal muscle proteolysis in response to short-term unloading in humans. J Appl Physiol 105:902-906 (2008).
Vamecq et al. Medical Significance of Peroxisome Proliferator-Activated Receptors the Lancet, 354:141-148 (1999).
Vippagunta et al. Crystalline Solids. Advanced Drug Delivery Reviews 48:3-26 (2001).
Vockley et al. Mammalian branched-chain acyl-CoA dehydrogenases: molecular cloning and characterization of recombinant enzymes, Methods Enzymol. 324:241-58 (2000).
Wahli. Peroxisome Proliferator-Activated Receptors (PPARs): from metabolic control to epidermal wound healing. Swiss Med Weekly 132:83-91 (2002).
Wallace. Diseases of the mitochondrial DNA. Annu. Rev. Biochem. 61:1175-1212 (1992).
Wang et al. Peroxisome-proliferator-activated receptor delta activates fat metabolism to prevent obesity. Cell 113:159-170 (2003).
Wang et al. Regulation of Muscle Fiber Type and Running Endurance by PPAR-delta. PLoS Biol. 2:e294 (2004).
Watkins et al. Peroxisomal fatty acid beta-oxidation in HepG2 cells. Arch Biochem Biophys 289:329-336 (1991).
Watt et al. Suppression of plasma free fatty acids upregulates peroxisome proliferator-activated receptor (PPAR) alpha and delta and PPAR coactivator 1alpha in human skeletal muscle, but not lipid regulatory genes. J Mol Endocrinol 33:533-544 (2004).
Webster et al. Nucleotide sequence of the galactose gene cluster of Kluyveromyces lactis. Nucleic Acids Res. 16:8192-8194 (1988).
Wenz et al., Increased muscle PGC-1α expression protects from sarcopenia and metabolic disease during aging. PNAS USA 106(48):20405-10 (2009).
Wilson et al. The PPARs: From Orphan Receptors to Drug Discovery. J Med Chem 43(4):527-550 (2000).
Wolfram. Effects of the PPAR delta agonist GW501516 on exercise performance of mice. FASEB J 21(5):A580 (Abstract No. 615.26. Experimental Biology 2007 Annual Meeting; Washington, D.C. Apr. 28, 2007 to May 2, 2007.
Wu et al. Structural basis for specific ligation of the peroxisome proliferator-activated receptor σ. PNAS USA 114(13):E2563-E2570 (2017).
Yamaguchi et al. Bezafibrate can be a new treatment option for mitochondrial fatty acid oxidation disorders: Evaluation by in vitro probe acylcarnitine assay. Mol Genet Metab 107(1-2):87-91 (2012).
Yasuda et al. Sex-based differences in skeletal muscle function and morphology with short-term limb immobilization. J Appl Physiol 99: 1085-1092 (2005).
Zingarelli et al. Peroxisome Proliferator-Activated Receptor delta Regulates Inflammation via NF-kappa-B Signaling in Polymicrobial Sepsis. The American Journal of Pathology 177(4):1834-1847 (2010).
PCT/US2023/061180 International Invitation to Pay Additional Fees dated Apr. 12, 2023.
PCT/US2023/061180 International Search Report and Written Opinion dated Jun. 28, 2023.

\* cited by examiner

USE OF PPAR-DELTA AGONISTS IN THE TREATMENT OF DISEASE

CROSS-REFERENCE

This application claims the benefit of U.S. Provisional Application No. 63/302,894, filed Jan. 25, 2022, and U.S. Provisional Application No. 63/391,429, filed Jul. 22, 2022, which applications are incorporated herein by reference.

FIELD OF THE INVENTION

Described herein are methods of using a peroxisome proliferator-activated receptor delta (PPARδ) agonist compound in the treatment or prevention of diseases or disorders.

BACKGROUND OF THE INVENTION

PPARδ, a member of the nuclear regulatory superfamily of ligand-activating transcriptional regulators, is expressed throughout the body. PPARδ agonists induce genes related to fatty acid oxidation and mitochondrial biogenesis. PPARδ also has anti-inflammatory properties.

SUMMARY OF THE INVENTION

In one aspect, described herein is a method for treating a disease or disorder in a mammal comprising administering to the mammal a therapeutically effective amount of sodium (E)-2-(4-((3-(4-fluorophenyl)-3-(4-(3-morpholinoprop-1-yn-1-yl)phenyl)allyl)oxy)-2-methylphenoxy)acetate (Compound II), wherein the disease or disorder is: muscle atrophy, a primary mitochondrial myopathy, a fatty acid oxidation disorder (FAOD), a kidney disease, a glycogen storage disease (GSD), Barth syndrome, diabetic cardiomyopathy, muscular dystrophy, a neuronal activation disorder, a neurodegenerative disorder, sarcopenia, or chronic fatigue syndrome.

In some embodiments, the disease or disorder is a primary mitochondrial myopathy and the mammal with a primary mitochondrial myopathy has: at least one mutation or deletion in at least one mitochondrial DNA (mtDNA) gene; at least one mitochondrial DNA (mtDNA) defect; at least one mutation or deletion in at least one nuclear DNA (nDNA) gene involved in mitochondrial function; or a combination thereof.

In some embodiments, the disease or disorder is a primary mitochondrial myopathy and the mammal has been diagnosed with Kearns-Sayre syndrome (KSS), Leigh syndrome, maternally inherited Leigh syndrome (MILS), Mitochondrial DNA depletion syndrome (MDS), Mitochondrial encephalomyopathy, lactic acidosis and stroke-like episodes (MELAS), Mitochondrial neurogastrointestinal encephalomyopathy (MNGIE), Myoclonus epilepsy with ragged red fibers (MERRF), Neuropathy ataxia and retinitis pigmentosa (NARP), Pearson syndrome, or Progressive external ophthalmoplegia (PEO).

In some embodiments, the disease or disorder is a long-chain fatty acid oxidation disorder (LC-FOAD).

In some embodiments, the disease or disorder is a FAOD and the FAOD comprises one or more defects in one or more of the enzymes or proteins involved in the entry of long-chain fatty acids into mitochondria, intramitochondrial β-oxidation defects of long-chain fatty acids affecting membrane bound enzymes, β-oxidation defects of short- and medium-chain fatty acids affecting enzymes of the mitochondrial matrix, defects in the enzymes or proteins involved with electron transfer to the respiratory chain from mitochondrial β-oxidation, or a combination thereof. In some embodiments, the disease or disorder is a FAOD and the FAOD comprises carnitine transporter deficiency, carnitine/acylcarnitine translocase deficiency, carnitine palmitoyl transferase deficiency Type 1, carnitine palmitoyl transferase deficiency Type 2, glutaric acidemia Type 2, long-chain 3-hydroxyacyl CoA dehydrogenase deficiency, medium-chain acyl CoA dehydrogenase deficiency, short-chain acyl CoA dehydrogenase deficiency, short-chain 3-hydroxyacyl CoA dehydrogenase deficiency, trifunctional protein deficiency, or very long-chain acyl CoA dehydrogenase deficiency, or a combination thereof. In some embodiments, the disease or disorder is a FAOD and the FAOD comprises carnitine palmitoyltransferase II (CPT2) deficiency, very long-chain Acyl-CoA dehydrogenase (VLCAD) deficiency, long-chain 3-hydroxyacyl-CoA dehydrogenase (LCHAD) deficiency, Trifunctional Protein (TFP) Deficiency; or a combination thereof. In some embodiments, the disease or disorder is a FAOD and the mammal has one or more mutations in one or more of the enzymes or proteins of the mitochondrial fatty acid beta-oxidation pathway, wherein the one or more enzymes or proteins of the mitochondrial fatty acid beta-oxidation pathway are selected from the group consisting of short-chain acyl-CoA dehydrogenase (SCAD), medium-chain acyl-CoA dehydrogenase (MCAD), long-chain 3-hydroxyacyl-CoA dehydrogenase (LCHAD), very long-chain acyl-CoA dehydrogenase (VLCAD), mitochondrial trifunctional protein (TFP), carnitine transporter (CT), Carnitine palmitoyltransferase I (CPT I), carnitine-acylcarnitine translocase (CACT), carnitine palmitoyltransferase II (CPT II), isolated long-chain L3-hydroxyl-CoA dehydrogenase, medium-chain L3-hydroxyl-CoA dehydrogenase, short-chain L3-hydroxyl-CoA dehydrogenase, medium-chain 3-ketoacylCoA thiolase, and long-chain 3-ketoacylCoA thiolase (LCKAT).

In some embodiments, the disease or disorder is a glycogen storage disease (GSD) and the GSD is GSD Type II (Pompe disease), Type III (Fobes-Cori disease), Type IV (Andersen disease), Type V (McArdle disease), and Tyle VII (Tarui disease). In some embodiments, the disease or disorder is McArdle disease. In some embodiments, the mammal with McArdle disease has at least one mutation or deletion in at least one myophosphoylase (PGYM) gene, and wherein the at least one mutation in at least one PGYM gene comprises a mutation selected from p.R50X, p.G206S, p.K543T, p.F710del, p.W798R, p.R270X, p.L397P, c.1768+1G>A, c.2262delA and a combination thereof.

In some embodiments, the disease or disorder is a muscular dystrophy and the muscular dystrophy is Duchenne muscular dystrophy or Becker muscular dystrophy.

In some embodiments, the disease or disorder is a neuronal activation disorder or a neurodegenerative disorder that is Huntington's disease.

In some embodiments, the disease or disorder is sarcopenia or chronic fatigue syndrome.

In some embodiments, the disease or disorder is muscle atrophy, and wherein the muscle atrophy is secondary to a chronic disease. In some embodiments, the chronic disease is multiple sclerosis, amyotrophic lateral sclerosis, spinal muscular atrophy, critical illness neuropathy, cancer, congestive heart failure, chronic pulmonary disease, chronic renal failure, chronic liver disease, diabetes mellitus, Cushing syndrome, chronic infection, glucocorticoid-induced myopathy, statin-induced myopathy, polymyositis or dermatomyositis. In some embodiments, the disease or disorder is muscle atrophy, wherein the muscle atrophy is secondary to a genetic disease that primarily affect skeletal muscle.

In some embodiments, the disease or disorder is muscle atrophy, wherein the muscle atrophy results from a muscle disease, and wherein the muscle disease is muscular dystrophy, sarcopenia, polymyositis, or myotonia.

In some embodiments, the disease or disorder is a kidney disease, wherein the kidney disease is Alport syndrome, Goodpasture syndrome, thin basement membrane nephropathy (TBMN), focal segmental glomerulosclerosis (FSGS), benign familial hematuria (BFH), or post-transplant anti-GBM (Glomerular Basement Membrane) nephritis. In some embodiments, the kidney disease is X-linked Alport syndrome (XLAS), autosomal recessive Alport syndrome (ARAS) or autosomal dominant Alport syndrome (ADAS).

In some embodiments, the mammal has elevated creatine kinase (CPK) levels, hepatic dysfunction, cardiomyopathy, hypoglycemia, rhabdomyolysis, acidosis, decreased muscle tone (hypotonia), muscle weakness, exercise intolerance, or combinations thereof.

In some embodiments, treating the disease or disorder comprises increasing oxidative phosphorylation (OXPHOS) in the mammal, improving whole-body fatty acid oxidation (FAO) in the mammal, improving the mammal's exercise tolerance, improving muscle histology, improving mitochondrial DNA copy number, improving heteroplasmy levels, improving the quality of mitochondria, decreasing pain, decreasing fatigue, improving cognition, improving overall well-being, a reduction in myoglobinuria, reducing tachycardia, a reduction in rhabdomyosis, a reduction in muscle contracture, increasing survival or a combination thereof.

In some embodiments, improving the mammal's exercise tolerance comprises increasing the distance walked during a about a 6-minute walk test, increasing the distance walked during about a 12-minute walk test, increasing stair climbing capacity, increasing the number of stands in a 30 second sit to stand test, decreasing the feeling of exhaustion during exercise, or a combination thereof.

In some embodiments, sodium (E)-2-(4-((3-(4-fluorophenyl)-3-(4-(3-morpholinoprop-1-yn-1-yl)phenyl)allyl)oxy)-2-methylphenoxy)acetate (Compound II) is crystalline sodium (E)-2-(4-((3-(4-fluorophenyl)-3-(4-(3-morpholinoprop-1-yn-1-yl)phenyl)allyl)oxy)-2-methylphenoxy)acetate (Compound II).

In some embodiments, crystalline Compound II is crystalline Form 1 of Compound II and is characterized as having an XRPD pattern substantially the same as shown in FIG. 1 as measured using Cu Kα radiation. In some embodiments, crystalline Compound II is crystalline Form 1 of Compound II and is characterized as having an XRPD pattern with peaks at about 2.8° 2-Theta, about 7.2° 2-Theta, about 13.4° 2-Theta, about 17.8° 2-Theta, about 19.7° 2-Theta, about 19.9° 2-Theta, and about 20.6° 2-Theta as measured using Cu Kα radiation. In some embodiments, crystalline Form 1 of Compound II is further characterized as having a DSC thermogram substantially the same as shown in FIG. 2 or a DSC thermogram with an endotherm having onset at about 179.5° C. and peak at about 181.6° C. In some embodiments, crystalline Form 1 of Compound II is further characterized as having a TGA pattern substantially the same as shown in FIG. 3 or a TGA pattern with a 0.1% w/w loss from 25 to 60° C. and degradation onset at about 250° C. In some embodiments, crystalline Form 1 of Compound II is further characterized as having an FTIR spectroscopy pattern substantially the same as shown in FIG. 4 or an FTIR spectroscopy pattern with peaks at about 103 cm$^{-1}$, about 838 cm$^{-1}$, about 1220 cm$^{-1}$, about 1504 cm$^{-1}$, and about 1612 cm$^{-1}$. In some embodiments, crystalline Form 1 of Compound II is further characterized as having a Raman spectroscopy pattern substantially the same as shown in FIG. 5 or a Raman spectroscopy pattern with peaks at about 103 cm$^{-1}$, about 126 cm$^{-1}$, about 810 cm$^{-1}$, about 1158 cm$^{-1}$, about 1238 cm$^{-1}$, about 1604 cm$^{-1}$, and about 1629 cm$^{-1}$. In some embodiments, crystalline Form 1 of Compound II is unsolvated. In some embodiments, crystalline Form 1 of Compound II is an acetone solvate, 1-propanol solvate, 2-methyltetrahydrofuran solvate, methyl isobutyl ketone solvate, 1,4-dioxane solvate, chloroform solvate, tetrahydrofuran solvate, dichloromethane solvate, or a hydrate.

In some embodiments, crystalline Compound II is crystalline Form 2 of Compound II and is characterized as having an XRPD pattern substantially the same as shown in FIG. 6 as measured using Cu Kα radiation. In some embodiments, crystalline Compound II is crystalline Form 2 of Compound II and is characterized as having an XRPD pattern with peaks at about 4.5 2-Theta, about 13.8° 2-Theta, about 17.6° 2-Theta, about 19.0° 2-Theta, about 19.6° 2-Theta, about 19.9° 2-Theta, about 20.5° 2-Theta, and about 23.0° 2-Theta as measured using Cu Kα radiation. In some embodiments, crystalline Form 2 of Compound II is further characterized as having a DSC thermogram substantially the same as shown in FIG. 7; or a DSC thermogram with six endothermic events having: an onset at about 44.1° C. and a peak at about 72.4° C.; a peak at about 92.4° C.; an onset at about 107.0° C. and a peak at about 118.5° C.; an onset at about 127.6° C. and a peak at about 130.0° C.; an onset at about 146.9° C. and a peak at about 149.9° C.; and an onset at about 179.5° C. and a peak at about 181.1° C. In some embodiments, crystalline Form 2 of Compound II is further characterized as having a TGA pattern substantially the same as shown in FIG. 8; or a TGA pattern with a 17.2% w/w loss from 25 to 145° C., and degradation onset at about 275° C. In some embodiments, crystalline Form 2 of Compound II is a 2-methyltetrahydrofuran solvate.

In some embodiments, crystalline Compound II is crystalline Form 3 of Compound II and is characterized as having an XRPD pattern substantially the same as shown in FIG. 9 as measured using Cu Kα radiation. In some embodiments, crystalline Form 3 of Compound II is further characterized as having a DSC thermogram substantially the same as shown in FIG. 10; or a DSC thermogram with three endothermic events having: an onset at about 58.7° C. and a peak at about 73.2° C.; an onset at about 114.5° C. and a peak at about 136.2° C.; and an onset at about 172.5° C. and a peak at about 178.6° C. In some embodiments, crystalline Form 3 of Compound II is further characterized as having a TGA pattern substantially the same as shown in FIG. 11; or a TGA pattern with a 2.3% w/w loss from 25 to 82° C., a further 3.8% w/w loss from 82° C. to 155° C., and a degradation onset at about 275° C. In some embodiments, crystalline Form 3 of Compound II is a tetrahydrofuran solvate.

In some embodiments, crystalline Compound II is crystalline Form 4 of Compound II and is characterized as having an XRPD pattern substantially the same as shown in FIG. 12 as measured using Cu Kα radiation. In some embodiments, crystalline Compound II is crystalline Form 4 of Compound II and is characterized as having an XRPD pattern with peaks at about 3.3° 2-Theta, about 6.7° 2-Theta, about 20.1° 2-Theta, and about 20.7° 2-Theta as measured using Cu Kα radiation. In some embodiments, crystalline Form 4 of Compound II is further characterized as having a DSC thermogram substantially the same as shown in FIG.

13; or a DSC thermogram with two endothermic events having: an onset at about 111.7° C. and a peak at about 114.5° C. with a broad shoulder starting at about 70° C.; and an onset at about 142.5° C. and a peak at about 147.2° C. with a broad shoulder starting at about 130.6° C. In some embodiments, crystalline Form 4 of Compound II is further characterized as having a TGA pattern substantially the same as shown in FIG. 14; or a TGA pattern with a 14.3% w/w loss from 25 to 175° C., and degradation onset at about 285° C. In some embodiments, crystalline Form 4 of Compound II is an acetone solvate.

In some embodiments, crystalline Compound II is crystalline Form 5 of Compound II and is characterized as having an XRPD pattern substantially the same as shown in FIG. 15 as measured using Cu Kα radiation. In some embodiments, crystalline Compound II is crystalline Form 5 of Compound II and is characterized as having an XRPD pattern with peaks at about 2.8 2-Theta, about 8.3° 2-Theta, about 8.7° 2-Theta, about 13.1° 2-Theta, about 19.4° 2-Theta, about 20.2° 2-Theta, about 21.3° 2-Theta, and about 24.6° 2-Theta as measured using Cu Kα radiation. In some embodiments, crystalline Form 5 of Compound II is further characterized as having a DSC thermogram substantially the same as shown in FIG. 16; or a DSC thermogram with two endothermic events having: an onset at 75.8° C. and two peaks at about 85.8° C. and 97.2° C.; and onset at 180.4° C. and a peak at 182.2. In some embodiments, crystalline Form 5 of Compound II is further characterized as having an FTIR spectroscopy pattern substantially the same as shown in FIG. 17; or an FTIR spectroscopy pattern with peaks at about 810 $cm^{-1}$, about 838 $cm^{-1}$, about 1220 $cm^{-1}$, about 1504 $cm^{-1}$, and about 1612 $cm^{-1}$.

In some embodiments, crystalline Compound II is substantially free of impurities. In some embodiments, crystalline Compound II is at least about 90% pure. In some embodiments, crystalline Compound II is at least about 95%, about 96%, about 97%, about 98%, or about 99% pure.

In some embodiments, sodium (E)-2-(4-((3-(4-fluorophenyl)-3-(4-(3-morpholinoprop-1-yn-1-yl)phenyl)allyl)oxy)-2-methylphenoxy)acetate (Compound II) is amorphous sodium (E)-2-(4-((3-(4-fluorophenyl)-3-(4-(3-morpholinoprop-1-yn-1-yl)phenyl)allyl)oxy)-2-methylphenoxy)acetate (Compound II). In some embodiments, amorphous Compound II is characterized as having an XRPD pattern showing a lack of crystallinity. In some embodiments, amorphous Compound II is further characterized as having a DSC thermogram substantially the same as shown in FIG. 22; or a DSC thermogram with: a broad endotherm with onset at 43.1° C. and peak at about 60.3° C.; a broad exotherm with onset at 107.0° C. and peak at 112.9° C.; and an endotherm with onset at 125.0° C. peak a 130.4° C. In some embodiments, amorphous Compound II is further characterized as having a TGA pattern substantially the same as shown in FIG. 23; or a TGA pattern with a 3.7% w/w loss from 25 to 150° C., and a degradation onset at about 260° C. In some embodiments, amorphous Compound II is substantially free of impurities. In some embodiments, amorphous Compound II is at least about 95%, about 96%, about 97%, about 98%, or about 99% pure.

In some embodiments, Compound II is administered to the mammal at a dose of about 10 mg to about 500 mg. In some embodiments, Compound II is administered to the mammal at a dose of about 50 mg to about 200 mg. In some embodiments, Compound II is administered to the mammal at a dose of about 75 mg to about 125 mg. In some embodiments, Compound II is administered to the mammal at a dose of about 50 mg. In some embodiments, Compound II is administered to the mammal at a dose of about 100 mg.

In some embodiments, Compound II is systemically administered to the mammal in the form an oral solution, oral suspension, powder, pill, tablet or capsule. In some embodiments, the pharmaceutical composition is in the form of a solid form pharmaceutical composition. In some embodiments, the pharmaceutical composition is in the form of a tablet, a pill, or a capsule. In some embodiments, Compound II is administered to the mammal daily. In some embodiments, Compound II is administered to the mammal once daily.

In some embodiments, the method further comprises administering at least one additional therapeutic to the mammal. In some embodiments, the at least one additional therapeutic is ubiquinol, ubiquinone, niacin, riboflavin, creatine, L-carnitine, acetyl-L-carnitine, biotin, thiamine, pantothenic acid, pyridoxine, alpha-lipoic acid, n-heptanoic acid, CoQ10, vitamin E, vitamin C, methylcobalamin, folinic acid, N-acetyl-L-cysteine (NAC), zinc, folinic acid/leucovorin calcium, resveratrol, acipimox, elamipretide, cysteamine, succinate, NAD agonists, vatiquinone (EPI-743), omaveloxolone (RTA-408), nicotinic acid, nicotinamide, elamipretide, KL133, KH176, or a combination thereof. In some embodiments, the at least one additional therapeutic is an odd-chain fatty acid, odd-chain fatty ketone, L-carnitine, or combinations thereof. In some embodiments, the at least one additional therapeutic is triheptanoin, n-heptanoic acid, a triglyceride, or a salt or thereof, or combinations thereof. In some embodiments, the at least one additional therapeutic is a creatine supplement, a vitamin B-6 supplement, glucagon, sucrose, ribose, an odd-chain fatty acid, odd-chain fatty ketone, L-carnitine, an ACE inhibitor or a combination thereof.

In some embodiments, the method further comprises administering a high protein diet, high fat diet, or combination thereof, to the mammal.

In some embodiments, the mammal is a human.

Other objects, features and advantages of the compounds, methods and compositions described herein will become apparent from the following detailed description. It should be understood, however, that the detailed description and the specific examples, while indicating specific embodiments, are given by way of illustration only, since various changes and modifications within the spirit and scope of the instant disclosure will become apparent to those skilled in the art from this detailed description.

Figure 1:
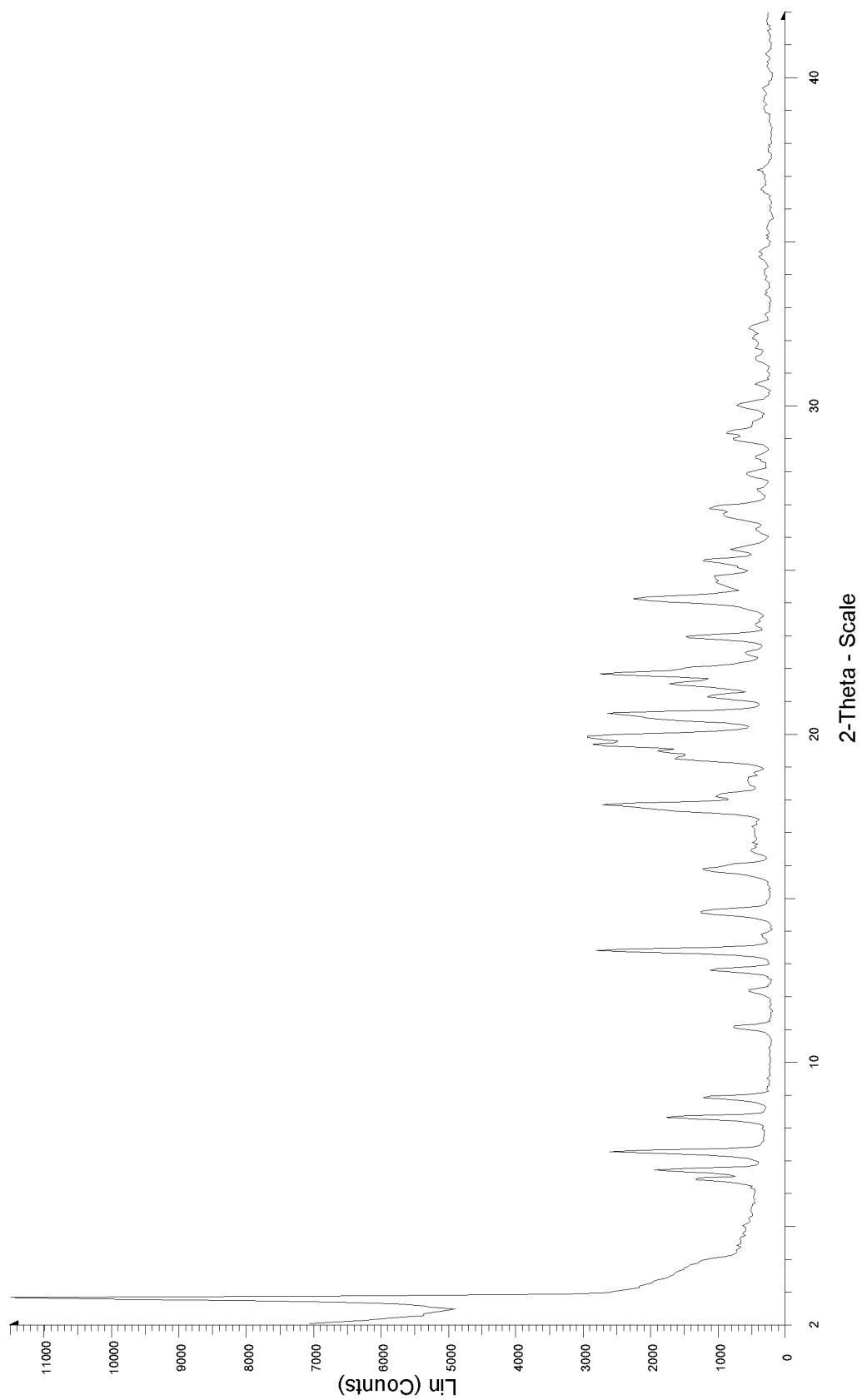
FIG. 1 illustrates a representative XRPD pattern for Form 1 of Compound II.

DETAILED DESCRIPTION OF THE INVENTION (E)-2-(4-((3-(4-Fluorophenyl)-3-(4-(3-morpholinoprop-1-yn-1-yl)phenyl)allyl)oxy)-2-methylphenoxy)acetic acid (Compound I) is a potent, selective and orally bioavailable PPARδ agonist compound. The PPARs are members of the nuclear receptor superfamily, which are ligand-modulated transcription factors that regulate gene expression of many cellular processes. The three PPARs, α, γ, and δ, are activated by lipids and are targets for current drug therapies for components of the metabolic syndrome. PPARα, a target for the fibrate class of triglyceride (TG)-lowering drugs, is primarily expressed in liver, where it upregulates genes involved in lipid oxidation in the fasted state. PPARγ is highly expressed in adipose tissue and regulates adipogenesis and insulin sensitivity. Pioglitazone is a drug from the thiazolidinedione class that increase insulin sensitivity through activating PPARγ. Compound I exhibits a significantly greater selectivity for PPARδ over PPARα and PPARγ (by 100-fold and 400-fold, respectively), and acts as a full agonist of PPARδ and only a partial agonist for both PPARα and PPARγ.

PPARδ controls genes involved in cellular metabolic processes such as glucose homeostasis, fatty acid synthesis and storage, and fatty acid mobilization and metabolism. PPARδ is expressed in several metabolically active tissues including liver, muscle, and fat. It is the most abundant PPAR isoform in skeletal muscle and has a higher expression in oxidative type I muscle fibers compared with glycolytic type II muscle fibers. A number of different physiological and pathological factors are reported to influence skeletal muscle PPARδ content. Both short term exercise and endurance training lead to increased PPARδ expression in human and rodent skeletal muscle. There is currently no marketed drug available targeting PPARδ.

Both genetic overexpression and pharmacological activation of PPARδ in mouse muscles results in increased number of fibers with high mitochondrial content and improves fatty acid oxidation. Overexpression of a constitutively active PPARδ (VP16-PPARδ) in skeletal muscles of transgenic mice pre-programs an increase in oxidative muscle fibers, enhancing running endurance in untrained adult mice (Wang, Y.-X., et al. (2004). Regulation of muscle fiber type and running endurance by PPARδ. *PLoS Biol.* 2, e294). The PPARδ agonist compound, GW1516, in combination with exercise (for 4 weeks) synergistically induced fatigue-resistant oxidative muscle fibers and mitochondrial biogenesis in mice, and therefore enhanced physical performance (Narkar, V. A., et al. (2008). AMPK and PPARδ agonists are exercise mimetics. *Cell* 134, 405-415). When mice were treated with GW1516 for a longer time (8 weeks compared to 4 weeks) a clear shift in energy substrate usage from glucose to fatty acid oxidation to a level similar to exercise training was observed, indicative of increased fatty acid metabolism (Fan, W., et al. (2017). PPARδ Promotes Running Endurance by Preserving Glucose. *Cell Metab.* 25, 1186-1193.e4).

Compound I

Compound I is a PPARδ agonist compound that is useful in the methods of treatment described herein. Compound I refers to (E)-2-(4-((3-(4-fluorophenyl)-3-(4-(3-morpholinoprop-1-yn-1-yl)phenyl)allyl)oxy)-2-methylphenoxy)acetic acid, which has the chemical structure shown below.

Compound I

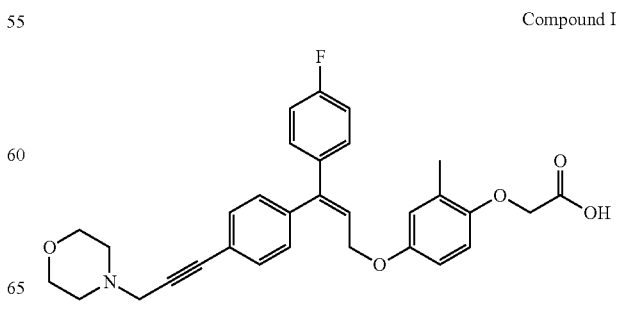

In some embodiments, Compound I exists in a zwitterionic form.

Compound I was tested on all three human PPAR subtypes (hPPAR): hPPARα, hPPARγ, and hPPARδ in vitro assays testing for such activity. Compound I exhibited a significantly greater selectivity for PPARδ over PPARα and PPARγ in humans, monkey, and mouse (see Table 1A). In some cases, Compound I acts as a full agonist of PPARδ and only a partial agonist for both PPARα and PPARγ. In some cases, Compound I demonstrates negligible activity on PPARα and/or PPARγ in transactivation assays testing for such activity.

TABLE 1A

Potency of Compound I in Human, Monkey and Mouse PPAR Receptor Transactivation Assays

| Species | PPAR Receptor Subtype | $EC_{50}$ (nM) Mean |
| --- | --- | --- |
| Human | PPARα | >10,000 |
| Human | PPARγ | >10,000 |
| Human | PPARδ | 31 ± 3 |
| Monkey | PPARα | >1000 |
| Monkey | PPARγ | >1000 |
| Monkey | PPARδ | 6.6 |
| Mouse | PPARα | >10,000 |
| Mouse | PPARγ | >10,000 |
| Mouse | PPARδ | 240 |

In some embodiments, Compound I did not show any human retinoid X receptor (hRXR) activity, or activity on the nuclear receptors FXR, LXRα or LXRβ. as a full agonist of PPARδ and only a partial agonist for both PPARα and PPARγ.

In vivo experiments demonstrated that Compound I treatment altered the expression patterns of several well-known PPARδ regulated genes in pathways involved in the beta-oxidation of long chain fatty acids (CPT1b) and mitochondrial biogenesis (PGC-1α) in mice muscle. In rat muscle, Compound I treatment increased the expression of a known PPAR regulated target gene, Angiopoietin-like 4 (ANGPTL4). In some embodiments, Compound I is used in the treatment of muscle diseases or conditions in a mammal. In some embodiments, Compound I is used to treat a disease or condition that would benefit from improvements in fatty acid oxidation or mitochondrial content or performance. In some embodiments, Compound I is used to improve in fatty acid oxidation or mitochondrial content or performance in a mammal.

Compound II refers to sodium (E)-2-(4-((3-(4-fluorophenyl)-3-(4-(3-morpholinoprop-1-yn-1-yl)phenyl)allyl)oxy)-2-methylphenoxy)acetate, which has the chemical structure shown below.

Compound II

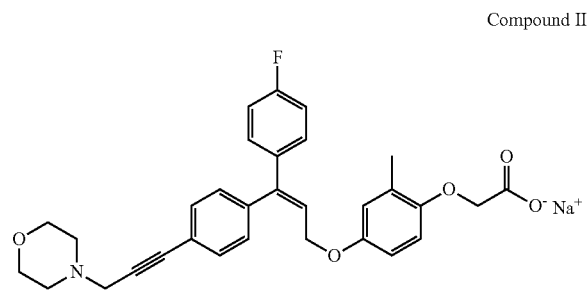 [SMILES: Cc1cc(OC/C=C(/c2ccc(F)cc2)c2ccc(C#CCN3CCOCC3)cc2)ccc1OCC(=O)[O-] ; [Na+]]

In some embodiments, Compound II is amorphous.

As used herein, the term "amorphous" or "amorphous solid form" refers to a solid form lacking crystallinity.

In some embodiments, Compound II is crystalline.

In some embodiments, crystallinity of a solid form is determined by methods known in the art. In some embodiments, crystallinity of a solid form is determined by X-Ray Powder Diffraction (XRPD). In some embodiments, crystallinity of a solid form is determined by solid state NMR.

Amorphous Compound II

Provided herein is the amorphous Compound II. Some embodiments provide a composition comprising amorphous Compound II.

Figure 22:
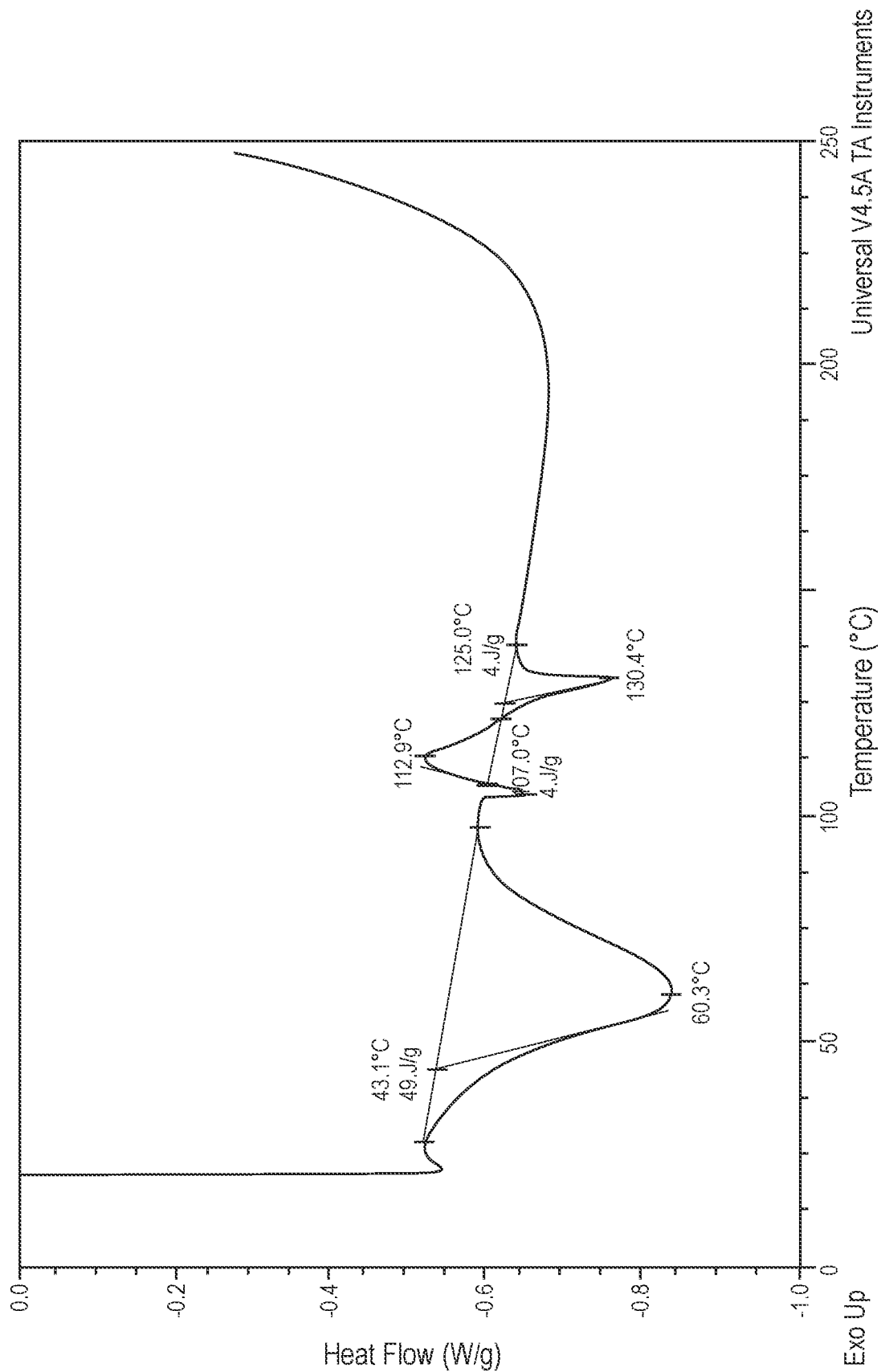
FIG. 22 illustrates a representative DSC thermogram for amorphous Compound II.

In some embodiments, amorphous Compound II is characterized as having an XRPD pattern showing a lack of crystallinity. In some embodiments, amorphous Compound II is further characterized as having a DSC thermogram substantially the same as shown in FIG. 22.

Figure 23:
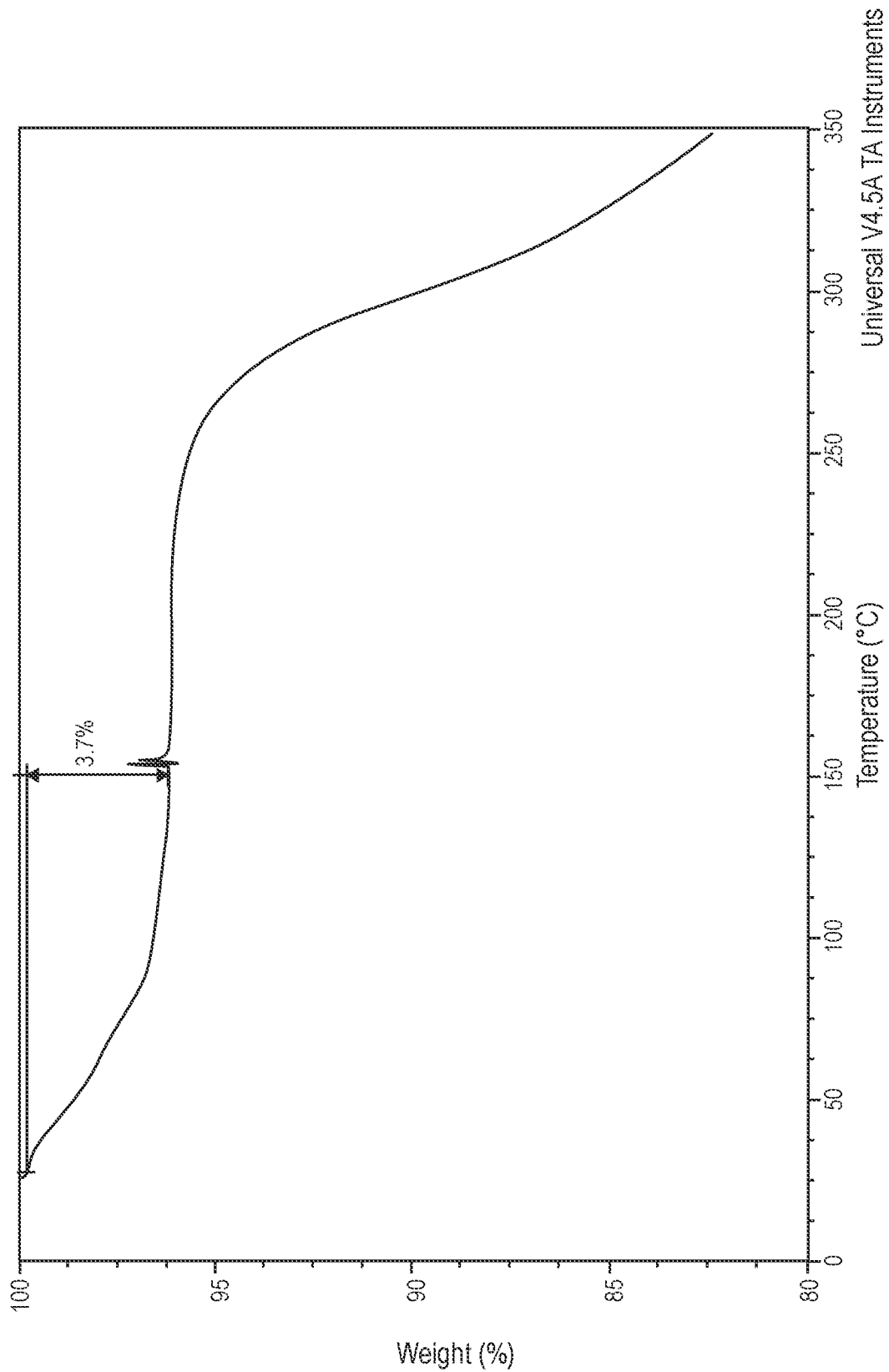
FIG. 23 illustrates a representative TGA thermogram for amorphous Compound II.

In some embodiments, amorphous Compound II is further characterized as having a DSC thermogram with: a broad endotherm with onset at 43.1° C. and peak at about 60.3° C.; a broad exotherm with onset at 107.0° C. and peak at 112.9° C.; and an endotherm with onset at 125.0° C. peak a 130.4° C. In some embodiments, amorphous Compound II is further characterized as having a TGA pattern substantially the same as shown in FIG. 23. In some embodiments, amorphous Compound II is further characterized as having a TGA pattern with a 3.7% w/w loss from 25 to 150° C., and a degradation onset at about 260° C. In some embodiments, amorphous Compound II is further characterized as having an unchanged XRPD after storage at ambient temperature over 24 hours, 48 hours, 7 days, or 10 days. In some embodiments, amorphous Compound II is further characterized as having an unchanged XRPD after storage at 75% RH and 40° C. over 10 days.

In some embodiments, amorphous Compound II is substantially free of impurities. In some embodiments, amorphous Compound II is at least about 90% pure. In some embodiments, amorphous Compound II is at least about 95%, about 96%, about 97%, about 98%, or about 99% pure. In some embodiments, amorphous Compound II is at least about 95% pure. In some embodiments, amorphous Compound II is at least about 96% pure. In some embodiments, amorphous Compound II is at least about 97% pure. In some embodiments, amorphous Compound II is at least about 98% pure. In some embodiments, amorphous Compound II is at least about 99% pure. In some embodiments, amorphous Compound II is at least about 99.1%, about 99.2%, about 99.3%, about 99.4%, about 99.5%, about 99.6%, about 99.7%, about 99.8%, about 99.9%, or about 100% pure.

Crystalline Compound II

Also provided herein is crystalline Compound II. In some embodiments, the crystalline Compound II is unsolvated.

In some embodiments, the crystalline Compound II is solvated. In some embodiments, the crystalline Compound II is an acetone solvate, 1-propanol solvate, 2-methyltetrahydrofuran solvate, methyl isobutyl ketone solvate, 1,4-dioxane solvate, chloroform solvate, tetrahydrofuran solvate, or dichloromethane solvate. In some embodiments, the crystalline Compound II is an acetone solvate. In some embodiments, the crystalline Compound II is a 2-methyltetrahydrofuran solvate. In some embodiments, the crystalline Compound II is a tetrahydrofuran solvate.

In some embodiments, the crystalline Compound II is a hydrate.

In some embodiments, amorphous Compound II is substantially free of impurities. In some embodiments, amorphous Compound II is at least about 90% pure. In some embodiments, amorphous Compound II is at least about 95%, about 96%, about 97%, about 98%, or about 99% pure. In some embodiments, amorphous Compound II is at least about 95% pure. In some embodiments, amorphous Compound II is at least about 96% pure. In some embodiments, amorphous Compound II is at least about 97% pure. In some embodiments, amorphous Compound II is at least about 98% pure. In some embodiments, amorphous Compound II is at least about 99% pure. In some embodiments, amorphous Compound II is at least about 99.1%, about 99.2%, about 99.3%, about 99.4%, about 99.5%, about 99.6%, about 99.7%, about 99.8%, about 99.9%, or about 100% pure.

Crystalline Form 1 of Compound II

In some embodiments, the crystalline Compound II is crystalline Form 1 of Compound II. In some embodiments, described herein is a composition comprising crystalline Form 1 of Compound II.

Figure 2:
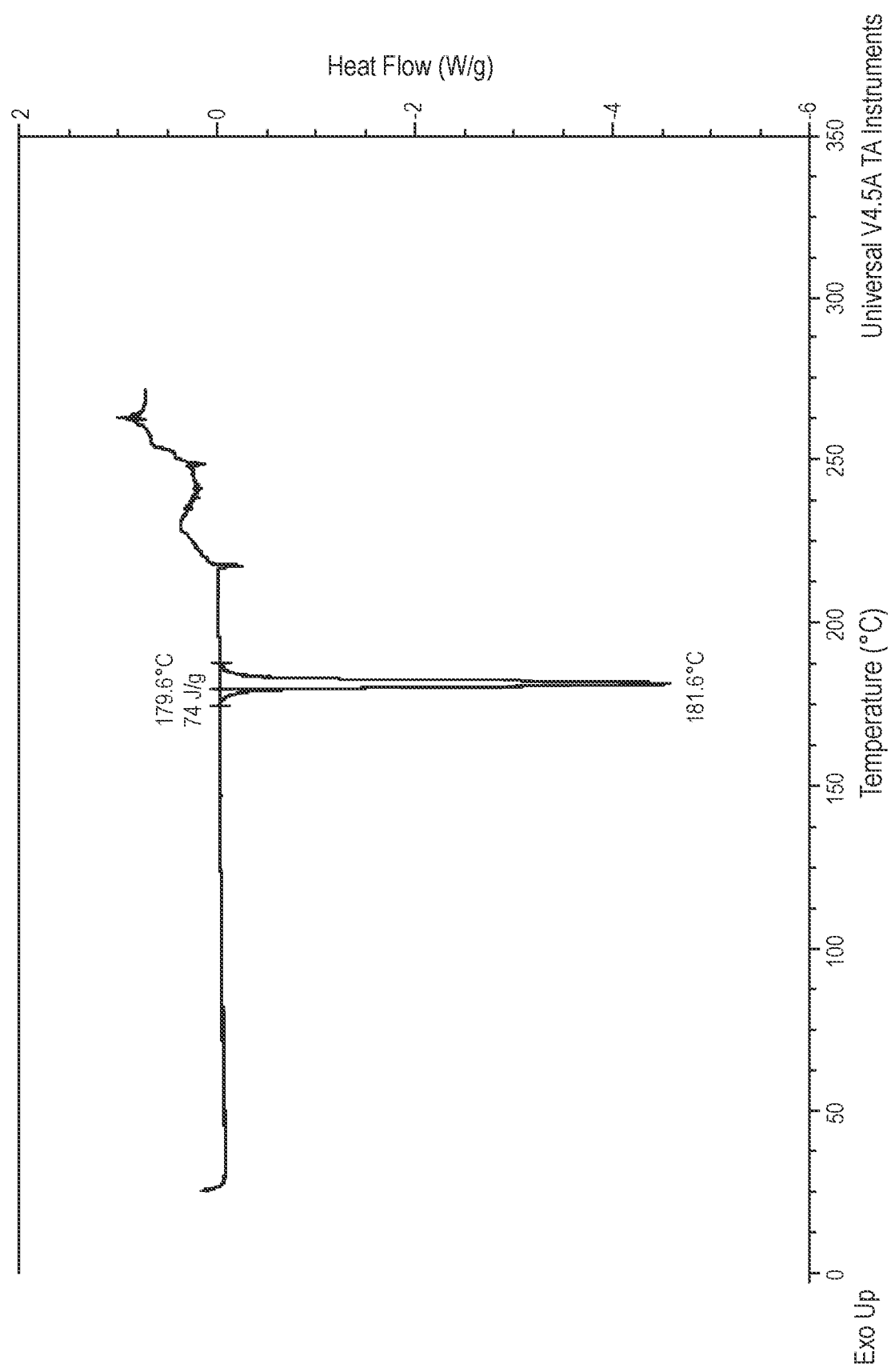
FIG. 2 illustrates a representative DSC thermogram for Form 1 of Compound II.
Figure 3:
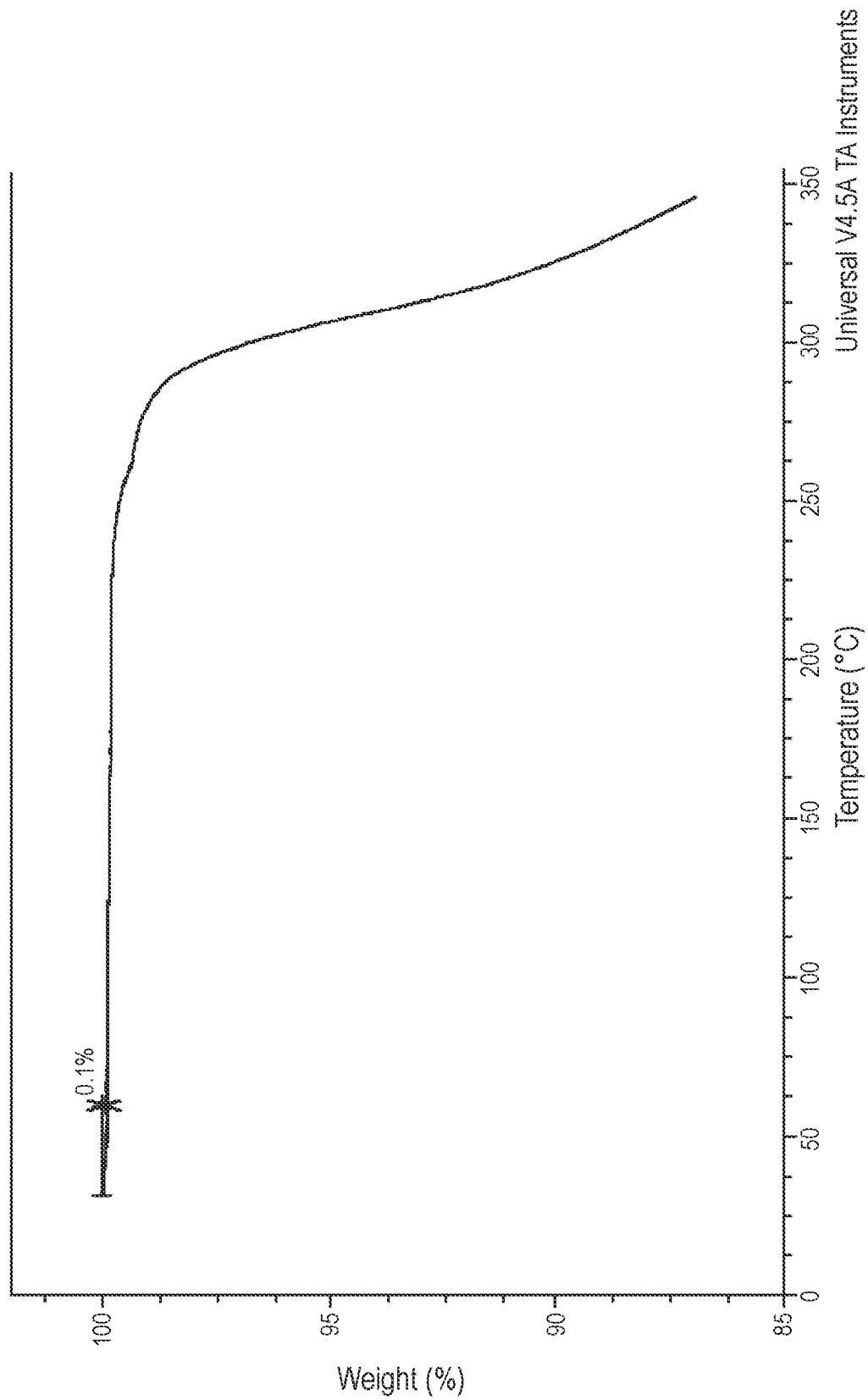
FIG. 3 illustrates a representative TGA thermogram for Form 1 of Compound II.
Figure 4:
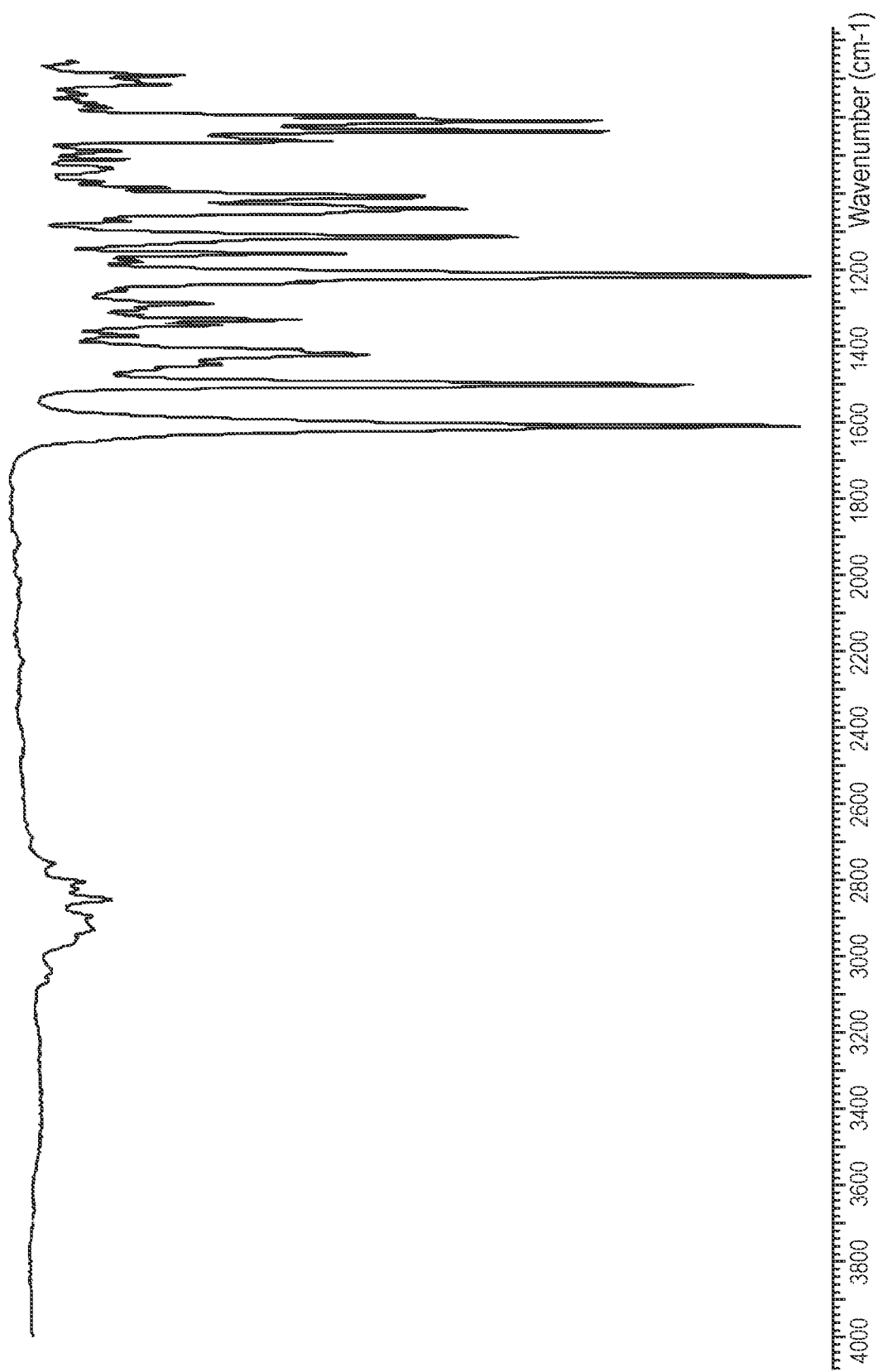
FIG. 4 illustrates a representative FTIR spectrum for Form 1 of Compound II.
Figure 5:
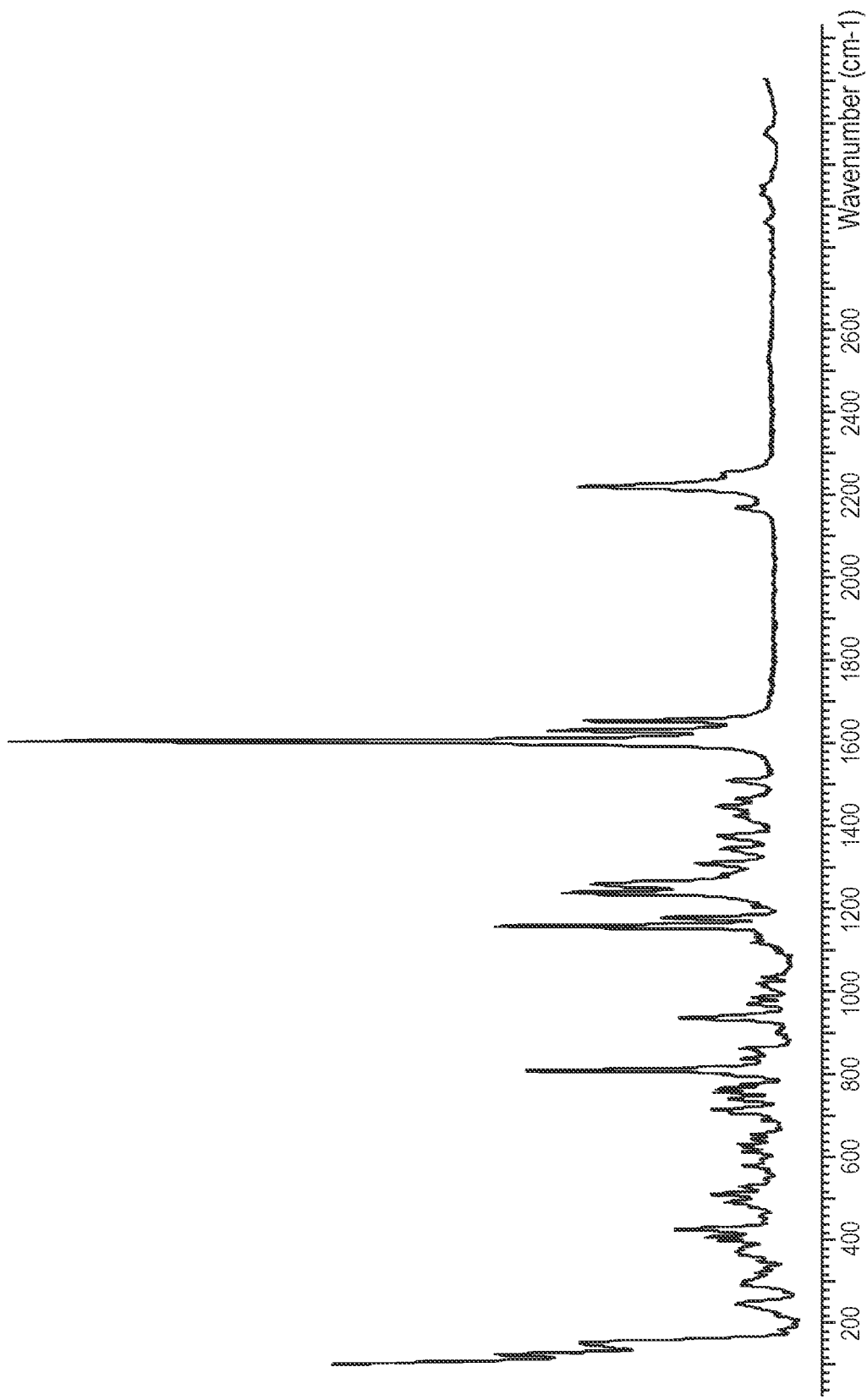
FIG. 5 illustrates a representative Raman spectrum for Form 1 of Compound II.

In some embodiments, crystalline Form 1 of Compound II is characterized as having an XRPD pattern substantially the same as the XRPD pattern shown in FIG. 1 as measured using Cu Kα radiation. In some embodiments, crystalline Form 1 of Compound II is further characterized as having a DSC thermogram substantially the same as shown in FIG. 2. In some embodiments, crystalline Form 1 of Compound II is further characterized as having a TGA pattern substantially the same as shown in FIG. 3. In some embodiments, crystalline Form 1 of Compound II is further characterized as having an FTIR spectroscopy pattern substantially the same as shown in FIG. 4. In some embodiments, crystalline Form 1 of Compound II is further characterized as having a Raman spectroscopy pattern substantially the same as shown in FIG. 5. In some embodiments, crystalline Form 1 of Compound II is further characterized as having a reversible water uptake (~13.0% w/w) between 0 and 90% Relative Humidity (RH).

In some embodiments, crystalline Form 1 of Compound II is characterized as having an XRPD pattern with peaks at about 2.8° 2-Theta, about 7.2° 2-Theta, about 13.4° 2-Theta, about 17.8° 2-Theta, about 19.7° 2-Theta, about 19.9° 2-Theta, and about 20.6° 2-Theta as measured using Cu Kα radiation. In some embodiments, crystalline Form 1 of Compound II is further characterized as having a DSC thermogram with an endotherm having onset at about 179.5° C. and peak at about 181.6° C. In some embodiments, crystalline Form 1 of Compound II is further characterized as having a TGA pattern with a 0.1% w/w loss from 25 to 60° C. and degradation onset at about 250° C. In some embodiments, crystalline Form 1 of Compound II is further characterized as having an FTIR spectroscopy pattern with peaks at about 103 cm$^{-1}$, about 838 cm$^{-1}$, about 1220 cm$^{-1}$, about 1504 cm$^{-1}$, and about 1612 cm$^{-1}$. In some embodiments, crystalline Form 1 of Compound II is further characterized as having a Raman spectroscopy pattern with peaks at about 103 cm$^{-1}$, about 126 cm$^{-1}$, about 810 cm$^{-1}$, about 1158 cm$^{-1}$, about 1238 cm$^{-1}$, about 1604 cm$^{-1}$, and about 1629 cm$^{-1}$. In some embodiments, crystalline Form 1 of Compound II is further characterized as having a reversible water uptake (~13.0% w/w) between 0 and 90% Relative Humidity (RH).

In some embodiments, crystalline Form 1 of Compound II has unit cell parameters substantially equal to the following at 100 K:

| | |
|---|---|
| Crystal System | Monoclinic |
| Space Group | P2/c |
| a (Å) | 31.581(3) |
| b (Å) | 6.1180(4) |
| c (Å) | 27.2046(18) |
| α° | 90 |
| β° | 94.447(7) |
| γ° | 90 |
| V (Å$^3$) | 5240.4(7) |
| Z | 8 |
| Calculated Density (Mg/m$^3$) | 1.363 |
| Absorption coefficient (mm$^{-1}$) | 0.937 |
| F(000) | 2256 |

Crystalline Form 2 of Compound II

In some embodiments, crystalline Compound II is crystalline Form 2 of Compound II. Crystalline Form 2 is a hydrate of Compound II. In some embodiments, described herein is a composition comprising crystalline Form 2 of Compound II.

Figure 6:
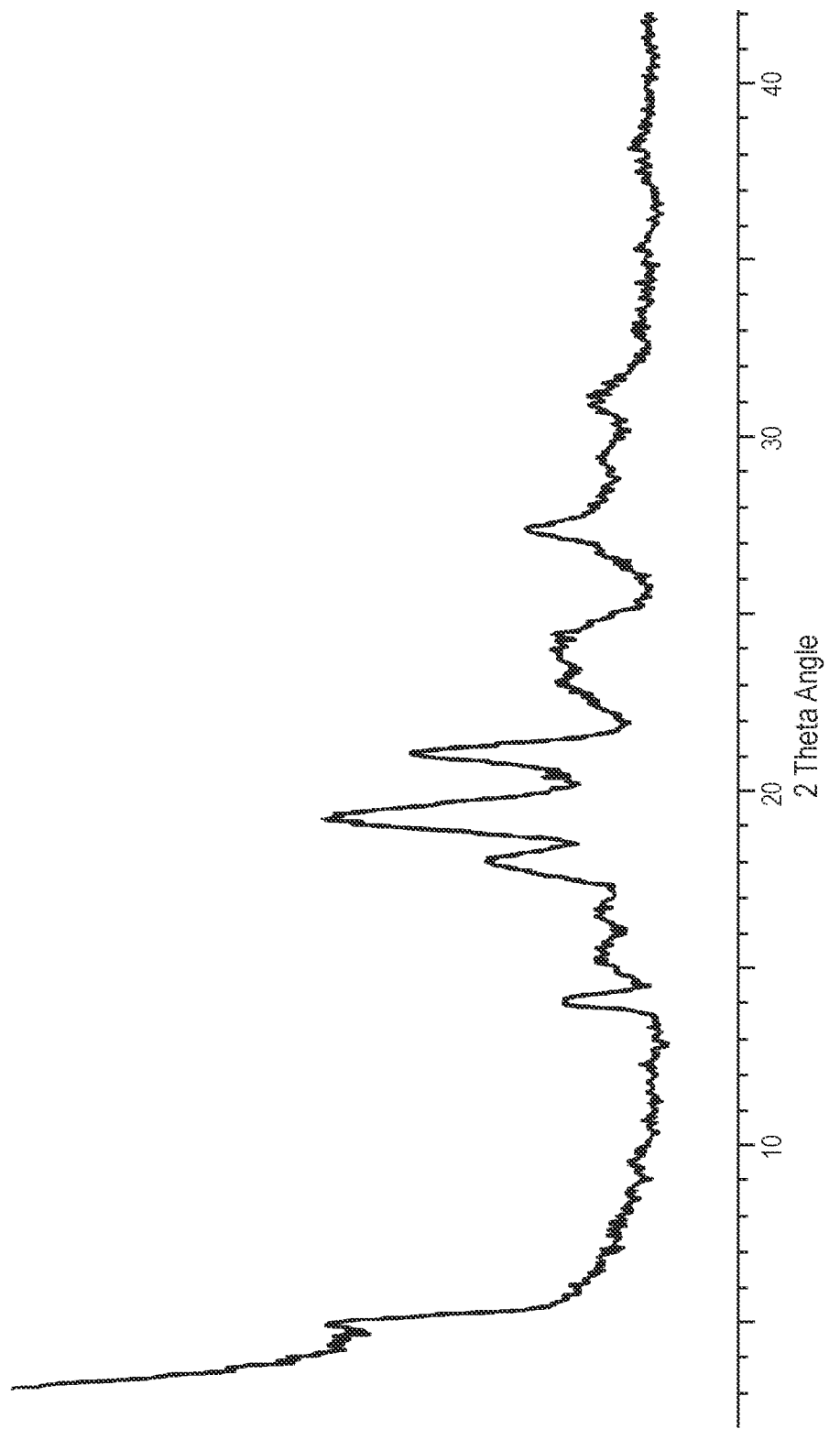
FIG. 6 illustrates a representative XRPD pattern for Form 2 of Compound II.
Figure 7:
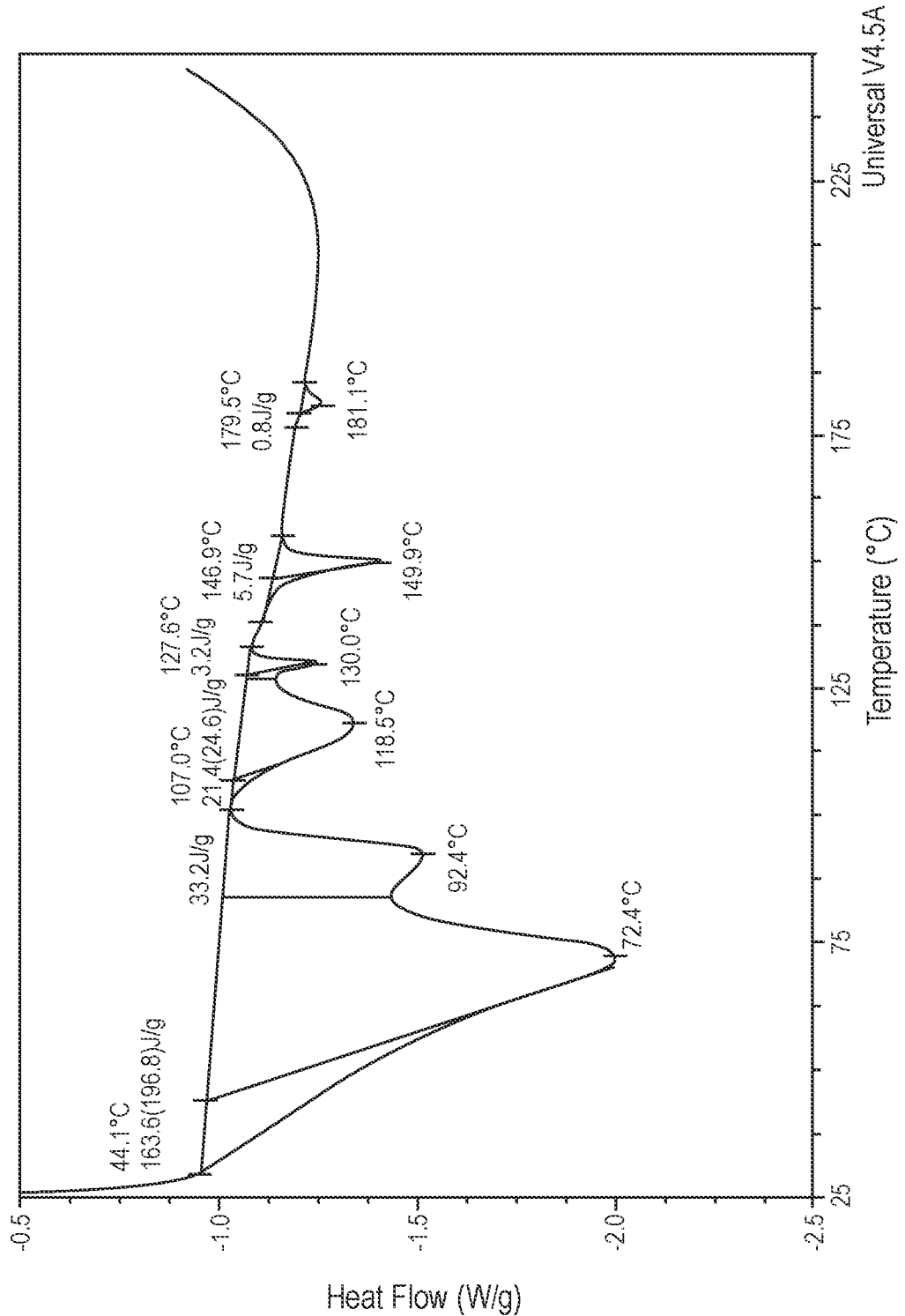
FIG. 7 illustrates a representative DSC thermogram for Form 2 of Compound II.
Figure 8:
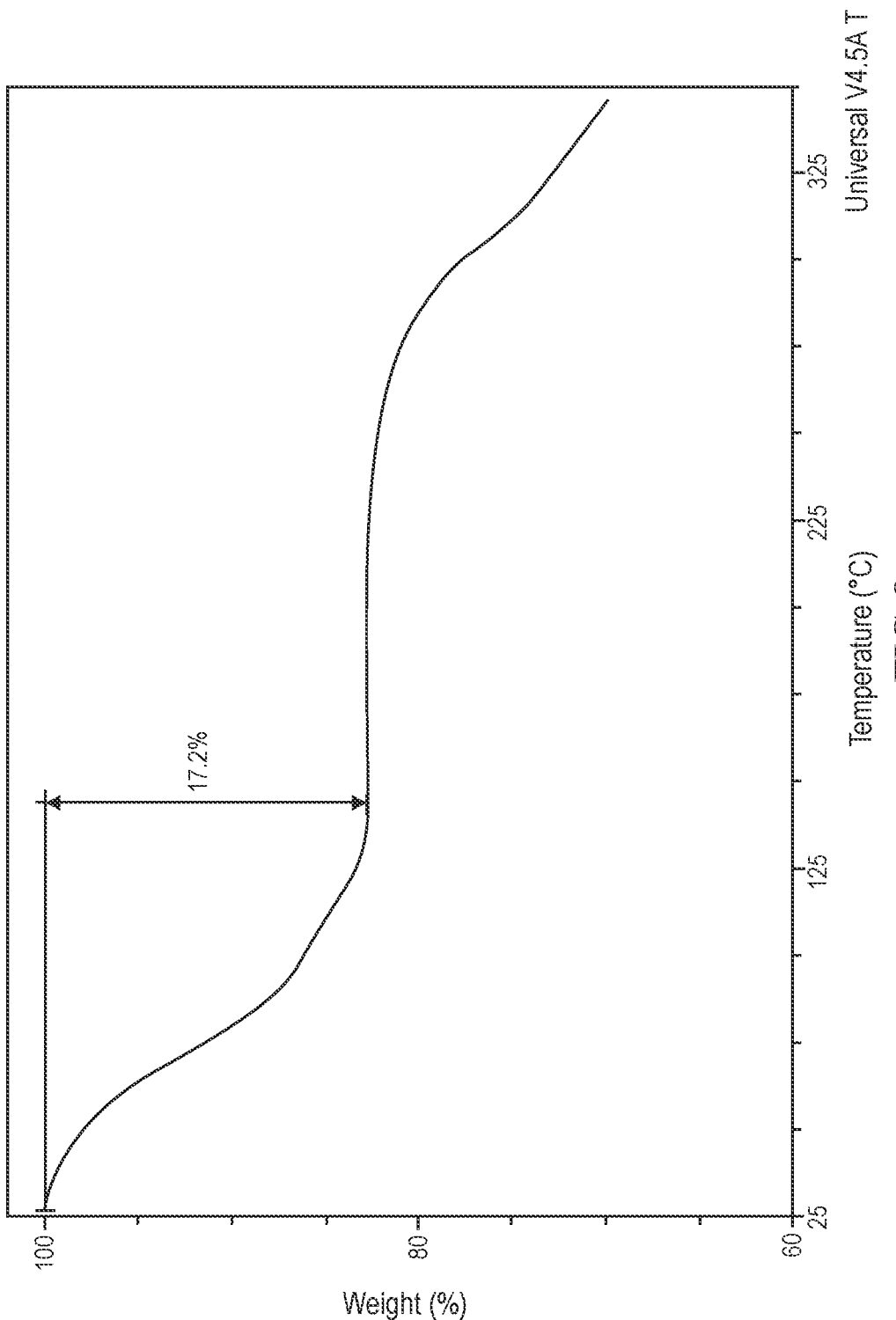
FIG. 8 illustrates a representative TGA thermogram for Form 2 of Compound II.

In some embodiments, crystalline Form 2 of Compound II is characterized as having an XRPD pattern substantially the same as the XRPD pattern shown in FIG. 6 as measured using Cu Kα radiation. In some embodiments, crystalline Form 2 of Compound II is further characterized as having a DSC thermogram substantially the same as shown in FIG. 7. In some embodiments, Form 2 of Compound II is further characterized as having a TGA pattern substantially the same as shown in FIG. 8.

In some embodiments, crystalline Form 2 of Compound II is characterized as having an XRPD pattern with peaks at about 4.5 2-Theta, about 13.8° 2-Theta, about 17.6° 2-Theta, about 19.0° 2-Theta, about 19.6° 2-Theta, about 19.9° 2-Theta, about 20.5° 2-Theta, and about 23.0° 2-Theta as measured using Cu Kα radiation. In some embodiments, crystalline Form 2 of Compound II is further characterized as having a DSC thermogram with six endothermic events having: an onset at about 44.1° C. and a peak at about 72.4° C.; a peak at about 92.4° C.; an onset at about 107.0° C. and a peak at about 118.5° C.; an onset at about 127.6° C. and a peak at about 130.0° C.; an onset at about 146.9° C. and a peak at about 149.9° C.; and an onset at about 179.5° C. and a peak at about 181.1° C. In some embodiments, crystalline Form 2 of Compound II is further characterized as having a TGA pattern with a 17.2% w/w loss from 25 to 145° C., and degradation onset at about 275° C.

In some embodiments, crystalline Form 2 of Compound II has reversible water uptake (~25% w/w) between 0 and 90% Relative Humidity (RH).

In some embodiments, crystalline Form 2 of Compound II an unchanged XRPD after GVS analysis at 90% RH and 25° C.

In some embodiments, crystalline Form 2 of Compound II has an unchanged XRPD after storage at 97% RH and 25° C. over 7 days.

In some embodiments, crystalline Form 2 of Compound II has an unchanged XRPD after storage at 75% RH and 40° C. over 7 days.

Crystalline Form 3 of Compound II

In some embodiments, crystalline Compound II is crystalline Form 3 of Compound II. Crystalline Form 3 of Compound II is a solvate of Compound II. In some embodiments, described herein is a composition comprising crystalline Form 3 of Compound II. In some embodiments, crystalline Form 3 of Compound II is an isostructural solvate form that is formed with multiple solvents. In some embodiments, crystalline Form 3 of Compound II is a solvate with toluene, methyl isobutyl ketone (MIBK), or 2-methyltetrahydrofuran.

In some embodiments, crystalline Form 3 of Compound II is a crystalline 2-methyltetrahydrofuran solvate of Compound II.

Figure 9:
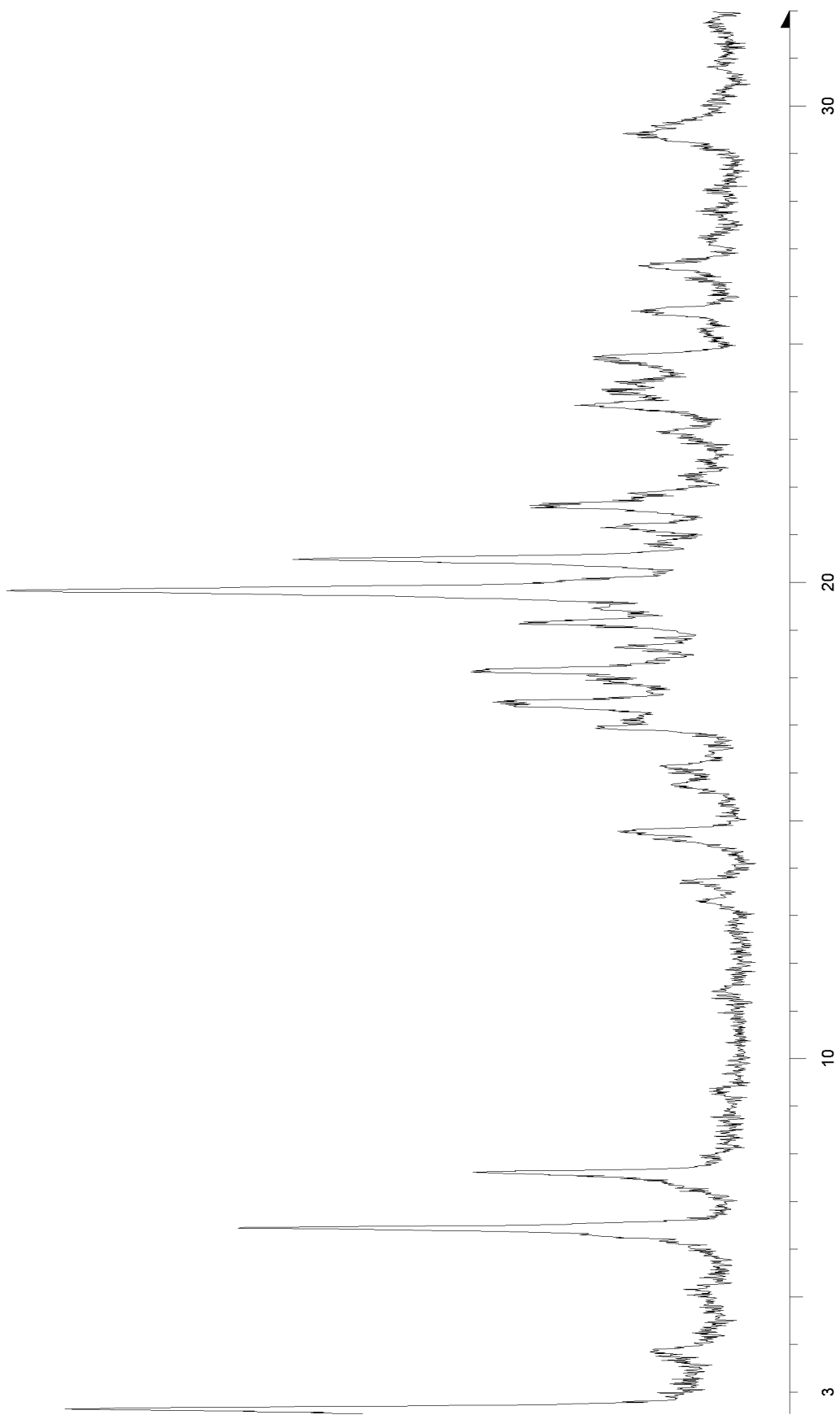
FIG. 9 illustrates a representative XRPD pattern for Form 3 of Compound II.
Figure 10:
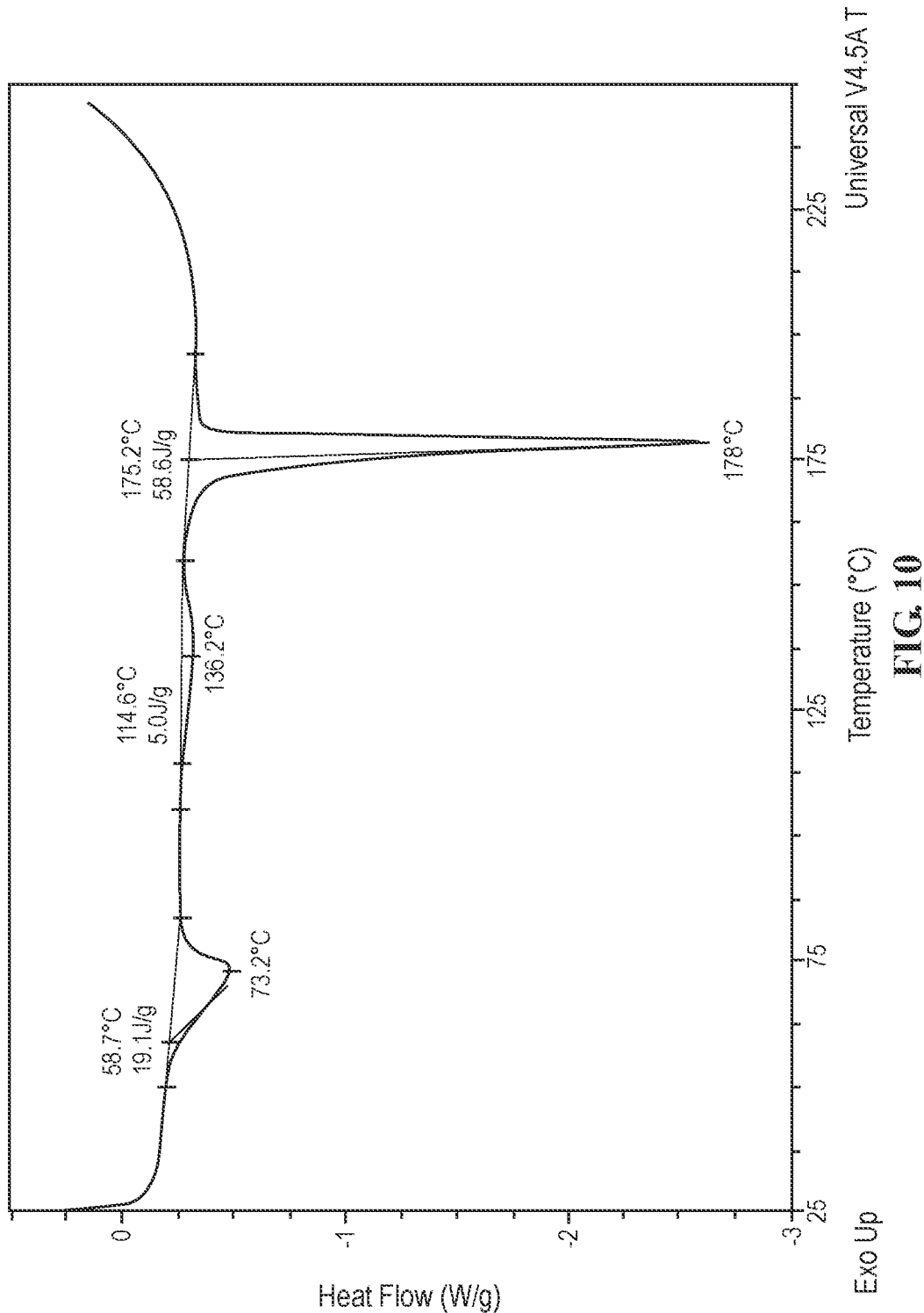
FIG. 10 illustrates a representative DSC thermogram for Form 3 of Compound II.
Figure 11:
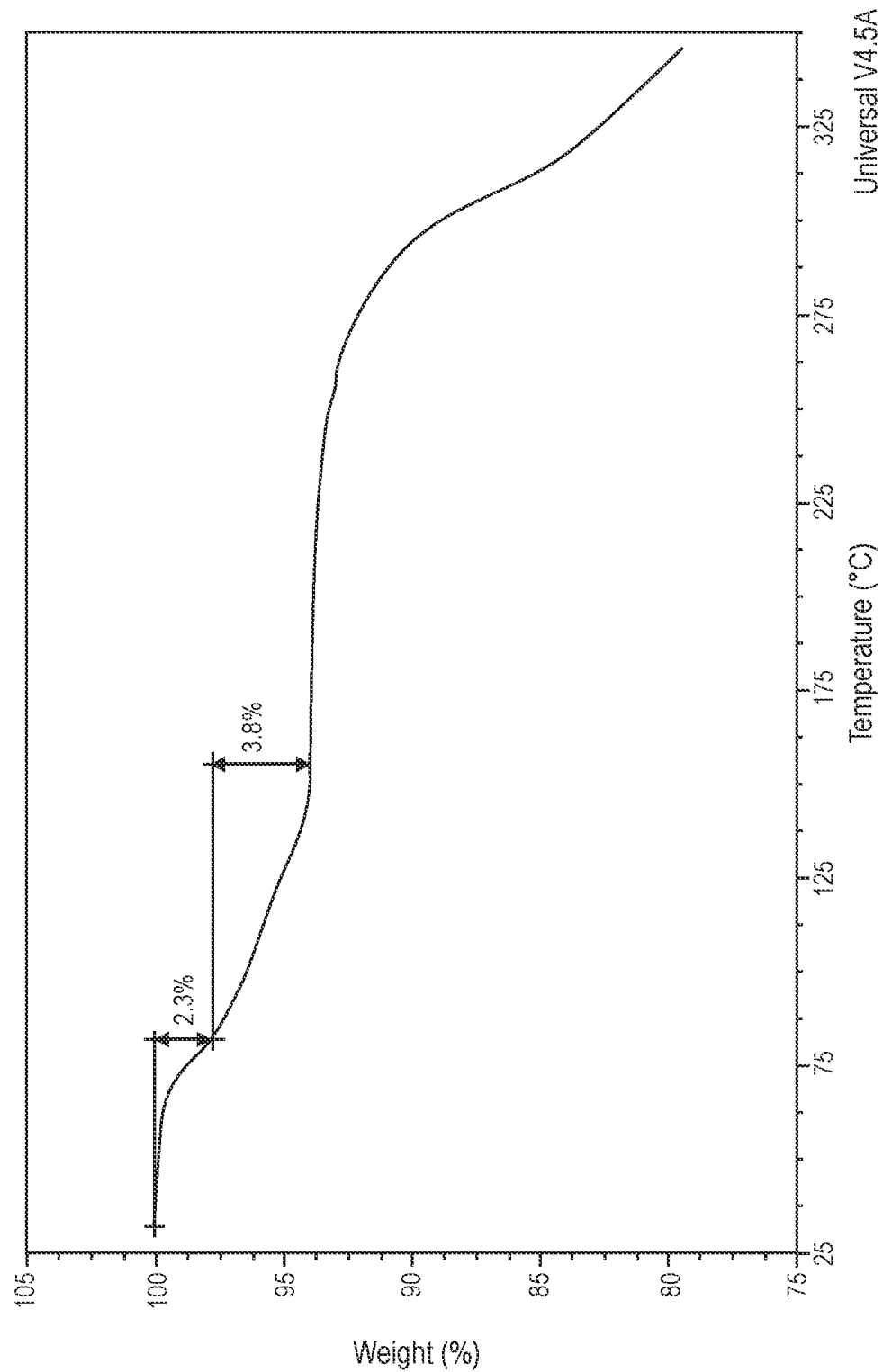
FIG. 11 illustrates a representative TGA thermogram for Form 3 of Compound II.

In some embodiments, crystalline Form 3 of Compound II is characterized as having an XRPD pattern substantially the same as the XRPD pattern shown in FIG. 9 as measured using Cu Kα radiation. In some embodiments, crystalline Form 3 of Compound II is further characterized as having a DSC thermogram substantially the same as shown in FIG. 10. In some embodiments, crystalline Form 3 of Compound II is further characterized as having a TGA pattern substantially the same as shown in FIG. 11.

In some embodiments, crystalline Form 3 of Compound II is characterized as having a DSC thermogram with three endothermic events having: an onset at about 58.7° C. and a peak at about 73.2° C.; an onset at about 114.5° C. and a peak at about 136.2° C.; an onset at about 172.5° C. and a peak at about 178.6° C. In some embodiments, crystalline Form 3 of Compound II is further characterized as having a TGA pattern with a 2.3% w/w loss from 25 to 82° C., a further 3.8% w/w loss from 82° C. to 155° C., and a degradation onset at about 275° C.

In some embodiments, crystalline Form 3 of Compound II has reversible water uptake (~9.0% w/w) between 0 and 90% Relative Humidity (RH).

In some embodiments, crystalline Form 3 of Compound II has an XRPD that converts to Form 1 after GVS analysis at 90% RH and 25° C.

In some embodiments, crystalline Form 3 of Compound II has an XRPD that converts to Form 1 after storage at 75% RH and 40° C. for 7 days.

In some embodiments, the crystalline Form 3 of Compound II is unstable and converts to Form 1 on drying.

In some embodiments, the crystalline Form 3 of Compound II is unstable and converts to Form 1 on standing in ambient conditions.

Crystalline Form 4 of Compound II

In some embodiments, crystalline Compound II is crystalline Form 4 of Compound II. Crystalline Form 4 of Compound II is a solvate. In some embodiments, described herein is a composition comprising crystalline Form 4 of Compound II. In some embodiments, crystalline Form 4 of Compound II is an isostructural solvate form that is formed with multiple solvents. In some embodiments, crystalline Form 4 of Compound II is solvated with methyl isobutyl ketone, 1,4-dioxane, chloroform, tetrahydrofuran, or dichloromethane.

In some embodiments, crystalline Form 4 of Compound II is a tetrahydrofuran solvate.

Figure 12:
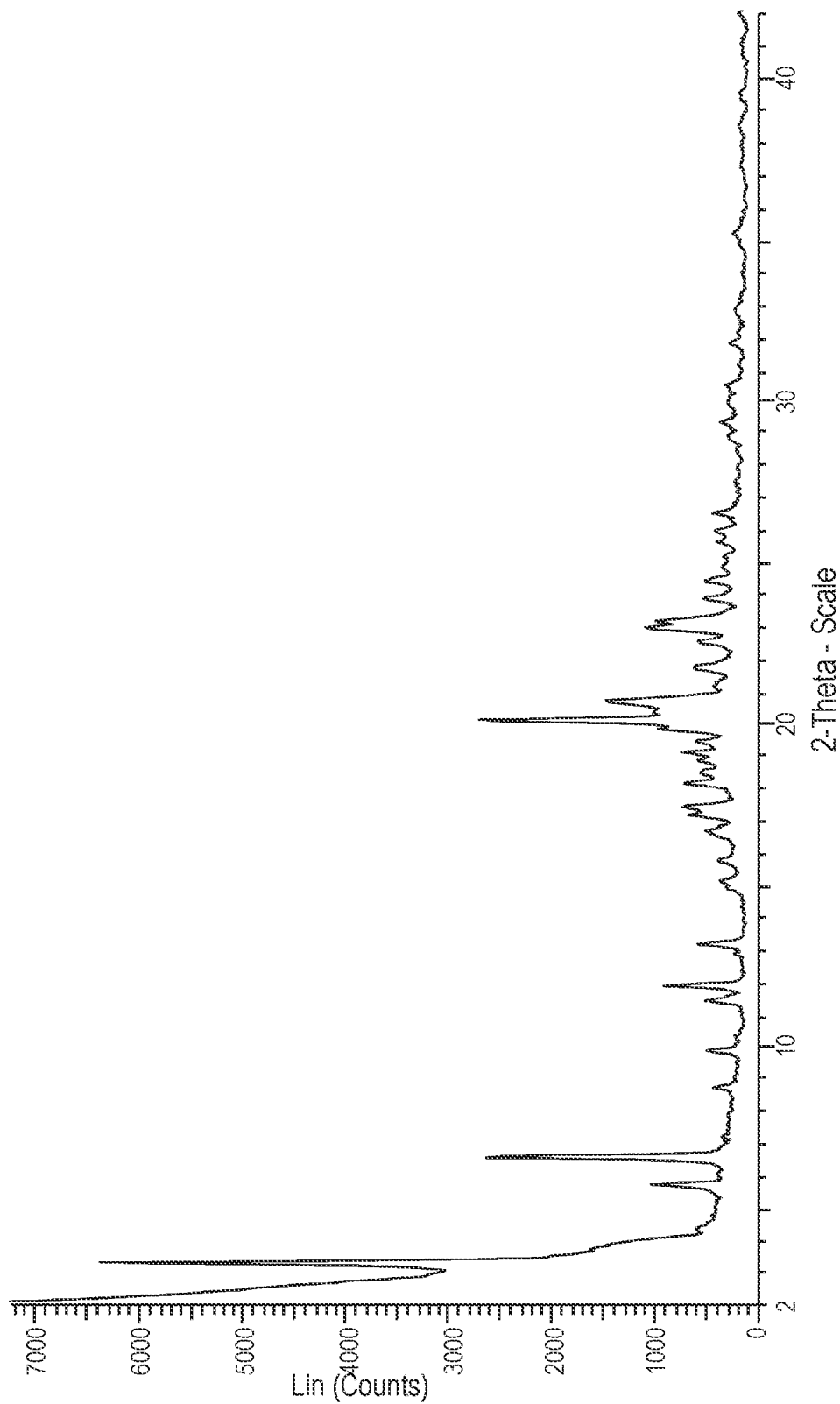
FIG. 12 illustrates a representative XRPD pattern for Form 4 of Compound II.
Figure 13:
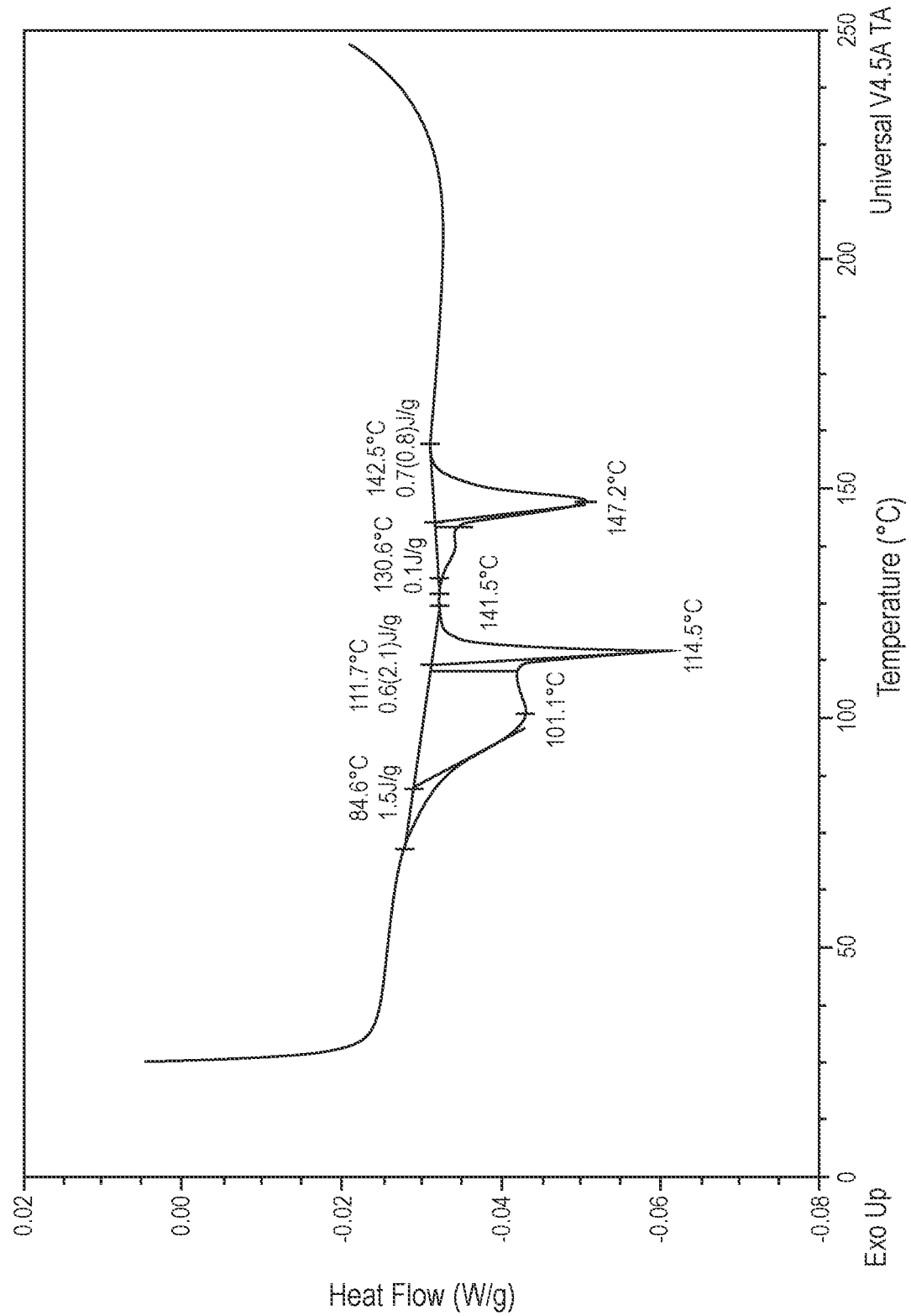
FIG. 13 illustrates a representative DSC thermogram for Form 4 of Compound II.
Figure 14:
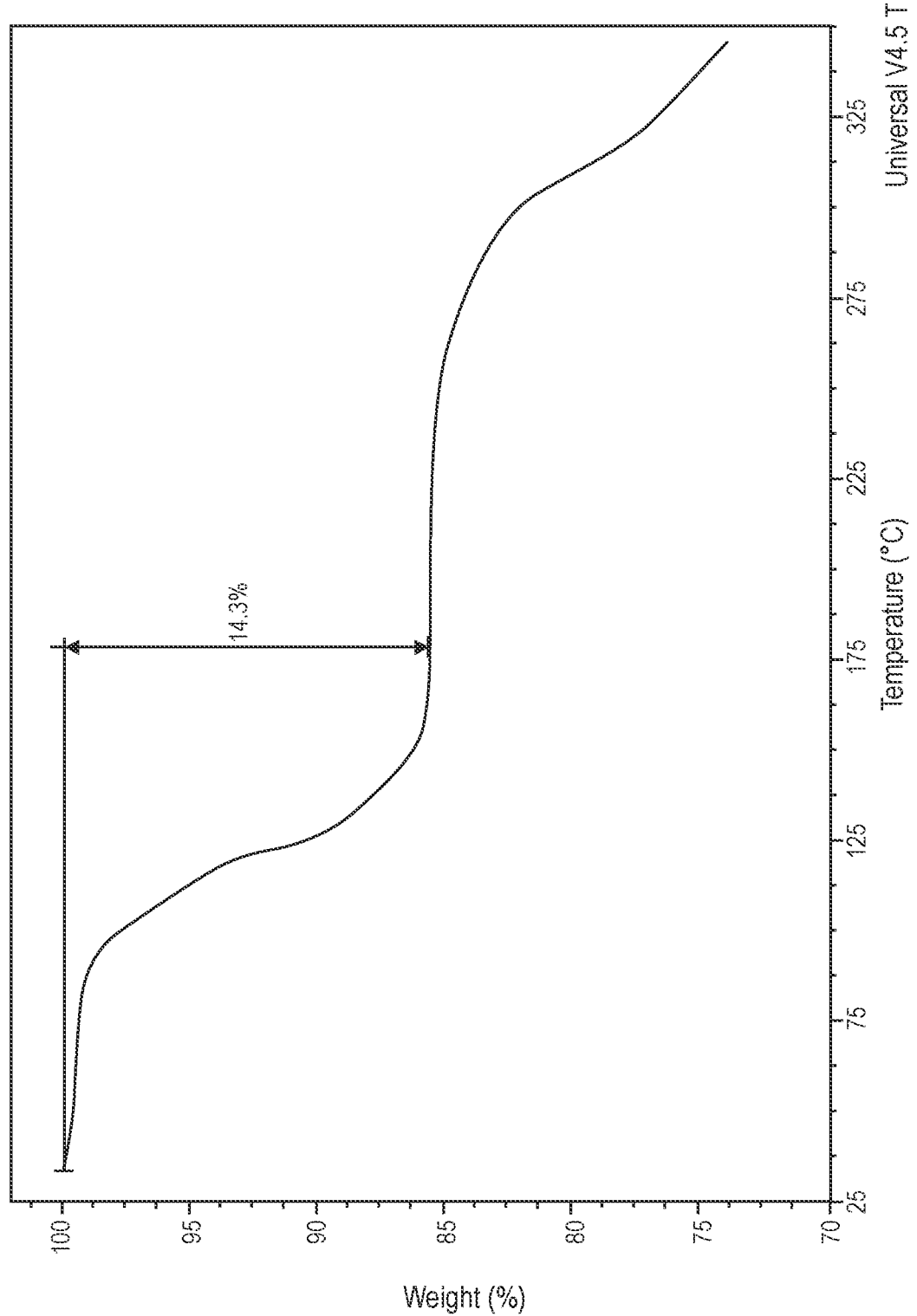
FIG. 14 illustrates a representative TGA thermogram for Form 4 of Compound II.

In some embodiments, crystalline Form 4 of Compound II is characterized as having an XRPD pattern substantially the same as the XRPD pattern shown in FIG. 12 as measured using Cu Kα radiation. In some embodiments, crystalline Form 4 of Compound II is further characterized as having a DSC thermogram substantially the same as shown in FIG. 13. In some embodiments, crystalline Form 4 of Compound II is further characterized as having a TGA pattern substantially the same as shown in FIG. 14.

In some embodiments, crystalline Form 4 of Compound II is characterized as having an XRPD pattern with peaks at about 3.3° 2-Theta, about 6.7° 2-Theta, about 20.1° 2-Theta, and about 20.7° 2-Theta as measured using Cu Kα radiation. In some embodiments, crystalline Form 4 of Compound II is further characterized as having a DSC thermogram with two endothermic events having: an onset at about 111.7° C. and a peak at about 114.5° C. with a broad shoulder starting at about 70° C.; and an onset at about 142.5° C. and a peak at about 147.2° C. with a broad shoulder starting at about 130.6° C. In some embodiments, crystalline Form 4 of Compound II is further characterized as having a TGA pattern with a 14.3% w/w loss from 25 to 175° C., and degradation onset at about 285° C.

In some embodiments, crystalline Form 4 of Compound II has reversible water uptake (~23% w/w) between 0 and 90% Relative Humidity (RH).

In some embodiments, crystalline Form 4 of Compound II has an XRPD that converts to Form 2 after GVS analysis at 90% RH and 25° C.

In some embodiments, crystalline Form 4 of Compound II has an unchanged XRPD after heating to 110° C.

In some embodiments, crystalline Form 4 of Compound II has an XRPD that converts to Form 2 after storage at 97% RH and 25° C. over 7 days.

In some embodiments, crystalline Form 4 of Compound II has an XRPD that converts to Form 1 after storage at 75% RH and 40° C. over 7 days.

Crystalline Form 5 of Compound II

In some embodiments, crystalline Compound II is crystalline Form 5 of Compound II. Crystalline Form 5 of Compound II is a solvate. In some embodiments, described herein is a composition comprising crystalline Form 5 of Compound II. In some embodiments, crystalline Form 5 of Compound II is an isostructural solvate form that is formed with multiple solvents. In some embodiments, crystalline Form 5 of Compound II is solvated with acetone, methyl ethyl ketone, diethyl ether, or ethyl acetate.

In some embodiments, crystalline Form 5 of Compound II is an acetone solvate.

Figure 15:
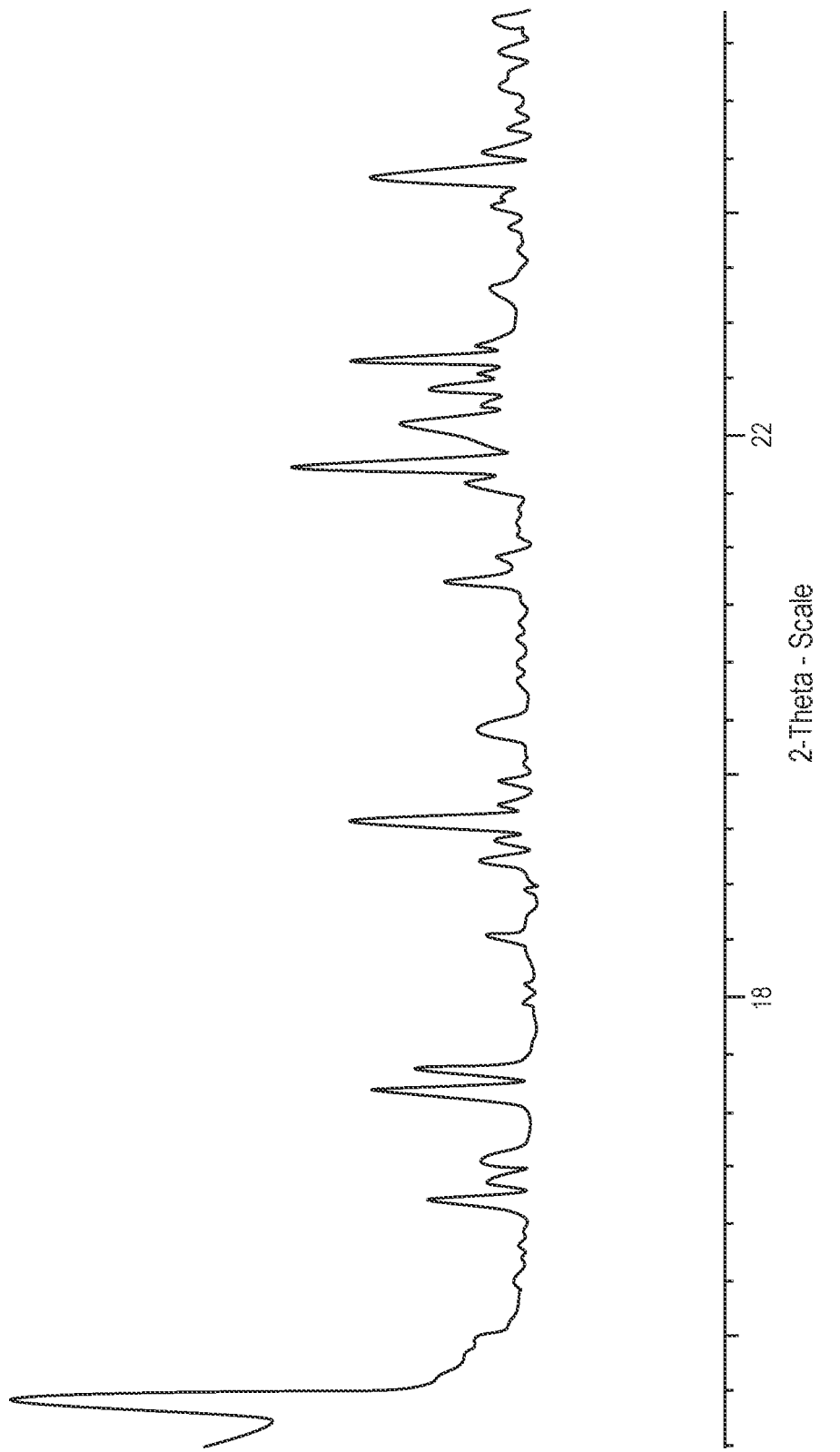
FIG. 15 illustrates a representative XRPD pattern for Form 5 of Compound II.
Figure 16:
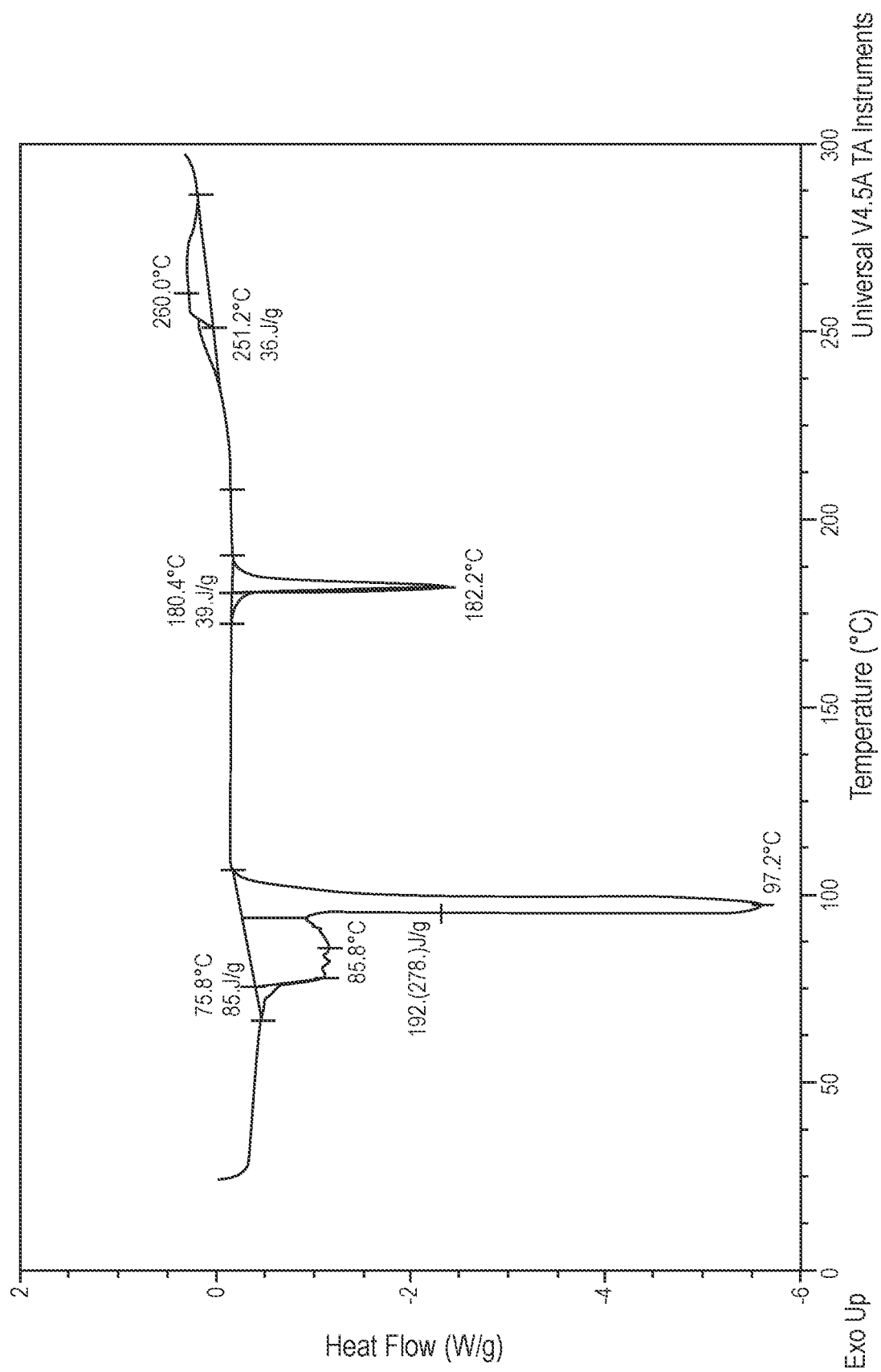
FIG. 16 illustrates a representative DSC thermogram for Form 5 of Compound II.
Figure 17:
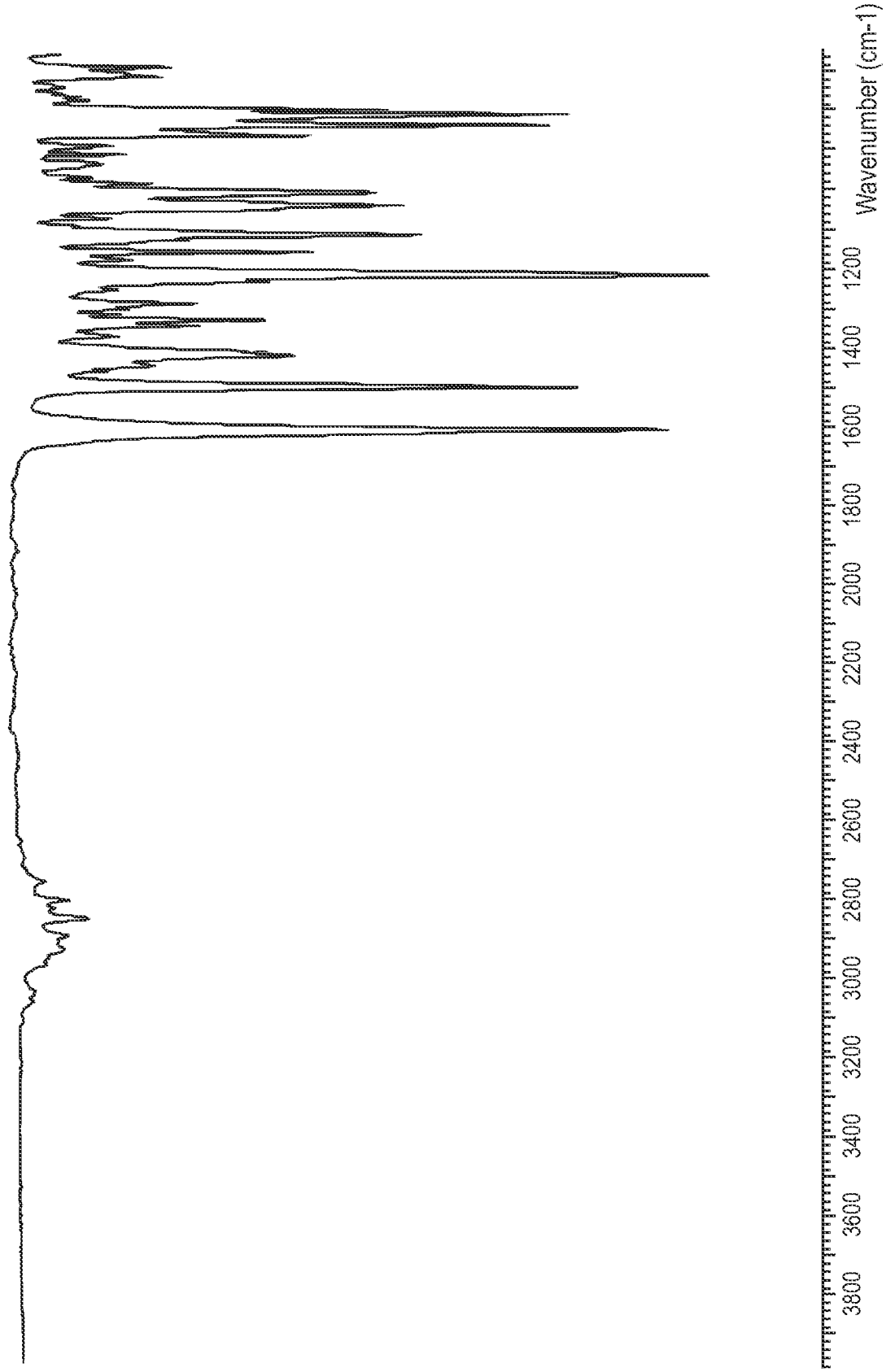
FIG. 17 illustrates a representative FTIR spectrum for Form 5 of Compound II.

In some embodiments, crystalline Form 5 of Compound II is characterized as having an XRPD pattern substantially the same as the XRPD pattern shown in FIG. 15 as measured using Cu Kα radiation. In some embodiments, crystalline Form 5 of Compound II is further characterized as having a DSC thermogram substantially the same as shown in FIG. 16. In some embodiments, crystalline Form 5 of Compound II is further characterized as having an FTIR spectroscopy pattern substantially the same as shown in FIG. 17.

In some embodiments, crystalline Form 5 of Compound II is characterized as having an XRPD pattern with peaks at about 2.8 2-Theta, about 8.3° 2-Theta, about 8.7° 2-Theta, about 13.1° 2-Theta, about 19.4° 2-Theta, about 20.2° 2-Theta, about 21.3° 2-Theta, and about 24.6° 2-Theta as measured using Cu Kα radiation. In some embodiments, crystalline Form 5 of Compound II is further characterized as having a DSC thermogram with two endothermic events having: an onset at 75.8° C. and two peaks at about 85.8° C. and 97.2° C.; and onset at 180.4° C. and a peak at 182.2. In some embodiments, crystalline Form 5 of Compound II is further characterized as having an FTIR spectroscopy pattern with peaks at about 810 cm-1, about 838 cm-1, about 1220 cm-1, about 1504 cm-1, and about 1612 cm-1.

In some embodiments, crystalline Form 5 of Compound II is unstable and converts to Form 1 on drying.

In some embodiments, crystalline Form 5 of Compound II has an XRPD that converts to Form 1 after drying.

In some embodiments, crystalline Form 5 of Compound II has an XRPD that converts to Form 1 after GVS analysis at 90% RH and 25° C.

In some embodiments, disclosed herein is crystalline Compound II solvate. In some embodiments, the crystalline Compound II solvate is an isostructural solvate that is formed with multiple solvents. In some embodiments, the crystalline Compound II solvate is a solvate with diethyl ether, ethyl acetate, methyl isobutyl ketone, methyl ethyl ketone,1-propanol, 1,4-dioxane, toluene, chloroform, tetrahydrofuran, dichloromethane, or 2-methyltetrahydrofuran. In some embodiments, the crystalline Compound II solvate is a crystalline solvate with 1,4-dioxane, tetrahydrofuran, or 2-methyltetrahydrofuran.

In some embodiments, disclosed herein is a crystalline Compound II hydrate.

Crystalline Pattern 9 of Compound II

In some embodiments, crystalline Compound II is crystalline Pattern 9 of Compound II. Pattern 9 of Compound II is a hydrate.

Figure 18:
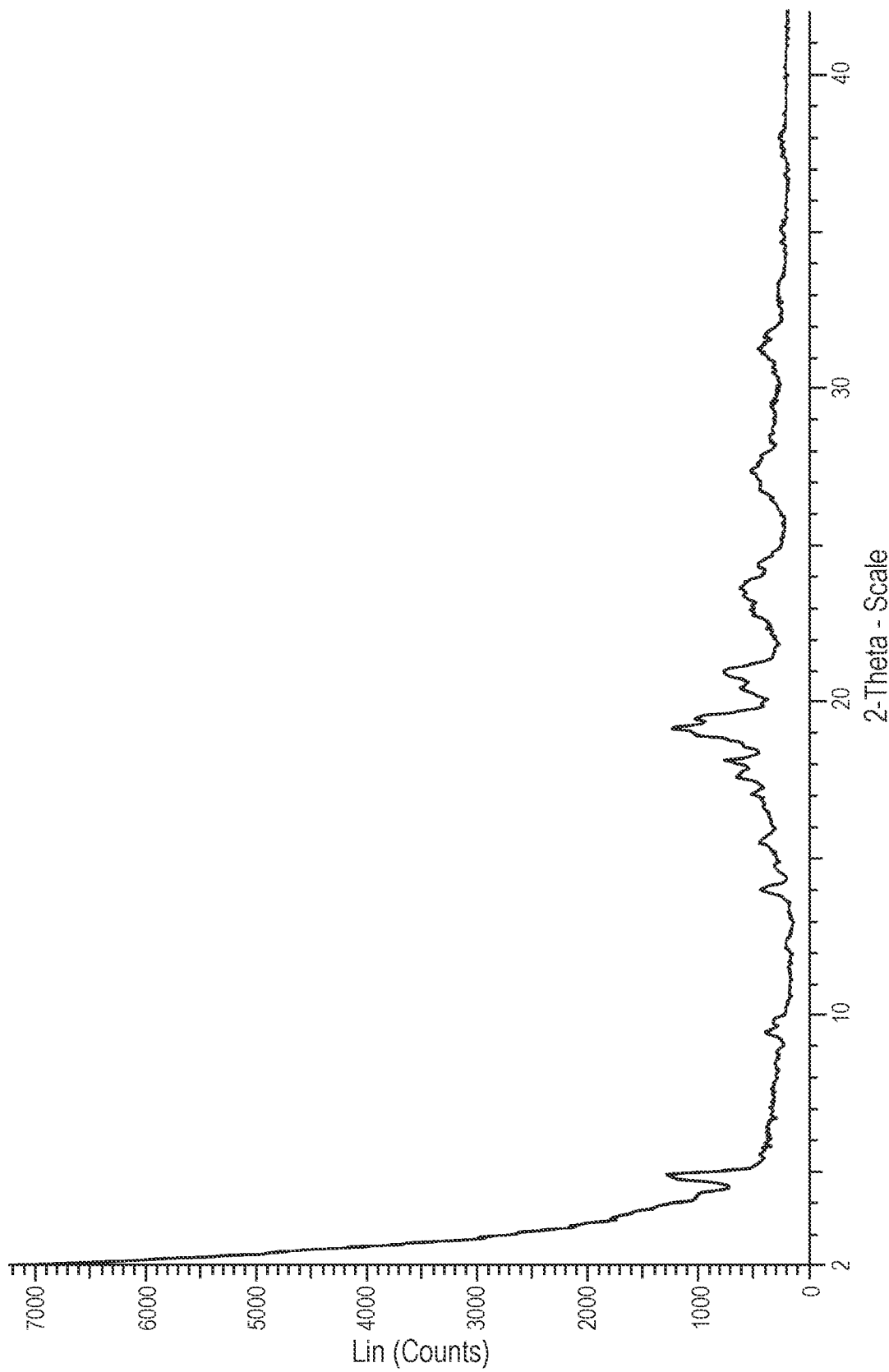
FIG. 18 illustrates a representative XRPD pattern for Pattern 9 of Compound II.
Figure 19:
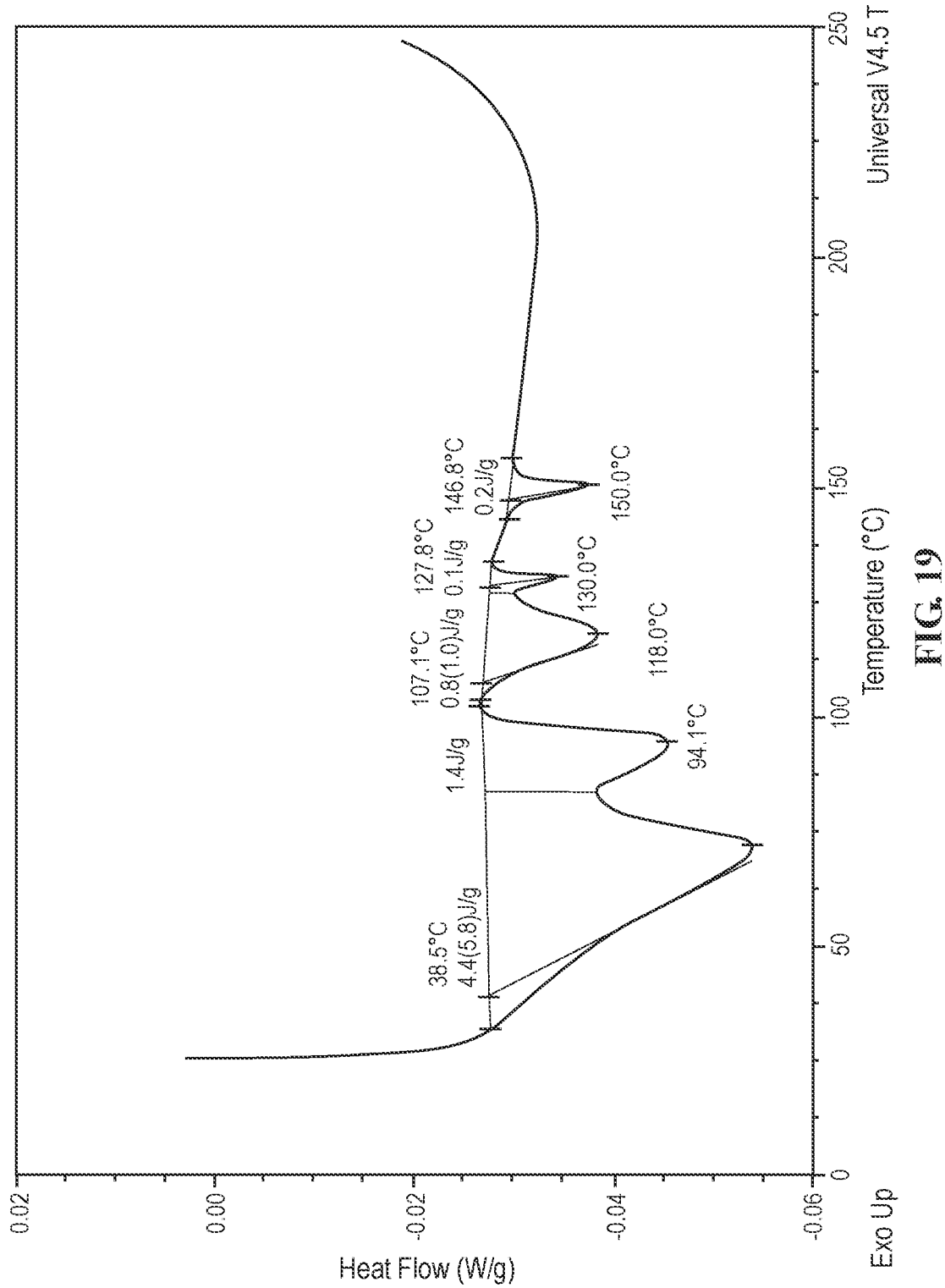
FIG. 19 illustrates a representative DSC thermogram for Pattern 9 of Compound II.
Figure 20:
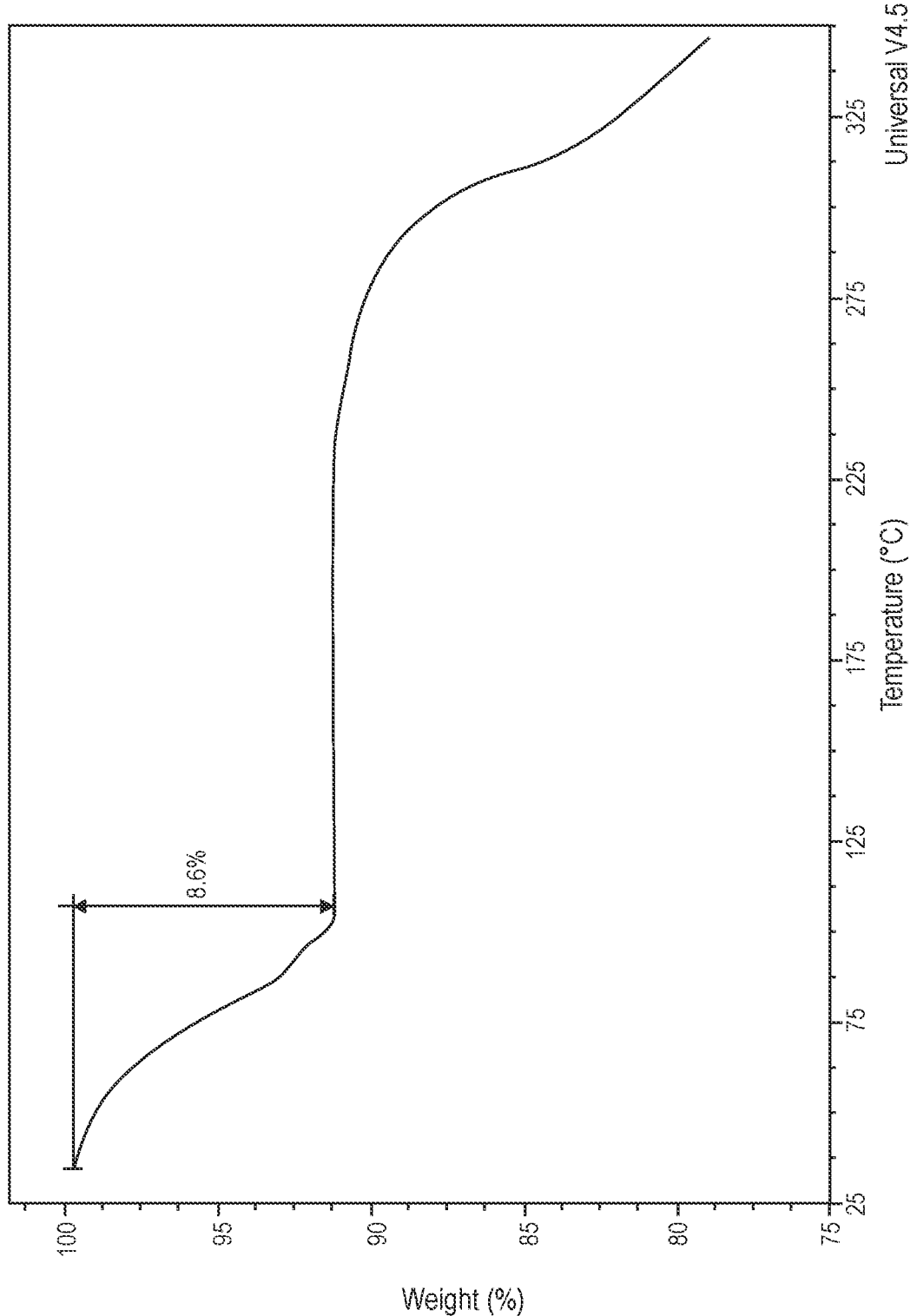
FIG. 20 illustrates a representative TGA thermogram for Pattern 9 of Compound II.

In some embodiments, crystalline Pattern 9 of Compound II is characterized as having an XRPD pattern substantially the same as the XRPD pattern shown in FIG. 18 as measured using Cu Kα radiation. In some embodiments, crystalline Pattern 9 of Compound II has a DSC thermogram substantially the same as the DSC thermogram shown in FIG. 19. In some embodiments, crystalline Pattern 9 of Compound II has a DSC thermogram with three endothermic events having: an onset at about 38.5° C. and two peaks at about 71.5° C. and 94.1° C.; an onset at about 107.1° C. and two peaks at about 118.0° C. and 130.0° C.; and an onset at about 146.8° C. and a peak at about 150.0° C. In some embodiments, crystalline Pattern 9 of Compound II has a TGA pattern substantially the same as shown in FIG. 20. In some embodiments, crystalline Pattern 9 of Compound II has a TGA pattern with a 8.6% w/w loss from 25 to 105° C., and degradation onset at about 270° C. In some embodiments, crystalline Pattern 9 of Compound II has reversible water uptake (~27% w/w) between 0 and 90% Relative Humidity (RH). In some embodiments, crystalline Pattern 9 of Compound II has an unchanged XRPD after GVS analysis at 90% RH and 25° C.

In some embodiments, provided herein is crystalline Compound II 2-methyltetrahydrofuran solvate (Pattern 5). In some embodiments, the crystalline Compound II 2-methyltetrahydrofuran solvate (Pattern 5) is unstable.

In some embodiments, provided herein is crystalline Compound II 1,4-dioxane solvate (Pattern 6). In some embodiments, the crystalline Compound II 1,4-dioxane solvate (Pattern 6) is unstable.

In some embodiments, provided herein is crystalline Compound II solvate Pattern 8. In some embodiments, crystalline Compound II solvate Pattern 8 is an isostructural solvate form that is formed with multiple solvents. In some embodiments, crystalline Compound II solvate Pattern 8 is a crystalline solvate with ethyl acetate. In some embodiments, the crystalline Compound II solvate Pattern 8 is unstable and converts to Form 1 on drying.

Figure 24:
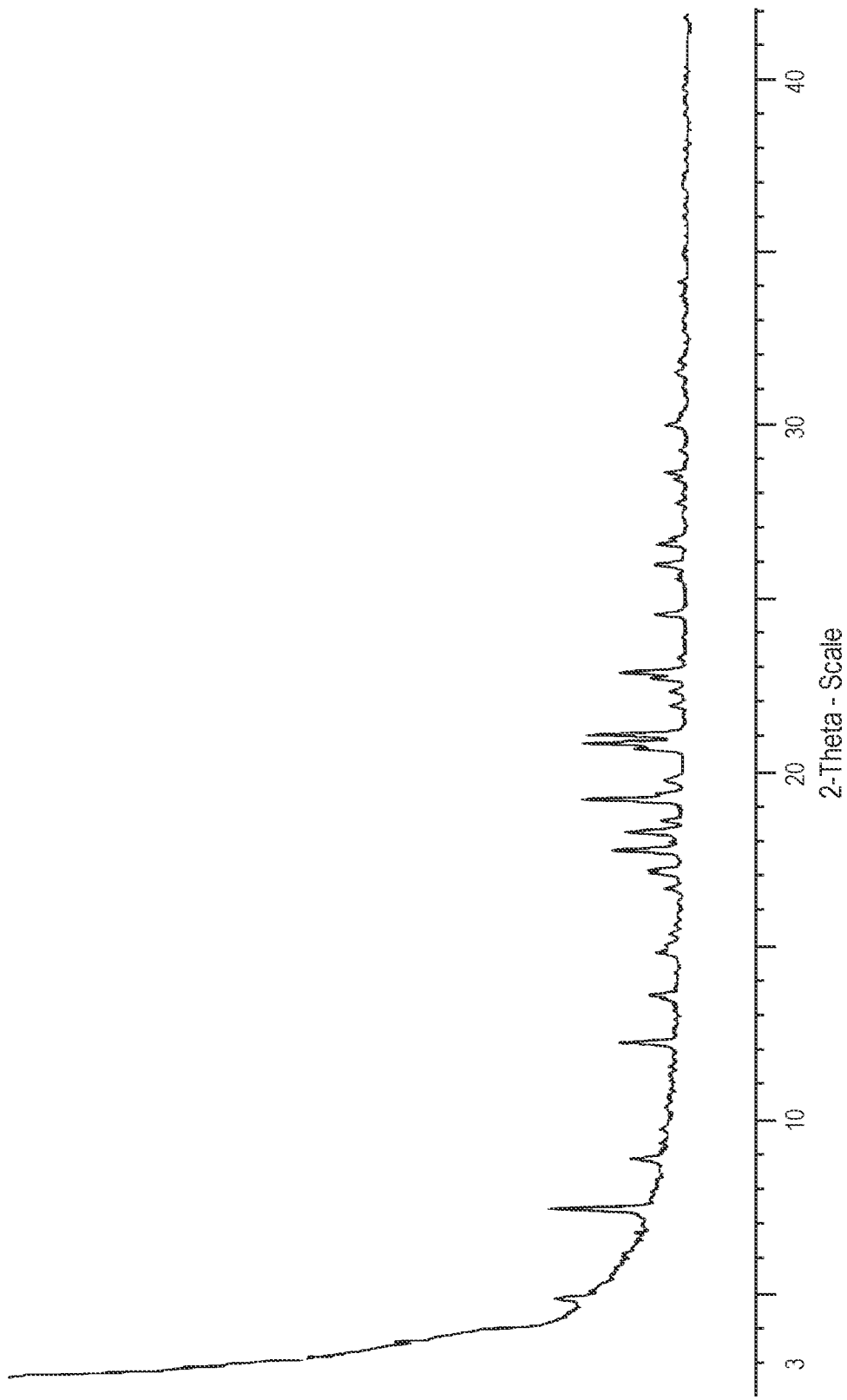
FIG. 24 illustrates a representative XRPD pattern for Pattern 12 of Compound II.
Figure 25:
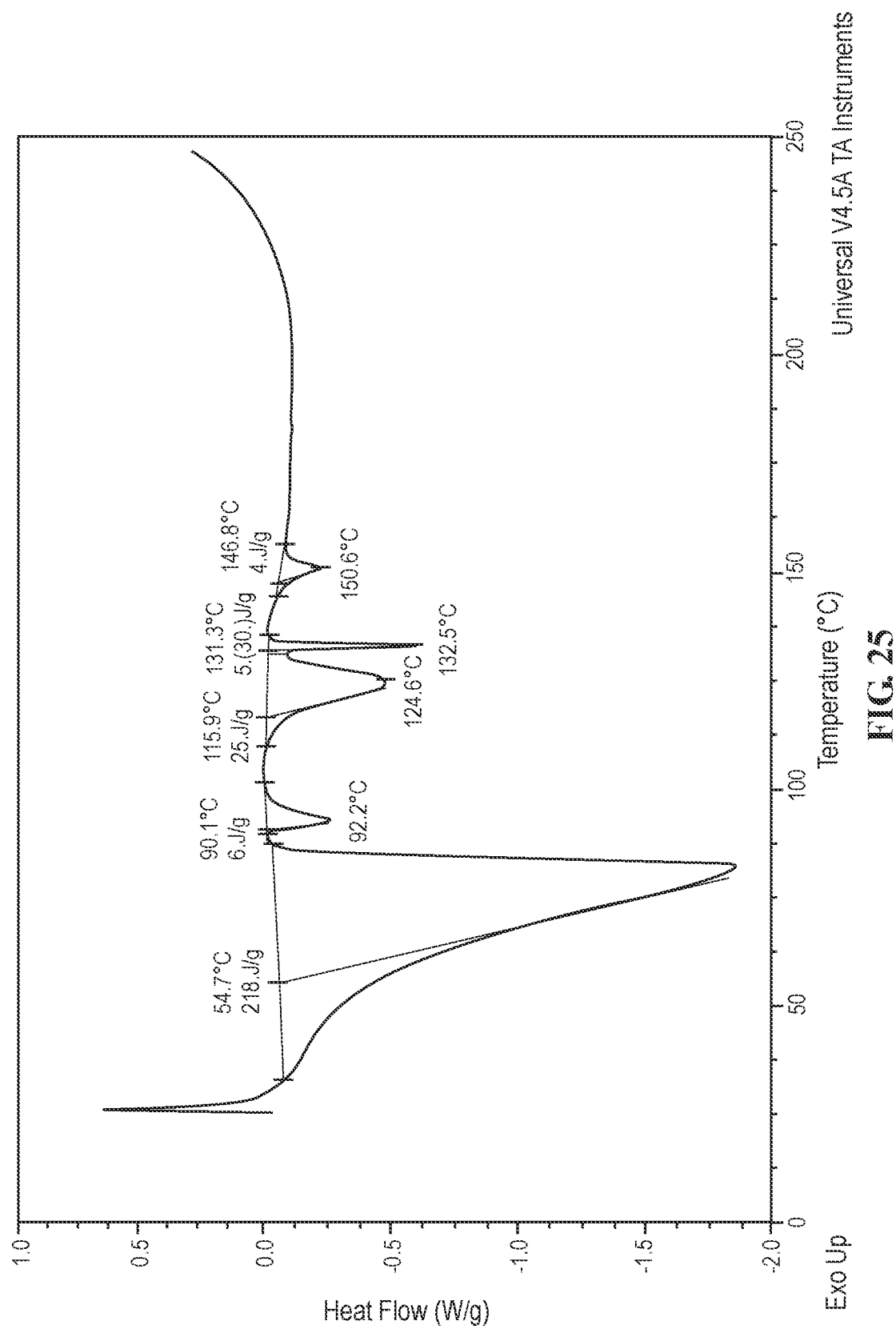
FIG. 25 illustrates a representative DSC thermogram for Pattern 12 of Compound II.

In some embodiments, provided herein is crystalline Compound II solvate Pattern 12. In some embodiments, crystalline Compound II Pattern 12 is characterized as having an XRPD pattern substantially the same as the XRPD pattern shown in FIG. 24 as measured using Cu Kα radiation. In some embodiments, crystalline Compound II Pattern 12 is further characterized as having a DSC thermogram substantially the same as shown in FIG. 25. In some embodiments, crystalline Compound II Pattern 12 is further characterized as having a DSC thermogram with five endothermic events having: an onset at about 54.7° C. and peak at about 81.5° C.; an onset at about 90.1° C. and peak at about 92.2° C.; an onset at about 115.9° C. and peak at about 124.6° C.; an onset at about 131.3° C. and peak at about 132.5° C.; and an onset at about 146.8° C. and peak at about 150.6° C.

Additional PPARδ Agonist Compounds

Other PPARδ agonist compounds, in addition to Compound I, or a pharmaceutically acceptable salt thereof (e.g., Compound II), are contemplated for use in treatment of any of the diseases or disorders described herein.

In some embodiments, the PPARδ agonist compound is a selective PPARδ agonist compound. As used herein, a selective PPARδ agonist compound is viewed as a chemical entity that binds to and activates the cellular PPARδ and does not substantially activate the cellular peroxisome proliferator activated receptors alpha (PPARα) and gamma (PPARγ). As used herein, a selective PPARδ agonist compound is a chemical entity that has at least a 10-fold maximum activation (as compared to endogenous receptor ligand) with a greater than 100-fold potency for activation of PPARδ relative to either or both of PPARα and PPARγ. In a further embodiment, a selective PPARδ agonist compound is a chemical entity that binds to and activates the cellular human PPARδ and does not substantially activate either or both of human PPARα and PPARγ. In a further embodiment, a selective PPARδ agonist compound is a chemical entity that has at least about a 10-fold, or about a 20-fold, or about a 30-fold, or about a 40-fold, or about a 50-fold, or about a 100-fold potency for activation of PPARδ relative to either or both of PPARα and PPARγ.

In some embodiments, a selective PPARδ agonist compound contemplated herein is capable of simultaneously contacting the amino-acid residues at positions VAL312, and ILE328 of PPARδ (hPPARδ numbering). In some embodiments, a selective PPARδ agonist compound is capable of simultaneously contacting the amino-acid residues at positions VAL298, LEU303, VAL312, and ILE328 (hPPARδ numbering).

In some embodiments, the PPARδ agonist compound is a PPARδ agonist compound disclosed in any of the following published patent applications: WO2014/165827; WO2016/057660; WO2016/057658; WO2017/180818; WO2017/062468; and WO/2018/067860 (each of which is incorporated herein for such PPARδ agonist compounds).

In some embodiments, the PPARδ agonist compound is a PPARδ agonist compound disclosed in any of the following published patent applications: United States Patent Application Publication Nos. 20160023991, 20170226154, 20170304255, and 20170305894 (each of which is incorporated herein for such PPARδ agonist compounds).

In some embodiments, the PPARδ agonist compound is a phenoxyalkylcarboxylic acid compound. In some embodiments, the phenoxyalkylcarboxylic acid compound is a 2-methylphenoxyalkylcarboxylic acid compound.

In some embodiments, the PPARδ agonist compound is a phenoxyalkylcarboxylic acid compound that is a phenoxyethanoic acid compound, phenoxypropanoic acid compound, phenoxypropenoic acid compound, phenoxybutanoic acid compound, phenoxybutenoic acid compound, phenoxypentanoic acid compound, phenoxypentenoic acid compound, phenoxyhexanoic acid compound, phenoxyhexenoic acid compound, phenoxyoctanoic acid compound, phenoxyoctenoic acid compound, phenoxynonanoic acid compound, phenoxynonenoic acid compound, phenoxydecanoic acid compound, or phenoxydecenoic acid compound. In some embodiments, the PPARδ agonist compound is a phenoxyethanoic acid compound or a phenoxyhexanoic acid compound. In some embodiments, the PPARδ agonist compound is a phenoxyethanoic acid compound. In some embodiments, the phenoxyethanoic acid compound is a 2-methylphenoxyethanoic acid compound. In some embodiments, the PPARδ agonist compound is a phenoxyhexanoic acid compound.

In some embodiments, the PPARδ agonist compound is a phenoxyethanoic acid compound, a ((benzamidomethyl) phenoxy)hexanoic acid compound, a ((heteroarylmethyl)-phenoxy)hexanoic acid compound, a methylthiophenoxyethanoic acid compound, or an allyloxyphenoxyethanoic acid compound.

In some embodiments, the PPARδ agonist compound is a ((benzamidomethyl)-phenoxy)hexanoic acid compound.

In some embodiments, the PPARδ agonist compound is a ((heteroarylmethyl)-phenoxy)hexanoic acid compound. In some embodiments, the PPARδ agonist compound is a ((imidazolylmethyl)phenoxy)hexanoic acid compound. In some embodiments, the PPARδ agonist compound is an imidazol-1-ylmethylphenoxyhexanoic acid compound. In some embodiments, the PPARδ agonist compound is a 6-(2-((2-phenyl-1H-imidazol-1-yl)methyl)phenoxy) hexanoic acid.

In some embodiments, the PPARδ agonist compound is an allyloxyphenoxyethanoic acid compound. In some embodiments, the allyloxyphenoxyethanoic acid compound is a 4-allyloxy-2-methylphenoxy)ethanoic acid compound.

In some embodiments, the PPARδ agonist compound is a methylthiophenoxyethanoic acid compound. In some embodiments, a PPARδ agonist compound is a 4-(methylthio)phenoxy)ethanoic acid compound.

In some embodiments, the PPARδ agonist compound is a phenoxyalkylcarboxylic acid compound selected from the group consisting of: (Z)-[2-Methyl-4-[3-(4-methylphenyl)-3-[4-[3-(morpholin-4-yl)propynyl]phenyl]allyloxy]-phen oxy]acetic acid; (E)-[2-Methyl-4-[3-[4-[3-(pyrazol-1-yl) prop-1-ynyl]phenyl]-3-(4-trifluoromethylphenyl)-allyloxy] phenoxy]acetic acid; (E)-[4-[3-(4-Fluorophenyl)-3-[4-[3-(morpholin-4-yl)propynyl]phenyl]allyloxy]-2-methyl-phe noxy]acetic acid (Compound I); (E)-[2-Methyl-4-[3-[4-[3-(morpholin-4-yl)propynyl]phenyl]-3-(4-trifluoromethylphenyl)allyloxy]-phenoxy]acetic acid; (E)-[4-[3-(4-Chlorophenyl)-3-[4-[3-(morpholin-4-yl)propynyl]phenyl]allyloxy]-2-methyl-phenoxy]acetic acid; (E)-[4-[3-(4-Chlorophenyl)-3-[4-[3-(morpholin-4-yl)propynyl]phenyl]allyloxy-2-methyl phenyl]-propionic acid; {4-[3-Isobutoxy-5-(3-morpholin-4-yl-prop-1-ynyl)-benzylsulfanyl]-2-methyl-phenoxy}-acetic acid; {4-[3-Isobutoxy-5-(3-morpholin-4-yl-prop-1-ynyl)-ph enylsulfanyl]-2-methyl-phenoxy}-acetic acid; and {4-[3,3-Bis-(4-bromo-phenyl)-allyloxy]-2-methyl-phenoxy}-acetic acid; (R)-3-methyl-6-(2-((5-methyl-2-(4-(trifluoromethyl) phenyl)-1H-imidazol-1-yl)methyl)phenoxy)hexanoic acid; (R)-3-methyl-6-(2-((5-methyl-2-(6-(trifluoromethyl)pyridi n-3-yl)-1H-imidazol-1-yl)methyl)phenoxy)hexanoic acid; (E)-[4-[3-(4-Fluorophenyl)-3-[4-[3-(morpholin-4-yl)propynyl]phenyl]allyloxy]-2-methyl-phenoxy]acetic acid (Compound I); 2-{4-[({2-[2-Fluoro-4-(trifluoromethyl)phenyl]-4-methyl-1,3-thiazol-5-yl}methyl)sulfanyl]-2-methylphenoxy}-2-methylpropanoic acid (sodelglitazar; GW677954); 2-[2-methyl-4-[[3-methyl-4-[[4-(trifluoromethyl)phenyl]methoxy]phenyl]thio]phenoxy]-acetic acid; 2-[2-methyl-4-[[[4-methyl-2-[4-(trifluoromethyl)phenyl]-5-thiazolyl]methyl]thio]phenoxy]-acetic acid (GW-501516); [4-[[[2-[3-Fluoro-4-(trifluoromethyl)phenyl]-4-methyl-5-thiazolyl]methyl]thio]-2-methylphenoxy]acetic acid (GW0742 also known as GW610742); 2-[2,6 dimethyl-4-[3-[4-(methylthio)phenyl]-3-oxo-1(E)-propenyl]phenoxyl]-2-methylpropanoic acid (elafibranor; GFT-505); {2-methyl-4-[5-methyl-2-(4-trifluoromethyl-phenyl)-2H-[1,2,3]triazol-4-ylmethylsulfanyl]-phenoxy}-acetic acid; and [4-({(2R)-2-Ethoxy-3-[4-(trifluoromethyl)phenoxy]propyl}sulfanyl)-2-methylphenoxy]acetic acid (seladelpar; MBX-8025); (S)-4-[cis-2,6-dimethyl-4-(4-trifluoromethoxy-phenyl)piperazine-1-sulfonyl]-indan-2-carboxylic acid or a tosylate salt thereof (KD-3010); (2s)-2-{4-butoxy-3-[({[2-fluoro-4-(Trifluoromethyl)phenyl]carbonyl}-amino)-methyl]benzyl}butanoic acid (TI-PP-204); [4-[3-(4-Acetyl-3-hydroxy-2-propylphenoxy)-propoxy]phenoxy]acetic acid (L-165,0411); 2-(4-{2-[(4-Chlorobenzoyl)amino]-ethyl}phenoxy)-2-methylpropanoic acid (bezafibrate); or a pharmaceutically acceptable salt thereof.

In another embodiment, the PPARδ agonist compound is a 2-methylphenoxy-alkylcarboxylic acid compound selected from the group consisting of (E)-[4-[3-(4-Fluoro-phenyl)-3-[4-[3-(morpholin-4-yl)propynyl]phenyl]allyloxy]-2-methylphenoxy]acetic acid (Compound I); 2-{4-[({2-[2-Fluoro-4-(trifluoromethyl)phenyl]-4-methyl-1,3-thiazol-5-yl}methyl) sulfanyl]-2-methylphenoxy}-2-methylpropanoic acid (sodelglitazar; GW677954); 2-[2-methyl-4-[[3-methyl-4-[[4-(trifluoromethyl)phenyl]methoxy]phenyl]thio]phenoxy]-acetic acid; 2-[2-methyl-4-[[[4-methyl-2-[4-(trifluoromethyl)phenyl]-5-thiazolyl]methyl]thio]-phenoxy]-acetic acid (GW-501516); [4-[[[2-[3-Fluoro-4-(trifluoromethyl)phenyl]-4-methyl-5-thiazolyl]methyl]thio]-2-methylphenoxy]acetic acid (GW0742 also known as GW610742); 2-[2,6 dimethyl-4-[3-[4-(methylthio)phenyl]-3-oxo-1(E)-propenyl]phenoxyl]-2-methylpropanoic acid (elafibranor; GFT-505); {2-methyl-4-[5-methyl-2-(4-trifluoromethyl-phenyl)-2H-[1,2,3]triazol-4-ylmethylsulfanyl]-phenoxy}-acetic acid; and [4-({(2R)-2-Ethoxy-3-[4-(trifluoro-methyl)phenoxy]propyl}sulfanyl)-2-methylphenoxy]acetic acid (seladelpar; MBX-8025).

In another embodiment, the PPARδ agonist compound is a compound selected from the group consisting of (S)-4-[cis-2,6-dimethyl-4-(4-trifluoromethoxy-phenyl)piperazine-1-sulfonyl]-indan-2-carboxylic acid or a tosylate salt thereof (KD-3010); (2s)-2-{4-butoxy-3-[({[2-Fluoro-4-(Trifluoromethyl)phenyl]carbonyl}amino)methyl]benzyl}butanoic acid (TIPP-204); [4-[3-(4-Acetyl-3-hydroxy-2-propylphenoxy)propoxy]phenoxy]acetic acid (L-165,0411); and 2-(4-{2-[(4-Chlorobenzoyl)amino]ethyl}phenoxy)-2-methylpropanoic acid (bezafibrate).

In another embodiment, the PPARδ agonist compound is a compound selected from the group consisting of sodelglitazar; lobeglitazone; netoglitazone; and isaglitazone; 2-(4-{2-[(4-Chlorobenzoyl)amino]ethyl}phenoxy)-2-methylpropanoic acid (bezafibrate); 2-[2-methyl-4-[[3-methyl-4-[[4-(trifluoromethyl)phenyl]methoxy]phenyl]thio]phenoxy]-acetic acid (See WO 2003/024395); (S)-4-[cis-2,6-dimethyl-4-(4-trifluoromethoxy-phenyl)piperazine-1-sulfonyl]-indan-2-carboxylic acid or a tosylate salt thereof (KD-3010); 4-butoxy-a-ethyl-3-[[[2-fluoro-4-(trifluoromethyl)benzoyl] amino]methyl]-benzenepropanoic acid (TIPP-204); 2-[2-methyl-4-[[[4-methyl-2-[4-(trifluoromethyl)phenyl]-5-thiazolyl]methyl]thio]phenoxy]-acetic acid (GW-501516); 2-[2,6 dimethyl-4-[3-[4-(methylthio)phenyl]-3-oxo-1(E)-propenyl]phenoxyl]-2-methyl-propanoic acid (GFT-505); {2-methyl-4-[5-methyl-2-(4-trifluoromethyl-phenyl)-2H-[1,2,3]triazol-4-ylmethylsylfanyl]-phenoxy}-acetic acid; and [4-({(2R)-2-Ethoxy-3-[4-(trifluoro-methyl)phenoxy]propyl}sulfanyl)-2-methylphenoxy]acetic acid (seladelpar; MBX-8025).

In some embodiments, the PPARδ agonist compound is (Z)-[2-Methyl-4-[3-(4-methylphenyl)-3-[4-[3-(morpholin- 4-yl)propynyl]phenyl]allyloxy]-phenoxy]acetic acid. In some embodiments, the PPARδ agonist compound is (E)-[2-Methyl-4-[3-[4-[3-(pyrazol-1-yl)prop-1-ynyl]phenyl]-3-(4-trifluoromethylphenyl)-allyloxy]phenoxy]acetic acid. In some embodiments, the PPARδ agonist compound is (E)-[2-Methyl-4-[3-[4-[3-(morpholin-4-yl)propynyl]phenyl]-3-(4-trifluoromethylphenyl)allyloxy]-phenoxy]acetic acid. In some embodiments, the PPARδ agonist compound is (E)-[4-[3-(4-Chlorophenyl)-3-[4-[3-(morpholin-4-yl)propynyl]phenyl]allyloxy]-2-methyl-phenoxy]acetic acid. In some embodiments, the PPARδ agonist compound is (E)-[4-[3-(4-Chlorophenyl)-3-[4-[3-(morpholin-4-yl)propynyl]phenyl]allyloxy]-2-methylphenyl]-propionic acid.

In some embodiments, the PPARδ agonist compound is {4-[3,3-Bis-(4-bromo-phenyl)-allyloxy]-2-methyl-phenoxy}-acetic acid. In some embodiments, a PPARδ agonist is {4-[3-Isobutoxy-5-(3-morpholin-4-yl-prop-1-ynyl)-benzylsulfanyl]-2-methyl-phenoxy}-acetic acid. In some embodiments, a PPARδ agonist compound is {4-[3-Isobutoxy-5-(3-morpholin-4-yl-prop-1-ynyl)-phenylsulfanyl]-2-methyl-phenoxy}-acetic acid.

In some embodiments, the PPARδ agonist compound is a compound selected from the group consisting of: (Z)-[2-Methyl-4-[3-(4-methylphenyl)-3-[4-[3-(morpholin-4-yl)propynyl]phenyl]allyloxy]-phenoxy]acetic acid; (E)-[2-Methyl-4-[3-[4-[3-(pyrazol-1-yl)prop-1-ynyl]phenyl]-3-(4-trifluoromethylphenyl)-allyloxy]phenoxy]acetic acid; (E)-[4-[3-(4-Fluorophenyl)-3-[4-[3-(morpholin-4-yl)propynyl]phenyl]allyloxy]-2-methyl-phenoxy]acetic acid; (E)-[2-Methyl-4-[3-[4-[3-(morpholin-4-yl)propynyl]phenyl]-3-(4-trifluoromethylphenyl)allyloxy]-phenoxy]acetic acid; (E)-[4-[3-(4-Chlorophenyl)-3-[4-[3-(morpholin-4-yl)propynyl]phenyl]allyloxy]-2-methyl-phenoxy]acetic acid; (E)-[4-[3-(4-Chlorophenyl)-3-[4-[3-(morpholin-4-yl)propynyl]phenyl]allyloxy]-2-methylphenyl]-propionic acid; {4-[3-Isobutoxy-5-(3-morpholin-4-yl-prop-1-ynyl)-benzylsulfanyl]-2-methyl-phenoxy}-acetic acid; {4-[3-Isobutoxy-5-(3-morpholin-4-yl-prop-1-ynyl)-phenylsulfanyl]-2-methyl-phenoxy}-acetic acid; and {4-[3,3-Bis-(4-bromo-phenyl)-allyloxy]-2-methyl-phenoxy}-acetic acid; or a pharmaceutically acceptable salt thereof.

In a further embodiment, the PPARδ agonist compound is (E)-[4-[3-(4-Fluorophenyl)-3-[4-[3-(morpholin-4-yl)propynyl]phenyl]allyloxy]-2-methyl-phenoxy]acetic acid or a pharmaceutically acceptable salt thereof. In some embodiments, the PPARδ agonist compound is (E)-[4-[3-(4-Fluorophenyl)-3-[4-[3-(morpholin-4-yl)propynyl]phenyl]allyloxy]-2-methyl-phenoxy]acetic acid sodium salt.

In a further embodiment, the PPARδ agonist compound is Compound 1, Compound 2, Compound 3, Compound 4, Compound 5, Compound 6, Compound 7, Compound 8, Compound 9, Compound 10, Compound 11, Compound 12, Compound 13, Compound 14, Compound 15, or Compound 16, disclosed in Wu et al. Proc Natl Acad Sci USA Mar. 28, 2017 114 (13) E2563-E2570.

In a further embodiment, a PPARδ agonist compound is (R)-3-methyl-6-(2-((5-methyl-2-(4-(trifluoromethyl)phenyl)-1H-imidazol-1-yl)methyl)phenoxy)hexanoic acid, or (R)-3-methyl-6-(2-((5-methyl-2-(6-(trifluoromethyl)pyridin-3-yl)-1H-imidazol-1-yl)methyl)phenoxy)hexanoic acid, or a pharmaceutically acceptable salt thereof.

In a further embodiment, the PPARδ agonist compound is (R)-3-methyl-6-(2-((5-methyl-2-(4-(trifluoromethyl)phenyl)-1H-imidazol-1-yl)methyl)phenoxy)hexanoic acid, or a pharmaceutically acceptable salt thereof. In some embodiments, the PPARδ agonist compound is the hemisulfate salt of (R)-3-methyl-6-(2-((5-methyl-2-(4-(trifluoromethyl)phenyl)-1H-imidazol-1-yl)methyl)phenoxy)hexanoic acid. In some embodiments, the PPARδ agonist compound is the meglumine salt of (R)-3-methyl-6-(2-((5-methyl-2-(4-(trifluoromethyl)phenyl)-1H-imidazol-1-yl)methyl)phenoxy) hexanoic acid.

In a further embodiment, the PPARδ agonist compound is (R)-3-methyl-6-(2-((5-methyl-2-(6-(trifluoromethyl)pyridin-3-yl)-1H-imidazol-1-yl)methyl)phenoxy)hexanoic acid, or a pharmaceutically acceptable salt thereof. In some embodiments, the PPARδ agonist compound is the hemisulfate salt of (R)-3-methyl-6-(2-((5-methyl-2-(6-(trifluoromethyl)pyridin-3-yl)-1H-imidazol-1-yl)methyl)phenoxy) hexanoic acid. In some embodiments, the PPARδ agonist compound is the meglumine salt of (R)-3-methyl-6-(2-((5-methyl-2-(6-(trifluoromethyl)pyridin-3-yl)-1H-imidazol-1-yl)methyl)phenoxy)hexanoic acid.

In a further embodiment, the PPARδ agonist compound is 2-(2-methyl-4-(((2-(4-(trifluoromethyl)phenyl)-2H-1,2,3-triazol-4-yl)methyl)thio)phenoxy)acetic acid, or a pharmaceutically acceptable salt thereof.

In a further embodiment, the PPARδ agonist compound is (R)-2-(4-((2-ethoxy-3-(4-(trifluoromethyl)phenoxy)propyl)thio)phenoxy)acetic acid, or a pharmaceutically acceptable salt thereof.

"Pharmaceutically acceptable," as used herein, refers a material, such as a carrier or diluent, which does not abrogate the biological activity or properties of the compound, and is relatively nontoxic, i.e., the material is administered to an individual without causing undesirable biological effects or interacting in a deleterious manner with any of the components of the composition in which it is contained.

The term "pharmaceutically acceptable salt" refers to a form of a therapeutically active agent that consists of a cationic form of the therapeutically active agent in combination with a suitable anion, or in alternative embodiments, an anionic form of the therapeutically active agent in combination with a suitable cation. Handbook of Pharmaceutical Salts: Properties, Selection and Use. International Union of Pure and Applied Chemistry, Wiley-VCH 2002. S. M. Berge, L. D. Bighley, D. C. Monkhouse, J. Pharm. Sci. 1977, 66, 1-19. P. H. Stahl and C. G. Wermuth, editors, Handbook of Pharmaceutical Salts: Properties, Selection and Use, Weinheim/Zurich: Wiley-VCH/VHCA, 2002. Pharmaceutical salts typically are more soluble and more rapidly soluble in stomach and intestinal juices than non-ionic species and so are useful in solid dosage forms. Furthermore, because their solubility often is a function of pH, selective dissolution in one or another part of the digestive tract is possible and this capability can be manipulated as one aspect of delayed and sustained release behaviors. Also, because the salt-forming molecule can be in equilibrium with a neutral form, passage through biological membranes can be adjusted.

In some embodiments, pharmaceutically acceptable salts are obtained by reacting a compound disclosed herein with an acid. In some embodiments, the compound disclosed herein (i.e. free base form) is basic and is reacted with an organic acid or an inorganic acid. Inorganic acids include, but are not limited to, hydrochloric acid, hydrobromic acid, sulfuric acid, phosphoric acid, nitric acid, and metaphosphoric acid. Organic acids include, but are not limited to, 1-hydroxy-2-naphthoic acid; 2,2-dichloroacetic acid; 2-hydroxyethanesulfonic acid; 2-oxoglutaric acid; 4-acetamidobenzoic acid; 4-aminosalicylic acid; acetic acid; adipic acid; ascorbic acid (L); aspartic acid (L); benzenesulfonic acid; benzoic acid; camphoric acid (+); camphor-10-sulfonic acid (+); capric acid (decanoic acid); caproic acid (hexanoic acid); caprylic acid (octanoic acid); carbonic acid; cinnamic acid; citric acid; cyclamic acid; dodecylsulfuric acid; ethane-1,2-disulfonic acid; ethanesulfonic acid; formic acid; fumaric acid; galactaric acid; gentisic acid; glucoheptonic acid (D); gluconic acid (D); glucuronic acid (D); glutamic acid; glutaric acid; glycerophosphoric acid; glycolic acid; hippuric acid; isobutyric acid; lactic acid (DL); lactobionic acid; lauric acid; maleic acid; malic acid (−L); malonic acid; mandelic acid (DL); methanesulfonic acid; naphthalene-1,5-disulfonic acid; naphthalene-2-sulfonic acid; nicotinic acid; oleic acid; oxalic acid; palmitic acid; pamoic acid; phosphoric acid; proprionic acid; pyroglutamic acid (−L); salicylic acid; sebacic acid; stearic acid; succinic acid; sulfuric acid; tartaric acid (+L); thiocyanic acid; toluenesulfonic acid (p); and undecylenic acid.

In some embodiments, a compound disclosed herein is prepared as a hydrochloride salt.

In some embodiments, pharmaceutically acceptable salts are obtained by reacting a compound disclosed herein with a base. In some embodiments, the compound disclosed herein is acidic and is reacted with a base. In such situations, an acidic proton of the compound disclosed herein is replaced by a metal ion, e.g., lithium, sodium, potassium, magnesium, calcium, or an aluminum ion. In some cases, compounds described herein coordinate with an organic base, such as, but not limited to, ethanolamine, diethanolamine, triethanolamine, tromethamine, meglumine, N-methylglucamine, dicyclohexylamine, tris(hydroxymethyl)methylamine. In other cases, compounds described herein form salts with amino acids such as, but not limited to, arginine, lysine, and the like. Acceptable inorganic bases used to form salts with compounds that include an acidic proton, include, but are not limited to, aluminum hydroxide, calcium hydroxide, potassium hydroxide, sodium carbonate, potassium carbonate, sodium hydroxide, lithium hydroxide, and the like. In some embodiments, the compounds provided herein are prepared as a sodium salt, calcium salt, potassium salt, magnesium salt, meglumine salt, N-methylglucamine salt or ammonium salt.

It should be understood that a reference to a pharmaceutically acceptable salt includes the solvent addition forms. In some embodiments, solvates contain either stoichiometric or non-stoichiometric amounts of a solvent, and are formed during the process of crystallization with pharmaceutically acceptable solvents such as water, ethanol, and the like. Hydrates are formed when the solvent is water, or alcoholates are formed when the solvent is alcohol. Solvates of compounds described herein are conveniently prepared or formed during the processes described herein. In addition, the compounds provided herein optionally exist in unsolvated as well as solvated forms.

Unless otherwise stated, the following terms used in this application have the definitions given below. The use of the term "including" as well as other forms, such as "include", "includes," and "included," is not limiting. The section headings used herein are for organizational purposes only and are not to be construed as limiting the subject matter described.

As used herein, "alkyl" refers to an aliphatic hydrocarbon group. The alkyl group is branched or straight chain. In some embodiments, the "alkyl" group has 1 to 10 carbon atoms, i.e. a C1-C10alkyl. In some embodiments, an alkyl is a C1-C6alkyl. In one aspect the alkyl is methyl, ethyl, propyl, iso-propyl, n-butyl, iso-butyl, sec-butyl, or t-butyl. Typical alkyl groups include, but are in no way limited to, methyl, ethyl, propyl, isopropyl, butyl, isobutyl, tert-butyl, isoamyl, pentyl, and hexyl.

The term "acceptable" with respect to a formulation, composition or ingredient, as used herein, means having no persistent detrimental effect on the general health of the subject being treated.

The term "modulate" as used herein, means to interact with a target either directly or indirectly so as to alter the activity of the target, including, by way of example only, to enhance the activity of the target, to inhibit the activity of the target, to limit the activity of the target, or to extend the activity of the target.

The term "modulator" as used herein, refers to a molecule that interacts with a target either directly or indirectly. The interactions include, but are not limited to, the interactions of an agonist, partial agonist, an inverse agonist, antagonist, degrader, or combinations thereof. In some embodiments, a modulator is an agonist.

The terms "administer," "administering", "administration," and the like, as used herein, refer to the methods that may be used to enable delivery of compounds or compositions to the desired site of biological action. These methods include, but are not limited to oral routes, intraduodenal routes, parenteral injection (including intravenous, subcutaneous, intraperitoneal, intramuscular, intravascular or infusion), topical and rectal administration. Those of skill in the art are familiar with administration techniques that can be employed with the compounds and methods described herein. In some embodiments, the compounds and compositions described herein are administered orally.

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered, which will relieve to some extent one or more of the symptoms of the disease or condition being treated. The result includes reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case is optionally determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The term "pharmaceutical combination" as used herein, means a product that results from the mixing or combining of more than one active ingredient and includes both fixed and non-fixed combinations of the active ingredients. The term "fixed combination" means that the active ingredients, e.g. a compound disclosed herein, or a pharmaceutically acceptable salt thereof, and a co-agent, are both administered to a patient simultaneously in the form of a single entity or dosage. The term "non-fixed combination" means that the active ingredients, e.g. a compound disclosed herein, or a pharmaceutically acceptable salt thereof, and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The terms "article of manufacture" and "kit" are used as synonyms.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one aspect, the mammal is a human.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

Diseases and Disorders

In one embodiment, the PPARδ agonist compounds disclosed herein (e.g., Compound I), or a pharmaceutically acceptable salt thereof (e.g., Compound II), are used in the preparation of medicaments for the treatment of diseases or conditions in a mammal that would benefit from modulation of PPARδ activity. Methods for treating any of the diseases or conditions described herein in a mammal in need of such treatment, involves administration of pharmaceutical compositions that include at least one compound disclosed herein or a pharmaceutically acceptable salt, active metabolite, prodrug, or pharmaceutically acceptable solvate thereof, in therapeutically effective amounts to said mammal.

In some embodiments, the PPARδ agonist compound disclosed herein (e.g., Compound I), or a pharmaceutically acceptable salt thereof (e.g., Compound II), is used in the treatment of a kidney disease in a mammal. In some embodiments, the kidney disease is Alport syndrome, Goodpasture syndrome, thin basement membrane nephropathy (TBMN), focal segmental glomerulosclerosis (FSGS), benign familial hematuria (BFH), post-transplant anti-GBM (Glomerular Basement Membrane) nephritis. In some embodiments, the kidney disease is X-linked Alport syndrome (XLAS), autosomal recessive Alport syndrome (ARAS) or autosomal dominant Alport syndrome (ADAS).

In some embodiments, the PPARδ agonist compound disclosed herein (e.g., Compound I), or a pharmaceutically acceptable salt thereof (e.g., Compound II), is used in the treatment of muscle atrophy in a mammal. In some embodiments, the muscle atrophy is secondary to a chronic disease. In some embodiments, the chronic disease is multiple sclerosis, amyotrophic lateral sclerosis, spinal muscular atrophy, critical illness neuropathy, cancer, congestive heart failure, chronic pulmonary disease, chronic renal failure, chronic liver disease, diabetes mellitus, Cushing syndrome, chronic infection, glucocorticoid-induced myopathy, statin-induced myopathy, polymyositis or dermatomyositis. In some embodiments, the chronic disease is a neurologic disease or drug-induced muscle disease. In some embodiments, the muscle atrophy is secondary to a genetic disease that primarily affect skeletal muscle. In some embodiments, the genetic disease is muscular dystrophy or myotonic dystrophy. In some embodiments, the muscle atrophy results from a muscle disease. In some embodiments, the muscle disease is muscular dystrophy, polymyositis, or myotonia. In some embodiments, the muscle disease occurs as a response to systemic illness. In some embodiments, the systemic illness is hypothyroidism, hyperthyroidism, adrenal gland depletion, diabetes mellitus, or an autoimmune disease. In some embodiments, the systemic illness is cancer, Acquired Immune Deficiency Syndrome (AIDS), chronic obstructive lung disease, congestive heart failure, cardiomyopathy, chronic liver disease, renal disease, emphysema, tuberculosis, osteomalacia, hormonal deficiency, anorexia nervosa, and generalized malnutrition.

In some embodiments, the PPARδ agonist compound disclosed herein (e.g., Compound I), or a pharmaceutically acceptable salt thereof (e.g., Compound II), is used in the treatment of a primary mitochondrial myopathy in a mammal. In some embodiments, the mammal has been diagnosed with Kearns-Sayre syndrome (KSS), Leigh syndrome, maternally inherited Leigh syndrome (MILS), Mitochondrial DNA depletion syndrome (MDS), Mitochondrial encephalomyopathy, lactic acidosis and stroke-like episodes (MELAS), Mitochondrial neurogastrointestinal encephalomyopathy (MNGIE), Myoclonus epilepsy with ragged red fibers (MERRF), Neuropathy ataxia and retinitis pigmentosa (NARP), Pearson syndrome, or Progressive external ophthalmoplegia (PEO).

In some embodiments, the PPARδ agonist compound disclosed herein (e.g., Compound I), or a pharmaceutically acceptable salt thereof (e.g., Compound II), is used in the treatment of a fatty acid oxidation disorder (FAOD) in a mammal. In some embodiments, the fatty acid oxidation disorder (FAOD) comprises carnitine transporter deficiency, carnitine/acylcarnitine translocase deficiency, carnitine palmitoyl transferase deficiency Type 1, carnitine palmitoyl transferase deficiency Type 2, glutaric acidemia Type 2, long-chain 3-hydroxyacyl CoA dehydrogenase deficiency, medium-chain acyl CoA dehydrogenase deficiency, short-chain acyl CoA dehydrogenase deficiency, short-chain 3-hydroxyacyl CoA dehydrogenase deficiency, trifunctional protein deficiency, or very long-chain acyl CoA dehydrogenase deficiency, or a combination thereof. In some embodiments, the fatty acid oxidation disorder comprises carnitine palmitoyltransferase II (CPT2) deficiency, very long-chain Acyl-CoA dehydrogenase (VLCAD) deficiency, long-chain 3-hydroxyacyl-CoA dehydrogenase (LCHAD) deficiency, Trifunctional Protein (TFP) Deficiency; or a combination thereof.

Primary Mitochondrial Myopathy

Healthy mitochondria are vital to normal cellular activities. Mitochondria harvest energy in the form of ATP and simultaneously regulate cellular metabolism. Mitochondria perform many key roles in the cell including oxidative phosphorylation, the oxidation of fatty acids (β-oxidation), central carbon metabolism, and the biosynthesis of intermediates for cell growth.

The prime pathway for the degradation of fatty acids is mitochondrial fatty acid β-oxidation (FAO). FAO is a key metabolic pathway for energy homoeostasis in organs such as the liver, heart and skeletal muscle. Fatty acid transport proteins (FATPs) are integral membrane proteins that enhance the uptake of long chain and very long chain fatty acids into cells. In the cytosol, fatty acids are activated to acyl-coenzyme A (CoA) esters by acyl-CoA synthetases before they can be directed into several different metabolic pathways, such as lipid synthesis and FAO. FAO requires mitochondrial import of acyl-CoA. Because the mitochondrial membrane is impermeable to acyl-CoAs, the carnitine cycle is needed for import into the mitochondria. This system requires L-carnitine and is composed of two acyltransferases, carnitine palmitoyltransferases 1 and 2 (CPT1 and CPT2), and carnitine acylcarnitine translocase (CACT). Inside the mitochondrion, acyl-CoAs are degraded via β-oxidation, which is a cyclic process of four enzymatic steps. Each cycle shortens the acyl-CoA by releasing the two carboxy-terminal carbon atoms as acetyl-CoA. FAO not only produces acetyl-CoA to fuel the Krebs cycle (also known as the tricarboxylic acid (TCA) cycle) and ketogenesis, but also reduces flavin adenine dinucleotide (to FADH2) and nicotinamide adenine dinucleotide (to NADH), and these reduced products directly feed into the electron transport chain (respiratory chain). To be able to fully degrade fatty acids, the β-oxidation machinery harbors different chain length-specific enzymes.

Oxidative phosphorylation (OXPHOS) is a metabolic pathway responsible for the generation of the majority of cellular energy in the form of ATP. The OXPHOS pathway includes complexes I-IV of the respiratory chain and complex V, an ATP synthase. Complex I (NADH:coenzyme Q oxidoreductase) oxidizes NADH with the reduction of coenzyme Q10 (also known as CoQ) from its ubiquinone (CoQ; Q) form to ubiquinol (QH2), generating an electrochemical gradient across the inner mitochondrial membrane. Complex II (succinate-CoQ oxidoreductase) intricately links the Krebs cycle (also known as the tricarboxylic acid (TCA) cycle) to the respiratory chain. Complex II oxidizes succinate with the reduction of CoQ from its ubiquinone (CoQ; Q) form to ubiquinol (QH2). Complex III (ubiquinol-cytochrome c oxidoreductase) catalyzes the reduction of cytochrome c by oxidation of ubiquinol with the generation of an electrochemical gradient. Complex IV (cytochrome c oxidase) is responsible for the terminal enzymatic reaction of the respiratory chain that transfers electrons (e−) to molecular oxygen and generates an electrochemical gradient. Complex V converts transmembrane electrochemical proton (H+) gradient energy into mechanical energy, which catalyses the chemical bond energy between ADP and phosphate (P) to form ATP.

Over 1,500 proteins are required for healthy mitochondrial function of which thirteen proteins are encoded by mitochondrial DNA (mtDNA) and the rest are encoded by nuclear (nDNA). About 100 proteins are directly involved in oxidative phosphorylation and the production of ATP. Mutations in nDNA or mtDNA genes that disrupt mitochondrial function lead to devastating mitochondrial diseases known as primary mitochondrial myopathies (PMM). In patients with mtDNA mutations, inheritance and clinical presentation are further complicated by the presence of multiple mtDNA genomes in an individual cell leading to a mixture of mutated and wild-type genomes (heteroplasmy) in the same cell or tissue.

Many common mitochondrial disorders are linked to dysfunction of the OXPHOS pathway. Such dysfunctions can include deficiencies in OXPHOS complex activity and/or reductions in steady-state levels of the OXPHOS complexes resulting in diminished ATP production or combinations thereof (Nsihia-Sefaa, A, and McKenzie, M, (2016), Biosci. Rep., 36, e00313, doi:10.1042/BSR20150295). The defects leading to these disorders can be caused by: 1) gene mutations of the protein subunits that encode the OXPHOS proteins; 2) mutations of the proteins required for OXPHOS complex biogenesis; or 3) mutations of the proteins necessary for replication, transcription and translation of mtDNA (id.) The OXPHOS complexes and FAO pathways are biochemically linked because NAD and FADH2 that are produced during FAO pass their electrons to the OXPHOS complexes. Studies have shown that primary disorders in one pathway cause secondary defects in the other pathway.

Because mitochondria are the main source of energy production in mammalian cells, clinical features of primary mitochondrial myopathy typically involve the tissues with the highest energy requirements. Furthermore, the presence of mtDNA in all human tissues means that dysfunction occurs in multiple organ systems. The most commonly affected organ systems are the nervous, muscular, cardiac, and endocrine systems. primary mitochondrial myopathies are usually progressive conditions which produce significant disability and, in some instances, premature death, often due to cardiac or neurological involvement such as arrhythmias or seizures. Myopathy can be the only clinical feature of a mitochondrial disease but may also be part of a component of other mitochondrial diseases or disorders.

PPARδ is the most abundant PPAR isoform in skeletal muscle and has a higher expression in oxidative type I muscle fibers compared with glycolytic type II muscle fibers. Both short-term exercise and endurance training lead to increased PPARδ expression in human and rodent skeletal muscle. Rodent studies suggest that a key feature of PPARδ activation is induction of skeletal muscle fatty acid oxidation. On activation of PPARδ in skeletal muscle in mice, the fiber composition changes toward the oxidative type I with induction of fatty acid oxidation, mitochondrial respiration, oxidative metabolism, and slow-twitch contractile apparatus. In addition to the metabolic effects of PPARδ activation, PPARδ also stimulates peroxisome proliferator-activated receptor gamma coactivator-1 alpha (PGC-1α), an effect accompanied by mitochondrial biogenesis. This type of adaptation is identical to that seen in response to physical exercise, and indeed, mice with transgenic (Tg) overexpression of PPARδ exhibit increased running endurance (Wang et al., PLoS Biol. 2:e294 (2004)).

The management of patients with mitochondrial diseases is focused on strategies to reduce morbidity and mortality and early treatment of organ-specific complications. Primary mitochondrial myopathies represent an area of significant unmet medical need; there is currently no available disease-modifying therapy for patients with primary mitochondrial myopathy.

Described herein, in some embodiments, are methods and compositions for treating primary mitochondrial myopathy in a mammal comprising administering to the mammal with a primary mitochondrial myopathy a PPARδ agonist compound disclosed herein (e.g., Compound I), or a pharmaceutically acceptable salt thereof (e.g., Compound II). Further described herein, in some embodiments, are methods and compositions for modulating PPARδ in a mammal with primary mitochondrial myopathy comprising administering to the mammal with primary mitochondrial myopathy a PPARδ agonist compound disclosed herein (e.g., Compound I), or a pharmaceutically acceptable salt thereof (e.g., Compound II). In some embodiments, modulating PPARδ in a mammal with primary mitochondrial myopathy leads to improvement in one or more symptoms associated with primary mitochondrial myopathy. In some embodiments, the mammal is a human.

In some embodiments, the mammal having primary mitochondrial myopathy has been diagnosed with Kearns-Sayre syndrome (KSS), Leigh syndrome, maternally inherited Leigh syndrome (MILS), Mitochondrial DNA depletion syndrome (MDS), Mitochondrial encephalomyopathy, lactic acidosis and stroke-like episodes (MELAS), Mitochondrial neurogastrointestinal encephalomyopathy (MNGIE), Myoclonus epilepsy with ragged red fibers (MERRF), Neuropathy ataxia and retinitis pigmentosa (NARP), Pearson syndrome, or Progressive external ophthalmoplegia (PEO).

In some embodiments, the mammal with a primary mitochondrial myopathy also comprises a secondary mitochondrial myopathy. In some embodiments, secondary mitochondrial myopathy refers to any abnormal mitochondrial function other than that resulting from a primary mitochondrial myopathy (see, for example, D. Niyazov et al. *Molecular Syndromology* 2016; 7; 122-137).

In some embodiments, the secondary mitochondrial myopathy is an inherited secondary mitochondrial myopathy. In some embodiments, the secondary mitochondrial myopathy involves mutations in non-OXPHOS genes. In some embodiments, the secondary mitochondrial myopathy involves secondary defects in OXPHOS function due to primary FAO deficiencies. In some embodiments, the secondary mitochondrial myopathy results from a primary OXPHOS deficiency that results in secondary FAO disease. In some embodiments, the secondary mitochondrial myopathy is an acquired secondary mitochondrial myopathy. For example, the acquired secondary mitochondrial myopathy is a result of environmental factors that cause oxidative stress including, but not limited to, aging, inflammation, and mitotoxic drugs. In some embodiments, the mitotoxic drug comprises corticosteroids, valproic acid, phenytoin, barbiturates, propofol, volatile anesthetics, nondepolarizing muscle relaxants, local anesthetics, statins, fibrates, biguanides, glitazones, beta-blockers, amiodarone, neuroleptics, antibiotics, or chemotherapeutics. In some embodiments, the chemotherapeutic is doxorubicin or a platinum based chemotherapeutic such as cisplatin.

In some embodiments, administration of a PPARδ agonist compound disclosed herein (e.g., Compound I), or a pharmaceutically acceptable salt thereof (e.g., Compound II) to a mammal with a disease or disorder described herein increases expression of PPARδ. In some embodiments, the PPARδ agonist compound increases activity of PPARδ. In some embodiments, the PPARδ agonist compound increases expression or activity of a gene or protein thereof involved in mitochondrial function. In some embodiments, the gene is a nuclear DNA (nDNA) gene. In some embodiments, the gene is a mitochondria DNA (mtDNA) gene.

In some embodiments, the PPARδ agonist compound increases expression or activity of a nDNA gene, wherein the nDNA gene includes, but not limited to, NDUFS1, NDUFS2, NDUFS3, NDUFS4, NDUFS6, NDUFS7, NDUFS8, NDUFV1, NDUFV2, NDUFA1, NDUFA2, NDUFA9, NDUFA10, NDUFA11, NDUFA12, NDUFA13, NDUFAF2, NDUFAF6, NDUFB11, SDHA, SDHB, SDHC, SDHD, SDHAF1, UQCRB, BCS1L, UQCRQ, UQCRC2, CYC1, TTC19, LYRM7, UQCC2, UQCC3, COA5, SURF1, COX10, COX14, COX15, COX20, COX6B1, FASTKD2, SCO1, SCO2, LRPPRC, TACO1, PET100, ATPAF2, TMEM70, ATP5E, ATP5A1, AARS2, DARS2, EARS2, RARS2, YARS2, FARS2, HARS2, LARS2, VARS2, TARS2, IARS2, CARS2, PARS2, NARS2, KARS, GARS, SARS2, MARS2, C12orf65, TUFM, TSFM, GFM1, MRPS16, MRPS22, MRPL3, MRP12, MRPL44, SLC19A3, SLC25A3, SLC25A19, AGK, SERAC1, TAZ, HIBCH, ECHS1, ETHE1, MPV17, GFER, ISCU, BOLA3, NFUJ, IBA57, MTO1, GTP3BP, TRMU, PUS1, MTFMT, TRIT1, TRNT1, TRMT5, LRPPRC, TACO1, ELAC2, PNPT1, HSD17B10, MTPAP, PTCD1, OPA1, MFN2, DGUOK, TK2, TYMP, MGME1, SUCLG1, SUCLA2, RNASEH1, C10orf2, POLG, POLG2, DNA2, RRM2B, FBXL4, AFG3L2, SPG7, and ANT1.

In some embodiments, the nDNA gene encodes complex I (NADH:ubiquinone oxidoreductase), complex II (succinate dehydrogenase), complex III (CoQ-cytochrome c reductase), complex IV (cytochrome c oxidase), complex V (ATP synthase), an aminoacyl-tRNA synthetase, a release factor, an elongation factor, a mitoribosomal protein, solute carriers of thiamine and phosphate, or a combination thereof. In some embodiments, the gene encoding the complex I comprises NDUFS1, NDUFS2, NDUFS3, NDUFS4, NDUFS6, NDUFS7, NDUFS8, NDUFV1, NDUFV2, NDUFA1, NDUFA2, NDUFA9, NDUFA10, NDUFA11, NDUFA12, NDUFA13, NDUFAF2, NDUFAF6, or NDUFB11. In some embodiments, the gene encoding the complex II comprises SDHA, SDHB, SDHC, SDHD, or SDHAF1. In some embodiments, the gene encoding the complex III comprises UQCRB, BCS1L, UQCRQ, UQCRC2, CYC1, TTC19, LYRM7, UQCC2, or UQCC3. In some embodiments, the gene encoding the complex IV comprises COA5, SURF1, COX10, COX14, COX15, COX20, COX6B1, FASTKD2, SCO1, SCO2, LRPPRC, TACO1, or PET1 00. In some embodiments, the gene encoding the complex V comprises ATPAF2, TMEM70, ATP5E, or ATP5A1. In some embodiments, the gene encoding the aminoacyl-tRNA synthetase comprises AARS2, DARS2, EARS2, RARS2, YARS2, FARS2, HARS2, LARS2, VARS2, TARS2, IARS2, CARS2, PARS2, NARS2, KARS, GARS, SARS2, or MARS2. In some embodiments, the gene encoding the release factor comprises C12orf65. In some embodiments, the gene encoding the elongation factor comprises TUFM, TSFM, or GFM1. In some embodiments, the gene encoding the mitoribosomal protein comprises MRPS16, MRPS22, MRPL3, MRP12, or MRPL44. In some embodiments, the gene encoding the solute carriers of thiamine and phosphate comprises SLC19A3, SLC25A3, or SLC25A19.

In some embodiments, the nDNA gene is involved in phospholipid metabolism, metabolism of toxic compounds, disulfide relay system, iron-sulfur protein assembly, tRNA modification, mRNA processing, mitochondrial fusion or fission, deoxynucleotide triphosphate synthesis, protein quality control and degradation, ATP and ADP transport, or a combination thereof. In some embodiments, the gene involved in the phospholipid metabolism comprises AGK, SERAC1, or TAZ. In some embodiments, the gene involved in the metabolism of toxic compounds comprises HIBCH, ECHS1, ETHE1, or MPV17. In some embodiments, the gene involved in the disulfide relay system comprises GFER. In some embodiments, the gene involved in the iron-sulfur protein assembly comprises ISCU, BOLA3, NFUJ, or IBA57. In some embodiments, the gene involved in the tRNA modification comprises MTO1, GTP3BP, TRMU, PUS1, MTFMT, TRIT1, TRNT1, or TRMT5. In some embodiments, the gene involved in the mRNA processing comprises LRPPRC, TACO1, ELAC2, PNPT1, HSD17B10, MTPAP, or PTCD1. In some embodiments, the gene involved in the mitochondrial fusion and fission comprises OPA1 or MFN2. In some embodiments, the gene involved in the deoxynucleotide triphosphate synthesis comprises DGUOK, TK2, TYMP, MGME1, SUCLG1, SUCLA2, RNASEH1, C10orf2, POLG, POLG2, DNA2, or RRM2B. In some embodiments, the gene involved in the protein quality control and degradation comprises FBXL4, AFG3L2, or SPG7. In some embodiments, the gene involved the ATP and ADP transport comprises ANT1.

Described herein, in some embodiments, are methods and compositions for treating a mammal with a disease or disorder described herein using a PPARδ agonist compound disclosed herein (e.g., Compound I), or a pharmaceutically acceptable salt thereof (e.g., Compound II), wherein the PPARδ agonist compound increases the expression or activity of a mitochondrial DNA (mtDNA) gene. In some embodiments, the mtDNA gene comprises at least one mutation, deletion, defect, or combination thereof. In some embodiments, the at least one mutation in at least one mitochondrial DNA (mtDNA) gene comprises a mutation selected from m.3243A>G, m.8344A>G, m.8993T>G, m.13513G>A, m.11778G>A, m.14484T>C, and a combination thereof. In some embodiments, the at least one mutation in at least one mitochondrial DNA (mtDNA) gene comprises mutation m.3243A>G. In some embodiments, the mtDNA gene comprises a mutation selected from an 8284 bp deletion, a 6277 bp deletion, a 4977 bp deletion, and a combination thereof.

In some embodiments, the PPARδ agonist compound increases a percentage of non-mutated mitochondrial DNA (mtDNA). In some embodiments, the PPARδ agonist compound increases the percentage of non-mutated mtDNA by at least or about 10%, 20%, 30%, 40%, 50%, 60%, 70%, 75%, 80%, 90%, 95%, or more than 95%. In some embodiments, the PPARδ agonist compound increases the percentage of non-mutated mtDNA in a range of about 10% to about 90%, about 20% to about 80%, about 30% to about 70%, or about 40% to about 60%. In some embodiments, the PPARδ agonist compound increases the percentage of non-mutated mtDNA such that a proportion of mtDNA in a cell is substantially non-mutated. In some embodiments, the proportion of non-mutated mtDNA to mutated mtDNA in a cell is at least or about 1.25:1, 1.5:1, 1.75:1, 2.0:1, 2.5:1, 3:1, 4:1, 5:1, 6:1, 7:1, 8:1, 9:1, 10:1, or more than 10:1. In some embodiments, the PPARδ agonist compound increases a percentage of non-mutated nuclear DNA (nDNA).

In some embodiments, the PPARδ agonist compound increases mitochondrial biogenesis. In some embodiments, the PPARδ agonist compound increases expression or activity of a gene or protein thereof involved in mitochondrial biogenesis. In some embodiments, the PPARδ agonist compound increases the transcription of a gene involved in mitochondrial biogenesis. In some embodiments, the PPARδ agonist compound increases the translation of a protein involved in mitochondrial biogenesis. In some embodiments, the protein is a transcription factor. In some embodiments, the protein is peroxisome proliferator-activated receptor gamma coactivator 1-alpha (PGC-1α).

The PPARδ agonist compound disclosed herein (e.g., Compound I), or a pharmaceutically acceptable salt thereof (e.g., Compound II), in some embodiments, modulates the expression or activity of PGC-1α. In some embodiments, the PPARδ agonist compound increases the transcription of the proliferator-activated receptor gamma coactivator 1-alpha gene. In some embodiments, the PPARδ agonist compound increases the translation of PGC-1a protein. In some embodiments, the PPARδ agonist compound modulates post-translation modifications of PGC-1α. For example, the PPARδ agonist compound modulates PGC-1α phosphorylation, acetylation, deacetylation, SUMOylation, ubiquitination, O-linked β-N-acetyl glucosamination, methylation, or a combination thereof.

In some embodiments, the PPARδ agonist compound reduces a rate of decrease in mitochondrial biogenesis. In another embodiment, described herein is a method of increases mitochondrial biogenesis in one or more tissues of a mammal relative to a control, wherein the increases in mitochondrial biogenesis comprises a comparison of one or more measurements of mitochondrial biogenesis in the mammal after treatment with a PPARδ agonist compound to a baseline measurement of mitochondrial biogenesis in the same mammal. In some embodiments, the tissues of the mammal comprise muscle tissues. In another embodiment, reducing the rate of increase in mitochondrial biogenesis in the mammal comprises a return to the mammal's baseline measurement of mitochondrial biogenesis faster than the control. In a further embodiment, increasing the rate of decrease in mitochondrial biogenesis in the mammal comprises a return to the mammal's baseline measurement of mitochondrial biogenesis following a period of time in less than 95%, or less than 90%, or less than 85%, or less than 80%, or less than 75%, or less than 70%, or less than 65%, or less than 60%, or less than 55%, or less than 50% of the time to return to baseline for a control. In another embodiment, the increase in mitochondrial biogenesis in the mammal is more than the increase in mitochondrial biogenesis relative to the control. In a further embodiment, the increase in mitochondrial biogenesis in the mammal comprises more than a 1%, more than a 2%, more than a 3%, more than a 4%, more than a 5%, more than a 6%, more than a 7%, more than an 8%, more than a 9%, more than a 10%, more than a 15%, more than a 20%, more than a 25%, more than a 30%, more than a 35%, more than a 40%, more than a 45%, or more than a 50% increase in mitochondrial biogenesis relative to the mammal's baseline measurement of mitochondrial biogenesis prior to treatment with a PPARδ agonist compound.

Muscle tissue is soft tissue found in most animals comprising muscle cells. Muscle cells contain protein filaments that can slide past one another and produce a contraction that changes both the length and shape of the muscle cell. Muscles function to produce force and motion. There are three types of muscles in the body: a) skeletal muscle (the muscle responsible for moving extremities and external areas of the bodies); b) cardiac muscle (the heart muscle); and c) smooth muscle (the muscle that is in the walls of arteries and bowel).

The term "muscle cell" as used herein refers to any cell that contributes to muscle tissue. Myoblasts, satellite cells, myotubes, and myofibril tissues are all included in the term "muscle cells" and may all be treated using the methods described herein. Muscle cell effects may be induced within skeletal, cardiac, and smooth muscles.

Skeletal muscle, or voluntary muscle, is generally anchored by tendons to bone and is generally used to effect skeletal movement such as locomotion or in maintaining posture. Although some control of skeletal muscle is generally maintained as an unconscious reflex (e.g., postural muscles or the diaphragm), skeletal muscles react to conscious control. Smooth muscle, or involuntary muscle, is found within the walls of organs and structures such as the esophagus, stomach, intestines, uterus, urethra, and blood vessels. Unlike skeletal muscle, smooth muscle is not under conscious control. Cardiac muscle is also an involuntary muscle but more closely resembles skeletal muscle in structure and is found only in the heart. Cardiac and skeletal muscles are striated in that they contain sarcomeres that are packed into highly regular arrangements of bundles. By contrast, the myofibrils of smooth muscle cells are not arranged in sarcomeres and therefore are not striated.

Skeletal muscle is further divided into two broad types: Type I (or "slow twitch") and Type II (or "fast twitch"). Type I muscle fibers are dense with capillaries and are rich in mitochondria and myoglobin, which gives Type I muscle tissue a characteristic red color. Type I muscle fibers can carry more oxygen and sustain aerobic activity using fats or carbohydrates for fuel. Type I muscle fibers contract for long periods of time but with little force. Type II muscle fibers may be subdivided into three major subtypes (IIa, Ix, and IIb) that vary in both contractile speed and force generated. Type II muscle fibers contract quickly and powerfully but fatigue very rapidly, and therefore produce only short, anaerobic bursts of activity before muscle contraction becomes painful.

Mitochondrial biogenesis is measured by mitochondrial mass and volume through histological section staining using a fluorescently labeled antibody specific to the oxidative-phosphorylation complexes, such as the Anti-OxPhox Complex Vd subunit antibody from Life Technologies or using mitochondrial specific dyes in live cell staining, such as the Mito-tracker probes from Life Technologies. Mitochondrial biogenesis can also be measured by monitoring the gene expression of one or more mitochondrial biogenesis related transcription factors such as PGC1α, NRF1, or NRF2 using a technique such as QPCR.

FAO is crucial for ATP production in muscle mitochondria, particularly during exercise, by providing substrates for the respiratory chain. The sources of fatty acids differ depending on the exercise intensity, with the contribution of free fatty acids increasing with exercise intensity. Mutations in any of the enzymes involved in FAO may lead to a variety of clinical symptoms in particular during fasting and in organs with high energy needs. During infancy, patients may present with cardiac symptoms such as dilated or hypertrophic cardiomyopathy and/or arrhythmias. Alternatively, FAO defects might present as a milder, later ('adult') onset disease, characterized by exercise-induced myopathy and rhabdomyolysis.

The PPARs (PPAR-α, PPAR-δ, PPAR-γ) are known for their transcriptional regulation of FAO. Activation of PPARs may trigger an up-regulation of gene expression of the enzymes involved in FAO resulting in an increase in residual enzyme activity and thereby correction of FAO flux in treated cells. In a study using cultured patient muscle cells, specific agonists of PPARδ (GW 072) and to a lower extent PPARα (GW 7647) stimulated FAO in control myoblasts (Djouadi, F., et al. J. Clin. Endocrinol. Metab. 90, 1791-1797, 2005).

In vitro studies with Compound I have demonstrated its ability to elicit a dose-dependent increase in fatty acid oxidation in human and rat muscle cell lines. In addition, Compound I treatment altered the expression patterns of several well-known PPARδ regulated genes in pathways important for fatty acid metabolism (CPT1b) and mitochondrial biogenesis (PGC1α) in vivo.

In some embodiments, deficiencies in FAO capacities are measured by comparing FAO capacities of a mammal identified as having a primary mitochondrial myopathy to the FAO capacities of a mammal without a primary mitochondrial myopathy (i.e. a control). In some embodiments, described herein are methods of increasing FAO capacities in a mammal with a primary mitochondrial myopathy comprising administering a PPARδ agonist compound (e.g., Compound I, or a pharmaceutically acceptable salt thereof) to a mammal with a primary mitochondrial myopathy. In some embodiments, described herein are methods of increasing FAO capacities in a mammal with a primary mitochondrial myopathy by about 5%, about 10%, about 15%, about 20%, about 25%, about 30%, about 35%, about 40%, about 45%, about 50%, about 55%, about 60%, about 75%, about 80%, about 95%, about 100%, or more than 100% of the levels observed for a mammal without a primary mitochondrial myopathy. In some embodiments, described herein are methods of increasing FAO capacities in a mammal with a primary mitochondrial myopathy to a level substantially similar to that observed for a mammal without a primary mitochondrial myopathy comprising administering a PPARδ agonist compound (e.g., Compound I, or a pharmaceutically acceptable salt thereof) to a mammal with a primary mitochondrial myopathy. In some embodiments, described herein are methods of restoring (i.e. normalizing by improving or increasing) FAO capacities in a mammal with a primary mitochondrial myopathy to a level substantially similar to that observed for a mammal without a primary mitochondrial myopathy comprising administering a PPARδ agonist compound (e.g., Compound I, or a pharmaceutically acceptable salt thereof) to a mammal with a primary mitochondrial myopathy.

In some embodiments, administration of a PPARδ agonist compound disclosed herein (e.g., Compound I), or a pharmaceutically acceptable salt thereof (e.g., Compound II), to a mammal with a primary mitochondrial myopathy restores (i.e., normalizes by increasing) a deficiency in the activity of one or more enzymes of proteins involved in the fatty acid p-oxidation pathway. In some embodiments, restoring activity comprises increasing the activity to substantially similar levels observed in a mammal without a primary mitochondrial myopathy.

Fatty Acid Oxidation Disorders (FAOD)

Mitochondria are the main site for the oxidation of fatty acids and triglycerides through a series of four enzyme reactions called β-oxidation. The β-oxidation pathway is a cyclic process in which two carboxy-terminal carbon atoms are released from fatty acids as acetyl-CoA units each time a cycle is fully completed. The acetyl-CoA can enter the citric acid cycle and the electron carriers deliver the electrons to the electron transport chain. Fatty acid oxidation (FAO) both produces acetyl-CoA to fuel the tricarboxylic acid (TCA) cycle and ketogenesis, and reduces flavin adenine dinucleotide (to FADH2) and nicotinamide adenine dinucleotide (to NADH); these reduced products directly feed into the respiratory chain. As the acyl-CoA gets shorter, its physicochemical properties change. To be able to fully degrade fatty acids, the β-oxidation machinery harbors different chain length-specific enzymes. Inherited defects for most of the β-oxidation enzymes have been identified and characterized (see for example, S. M. Houten, et al., The Biochemistry and Physiology of Mitochondrial Fatty Acid β-Oxidation and Its Genetic Disorders. *Annual Review of Physiology* 2016 78:1, 23-44).

FAO is crucial for ATP production in muscle, particularly during exercise. The sources of fatty acids differ depending on the exercise intensity, with the contribution of free fatty acids increasing with exercise intensity. Mutations in any of the enzymes involved in FAO, in some cases, lead to a variety of clinical symptoms in particular during fasting and in organs with high energy needs. During infancy, patients, in some cases, present with cardiac symptoms such as dilated or hypertrophic cardiomyopathy and/or arrhythmias. Alternatively, FAO defects, in some cases, present as a milder, later ('adult') onset disease, characterized by exercise-induced myopathy and rhabdomyolysis. Human inherited defects have been described for almost all enzymes and transporters involved in FAO.

In most FAO defects, disease-causing mutations have been characterized that result in absent or non-functional protein, or variable levels of residual enzyme activity. The PPARs (PPAR-α, PPAR-δ, PPAR-γ) are known for their transcriptional regulation of FAO. Activation of PPARs, in some cases, trigger an up-regulation of gene expression of the enzymes involved in FAO resulting in an increase in residual enzyme activity and thereby correction of FAO flux in treated cells. This is the case for the defect in CPT2. CPT2 is an inner mitochondrial membrane enzyme involved in the transfer of long-chain fatty acids from cytosol to the mitochondrial matrix, in concert with its outer membrane counterpart, CPT1. Using the PPAR agonist compound bezafibrate, pharmacological enhancement of a deficient enzyme could be achieved in cultured patient fibroblasts carrying mild mutations of the CPT2 gene (Djouadi, F., et al. *Pediatr. Res.* 54, 446-451, 2003). Bezafibrate is a pan-PPAR agonist compound with limited selectivity for any of the three receptor subtypes. In a follow up study (Djouadi, F., et al. *J. Clin. Endocrinol. Metab.* 90, 1791-1797, 2005) using cultured patient muscle cells, specific agonists of PPARδ (GW 072) and, to a lower extent, PPARα (GW 7647) stimulated FAO in control myoblasts. However, when tested in CPT2-deficient myoblasts, both bezafibrate and the PPARδ agonist compound were able to restore FAO, whereas the PPARα agonist compound had no effect. The PPARδ selective agonist compound increased residual CPT2 activity and normalized long-chain acylcarnitine production by deficient cells. In some embodiments, selective PPARδ agonists are therapeutic options for correction of FAO defects.

Pharmacological rescue of residual enzyme activity, in some cases, is potentially extended to other FAO gene defects, such as VLCAD, because the PPAR signaling pathway controls several enzymes of the β-oxidation pathway. For example, using the PPARδ agonist compound MA-0211, improvements in fatty acid oxidation were observed in fibroblasts derived from patients with very long-chain Acyl-CoA dehydrogenase (VLCAD), long-chain 3-hydroxylacyl-CoA dehydrogenase (LCHAD) and mitochondrial trifunctional protein (TFP) deficiencies were observed (see Goddeeris, M., et al., A Novel Small-Molecule PPARδ Modulator for the Treatment of Fatty Acid Oxidation Disorders. Poster Session presented at INFORM: International Network for Fatty Acid Oxidation Research and Management; Rio de Janeiro, Brazil, Sep. 4, 2017).

Figure 21:
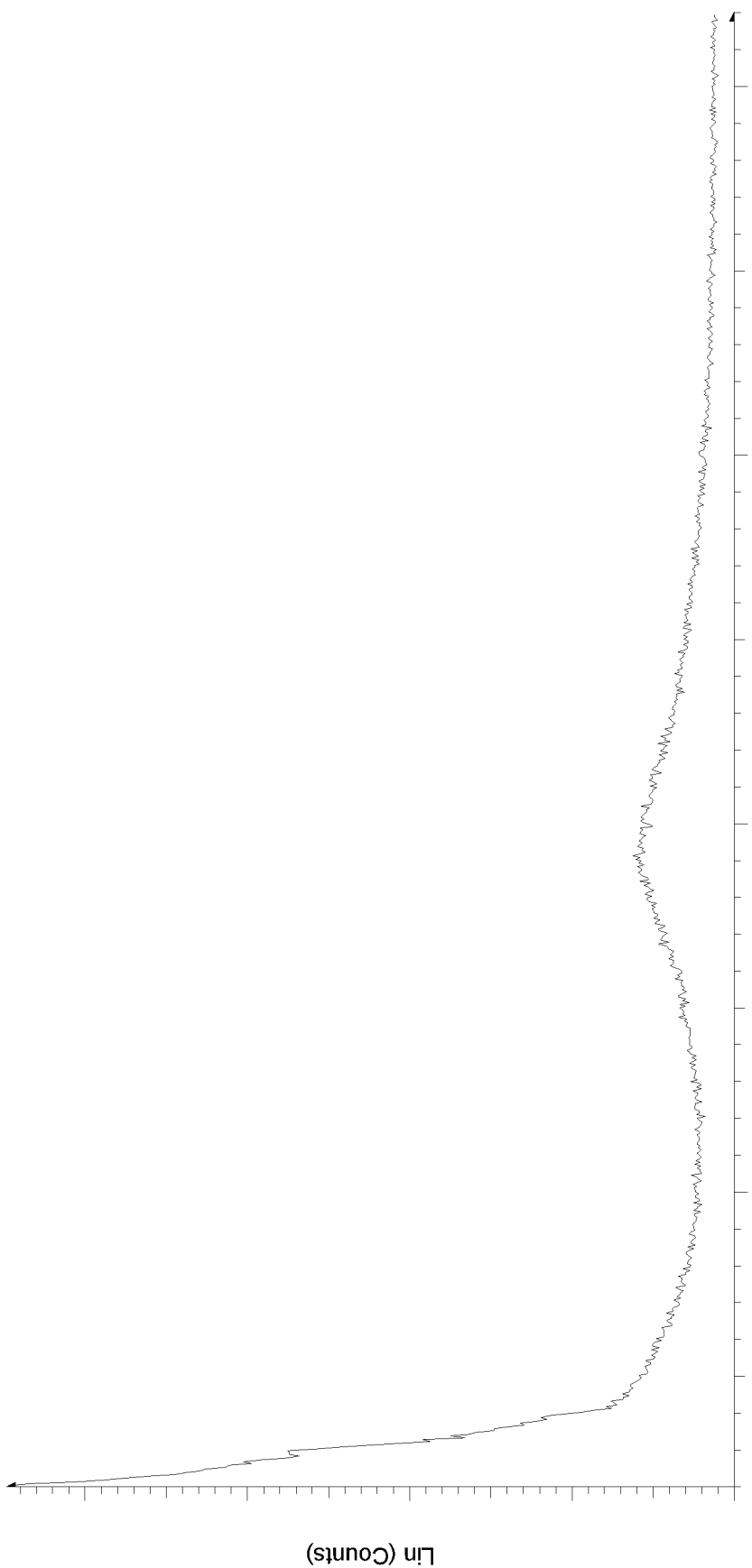
FIG. 21 illustrates a representative XRPD pattern for amorphous Compound II.

Using the VLCAD deficient cell line FB833, the following PPARδ agonist compounds were shown to increase VLCAD enzyme activity: 2-[2-Methyl-4-[[[4-methyl-2-[4-(trifluoromethyl)phenyl]-5-thiazolyl]methyl]thio]phenoxy] acetic acid (GW501516), [4-[[[2-[3-Fluoro-4-(trifluoromethyl)phenyl]-4-methyl-5-thiazolyl]methyl]thio]-2-methylphenoxy]acetic acid (GW0742 also known as GW610742), and [4-[3-(4-Acetyl-3-hydroxy-2-propylphenoxy)propoxy] phenoxy]acetic acid (L-165,0411) (See FIGS. 20 and 21 of International publication no. WO18093839).

In vitro studies with Compound I have demonstrated its ability to elicit a dose-dependent increase in fatty acid oxidation in human and rat muscle cell lines. In addition, Compound I treatment altered the expression patterns of several well-known PPARδ regulated genes in pathways important for fatty acid metabolism (CPT1b) and mitochondrial biogenesis (PGC1α) in vivo.

In vitro studies with cultured fibroblasts obtained from symptomatic patients with FAOD due to very long-chain acyl-CoA dehydrogenase (VLCAD) deficiency, Compound I increased VLCAD enzymatic activity. In some embodiments, Compound I increases the activity of mutated but catalytically active enzymes and transporters in the FAO pathway in subjects with a FAOD. In some embodiments, Compound I increases the activity of mutated but catalytically active enzymes and transporters in the FAO pathway in symptomatic patients with FAOD due to very long-chain acyl-CoA dehydrogenase (VLCAD) deficiency. In some embodiments, Compound I improves whole-body fatty acid oxidation, and thus decreases disease severity in VLCAD patients.

Described herein, in some embodiments, are methods of pharmacological rescue of residual enzyme activity of enzymes involved in the fatty acid β-oxidation pathway. In some embodiments, certain cells bearing mutations are expected to have some residual enzymatic activity. For example, in some embodiments, low residual enzymatic activity of VLCAD is observed in fibroblasts obtained from patients bearing missense mutations (Goetzman E S. Advances in the Understanding and Treatment of Mitochondrial Fatty Acid Oxidation Disorders. *Curr Genet Med Rep.* 2017; 5(3):132-142). In some embodiment, described herein are methods of increasing residual enzyme activity of one or more enzymes involved in the fatty acid β-oxidation pathway in a mammal with a FAOD comprising administering a PPARδ agonist compound disclosed herein (e.g., Compound I), or a pharmaceutically acceptable salt thereof (e.g., Compound II), to a mammal with a FAOD. In some embodiment, described herein are methods of increasing residual enzyme activity of one or more enzymes involved in the fatty acid β-oxidation pathway in a mammal with a FAOD by about 5%, about 10%, about 15%, about 20%, about 25%, about 30%, about 35%, about 40%, about 45%, about 50%, about 55%, about 60%, about 75%, about 80%, about 95%, about 100%, or more than 100% of the enzyme activity levels observed for a mammal without a FAOD comprising administering a PPARδ agonist compound disclosed herein (e.g., Compound I), or a pharmaceutically acceptable salt thereof (e.g., Compound II), to a mammal with a FAOD.

In some embodiments, deficiencies in FAO capacities are measured by comparing FAO capacities of a mammal identified as having a FAOD to the FAO capacities of a mammal without a FAOD (i.e. a control). In some embodiments, described herein are methods of increasing FAO capacities in a mammal with a FAOD comprising administering a PPARδ agonist compound disclosed herein (e.g., Compound I), or a pharmaceutically acceptable salt thereof (e.g., Compound II), to a mammal with a FAOD. In some embodiments, described herein are methods of increasing FAO capacities in a mammal with a FAOD by about 5%, about 10%, about 15%, about 20%, about 25%, about 30%, about 35%, about 40%, about 45%, about 50%, about 55%, about 60%, about 75%, about 80%, about 95%, about 100%, or more than 100% of the levels observed for a mammal without a FAOD. In some embodiments, described herein are methods of increasing FAO capacities in a mammal with a FAOD to a level substantially similar to that observed for a mammal without a FAOD comprising administering a PPARδ agonist compound disclosed herein (e.g., Compound I), or a pharmaceutically acceptable salt thereof (e.g., Compound II), to a mammal with a FAOD. In some embodiments, described herein are methods of restoring (i.e. normalizing) FAO capacities in a mammal with a FAOD to a level substantially similar to that observed for a mammal without a FAOD comprising administering a PPARδ agonist compound disclosed herein (e.g., Compound I), or a pharmaceutically acceptable salt thereof (e.g., Compound II), to a mammal with a FAOD.

In some embodiments, administration of a PPARδ agonist compound disclosed herein (e.g., Compound I), or a pharmaceutically acceptable salt thereof (e.g., Compound II), to a mammal with a FAOD restores (i.e., normalizes) a deficiency in the activity of one or more enzymes of proteins involved in the fatty acid β-oxidation pathway. In some embodiments, restoring activity comprises increasing the activity to substantially similar levels observed in a mammal without a FAOD.

Described herein, in some embodiments, are methods and compositions for treating a fatty acid oxidation (FAO) disorder. In some embodiments, the FAO disorder is caused by a mutation in a gene involved in FAO. In some embodiments, the mutation causes the gene to encode a non-functional protein or a protein with reduced activity. In some embodiments, methods comprise administering a peroxisome proliferator-activated receptor delta (PPARδ). In some embodiments, administration of a PPARδ agonist compound disclosed herein (e.g., Compound I), or a pharmaceutically acceptable salt thereof (e.g., Compound II), increases the expression of the gene involved in FAO. In some embodiments, administration of the PPARδ increases the activity of the protein involved in FAO.

Methods described herein, in some embodiments, comprise treating a FAO disorder caused by a mutation in a gene of interest. In some embodiments, the mutation is a gene mutation. In some embodiments, the mutation is a missense mutation, a nonsense mutation, an insertion, a deletion, a duplication, a frameshift mutation, a repeat expansion, a splicing mutation, or a whole gene deletion. In some embodiments, the FAO disorder is caused by one or more mutations in the gene of interest.

In some embodiments, the gene of interest is a gene involved in fatty acid oxidation. In some embodiments, the gene of interest encodes for a protein involved in fatty acid oxidation. In some embodiments, the gene of interest encodes for a protein that functions as a carnitine shuttle. In some embodiments, the gene of interest encodes for a protein that functions in the fatty acid oxidation cycle. In some embodiments, the gene of interest encodes for a protein that functions as an auxiliary enzyme. In some embodiments, the mutation in a gene of interest encodes for a protein with increased activity. In some embodiments, the mutation in a gene of interest encodes for a protein with reduced activity.

Methods described herein, in some embodiments, comprise treating a FAO disorder caused by a mutation in a gene of interest, wherein the gene of interest encodes for a protein that functions as a carnitine shuttle. Exemplary genes that encode for a protein that functions as a carnitine shuttle include, but not limited to, CPT1A, CPT1B, SLC25A20, CPT2, and SLC22A5. In some embodiments, the mutation is in CPT1A. In some embodiments, the mutation is in CPT1B. In some embodiments, the mutation is in SLC25A20. In some embodiments, the mutation is in CPT2. In some embodiments, the mutation is in SLC22A5. In some embodiments, the mutation is in one or more genes selected from the group consisting of CPT1A, CPT1B, SLC25A20, CPT2, and SLC22A5.

CPT1A, also known as carnitine palmitoyltransferase 1A, encodes the CPT1A protein. CPT1B, also known as carnitine palmitoyltransferase 1B, encodes the CPT1B protein. CTP1 is an outer-mitochondrial-membrane protein and catalyzes the transesterification of the acyl-CoA to acylcarnitine. In some embodiments, a mutation is in CPT1A. In some embodiments, a mutation in CPT1A results in a decrease or loss of activity in CPT1A.

In some embodiments, a mutation is in CPT1B. In some embodiments, a mutation in CPT1B is a mutation in a peptide sequence.

SLC25A20, also known as solute Carrier Family 25 Member 20 or carnitine acylcarnitine translocase (CACT), encodes the CACT protein. CACT carries out the transport of acylcarnitines across the inner mitochondrial membrane in exchange for a free carnitine molecule.

CPT2, also known as carnitine O-palmitoyltransferase 2, encodes the CPT2 protein. CPT2 is a peripheral inner-mitochondrial-membrane protein and completes the fatty acid oxidation cycle by reconverting the acylcarnitine into an acyl-Co. In some embodiments, a mutation is in CPT2.

SLC22A5, also known as solute carrier family 22 member 5, encodes OCTN2 protein. OCTN2 functions to transport carnitine across the plasma membrane.

Methods described herein, in some embodiments, comprise treating a FAO disorder caused by a mutation in a gene of interest, wherein the gene of interest encodes for a protein that functions in the fatty acid oxidation cycle. Exemplary genes that encode for a protein that functions in the fatty acid oxidation cycle include, but not limited to, ACADVL, ACADM, ACADS, HADHA, HADHB, ECHS1, HADH, ACAA2, ACAT1, ACADL, and ACAD9. In some embodiments, the mutation is in ACADVL. In some embodiments, the mutation is in ACADM In some embodiments, the mutation is in ACADS. In some embodiments, the mutation is in HADHA. In some embodiments, the mutation is in HADHB. In some embodiments, the mutation is in ECHS1. In some embodiments, the mutation is in HADH. In some embodiments, the mutation is in ACAA2. In some embodiments, the mutation is in ACAT1. In some embodiments, the mutation is in ACADL. In some embodiments, the mutation is in ACAD9. In some embodiments, the mutation is in one or more genes selected from the group consisting of ACADVL, ACADM, ACADS, HADHA, HADHB, ECHS1, HADH, ACAA2, ACAT1, ACADL, and ACAD9.

ACADVL, also known as very long chain acyl-CoA dehydrogenase, encodes the VLCAD protein. VLCAD is a member of the acetyl-CoA dehydrogenase family and metabolizes acetyl-CoA's from long chain acyl CoA. In some embodiments, a mutation is in ACADVL.

ACADM, also known as medium-chain specific acyl-CoA dehydrogenase, encodes the MCAD protein. MCAD is a member of the acetyl-CoA dehydrogenase family and metabolizes acetyl-CoA's from medium chain acyl CoA. In some embodiments, a mutation is in ACADM.

ACADS, also known as short-chain specific acyl-CoA dehydrogenase, encodes for the SCAD protein. SCAD is a member of the acetyl-CoA dehydrogenase family and metabolizes acetyl-CoA's from short chain acyl CoA. In some embodiments, a mutation is in ACADS.

HADHA, also known as hydroxyacyl-CoA dehydrogenase trifunctional multienzyme complex subunit alpha, encodes the protein MTPα. MTPα is a subunit of MTP, which is located at mitochondrial inner membrane and metabolizes long chain intermediates. In some embodiments, a mutation is in MTPα.

HADHB, also known as hydroxyacyl-CoA dehydrogenase trifunctional multienzyme complex subunit beta, encodes the protein MTPβ. MTPβ is a subunit of MTP. In some embodiments, a mutation is in MTPβ.

ECHS1, also known as enoyl-CoA hydratase, short chain, encodes the Crotonase protein, short chain protein. Crotonase functions to metabolize fatty acids during fatty acid oxidation to generate acetyl CoA. In some embodiments, a mutation is in crotonase.

HADH, also known as short-chain (S)-3-hydroxyacyl-CoA dehydrogenase, encodes the SCHAD protein, short chain protein. SCHAD functions in the beta oxidation of short chain fatty acids. In some embodiments, a mutation is in SCHAD.

ACAA2, also known as medium-chain 3-ketoacyl-CoA thiolase, encodes the MCKAT protein, short chain protein. MCKAT catalyzes ketoacyl-CoA. In some embodiments, a mutation is in SCHAD.

ACAT1, also known as acetoacetyl-CoA thiolase or acetyl-CoA acetyltransferase 1, encodes the acetyl-CoA acetyltransferase protein. Acetyl-CoA acetyltransferase functions in ketone body metabolism. In some embodiments, a mutation is in acetoacetyl-CoA thiolase.

ACADL, also known as acyl-CoA dehydrogenase long chain, encodes the LCAD protein. LCAD catalyzes the beta oxidation of straight chain fatty acids. In some embodiments, a mutation is in LCAD.

ACAD9, also known as acyl-CoA dehydrogenase family, member 9, encodes the ACAD9 protein. ACAD9 is a member of the ACAD family that act on fatty acids comprising 14-20 carbons. In some embodiments, a mutation is in ACAD9.

Methods described herein, in some embodiments, comprise treating a FAO disorder caused by a mutation in a gene of interest, wherein the gene of interest encodes for a protein that functions as an auxiliary enzyme. Exemplary genes that encode for a protein that functions as an auxiliary enzyme include, but not limited to, ECI1, ECI2, DECR1, and ECH1. In some embodiments, the mutation is in ECI1. In some embodiments, the mutation is in ECI2. In some embodiments, the mutation is in DECR1. In some embodiments, the mutation is in ECH1. In some embodiments, the mutation is in one or more genes selected from the group consisting of ECI1, ECI2, DECR1, and ECH1.

ECI1, also known as enoyl-CoA delta isomerase 1, encodes for the protein DCI. DCI is a mitochondrial enzyme involved in beta oxidation of unsaturated fatty acids. In some embodiments, a mutation is in DCI.

ECI2, also known as enoyl-CoA delta isomerase 2, encodes for the protein PECI. PECI is a mitochondrial enzyme involved in beta oxidation of unsaturated fatty acids. In some embodiments, a mutation is in PECI.

DECR1, also known as 2,4-dienoyl-CoA reductase, encodes for the protein DECR. DECR participates in the metabolism of unsaturated fatty enoyl-CoA esters having double bonds in both even- and odd-numbered positions. In some embodiments, a mutation is in DECR.

ECH1, also known as enoyl-CoA hydratase 1, encodes for the protein ECH1. ECH1 functions in the auxiliary step of the fatty acid oxidation pathway. In some embodiments, a mutation is in ECH1.

Glycogen Storage Diseases

Carbohydrate is a major substrate in mammalian metabolism, and reduced access to stored carbohydrate results in pathologically restricted physical activity. Numerous pathogenic genetic variants affecting enzymes of carbohydrate metabolism and synthesis that result in glycogen storage diseases (GSDs) have been identified. Over 10 different GSDs have been documented, some of which primarily manifest as muscle disorders caused by enzyme deficiencies associated with glycolysis and glycogenolysis. Several glycogen storage diseases affect the muscle including GSD type II (Pompe disease), Type III (Fobes-Cori disease), Type IV (Andersen disease), Type V (McArdle disease), and Tyle VII (Tarui disease).

The most common feature of the muscle-related GSDs is exercise intolerance, which is usually accompanied by discomfort, muscle weakness and/or pain and, when combined with persistent exercise despite the symptoms, leads to muscle damage, which often manifests as elevated CK and myoglobinuria. At the start of activity, including but not limited, ascending and descending steps, getting out of bed, brushing teeth, aerobic exercise (such as walking or jogging), muscle contraction is fueled by ATP already available within the muscle fiber. ATP is hydrolyzed to ADP, and the breaking of a phosphate bond provides the free energy for the 'power stroke', with actual movement seen in the shortening of the sarcomere. ATP is reconstituted from intramuscular stores of creatine phosphate by donation of an inorganic phosphate group. However, this process is soon outstripped by demand, and people with GSD disease are unable to mobilize ATP from other sources, leading to an energy crisis that causes the heart rate to increase sharply, together with symptoms of discomfort, pain and fatigue in the exercising muscle. The patient must, therefore, slow down or to stop the activity, allowing the symptoms to subside or disappear before exercise can continue. On recommencement of physical activity, the symptoms may reappear but should soon diminish, alongside a decrease in heart rate (at 8-10 min into continuous physical activity), as a result of an augmented supply of ATP associated with increased efficiency of fat oxidation and improved muscle blood supply. The 8-10 min lag represents the time taken to increase the rate of fat oxidation to an appropriate level to meet a relatively modest demand, with respect to intensity of effort. Without careful management during the early stages of physical activity to ensure that the second wind is achieved, individuals with GSD disease are at substantial risk of contracture and rhabdomyolysis.

Patients with GSD typically experience activity/exercise intolerance in the form of reversible acute crises of early fatigue and contractures that can result in rhabdomyolysis and myoglobinuria. When muscle damage is severe, myoglobinuria can lead to acute renal failure requiring dialysis. A cardinal feature of this disorder, which distinguishes it from other conditions, is the 'second wind' phenomenon. This denotes marked improvement in tolerance to aerobic exercise, such as walking, jogging or cycling, after about 8-10 minutes of exercise, with disappearance or diminution or exercise intolerance and/or exaggerated cardiovascular response (e.g. high heart rate) and/or fatigue that were triggered by the start of exertion. The second wind occurs as a consequence of increased availability and metabolism of alternative fuel substrates namely free fatty acids metabolized through oxidative phosphorylation and glucose supplied from the liver. Patients with GSD present with high total creatinine kinase (CK or formerly known as phosphocreatine (CPK)) serum levels even in the absence of heavy exercise in the previous few hours or days. Taking glucose prior to exercise may alleviate muscle symptoms but this is not a good strategy over the long term as it may result in significant weight gain. There is limited evidence for subjective benefit from creatine supplementation from a small randomized controlled trial, although this has not been confirmed in the clinic setting. Currently, there are no satisfactory treatments or approved drugs for the condition.

Without being bound to any theory or mechanism, the rationale for the use of a PPARδ agonist compound in patients with GSD is based on the following pharmacological effects of a PPARδ agonist compound, namely: a PPARδ agonist compound may increase FAO and oxidative phosphorylation (OXPHOS) activity resulting in enhanced mitochondrial ATP; a PPARδ agonist compound may increase mitochondrial biogenesis which would enhance the cellular ATP synthesis capacity; and a PPARδ agonist compound may directly or indirectly activate the transcription of multiple genes involved in energy metabolism and fatty acid oxidation.

Described herein, in some embodiments, are methods and compositions for treating a glycogen storage disease in a mammal comprising administering to the mammal with a glycogen storage disease a PPARδ agonist compound disclosed herein (e.g., Compound I), or a pharmaceutically acceptable salt thereof (e.g., Compound II). Further described herein, in some embodiments, are methods and compositions for modulating PPARδ in a mammal with a glycogen storage disease comprising administering to the mammal with glycogen storage disease a PPARδ agonist compound disclosed herein (e.g., Compound I), or a pharmaceutically acceptable salt thereof (e.g., Compound II). In some embodiments, modulating PPARδ in a mammal with glycogen storage disease leads to improvement in one or more symptoms associated with glycogen storage disease. In some embodiments, the glycogen storage disease comprises a glycogen storage disease that compromises muscle function in the mammal. In some embodiments, the glycogen storage disease is GSD type II (Pompe disease), Type III (Fobes-Cori disease), Type IV (Andersen disease), Type V (McArdle disease), and Tyle VII (Tarui disease).

In some embodiments, a PPARδ agonist compound disclosed herein (e.g., Compound I), or a pharmaceutically acceptable salt thereof (e.g., Compound II) is used in the treatment of a glycogen storage disease (GSD) in a mammal. In some embodiments, the glycogen storage disease compromises muscle function in the mammal. In some embodiments, the glycogen storage disease comprises a glycogen storage disease that compromises muscle function in the mammal. In some embodiments, the glycogen storage disease is GSD Type II (Pompe disease), Type III (Fobes-Cori disease), Type IV (Andersen disease), Type V (McArdle disease), and Tyle VII (Tarui disease). In some embodiments, the glycogen storage disease is McArdle disease or Pompe disease in the mammal. In some embodiments, the glycogen storage disease is McArdle disease.

In some embodiments, a PPARδ agonist compound disclosed herein (e.g., Compound I), or a pharmaceutically acceptable salt thereof (e.g., Compound II) is used in the treatment of a glycogen storage disease Type II in a mammal. Glycogen storage disease Type II, also known as Pompe disease, is caused by the deficiency of acid alpha glucosidase (GAA), an enzyme that is responsible for the breakdown of the α-1,4- and α-1,6-glycosidic bonds of glycogen to glucose. The deficiency of GAA causes glycogen to accumulate within the lysosomes in multiple tissues, resulting in cellular malfunction, cellular damage, tissue damage, and ultimately organ dysfunction. In Pompe disease, the organ dysfunction is primarily manifested by muscle weakness and muscle wasting in cardiac and skeletal muscles.

Pompe disease is divided into three subcategories, which differ in severity and the age at which they appear. These types are known as classic infantile-onset, non-classic infantile-onset, and late-onset.

The classic form of infantile-onset Pompe disease begins shortly after birth. Infants with this disorder typically experience generalized muscle weakness (myopathy), poor muscle tone (hypotonia), enlarged liver (hepatomegaly), and heart defects. Affected infants may also fail to grow at the expected rate (failure to thrive) and have breathing problems.

The non-classic form of infantile-onset Pompe disease usually appears by age 1. It is characterized by delayed motor skills (such as rolling over and sitting) and progressive muscle weakness. The muscle weakness in this disorder leads to serious respiratory problems and the heart may be abnormally large (cardiomegaly).

The late-onset type of Pompe disease may not become apparent until later in childhood, adolescence, or adulthood. Late-onset Pompe disease is a clinically milder form of the disorder and is less likely to involve the heart defects. Individuals with late-onset Pompe disease often experience progressive muscle weakness, especially in the legs and the trunk, including the muscles that control breathing. As the disorder progresses, breathing problems can lead to respiratory failure.

In some embodiments, a PPARδ agonist compound disclosed herein (e.g., Compound I), or a pharmaceutically acceptable salt thereof (e.g., Compound II) is used in the treatment of a glycogen storage disease Type III in a mammal. Glycogen storage disease Type III, also known as Fobes-Cori disease, is caused by mutations in the AGL gene, which is responsible for the production of the debranching enzyme. The debranching enzyme has two active sites called amylo-1,6-glucosidase and 4-alpha-glucanotransferase. The mutations in the AGL gene leads to the deficient function of the debranching enzyme, resulting in excessive accumulation of an abnormal glycogen in the liver, muscles, and, in some cases, the heart. Most common symptoms of the glycogen storage disease Type III include enlarged liver (hepatomegaly), low blood sugar (hypoglycemia), failure to thrive, and recurrent illness and/or infections. In some embodiments, the amount of glycogen stored in the liver and muscles is abnormally high, resulting in the enlarged liver and swollen abdomen. In some embodiments, the symptoms of glycogen storage disease Type III include muscle weakness. The typical signs and symptoms observed in child with glycogen storage disease Type III include short stature, low blood sugar after fasting, and an elevated level of fatty substances in the blood (hyperlipidemia). In some embodiments, individuals with glycogen storage disease Type III may experience unusually frequent nosebleeds. Enlarged heart muscle (cardiac hypertrophy) is common in those with glycogen storage disease Type III and may appear in in early childhood. In most cases, however, heart function remains within normal limits.

In some embodiments, a PPARδ agonist compound disclosed herein (e.g., Compound I), or a pharmaceutically acceptable salt thereof (e.g., Compound II) is used in the treatment of a glycogen storage disease Type IV in a mammal. Glycogen storage disease Type IV, also known as Andersen disease, is caused by mutations in the GBE1 gene. The GBE1 gene provides instructions for making the glycogen branching enzyme. The glycogen branching enzyme is necessary for making glycogen, a major source of stored energy in the body. The glycogen branding enzyme makes glycogen more compact for storage and allows it to break down more easily when it is needed for energy. The mutations in the GBE1 gene lead to the deficient activity of the glycogen-branching enzyme, resulting in accumulation of abnormal glycogen in the liver, muscle, and/or other tissues.

Clinically, the symptoms and findings become apparent in the first months of life. The signs and symptoms of Andersen disease include progressive cirrhosis of the liver, enlarged liver and spleen (hepatosplenomegaly), liver failure, abnormal fluid build-up in the abdomen (ascites), and enlarged veins in the wall of the esophagus (esophageal varices). In some embodiments, the signs and symptoms of Andersen disease include skeletal muscle or heart muscle disease (myopathy or cardiomyopathy) caused by the excessive accumulation of glycogen in the muscle tissue. In some embodiments, the signs and symptoms of Andersen disease include muscle weakness, fatigue, exercise intolerance, and muscle wasting (atrophy). In some embodiments, the signs and symptoms of Andersen include heart failure.

In some embodiments, a PPARδ agonist compound disclosed herein (e.g., Compound I), or a pharmaceutically acceptable salt thereof (e.g., Compound II) is used in the treatment of a glycogen storage disease Type V in a mammal. Of the glycogenolytic and glycolytic disorders (GSDs), McArdle disease (GSD V, myophosphorylase deficiency or glycogenosis type 5) is the result of autosomal recessive mutations in PYGM, the gene encoding the muscle form of glycogen phosphorylase. Myophosphorylase catalyzes and regulates the breakdown of glycogen to glucose-1-phosphate in skeletal muscle. PYGM is located at chromosome 11q13. Researchers have identified many pathogenic mutations in the gene, which spans 20 exons, and most are population specific. The most common mutation in Northern Europe and North American patients is a nonsense mutation at Arg50X (R50X) in exon 1 (previously referred to as R49X). A second frequent mutation in this population and in Spanish patients is Gly205Ser (G205S). The prevalence of McArdle disease is believed to be in the range of 1 in 100,000 to 1 in 167,000, but precise epidemiological data are lacking.

In some embodiments, the mammal having McArdle disease has been classified up a severity from Type 0 to Type IV. In some embodiments, Type 0 disease severity comprises asymptomatic or virtually asymptomatic (mild exercise intolerance but not functional limitation in any daily life activity) disease. In some embodiments, Type 1 disease severity comprises exercise intolerance, contractures, myalgia, and limitation of acute strenuous exercise and occasionally in daily life activities; no record of myoglobinuria, no muscle wasting or weakness. In some embodiments, Type 2 disease severity comprises Type 1 disease severity with also recurrent exertional myoglobinuria, moderate restriction in exercise and limitation in daily life activities. In some embodiments, Type III disease severity comprises Type 2 disease severity with fixed muscle weakness, with or without wasting, and severe limitations on exercise and most daily life activities.

In some embodiments, the mammal with McArdle disease has at least one mutation or deletion in at least one myophosphorylase (PGYM) gene. In some embodiments, the mammal with McArdle disease has at least one mutation or deletion in at least two copies of the PGYM gene. In some embodiments, the at least one mutation in at least one PGYM gene comprises a mutation selected from p.R50X, p.G206S, p.K543T, p.F710del, p.W798R, p.R270X, p.L397P, c.1768+1G>A, c.2262delA and a combination thereof.

In some embodiments, a PPARδ agonist compound disclosed herein (e.g., Compound I), or a pharmaceutically acceptable salt thereof (e.g., Compound II) is used in the treatment of a glycogen storage disease Type VII in a mammal. Glycogen storage disease Type VII, also known as Tauri disease, is caused by mutations in the gene for muscle phosphofructokinase (PFKM). This leads to the deficient function of phosphofructokinase enzyme, which is responsible for breaking down glycogen to glucose. The mutations in the PFKM gene lead to a decreased amount of energy of muscles to use during exercise, resulting in muscle pain and cramps. The signs and symptoms usually begin in childhood. The most common signs and symptoms include muscle weakness, pain, and stiffness during exercise. Other symptoms include nausea; vomiting; dark, reddish brown-colored urine (myoglobinuria); yellowing of the skin (jaundice); low number of red blood cells (anemia); large amount of glycogen in the muscle; break down of muscle tissue (rhabdomyolysis); and high amount of uric acid in the blood (hyperuricemia). The symptoms of infant glycogen storage disease Type VII include loss of muscle tone (hypotonia), muscle weakness (including in the heart), breathing problems that may lead to death, curving of the joints (arthrogryposis), and intellectual disability. The symptoms of late-onset (adult) glycogen storage disease Type VII include muscle weakness, pain, and tiredness. Individuals with hemolytic glycogen storage disease Type VII do not have muscle symptoms but have anemia due to break down of red blood cells.

In some embodiments, a PPARδ agonist compound disclosed herein (e.g., Compound I), or a pharmaceutically acceptable salt thereof (e.g., Compound II), is used in the treatment of a lysosomal storage disorder (LSD) in a mammal. Lysosomes are small compartments inside the cells that contain digestive enzymes. Lysosomes are involved in various cell processes, such as degrading and recycling cellular waste, cellular signaling and energy metabolism. Defects in genes encoding lysosomal proteins cause lysosomal storage disorders.

Muscular Dystrophy

In some embodiments, a PPARδ agonist compound disclosed herein (e.g., Compound I), or a pharmaceutically acceptable salt thereof (e.g., Compound II) is used in the treatment of a muscular dystrophy in a mammal. Muscle dystrophies are genetic conditions that are characterized by progressive muscle weakness and wasting, primarily in cardiac and skeletal muscles. Muscle weakness is initially observed in the hips and upper leg muscles, but most voluntary muscles, including muscles of respiration and heart, will be affected over time. Weakened heart muscle prevents the heart from pumping blood to the rest of the body, resulting in the development of cardiomyopathy and heart failure.

In some embodiments, the muscular dystrophy is Duchenne muscular dystrophy or Becker muscular dystrophy. These are two forms of muscular dystrophy, which have similar signs and symptoms but differ in their severity, age of onset, and rate of progression. The Becker muscular dystrophy has milder and more varied signs and symptoms. Duchenne and Becker muscular dystrophies are caused by different mutations in a protein called dystrophin. In Duchenne muscular dystrophy, functioning dystrophin is completely absent in muscle whereas in Becker muscular dystrophy some dystrophin is present but not enough for normal muscle function.

Dystrophin is a 427 kDa cytoplasmic protein, which is a vital component of the dystrophin-associated protein complex (DAPC) at the sarcolemma, connecting the internal cytoskeleton to the surrounding extracellular matrix. Dystrophin provides structural stability to the skeletal muscle, maintains strength and flexibility and protects the sarcolemma from contraction-induced injury. Absence of dystrophin and subsequent loss of the DAPC leads to progressive defects including perturbation of the calcium homeostasis, activation of proteases and pro-inflammatory cytokines, and mitochondrial dysfunction resulting in continual influx of inflammation, fibrosis, repeated cycles of necrosis and altered regeneration, with impaired vascular adaptation. The myofibres become more susceptible to contraction-induced injury, which results in premature death, muscle wasting and fatty tissue replacement.

Utrophin is the autosomal homologue of dystrophin and enhancing its expression by moderate amounts (2-fold) in animal models of DMD can compensate for the lack of dystrophin in skeletal muscle fibers and alleviate the muscle pathology. Slow-twitch muscle fibers in both the dystrophin-negative mdx mouse model of muscular dystrophy and DMD patients show reduced damage in comparison to their fast-twitch counterparts. The peroxisome proliferator-activated receptor gamma coactivator 1-a (PGC-1a) is a key factor that can also drive the formation of slow oxidative muscle fiber.

PPARδ promotes the formation of slow-twitch, more oxidative muscle fiber. The PPARδ specific agonist compound GW501516 has been shown to increase the number of slow oxidative fibers and enhance running endurance in adult mice when combined with exercise training.

Other Muscle Diseases and Disorders

In some embodiments, a PPARδ agonist compound disclosed herein (e.g., Compound I), or a pharmaceutically acceptable salt thereof (e.g., Compound II) is used in the treatment of a muscle structure disorder, a muscle fatigue disorder, a muscle mass disorder, a beta oxidation disease, a vascular disease, an ocular vascular disease, or a muscular eye disease in a mammal. In some embodiment, the mammal manifests signs and symptoms of a sarcopenia, muscle wasting, muscle mass loss, fatigue, chronic fatigue syndrome.

Muscle wasting occurs in many inflammatory diseases associated to inter- and intra-muscular fat deposition. In some embodiments, muscle wasting occurs during aging. During aging, muscle mass gradually decreases but may be accelerated by periods of physical inactivity as a result of reduced physical exercise, physical disability, or poor quality of lifestyle. Muscle mass loss is responsible for functional impairment with loss of strength, increased likelihood of falls and loss of autonomy.

Sarcopenia

Sarcopenia is defined as an ageing-related loss of both muscle mass and strength below a threshold level. It is an important predictor of adverse outcomes such as limited mobility, increased risk of falls, decreased quality of life (QoL), hospitalization and mortality. Muscle weakness and skeletal muscle atrophy are overt characteristics of this geriatric syndrome.

Sarcopenia is a muscular disease defined by loss of muscle mass, muscle strength and endurance. In some embodiments, sarcopenia is characterized by the presence of low skeletal muscle mass, low muscle strength, low muscle performance, or a combination thereof. In some embodiments, sarcopenia is age-related (e.g., decreased physical activity, mitochondrial dysfunction, anorexia of aging, apoptosis) but can be accelerated by other factors, such as neuronal degeneration (e.g., loss of motor end plates, peripheral neuropathy), weight loss (e.g., diet, malabsorption, disease-related), inflammation (e.g., interleukin-1, interleukin-6, tumor necrosis factor-alpha), hormones (e.g., low testosterone, low growth hormone, low IGF-1, increased cortisol, low vitamin D), and vascular conditions (e.g., peripheral vascular disease, decreased capillary function).

Certain human skeletal muscles undergo decline in muscle mass between the ages of 20 and 80 years. In some embodiments, certain human skeletal muscles undergo up to 40% decline in muscle mass between the ages of 20 and 80 years.

Among other factors, abrogation of mitochondrial energy production in the muscle is implicated as a major driver of sarcopenia. Reduction in mitochondrial energy production is caused by several factors, including genetic mutation and deletions in mitochondrial DNA (mtDNA) and nuclear DNA (nDNA), reduced mitochondrial mass, reduced OXPHOS activity and ATP production, and reduced activity of important mitochondrial support proteins (e.g., PGC-1α).

Although the molecular events responsible for sarcopenia are unknown, the muscle mass loss is due to fiber atrophy and fiber loss. A variety of mechanisms have been proposed for fiber loss. These include contraction-induced injury, deficient satellite cell recruitment, denervation/renervation, endocrine changes, oxidative stress and mitochondrial DNA damage.

In some embodiments, oxidative stress and mitochondrial DNA damage contribute to the progressive age-related loss of muscle mass. In some embodiments, oxidative damage to the mitochondrial genome has the potential to trigger mtDNA deletion mutations, the accumulation of which would cause a decline in the energy production of the affected cell(s), result in abnormal electron transport system (ETS) enzyme phenotypes, atrophy and would, ultimately, lead to fiber loss.

mtDNA mutations have been shown, in humans, to result in a number of diseases including myopathies and encephalopathies, a broad class of conditions characterized by muscle weakness and central nervous system dysfunction. Myopathies can be divided into two major groups: (a) those caused by a single mtDNA base substitution, such as Leber's hereditary optic nerve atrophy and myoclonic epilepsy and ragged red fiber (MERRF); and (b) diseases caused by large mtDNA deletion mutations such as chronic progressive external ophthalmoplegia (CPEO) and Kearns-Sayre Syndrome (KSS). In myopathy patients, the levels of the mutated mtDNA genomes are very high, 73-98% mutated mtDNA in symptomatic MERRF patients. Deletion mutations are generally present as 20-80% of all mtDNA genomes in KSS patients.

Age-associated mtDNA alterations have been identified, including mtDNA alterations in the mitochondrial myopathies (Wallace, D. C. (1992) Diseases of the mitochondrial DNA. *Annu. Rev. Biochem.* 61, 1175-1212). The mtDNA4977 deletion mutation was found to accumulate, with age, in a variety of human tissues, the highest levels were detected in nerve and muscle tissue (Lee, C. M., et al., (1993) Multiple mitochondrial DNA deletions associated with age in skeletal muscle of rhesus monkeys. *J. Gerontol.* 48, B201-B205.), the same tissues in which mitochondrial enzyme activities were observed to decline with age. Additional mtDNA deletion mutations have been identified in a variety of other species, including rhesus monkeys, mice, and rats.

In addition to the increases in mtDNA deletion mutations with age, skeletal muscle mtDNA content decreases with age (Allen Herbst, et al., Geroscience. 2021 June; 43(3): 1253-1264). Furthermore, skeletal muscle mitochondrial density decreases in sarcopenic subjects. For example, the activity of citrate synthase (CS), a validated biomarker for mitochondrial density in skeletal muscle, is reduced by about 60% in sedentary old adults compared to active adults. Citrate synthase is an enzyme responsible for catalyzing the first reaction of the citric acid cycle (condensation of acetyl-CoA and oxaloacetate to form citrate). Succinate dehydrogenase (SDH), also known as succinate-coenzyme Q reductase (SQR) or respiratory complex II, is an enzyme complex which participates in both the citric acid and the electron transport chain. Both CS and succinate dehydrogenase activity are reduced in muscle from elderly adults with sarcopenia.

In some embodiments, the PPARδ agonist compound disclosed herein (e.g., Compound I), or a pharmaceutically acceptable salt thereof (e.g., Compound II) is used in the treatment of sarcopenia by increasing or improving mitochondrial mass or mitochondrial density.

In some embodiments, mtDNA content and quality correlate with $VO_2$ max and lean muscle mass. In some embodiments, improving mtDNA content and quality in a sarcopenic subject improves the $VO_2$ max in the sarcopenic subject.

In some embodiments, the PPARδ agonist compound disclosed herein (e.g., Compound I), or a pharmaceutically acceptable salt thereof (e.g., Compound II) improves muscle performance in a sarcopenic subject. In some embodiments, muscle performance is assessed with walk speed test. In some embodiments, patients with sarcopenia walk roughly 20-25% slower when compared to age-matched normal group without sarcopenia. In some other embodiments, muscle performance is assessed with exercise tolerance using $VO_2$ max or peak $VO_2$. $VO_2$ max (or peak $VO_2$) is the measurement of the maximum amount of oxygen a person can utilize during intense exercise. It is a common measurement used to establish the aerobic capacity of a person prior to or during the course of exercise. $VO_2$ max (or peak $VO_2$) is expressed either as an absolute rate (for example, liters of oxygen per minute (e.g. L/min)) or as a relative rate (for example, milliliters of oxygen per kilogram of body mass per minute (e.g., mL/min/kg min)). In some embodiments, patients with sarcopenia show lower $VO_2$ max (or peak $VO_2$) compared to age-matched subjects without sarcopenia.

OXPHOS proteins decline in sarcopenic and aged human muscle. For example, complex I, II, III, and V protein levels are downregulated in sarcopenic muscle (Migliavacca, E., et al. Nat Commun 10, 5808 (2019)). In addition, OXPHOS activity declines with age and is lower in low-functioning elderly adults. In addition, ATP synthesis rate declines with age, as well as ATP synthesizing capacity decreases with age. In some embodiments, the PPARδ agonist compound disclosed herein (e.g., Compound I), or a pharmaceutically acceptable salt thereof (e.g., Compound II), is used to improve the decline in OXPHOS activity and/or ATP production in a sarcopenic subject. In some embodiments, improving the decline in OXPHOS activity and/or ATP production treats sarcopenia. In some embodiments, the PPARδ agonist compound described herein increases or improves oxidative phosphorylation (OXPHOS) activity resulting in enhanced mitochondrial ATP. In some embodiments, the PPARδ agonist compound enhances the cellular ATP synthesis capacity. In some embodiments, the PPARδ agonist compound directly or indirectly activates the transcription of multiple genes involved in OXPHOS pathway.

The peroxisome proliferator-activated receptor-γ coactivator-1α (PGC-1α) is involved in the transcriptional regulation of numerous nuclear and mitochondrial gene products that are responsible for muscle mass and muscle performance. Maintaining an optimal intracellular PGC-1α level is crucial in protecting the muscle from many degradative and destructive processes, such as proteolysis, oxidative damage, inflammation, uncontrolled autophagy and apoptosis. Overexpression of PGC-1a in skeletal muscle activates mitochondrial oxidative metabolism, leading to significant increase in physical endurance.

PGC-1a protein levels are decreased in sedentary old human subjects and low functioning elderly subjects relative to both young and active old subjects. Furthermore, PGC-1α mRNA levels are decreased in sarcopenic human muscle and correlate with downregulation of genes controlled by PGC-1α. Interestingly, overexpression of PGC-1a in transgenic animals preserved mitochondrial function, neuromuscular junctions, and muscle integrity during aging and protects from sarcopenia. (T. Wenz, et al., Proc Natl Acad Sci USA. 2009 Dec. 1; 106(48):20405-10). In some embodiments, the PPARδ agonist compound disclosed herein (e.g., Compound I), or a pharmaceutically acceptable salt thereof (e.g., Compound II), modulates the expression or activity of PGC-1a in a sarcopenic subject.

In some embodiments, the PPARδ agonist compound disclosed herein (e.g., Compound I), or a pharmaceutically acceptable salt thereof (e.g., Compound II), the PPARδ agonist compound can treat, prevent, or ameliorate one or more symptoms and conditions associated with sarcopenia by increasing or improving the activity of mitochondrial support proteins. In some embodiments, the mitochondrial support proteins increase the translation of a protein involved in mitochondrial biogenesis. In some embodiments, the mitochondrial support protein is a transcription factor. In some embodiments, the protein is peroxisome proliferator-activated receptor gamma coactivator 1-alpha (PGC-1α).

Compound I has been shown to treat muscle atrophy in other conditions that may resemble muscle atrophy observed in sedentary sarcopenic subjects. For example, compound I has been shown to treat muscle atrophy associated with limb immobilization. In a prior clinical trial in healthy volunteers, Compound I was administered at dose of 100 mg twice daily for 28 days in healthy volunteers during and after a single limb immobilization (see NCT01524406). The study was conducted to evaluate the impact of Compound I on the recovery of muscle atrophy from leg immobilization, and improvements in cross section area (CSA) and muscle strength parameters expected in patients treated with study drug compared to those given placebo. Subjects treated with Compound I had a significant increase in mean knee extension strength at Day 21 from baseline vs placebo. Analysis of gene expression in muscle biopsies indicated significant increases in the expression of known PPAR regulated target genes (e.g. ANGPTL4) and genes involved in fatty acid metabolism (e.g. pyruvate dehydrogenase kinase 4, PDK4) in subjects treated with Compound I.

In addition, as noted in Example B-4, improvements in exercise tolerance were observed in subjects with PMM due to mitochondrial gene defects following administration of Compound I. Subjects were able to increase the distance walked during a 12-minute walk test. In this same group of subjects, trends towards increases in peak $VO_2$ were observed for many subjects that received 100 mg of Compound I.

In some cases, some individuals are more susceptible to sarcopenia than others. For example, elderly women may be more susceptible to sarcopenia. The different susceptibility is due to a combination of factors, including age, gender, genetics, hormones, lifestyle, diet, physical activity, and sedentary behavior. Individuals carrying certain genes are more susceptible to sarcopenia. For example, ACTN3 and VDR genotype are associated with sarcopenia. Other examples of SNPs associated with sarcopenia include, but not limited to, FTO rs9939609, ESR1 rs4870044, NOS3 rs1799983 and TRHR rs7832552.

In some embodiments, Compound I), or a pharmaceutically acceptable salt thereof (e.g., Compound II), is used to treat sarcopenia in a subject. In some embodiments, treating sarcopenia comprises improving exercise endurance, muscle mass, or a combination thereof. In some embodiments, the subject is male human. In some embodiments, the subject is female human. In some embodiments, the subject is at least 40, at least 50, at least 60, at least 70, or at least 80 years old. In some embodiments, the subject is greater than 40, greater than 50, greater than 60, greater than 70, or greater than 80 years old.

Chronic Fatigue Syndrome

Fatigue is a feeling of weariness, tiredness, or lack of energy resulting from mental or physical exertion or illness. Chronic fatigue syndrome (CFS) is a complicated disorder in which symptoms of fatigue persist at least six months. Common symptoms include extreme exhaustion after physical or mental exercise, problems with memory or concentration, sleep disturbances, irritable bowel syndrome, sore throat, headaches, tender lymph nodes in the neck or armpits, muscle pain, joint pain, and irregular heartbeat. In some embodiments, CFS is a metabolic mitochondrial dysfunction resulting in insufficient energy production. In some embodiments, CFS is an acquired metabolic mitochondrial dysfunction. Symptoms associated with CFS such as fatigue, exercise intolerance and myalgia are also shared by patients with primary mitochondrial diseases which are known to be caused by mitochondrial dysfunction resulting from either nuclear or mitochondrial DNA (mtDNA) mutations.

In some embodiments, acquired mitochondrial dysfunction occurs concurrently with or following a viral infection. In some such embodiments, a transition in metabolism from fatty acid oxidation to carbohydrate oxygen occurs suggesting metabolic reprogramming and dysfunctional mitochondria. In some embodiments, metabolic reprogramming is characterized by an inability to restore optimal mitochondrial function and is biased towards glycolysis. Chronic fatigue syndrome may occur following acute infection with severe acute respiratory syndrome coronavirus 2 (SARS-CoV-2). Chronic fatigue syndrome may be associated with post-COVID-19 syndrome.

Chronic fatigue syndrome may be associated with dysfunctional mitochondria or decreased mitochondrial function, decreased mitochondrial number, or combinations thereof. Subjects may have an elevated lactate level at low exercise intensity. Subjects may have reduced levels of lactate clearance. Subjects may have abnormal fatty acid oxidation. Subjects may have reduced levels of fatty acid oxidation.

In some embodiments, a PPARδ agonist compound disclosed herein (e.g., Compound I), or a pharmaceutically acceptable salt thereof (e.g., Compound II) increases or maintains muscle tone in a mammal by promoting the activity of PPARδ, which is the predominant PPAR isotype expressed in skeletal muscle. PPARδ controls energy metabolism, mitochondrial biogenesis, and fiber-type switching.

In some embodiments, a PPARδ agonist compound disclosed herein (e.g., Compound I), or a pharmaceutically acceptable salt thereof (e.g., Compound II) is used to treat, prevent, or ameliorate mitochondrial dysfunction in a mammal by promoting the activity of PPARδ.

In some embodiments, a PPARδ agonist compound disclosed herein (e.g., Compound I), or a pharmaceutically acceptable salt thereof (e.g., Compound II) is used to treat acquired mitochondrial dysfunction.

Additional Diseases and Disorders

In some embodiments, a PPARδ agonist compound disclosed herein (e.g., Compound I), or a pharmaceutically acceptable salt thereof (e.g., Compound II) increases or maintains muscle tone in a mammal by promoting the activity of PPARδ, which is the predominant PPAR isotype expressed in skeletal muscle. PPARδ controls energy metabolism, mitochondrial biogenesis, and fiber-type switching.

In some embodiments, a PPARδ agonist compound disclosed herein (e.g., Compound I), or a pharmaceutically acceptable salt thereof (e.g., Compound II) is used in the treatment of a Barth syndrome in a mammal. Barth syndrome (BTHS) is a metabolic genetic disease that affects multiple organs. The disease is caused by mutations in the tafazzin (Taz) gene on X-chromosome. Taz a mitochondrial transacylase, which is a critical enzyme in the biogenesis of mitochondrial phospholipid cardiolipin, the signature protein of the mitochondrial inner membrane. Cardiolipin plays a key role in the maintenance of mitochondrial cristae architecture, structural integrity of electron transfer chain (ETC) complexes, and mitochondrial ATP synthesis.

In some embodiments, a PPARδ agonist compound disclosed herein (e.g., Compound I), or a pharmaceutically acceptable salt thereof (e.g., Compound II) is used to treat, prevent, or ameliorate mitochondrial dysfunction in a mammal by promoting the activity of PPARδ.

In some embodiments, a PPARδ agonist compound disclosed herein (e.g., Compound I), or a pharmaceutically acceptable salt thereof (e.g., Compound II) is used in the treatment of a diabetic cardiomyopathy in a mammal. Diabetic cardiomyopathy is a disorder of the heart muscle in patients with diabetes. The disease is characterized by the existence of abnormal myocardial structure and often involves mitochondrial dysfunction. An altered mitochondrial structure and reduced expressions of genes involved in mitochondrial oxidative phosphorylation are caused by excessive fatty acid uptake in diabetic hearts.

The heart has perpetually high energy demands in order to support its role as a constantly active pump. The heart generates kilogram quantities of ATP each day and the vast majority of ATP in the cardiac myocyte is generated via oxidative phosphorylation (OXPHOS) pathway. The ATP generating pathway must respond to changing physiologic conditions, as well as alterations in oxygen and energy substrate availability. PPARδ is expressed abundantly in heart tissue and regulates transcriptional gene expression and free fatty acid (FFA) metabolism. Enhanced PPARδ signaling promotes FFA use whereas deletion of PPARδ decreases FFA oxidative gene expression and FFA oxidation. In some embodiments, PPARδ activity regulates glucose and FFA metabolism and cardiac function.

In some embodiments, a PPARδ agonist compound disclosed herein (e.g., Compound I), or a pharmaceutically acceptable salt thereof (e.g., Compound II) is used in the treatment of a neuronal activation disorder and a neurodegenerative disorder in a mammal. In some embodiments, the neurodegenerative disorder is Huntington's disease in the mammal. Huntington's disease is a progressive neurodegenerative disorder characterized by the gradual development of involuntary muscle movements affecting the hands, feet, and face of the mammal. The disease is caused by mutations of a gene known as huntingtin (htt) located on chromosome 4. The htt mutation that causes Huntington's disease contains abnormally long repeats of a specific DNA segment consisting of three nucleotide bases (cytosine, adenine, and guanine). This DNA segment is also known as a CAG trinucleotide repeat. This expanded repeats of the CAG trinucleotide result in the production of an abnormally long version of the huntingtin protein. The elongated protein is cut into small, toxic fragments that accumulate in neurons and disrupt the normal functions of these cells. The dysfunction of neurons in certain areas of the brain (e.g., basal ganglia, cerebral cortex) underlie the symptoms and physical features of Huntington's disease.

Neurons in the brain demand high energy and require mitochondrial production of ATP. Mitochondria as critical organelle control energy production, $Ca^{2+}$ buffering, ROS generation, and antioxidant activity. Accumulation of mutant huntingtin protein evokes mitochondrial dysfunction in neurons, which is manifested by decreased electron transport chain activity, oxygen consumption, $Ca^{2+}$ buffering and decreased ATP and $NAD^+$ production.

In some embodiments, a PPARδ agonist compound disclosed herein (e.g., Compound I), or a pharmaceutically acceptable salt thereof (e.g., Compound II) is used to treat, prevent, or ameliorate the mitochondrial dysfunction in a mammal by promoting the activity of PPARδ. This leads to the increased cell survival of neurons.

Pharmaceutical Compositions

In some embodiments, the PPARδ agonist compound disclosed herein (e.g., Compound I), or a pharmaceutically acceptable salt thereof (e.g., Compound II) is formulated into pharmaceutical composition. Pharmaceutical compositions are formulated in a conventional manner using one or more pharmaceutically acceptable inactive ingredients that facilitate processing of the active compounds into preparations that are used pharmaceutically. Proper formulation is dependent upon the route of administration chosen. A summary of pharmaceutical compositions described herein is found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

In some embodiments, the PPARδ agonist compound disclosed herein (e.g., Compound I), or a pharmaceutically acceptable salt thereof (e.g., Compound II) is administered either alone or in combination with pharmaceutically acceptable carriers, excipients or diluents, in a pharmaceutical composition. Administration of the compounds and compositions described herein can be effected by any method that enables delivery of the compounds to the site of action.

In some embodiments, pharmaceutical compositions suitable for oral administration are presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. In some embodiments, the active ingredient is presented as a bolus, electuary or paste.

Pharmaceutical compositions which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. In some embodiments, the tablets are coated or scored and are formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In some embodiments, stabilizers are added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or Dragee coatings for identification or to characterize different combinations of active compound doses.

It should be understood that in addition to the ingredients particularly mentioned above, the compounds and compositions described herein may include other agents conventional in the art having regard to the type of formulation in question, for example those suitable for oral administration may include flavoring agents.

Methods of Dosing and Treatment Regimens

In one embodiment, a PPARδ agonist compound disclosed herein (e.g., Compound I), or a pharmaceutically acceptable salt thereof (e.g., Compound II) is used in the preparation of medicaments for the treatment of diseases or conditions in a mammal that would benefit from modulation of PPARδ activity. Methods for treating any of the diseases or conditions described herein in a mammal in need of such treatment, involves administration of pharmaceutical compositions that include at least one compound disclosed herein or a pharmaceutically acceptable salt, or solvate thereof, in therapeutically effective amounts to said mammal.

In certain embodiments, the compositions containing a PPARδ agonist compound disclosed herein (e.g., Compound I), or a pharmaceutically acceptable salt thereof (e.g., Compound II) are administered for prophylactic and/or therapeutic treatments. In certain therapeutic applications, the compositions are administered to a patient already suffering from a disease or condition, in an amount sufficient to cure or at least partially arrest at least one of the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation and/or dose ranging clinical trial.

The amount of a given agent that corresponds to such an amount varies depending upon factors such as the particular compound, disease condition and its severity, the identity (e.g., weight, sex) of the subject or host in need of treatment, but nevertheless is determined according to the particular circumstances surrounding the case, including, the specific agent being administered, the route of administration, the condition being treated, and the subject or host being treated.

In general, however, doses of a PPARδ agonist compound disclosed herein (e.g., Compound I), or a pharmaceutically acceptable salt thereof (e.g., Compound II), employed for adult human treatment are typically in the range of 0.01 mg-500 mg per day. In one embodiment, the desired dose is conveniently presented in a single dose or in divided doses administered simultaneously or at appropriate intervals, for example as two, three, four or more sub-doses per day.

In one embodiment, the daily dosages appropriate for the PPARδ agonist compound disclosed herein (e.g., Compound I), or a pharmaceutically acceptable salt thereof (e.g., Compound II), are from about 0.01 to about 50 mg/kg per body weight. In some embodiments, the daily dosage or the amount of active in the dosage form are lower or higher than the ranges indicated herein, based on a number of variables in regard to an individual treatment regime. In various embodiments, the daily and unit dosages are altered depending on a number of variables including, but not limited to, the activity of the compound used, the disease or condition to be treated, the mode of administration, the requirements of the individual subject, the severity of the disease or condition being treated, and the judgment of the practitioner Alternatively, a suitable dose of a PPARδ agonist compound disclosed herein (e.g., Compound I), or a pharmaceutically acceptable salt thereof (e.g., Compound II), for administration to a human will be in the range of from about 0.1 mg/day to about 1000 mg/day; from about 1 mg/day to about 400 mg/day; or from about 1 mg/day to about 300 mg/day. In other embodiments, a suitable dose of a PPARδ agonist compound disclosed herein (e.g., Compound I), or a pharmaceutically acceptable salt thereof (e.g., Compound II), for administration to a human will be about 1 mg/day, about 2 mg/day, about 3 mg/day, about 4 mg/day, about 5 mg/day, about 6 mg/day, about 7 mg/day, about 8 mg/day, about 9 mg/day, about 10 mg/day, about 15 mg/day, about 20 mg/day, about 25 mg/day, about 30 mg/day, about 35 mg/day, about 40 mg/day, about 45 mg/day, about 50 mg/day, about 55 mg/day, about 60 mg/day, about 65 mg/day, about 70 mg/day, about 75 mg/day, about 80 mg/day, about 85 mg/day, about 90 mg/day, about 95 mg/day, about 100 mg/day, about 125 mg/day, about 150 mg/day, about 175 mg/day, about 200 mg/day, about 225 mg/day, about 250 mg/day, about 275 mg/day, about 300 mg/day, about 325 mg/day, about 350 mg/day, about 375 mg/day, about 400 mg/day, about 425 mg/day, about 450 mg/day, about 475 mg/day, or about 500 mg/day.

In some embodiments, the PPARδ agonist compound disclosed herein (e.g., Compound I), or a pharmaceutically acceptable salt thereof (e.g., Compound II), is administered is dose selected from about 25 mg, about 50 mg, about 75 mg, about 100 mg, about 125 mg, about 150 mg, about 175 mg, about 200 mg, about 225 mg, about 250 mg, about 275 mg, about 300 mg, about 325 mg, about 350 mg, about 375 mg, and about 400 mg. In some embodiments, the dose is administered once a day. In some embodiments, the dose is administered twice a day.

In one embodiment, a suitable dose of Compound II for administration to a human is about 25 mg/day, about 50 mg/day, about 75 mg/day, about 100 mg/day, about 125 mg/day, about 150 mg/day, about 175 mg/day, about 200 mg/day, about 225 mg/day, about 250 mg/day, about 275 mg/day, about 300 mg/day, about 325 mg/day, about 350 mg/day, about 375 mg/day, about 400 mg/day, about 425 mg/day, about 450 mg/day, about 475 mg/day, or about 500 mg/day. In one embodiment, a suitable dose of Compound II for administration to a human is about 100 mg twice/day (i.e., a total of about 200 mg/day). In another embodiment, a suitable dose of Compound II, for administration to a human is about 50 mg twice/day (i.e., a total of about 100 mg/day).

In any of the aforementioned aspects are further embodiments in which the effective amount of the PPARδ agonist compound disclosed herein (e.g., Compound I), or a pharmaceutically acceptable salt thereof (e.g., Compound II), is: (a) systemically administered to the mammal; and/or (b) administered orally to the mammal.

In prophylactic applications, compositions containing a PPARδ agonist compound disclosed herein (e.g., Compound I), or a pharmaceutically acceptable salt thereof (e.g., Compound II), are administered to a patient susceptible to or otherwise at risk of a particular disease, disorder or condition. Such an amount is defined to be a "prophylactically effective amount or dose." In this use, the precise amounts also depend on the patient's state of health, weight, and the like. When used in patients, effective amounts for this use will depend on the severity and course of the disease, disorder or condition, previous therapy, the patient's health status and response to the drugs, and the judgment of the treating physician. In one aspect, prophylactic treatments include administering to a mammal, who previously experienced at least one symptom of the disease being treated and is currently in remission, a pharmaceutical composition comprising a PPARδ agonist compound disclosed herein (e.g., Compound I), or a pharmaceutically acceptable salt thereof (e.g., Compound II), in order to prevent a return of the symptoms of the disease or condition.

In certain embodiments wherein the patient's condition does not improve, upon the doctor's discretion the administration of a PPARδ agonist compound disclosed herein (e.g., Compound I), or a pharmaceutically acceptable salt thereof (e.g., Compound II), is administered chronically, that is, for an extended period of time, including throughout the duration of the patient's life in order to ameliorate or otherwise control or limit the symptoms of the patient's disease or condition.

In certain embodiments wherein improvement in the status of the disease or condition in the human is not observed, the daily dose of a PPARδ agonist compound disclosed herein (e.g., Compound I), or a pharmaceutically acceptable salt thereof (e.g., Compound II), is increased. In some embodiments, a once-a-day dosing schedule is changed to a twice-a-day dosing schedule. In some embodiments, a three times a day dosing schedule is employed to increase the amount of the PPARδ agonist compound disclosed herein (e.g., Compound I), or a pharmaceutically acceptable salt thereof (e.g., Compound II), that is administered. In some embodiments, the frequency of administration by inhalation is increased in order to provide repeat high Cmax levels on a more regular basis. In some embodiments, the frequency of administration is increased in order to provide maintained or more regular exposure to the PPARδ agonist compound disclosed herein (e.g., Compound I), or a pharmaceutically acceptable salt thereof (e.g., Compound II). In some embodiments, the frequency of administration is increased in order to provide repeat high Cmax levels on a more regular basis and provide maintained or more regular exposure to the PPARδ agonist compound disclosed herein (e.g., Compound I), or a pharmaceutically acceptable salt thereof (e.g., Compound II).

In certain embodiments wherein a patient's status does improve, the dose of drug being administered is temporarily reduced or temporarily suspended for a certain length of time (i.e., a "drug holiday"). In specific embodiments, the length of the drug holiday is between about 2 days and about 1 year, including by way of example only, about 2 days, about 3 days, about 4 days, about 5 days, about 6 days, about 7 days, about 10 days, about 12 days, about 15 days, about 20 days, about 28 days, or more than about 28 days. The dose reduction during a drug holiday is, by way of example only, by about 10%-100%, including by way of example only about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, and about 100%.

Once improvement of the patient's conditions has occurred, a maintenance dose is administered if necessary. Subsequently, in specific embodiments, the dosage or the frequency of administration, or both, is reduced, as a function of the symptoms, to a level at which the improved disease, disorder or condition is retained. In certain embodiments, however, the patient requires intermittent treatment on a long-term basis upon any recurrence of symptoms.

In some embodiments, a PPARδ agonist compound disclosed herein (e.g., Compound I), or a pharmaceutically acceptable salt thereof (e.g., Compound II), is administered to the human on a continuous dosing schedule. In some embodiments, a PPARδ agonist compound disclosed herein (e.g., Compound I), or a pharmaceutically acceptable salt thereof (e.g., Compound II), is administered to the human on a continuous daily dosing schedule.

The term "continuous dosing schedule" refers to the administration of a particular therapeutic agent at regular intervals. In some embodiments, continuous dosing schedule refers to the administration of a particular therapeutic agent at regular intervals without any drug holidays from the particular therapeutic agent. In some other embodiments, continuous dosing schedule refers to the administration of a particular therapeutic agent in cycles. In some other embodiments, continuous dosing schedule refers to the administration of a particular therapeutic agent in cycles of drug administration followed by a drug holiday (for example, a wash out period or other such period of time when the drug is not administered) from the particular therapeutic agent. For example, in some embodiments the therapeutic agent is administered once a day, twice a day, three times a day, once a week, twice a week, three times a week, four times a week, five times a week, six times a week, seven times a week, every other day, every third day, every fourth day, daily for a week followed by a week of no administration of the therapeutic agent, daily for a two weeks followed by one or two weeks of no administration of the therapeutic agent, daily for three weeks followed by one, two or three weeks of no administration of the therapeutic agent, daily for four weeks followed by one, two, three or four weeks of no administration of the therapeutic agent, weekly administration of the therapeutic agent followed by a week of no administration of the therapeutic agent, or biweekly administration of the therapeutic agent followed by two weeks of no administration of the therapeutic agent. In some embodiments, daily administration is once a day. In some embodiments, daily administration is twice a day. In some embodiments, daily administration is three times a day. In some embodiments, daily administration is more than three times a day.

The term "continuous daily dosing schedule" refers to the administration of a particular therapeutic agent every day at roughly the same time each day. In some embodiments, daily administration is once a day. In some embodiments, daily administration is twice a day. In some embodiments, daily administration is three times a day. In some embodiments, daily administration is more than three times a day.

In some embodiments, the amount of a PPARδ agonist compound disclosed herein (e.g., Compound I), or a pharmaceutically acceptable salt thereof (e.g., Compound II), is administered once-a-day. In some other embodiments, the amount of a PPARδ agonist compound disclosed herein (e.g., Compound I), or a pharmaceutically acceptable salt thereof (e.g., Compound II), is administered twice-a-day. In some other embodiments, the amount of a PPARδ agonist compound disclosed herein (e.g., Compound I), or a pharmaceutically acceptable salt thereof (e.g., Compound II), is administered three times a day.

Diagnosis

In some embodiments, a diagnosis of the disease of disorder disclosed herein in a mammal is confirmed with a tissue biopsy and molecular genetic testing (e.g. Parikh S, et al. Diagnosis and management of mitochondrial disease: a consensus statement from the Mitochondrial Medicine Society. Genet Med. 2015; 17(9):689-701. doi:10.1038/gim.2014.177).

A human mitochondrial genome database is known, see for example, MITOMAP, a compendium of polymorphisms and mutations in human mitochondrial DNA. See also, Revised Cambridge Reference Sequence (rCRS) of the Human Mitochondrial DNA.

A tissue biopsy involves taking a small sample of affected tissue that is studied under a microscope. In some embodiments, chemical tests conducted on the tissue sample are also performed.

In some embodiments, a tissue biopsy comprises a muscle biopsy. In some embodiments, a variety of histological, biochemical, and genetic studies are performed on the tissue. Tissue testing allows for, but not limited to, detection of mtDNA mutations with tissue specificity or low-level heteroplasmy and quantification of mtDNA content (copy number). Tissue testing also allows for, but not limited to, detection of an accumulation of glycogen or an absence of functional muscle glycogen phosphorylase enzyme In some embodiments, muscle histology includes, but is not limited to, hematoxylin and eosin (H&E), Gomori trichrome (for ragged red fibers), SDH (for SDH-rich or ragged blue fibers), NADH-TR (NADH-tetrazolium reductase), COX (for COX negative fibers), and combined SDH/COX staining (COX intermediate fibers). Electron microscopy (EM) examines the mitochondria for inclusions and ultrastructural abnormalities.

In some embodiments, functional in vitro assays in tissue (typically muscle) are performed to measure mitochondrial function. These tests evaluate the various functions of the mitochondrial ETC or respiratory chain. Functional assays include enzyme activities of the individual components of the ETC, measurements of the activity of components, blue-native gel electrophoresis, measurement of the presence of various protein components within complexes and supercomplexes (achieved via western blots and gel electrophoresis), and consumption of oxygen using various substrates and inhibitors.

Treatment Outcomes

In some embodiments, methods for treating a disease or condition described herein with a PPARδ agonist compound disclosed herein (e.g., Compound I), or a pharmaceutically acceptable salt thereof (e.g., Compound II), result in improvements in muscle histology, increases in mitochondrial DNA copy number, improvements in heteroplasmy level, improvement (e.g. increases) in respiratory chain enzyme activity (such as, but not limited to, ATP-ADP levels, fatty acid oxidation gene expression or flux), and increases in mRNA levels (e.g. measured using transcriptomics).

In some embodiments, methods for treating a disease or condition described herein with a PPARδ agonist compound disclosed herein (e.g., Compound I), or a pharmaceutically acceptable salt thereof (e.g., Compound II), result in histological improvements in biopsied muscle samples taken from a mammal with a muscle mass disorder. In some embodiments, histological improvements in biopsied muscle samples comprises increasing the quality of mitochondria. In some embodiments, histological improvements in biopsied muscle samples comprises decreases in ragged red fibers. In some embodiments, histological improvements in biopsied muscle samples comprises decreases in glycogen accumulation.

In some embodiments, improvements or changes in treatment outcomes are measured after about 2 weeks, about 4 weeks, about 6 weeks, about 8 weeks, about 10 weeks, about 12 weeks, about 14 weeks, about 16 weeks, about 18 weeks, about 20 weeks, about 24 weeks, about 26 weeks, about 52 weeks, or more than about 52 weeks of daily administration of Compound I, or a pharmaceutically acceptable salt thereof (e.g., Compound II). In some embodiments, improvements or changes in treatment outcomes are measured after about 12 weeks of daily administration of Compound I, or a pharmaceutically acceptable salt thereof (e.g., Compound II). In some embodiments, improvements or changes in treatment outcomes are measured after about 24 weeks of daily administration of Compound I, or a pharmaceutically acceptable salt thereof (e.g., Compound II). In some embodiments, improvements or changes in treatment outcomes are measured after about 52 weeks of daily administration of Compound I, or a pharmaceutically acceptable salt thereof (e.g., Compound II). In some embodiments, improvements or changes in treatment outcomes are measured after daily administration of Compound II.

In some embodiments, histological improvements in biopsied muscle samples improve by at least or about 10%, 15%, 20%, 25%, 30%, 35% 40%, 45% 50%, 55%, 60%, 65%, 70%, 75%, 80%, 85%, 90%, 95%, or more than 95%.

In some embodiments, mitochondrial DNA copy number increase by at least or about 10%, 15%, 20%, 25%, 30%, 35%, 40%, 45%, 50%, 55%, 60%, 65%, 70%, 75%, 80%, 85%, 90%, 95%, or more than 95%. In some embodiments, the administration of a PPARδ agonist compound disclosed herein (e.g., Compound I), or a pharmaceutically acceptable salt thereof (e.g., Compound II), to a mammal with a muscle mass disorder results in mitochondrial DNA copy number improving by at least or about 0.5 fold, 1 fold, 1.5 fold, 2 fold, 2.5 fold, 3 fold, 3.5 fold, 4 fold, 5 fold, 6 fold, 7 fold, 8 fold, 9 fold, 10 fold, or more than 10 fold.

In some embodiments, heteroplasmy levels improve by at least or about 10%, 15%, 20%, 25%, 30%, 35%, 40%, 45%, 50%, 55%, 60%, 65%, 70%, 75%, 80%, 85%, 90%, 95%, or more than 95%. In some embodiments, the administration of a PPARδ agonist compound disclosed herein (e.g., Compound I), or a pharmaceutically acceptable salt thereof (e.g., Compound II), to a mammal with a muscle mass disorder results in heteroplasmy levels improving by at least or about 0.5 fold, 1 fold, 1.5 fold, 2 fold, 2.5 fold, 3 fold, 3.5 fold, 4 fold, 5 fold, 6 fold, 7 fold, 8 fold, 9 fold, 10 fold, or more than 10 fold.

In some embodiments, respiratory chain enzyme activity improves by at least or about 10%, 15%, 20%, 25%, 30%, 35%, 40%, 45%, 50%, 55%, 60%, 65%, 70%, 75%, 80%, 85%, 90%, 95%, or more than 95%. In some embodiments, the administration of a PPARδ agonist compound disclosed herein (e.g., Compound I), or a pharmaceutically acceptable salt thereof (e.g., Compound II), to a mammal with a muscle mass disorder results in respiratory chain enzyme improving by at least or about 0.5 fold, 1 fold, 1.5 fold, 2 fold, 2.5 fold, 3 fold, 3.5 fold, 4 fold, 5 fold, 6 fold, 7 fold, 8 fold, 9 fold, 10 fold, or more than 10 fold.

Improvements, in some embodiments, are compared to a control. In some embodiments, a control is an individual who does not receive a PPARδ agonist compound disclosed herein (e.g., Compound I), or a pharmaceutically acceptable salt thereof (e.g., Compound II). In some embodiments, the control is an individual who does not receive a full dose of a PPARδ agonist compound disclosed herein (e.g., Compound I), or a pharmaceutically acceptable salt thereof (e.g., Compound II). In some embodiments, the control is baseline for the individual prior to receiving a PPARδ agonist compound disclosed herein (e.g., Compound I), or a pharmaceutically acceptable salt thereof (e.g., Compound II).

In some embodiments, methods for treating disease or condition with a PPARδ agonist compound disclosed herein (e.g., Compound I), or a pharmaceutically acceptable salt thereof (e.g., Compound II), result in improvements in one or more treatment outcome measures. In some embodiments, outcomes measures include, but are not limited to: patient reported outcomes (PRO), exercise tolerance, whole body fatty acid oxidation (e.g. $^{13}CO_2$ production), blood acylcarnitines profiles, and blood inflammatory cytokines. In some embodiments, a baseline assessment is determined, typically prior to the administration of a PPARδ agonist compound. Improvements in outcome measures are assessed with repeated assessments taken during treatment with a PPARδ agonist compound and a comparison against the baseline assessment and/or any prior assessment(s).

In some embodiments, improvements in one or more outcome measures are by at least or about 10%, 15%, 20%, 25%, 30%, 35%, 40%, 45%, 50%, 55%, 60%, 65%, 70%, 75%, 80%, 85%, 90%, 95%, or more than 95%. In some embodiments, the administration of a PPARδ agonist compound disclosed herein (e.g., Compound I), or a pharmaceutically acceptable salt thereof (e.g., Compound II), to a mammal with a muscle mass disorder results in one or more outcome measures improving by at least or about 0.5 fold, 1 fold, 1.5 fold, 2 fold, 2.5 fold, 3 fold, 3.5 fold, 4 fold, 5 fold, 6 fold, 7 fold, 8 fold, 9 fold, 10 fold, or more than 10 fold.

In some embodiments, patient reported outcomes (PRO) are measured with questionnaires. In some embodiments, the questionnaire covers health concepts related to the disorder being treated. In some embodiments, the questionnaire covers health concepts related to the disorder being treated such as, but not, limited to: physical functioning, bodily pain, role limitations due to physical health problems, role limitations due to personal or emotional problems, emotional well-being, social functioning, energy/fatigue, and general health perceptions, including perceptions in change of health.

In some embodiments, outcome measures are assessed with tests that assess exercise tolerance or endurance. In some embodiments, exercise tolerance is assessed with exercise tests. Exercise tests include, but are not limited to, submaximal treadmill, walking tests (e.g. 1 minute, 2 minute, 3 minute, 6 minute; 10 minute, 12 minute or 1-12 minute and all times in between), run tests, treadmill and ergometry exercise testing. In some embodiments, exercise tests are used in combination with the Borg Scale of perceived exertion. In some embodiments, exercise tests are performed according to guidelines set forth by the American Thoracic Society (ATS).

In some embodiments, the mammal's exercise tolerance is measured with a rating of perceived Exertion (RPI).

In some embodiments, treating a muscle mass disorder comprises improving the mammal's exercise tolerance, sense of feeling well, cognition, decreasing pain, decreasing fatigue, increasing strength, increasing survival or a combination thereof.

In some embodiments, an improvement in a person's sense of well-being, pain, fatigue, and/or cognition is determined by asking the person treated to compare the aforementioned symptoms after treatment as compared to before treatment.

In some embodiments, an improvement in a person's symptoms can be determined by asking a caregiver to compare the subject's symptoms before and after treatment.

In some embodiments, improving the mammal's exercise tolerance comprises increasing endurance/exercise tolerance as measured by sit-stand tests, or the distance walked in a walking test such as about a 6-minute walk test or in a about 12-minute walk test. In some embodiments, the distance walked in such a walking test increases by at least about 1 meter, at least about 5 meters, at least about 10 meters, at least about 20 meters, at least about 30 meters, at least about 40 meters, at least about 50 meters, at least about 60 meters, at least about 70 meters, at least about 80 meters, at least about 90 meters, at least about 100 meters, or more than about 100 meters.

The 30 second sit to stand test is also known as 30 second chair stand test (30CST), is for testing leg strength and endurance in older adults. The 30CST involves recording the number of stands a person can complete in 30 seconds rather than the amount of time it takes to complete a pre-determined number of repetitions.

As used herein the term "about" means within +10% of the value.

In some embodiments, administration of a PPARδ agonist compound disclosed herein (e.g., Compound I), or a pharmaceutically acceptable salt thereof (e.g., Compound II) to a mammal with a GSD comprises improving the mammal's sense of feeling well, exercise tolerance, decreasing pain, decreasing fatigue, increasing strength, or a combination thereof. In some embodiments, the administration of a PPARδ agonist compound decreasing perceived pain or decreasing perceived fatigue during exercise before the second wind occurs in the mammal with the GSD.

In some embodiments, improving the mammal's exercise tolerance comprises decreases in heart rate during the 12-minute walk test. In some embodiments, heart rate decreases by 1 heart beat per minute, by 2 heart beats per minute, by 3 heart beats per minute, by 4 heart beats per minute, by 5 heart beats per minute, by at least about 10 heart beats per minute, or by at least about 20 heart beats per minute.

In some embodiments, improving the mammal's exercise tolerance comprises increasing the mammal's peak or maximal uptake of oxygen (peak $VO_2$ or $VO_2$ max). $VO_2$ max, also known as maximal oxygen uptake, is the measurement of the maximum amount of oxygen a person can utilize during intense exercise. It is a common measurement used to establish the aerobic capacity of a person prior to or during the course of exercise.

In some embodiments, peak $VO_2$ is expressed either as an absolute rate (for example, litres of oxygen per minute (e.g. L/min)) or as a relative rate (for example, milliliters of oxygen per kilogram of body mass per minute (e.g., mL/min/kg min)).

In some embodiments, improving the mammal's exercise tolerance comprises increasing the mammals peak $VO_2$ measurement by about 0.5 mL/min/kg, by about 1 mL/min/kg, by about 1.5 mL/min/kg, by about 2 mL/min/kg, by about 2.5 mL/min/kg, by about 3 mL/min/kg, by about 3.5 mL/min/kg, by about 4 mL/min/kg, by about 4.5 mL/min/kg, by about 5 mL/min/kg, or more than about 5 mL/min/kg.

In some embodiments, improving the mammal's exercise tolerance comprises decreases in measured respiratory exchange ratios (RER).

In some embodiments, the respiratory exchange ratio (RER) is measured to assess exercise tolerance. RER is the ratio between the amount of carbon dioxide ($CO_2$) produced in metabolism and oxygen ($O_2$) used. In some embodiments, the ratio is determined by comparing exhaled gases to room air.

PPAR agonists have demonstrated the ability to increase $^{13}CO_2$ production in clinical trials (Gillingham, M. B., et al., *Journal of Inherited Metabolic Disease*, Volume 40, Issue 6, November 2017, 831-843; Riserus, U., et al. *Diabetes* 2008 February; 57(2): 332-339; each of which is incorporated for such protocols). In some embodiments, stable isotope methods are used to measure in vivo residual fatty acid oxidation capacity. Enrichment of $^{13}CO_2$ only occurs by one complete round of fatty acid oxidation. A representative protocol is as follows. A fasting blood sample is obtained after an overnight fast. Prior to breakfast, a resting indirect calorimetry is measured. Subjects are then given a meal (e.g., a shake) containing 17-mg/kg $^{13}C$-oleic acid. Breath samples are collected prior to (time 0) and again hourly at 1, 2, 3, 4, 5, 6, 7, and 8 hours following the $^{13}C$-oleic administration. $^{13}C$ in breath samples are measured as a ratio of $^{13}C/^{12}C$ using the Delta Plus IRMS (Finnigan MAT, Bremen, Germany). Recovery is calculated as 13C divided by the dose of $^{13}C$ administered. The amount of excess $^{13}C$ in breath is a measure of residual fatty acid oxidation capacity in subjects with disorders of long-chain fatty acid oxidation.

In some embodiments, improvements in fatty acid oxidation in subjects with a FAOD that are treated with a PPARδ agonist compound disclosed herein (e.g., Compound I), or a pharmaceutically acceptable salt thereof (e.g., Compound II), are measured with a suitable $^{13}CO_2$ breath sample test. In some embodiments, a suitable $^{13}CO_2$ breath sample test comprises the steps of: 1) providing the subject a meal comprising $^{13}C$-enriched fatty acid(s); 2) administering to the subject a PPARδ agonist compound disclosed herein (e.g., Compound I), or a pharmaceutically acceptable salt thereof (e.g., Compound II), after the consumption of the meal; and 3) collecting breath samples from the subject at regular intervals and measuring the relative amount of $^{13}CO_2$ to $^{12}CO_2$ in the breath samples. In some embodiments, the breath samples are collected about every hour. In some embodiments, the meal is enriched with a 13C labeled fatty acid, wherein the fatty acid is butyric acid, caproic acid, caprylic acid, capric acid, lauric acid, myristic acid, palmitic acid, stearic acid, arachidic acid, behenic acid, lignoceric acid, caproleic acid, lauroleic acid, myristoleic acid, palmitoleic acid, oleic acid, elaidic acid, vaccenic acid, gadoleic acid, erucic acid, brassidic acid, nervonic acid, linoleic acid, alpha-linolenic acid, gamma-linolenic acid, columbinic acid, stearidonic acid, mead acid, dihomo-γ-linolenic acid, arachidonic acid, eicosapentaenoic acid, docosapentaenoic acid, or docosahexaenoic acid.

In some embodiments, the amount of $^{13}CO_2$ in breath samples is used as a diagnostic to guide treatment of the subject with a FAOD with a PPARδ agonist compound disclosed herein (e.g., Compound I), or a pharmaceutically acceptable salt thereof (e.g., Compound II). For example, if a subject or individual has a change in the amount of $^{13}CO_2$ of at least a specified percentage or level following the administration of a PPARδ agonist compound disclosed herein (e.g., Compound I), or a pharmaceutically acceptable salt thereof (e.g., Compound II), the subject or individual continues the treatment using the PPARδ agonist compound disclosed herein (e.g., Compound I), or a pharmaceutically acceptable salt thereof (e.g., Compound II). In some embodiments, modest increases in $^{13}CO_2$ in breath samples may necessitate an increase in the amount of the PPARδ agonist compound that is administered to the subject, an increase in the frequency of administering the PPARδ agonist compound, or both.

In some instances, the change in the amount of $^{13}CO_2$ is at least or about 10%, 15%, 20%, 25%, 30%, 35%, 40%, 45%, 50%, 55%, 60%, 65%, 70%, 75%, 80%, 85%, 90%, 95%, or more than 95% compared to baseline. In some instances, the change occurs after at least or about 1 hour, 2 hours, 3 hours, 4 hours, 5 hours, 6 hours, 7 hours, 8 hours, 12 hours, 16 hours, 20 hours, 1 day, 2 days, 3 days, 4 days, 5 days, 6 days, 1 week, 2 weeks, 3 weeks, 1 month, 2 months, 3 months, 4 months, or more than 4 months after initiation of treatment with a PPARδ agonist compound disclosed herein (e.g., Compound I), or a pharmaceutically acceptable salt thereof (e.g., Compound II) has begun. In some instances, a treatment regimen comprising a PPARδ agonist compound disclosed herein (e.g., Compound I), or a pharmaceutically acceptable salt thereof (e.g., Compound II) is continued if the change in the amount of $^{13}CO_2$ is at least or about 10%, 15%, 20%, 25%, 30%, 35%, 40%, 45%, 50%, 55%, 60%, 65%, 70%, 75%, 80%, 85%, 90%, 95%, or more than 95% compared to baseline after at least or about 1 hour, 2 hours, 3 hours, 4 hours, 5 hours, 6 hours, 7 hours, 8 hours, 12 hours, 16 hours, 20 hours, 1 day, 2 days, 3 days, 4 days, 5 days, 6 days, 1 week, 2 weeks, 3 weeks, 1 month, 2 months, 3 months, 4 months, or more than 4 months after initiation of treatment with a PPARδ agonist compound disclosed herein (e.g., Compound I), or a pharmaceutically acceptable salt thereof (e.g., Compound II) has begun. In some instances, the change is an increase in the levels of $^{13}CO_2$.

In some embodiments, increases of amount of $^{13}CO_2$ over time is indicative of a subject's responsive to the PPARδ agonist compound. In some instances, a subject is responsive to the PPARδ agonist compound if there is a change in the amount of $^{13}CO_2$ of at least or about 10%, 15%, 20%, 25%, 30%, 35%, 40%, 45%, 50%, 55%, 60%, 65%, 70%, 75%, 80%, 85%, 90%, 95%, or more than 95% compared to baseline in $^{13}CO_2$ levels. In some instances, the change in the amount of $^{13}CO_2$ occurs after at least or about 1 hour, 2 hours, 3 hours, 4 hours, 5 hours, 6 hours, 7 hours, 8 hours, 12 hours, 16 hours, 20 hours, 1 day, 2 days, 3 days, 4 days, 5 days, 6 days, 1 week, 2 weeks, 3 weeks, 1 month, 2 months, 3 months, 4 months, or more than 4 months after administration of the PPARδ agonist compound. In some instances, a subject is responsive if the change in the amount of $^{13}CO_2$ is at least or about 10%, 15%, 20%, 25%, 30%, 35%, 40%, 45%, 50%, 55%, 60%, 65%, 70%, 75%, 80%, 85%, 90%, 95%, or more than 95% compared to baseline after at least or about 1 hour, 2 hours, 3 hours, 4 hours, 5 hours, 6 hours, 7 hours, 8 hours, 12 hours, 16 hours, 20 hours, 1 day, 2 days, 3 days, 4 days, 5 days, 6 days, 1 week, 2 weeks, 3 weeks, 1 month, 2 months, 3 months, 4 months, or more than 4 months after initiation of treatment with a PPARδ agonist compound has begun. In some instances, the change is an increase in the amount of $^{13}CO_2$ in the breath samples overt time.

In some embodiments, treatment with a PPARδ agonist compound disclosed herein (e.g., Compound I), or a pharmaceutically acceptable salt thereof (e.g., Compound II) comprises a reduction in the cardiovascular response to exercise. In some embodiments, the cardiovascular response comprises monitoring heart rate, and cardiac output. In some embodiments, the cardiovascular response to exercise comprises an elevated heart rate. In some embodiments, treatment with a PPARδ agonist compound disclosed herein (e.g., Compound I), or a pharmaceutically acceptable salt thereof (e.g., Compound II) comprises a reduction in elevated heart rates in response to exercise to levels considered normal for healthy subjects performing the same exercise. In some embodiments, treatment with a PPARδ agonist compound disclosed herein (e.g., Compound I), or a pharmaceutically acceptable salt thereof (e.g., Compound II) comprises a reduction in the elevated of heart rate during exercise of about 10%, 15%, 20%, 25%, 30%, 35%, 40%, 45%, 50%, 55%, 60%, 65%, 70%, 75%, 80%, 85%, 90%, 95%, or more than 95%. In some embodiments, the administration of a PPARδ agonist compound disclosed herein (e.g., Compound I), or a pharmaceutically acceptable salt thereof (e.g., Compound II), to a mammal with a disease or disorder described herein results in a reduction of elevated heart rates during exercise by at least or about 0.5 fold, 1 fold, 1.5 fold, 2 fold, 2.5 fold, 3 fold, 3.5 fold, 4 fold, 5 fold, 6 fold, 7 fold, 8 fold, 9 fold, 10 fold, or more than 10 fold so that the heart rates during exercise approach heart rates observed for healthy subjects performing the same exercise.

In some embodiments, a mammal's pain is evaluated with Rating of Perceived Pain (RPP). In some embodiments, pain severity is measured on a ten-point scale. In some embodiments, treatment with a PPARδ agonist compound disclosed herein (e.g., Compound I), or a pharmaceutically acceptable salt thereof (e.g., Compound II), comprises decreases in RPP scores by 1, 2, 3, 4, 5 or more than 5.

In some embodiments, a mammal's pain is evaluated with a Brief Pain Inventory (BPI). BPI comprises a questionnaire that assesses the severity of pain and the impact of pain on daily functions that is experienced. In some embodiments, pain severity is measured on a ten-point scale. In some embodiments, the administration of a PPARδ agonist compound disclosed herein (e.g., Compound I), or a pharmaceutically acceptable salt thereof (e.g., Compound II), to a mammal with a disease or disorder described herein comprises decreases in BPI scores by 1, 2, 3, 4, 5 or more than 5.

In some embodiments, a mammal's fatigue or energy level is evaluated with a Fatigue Assessment Scale (FAS) (e.g., see J Psychosom Res. 2003 April; 54(4):345-52) or a Modified Fatigue Impact Scale (MFIS). Fatigue is a feeling of physical tiredness and lack of energy that many people experience from time to time. MFIS comprises a questionnaire that assesses the impact fatigue has on a person's daily life. The MFIS is a detailed tool, that is completed by the patient personally, rather than having an interview and thus, no training is required to deliver it. Scoring is simple, the score reflects functional limitation due to fatigue experienced within the previous month rather than a measure of the level of fatigue. It may be used in both the clinical and the research setting in people for whom fatigue is a predominant symptom. In some embodiments, the total MFIS score can range from 0 to 84. There are 21 items, each of which is scored 0 (no problem) to 4 (extreme problem). It is composed of three subscales that describe the impact of fatigue on physical, cognitive and psychosocial functioning: a) Physical functioning (9 items) reflects motivation, effort, stamina, and coordination. The physical subscale can range from 0 to 36. b) Cognitive functioning (10 items) concerns concentration, memory, thinking and organization of thoughts. The cognitive subscale ranges from 0 to 40. c) Psychosocial functioning (2 items) describes the impact of fatigue upon isolation, emotions, workload, and coping. The psychosocial subscale can range from 0 to 8.

In some embodiments, the administration of a PPARδ agonist compound disclosed herein (e.g., Compound I), or a pharmaceutically acceptable salt thereof (e.g., Compound II), to a mammal with a disease or disorder described herein comprises decreases in MFIS scores by 1, 2, 3, 4, 5, 6, 7, 8, 9, 10, 11, 12, 13, 14, 15, 16, 17, 18, 19, 20, or more than 20. In some embodiments, the administration of a PPARδ agonist compound disclosed herein (e.g., Compound I), or a pharmaceutically acceptable salt thereof (e.g., Compound II), to a mammal with a disease or disorder described herein comprises decreases in MFIS physical functioning subscores by 1, 2, 3, 4, 5, 6, 7, 8, 9, 10, or more than 10. In some embodiments, the administration of a PPARδ agonist compound disclosed herein (e.g., Compound I), or a pharmaceutically acceptable salt thereof (e.g., Compound II), to a mammal with a disease or disorder described herein comprises decreases in MFIS cognitive functioning subscores by 1, 2, 3, 4, 5, 6, 7, 8, 9, 10, or more than 10. In some embodiments, the administration of a PPARδ agonist compound disclosed herein (e.g., Compound I), or a pharmaceutically acceptable salt thereof (e.g., Compound II), to a mammal with a disease or disorder described herein comprises decreases in MFIS psychosocial functioning subscores by 1, 2, 3, 4, or more than 4.

In some embodiments, fatigue or energy level is evaluated with the PROMIS SF v1.0 Fatigue 13a, which is the FACIT-Fatigue adopted by the PROMIS Health Organization. This test has 13 items, a recall period of the past 7 days, and a response scale that is a 5 point Likert-type scale.

In some embodiments, administration of a PPARδ agonist compound disclosed herein (e.g., Compound I), or a pharmaceutically acceptable salt thereof (e.g., Compound II), to a mammal causes a reduction in rhabdomyolysis as compared to pre-treatment levels. The diagnosis of rhabdomyolysis is confirmed by detecting elevated muscle enzymes in blood, which include creatine phosphokinase (CPK), SGOT, SGPT, and LDH. The levels of these enzymes rise as the muscle is destroyed in rhabdomyolysis. In some embodiments, following treatment with a PPARδ agonist compound, the degree of rhabdomyolysis is reduced in the mammal as compared to a mammal who has not been administered a PPARδ agonist compound. In some embodiments, reduction of rhabdomyolysis comprises a reduction in the frequency of rhabdomyolysis, a reduction in the number of incidences of rhabdomyolysis, or a reduction in the intensity of rhabdomyolysis. In some embodiments, there is a reduction in rhabdomyolysis following exercise. In some embodiments, there is a reduction in rhabdomyolysis of about 10%, 15%, 20%, 25%, 30%, 35%, 40%, 45%, 50%, 55%, 60%, 65%, 70%, 75%, 80%, 85%, 90%, 95%, or more than 95%. In some embodiments, the administration of a PPARδ agonist compound disclosed herein (e.g., Compound I), or a pharmaceutically acceptable salt thereof (e.g., Compound II), to a mammal results in a reduction of rhabdomyolysis by at least or about 0.5 fold, 1 fold, 1.5 fold, 2 fold, 2.5 fold, 3 fold, 3.5 fold, 4 fold, 5 fold, 6 fold, 7 fold, 8 fold, 9 fold, 10 fold, or more than 10 fold.

In some embodiments, administration of a PPARδ agonist compound disclosed herein (e.g., Compound I), or a pharmaceutically acceptable salt thereof (e.g., Compound II), to a mammal decreases the intensity of, frequency of or incidences of muscle contracture (cramp) during exercise as compared to pretreatment levels. In some embodiments, there is a reduction in muscle contracture of about 10%, 15%, 20%, 25%, 30%, 35%, 40%, 45%, 50%, 55%, 60%, 65%, 70%, 75%, 80%, 85%, 90%, 95%, or more than 95%. In some embodiments, the administration of a PPARδ agonist compound disclosed herein (e.g., Compound I), or a pharmaceutically acceptable salt thereof (e.g., Compound II), to a mammal results in a reduction of the intensity of, frequency of or incidences of muscle contracture (cramp) during exercise by at least or about 0.5 fold, 1 fold, 1.5 fold, 2 fold, 2.5 fold, 3 fold, 3.5 fold, 4 fold, 5 fold, 6 fold, 7 fold, 8 fold, 9 fold, 10 fold, or more than 10 fold.

In some embodiments, following treatment with a PPARδ agonist compound disclosed herein (e.g., Compound I), or a pharmaceutically acceptable salt thereof (e.g., Compound II), the degree of myoglobinuria is reduced in the mammal as compared to pre-treatment levels. In some embodiments, reduction of myoglobinuria comprises a reduction in the frequency of myoglobinuria, a reduction in the number of incidences of myoglobinuria, or a reduction in the intensity of myoglobinuria. In some embodiments, treatment with a PPARδ agonist compound comprises a reduction in myoglobinuria following exercise. In some embodiments, treatment with a PPARδ agonist compound comprises a reduction in myoglobinuria by about 10%, 15%, 20%, 25%, 30%, 35%, 40%, 45%, 50%, 55%, 60%, 65%, 70%, 75%, 80%, 85%, 90%, 95%, or more than 95%. In some embodiments, treatment with a PPARδ agonist compound results in a reduction of myoglobinuria by at least or about 0.5 fold, 1 fold, 1.5 fold, 2 fold, 2.5 fold, 3 fold, 3.5 fold, 4 fold, 5 fold, 6 fold, 7 fold, 8 fold, 9 fold, 10 fold, or more than 10 fold.

In some embodiments, improvements in patient outcomes following the administration the administration of a PPARδ agonist compound disclosed herein (e.g., Compound I), or a pharmaceutically acceptable salt thereof (e.g., Compound II) is measured by a decrease in a Patient Global Impression of Severity (PGI-S), a Patient Global Impression of Impact (PGI-I), or a Patient Global Impression of Change (PGI-C). In some embodiments, the PGI-S asks a subject to describe the severity of symptoms over the past week on a scale comprising none, mild, moderate, severe, and very severe. In some embodiments, the PGI-I asks a subject to describe the impact of symptoms over the past week on the subject's quality of life on a scale comprising none, mild, moderate, severe, and very severe. In some embodiments, the PGI-C asks the subject to describe the change in severity of symptoms over a period of time on a scale comprising much improved, moderately improved, minimally improved, no change, minimally worse, moderately worse, and much worse. In some embodiments, the PGI-C asks the subject to describe the change in severity of symptoms over a period of about a week and is assessed weekly over a period of about twelve weeks, about thirteen weeks, about fourteen weeks, about fifteen weeks, about sixteen weeks, or over a period of more than sixteen weeks. In some embodiments, the PGI-C asks the subject to describe the change in severity of symptoms over a period of about a week and is assessed weekly over a period of about one month, two months, three months, four months, five months, six months or over a period of more than six months.

In some embodiments, improvements in patient outcomes following the administration the administration of a PPARδ agonist compound disclosed herein (e.g., Compound I), or a pharmaceutically acceptable salt thereof (e.g., Compound II) is measured by a change in the RAND 36-Item Health Survey. The RAND 36-Item Health Survey (Version 1.0) asks questions which cover eight health concepts: physical functioning, bodily pain, role limitations due to physical health problems, role limitations due to personal or emotional problems, emotional well-being, social functioning, energy/fatigue, and general health perceptions. It also includes a single item that provides an indication of perceived change in health.

In some embodiments, improvements in patient outcomes following the administration the administration of a PPARδ agonist compound disclosed herein (e.g., Compound I), or a pharmaceutically acceptable salt thereof (e.g., Compound II) is measured by a change in the 36 Item Health Survey V2.0@ (SF-36). The 36-Item Health Survey Version 2.0@ asks questions which cover eight health concepts: physical functioning, bodily pain, role limitations due to physical health problems, role limitations due to personal or emotional problems, emotional well-being, social functioning, energy/fatigue, and general health perceptions. It also includes a single item that provides an indication of perceived change in health. In some embodiments, a one-week recall period is used.

In some embodiments, improvements in treatment outcomes following the administration of a PPARδ agonist compound disclosed herein (e.g., Compound I), or a pharmaceutically acceptable salt thereof (e.g., Compound II) is measured by a decrease in the Work Productivity and Activity Impairment Questionnaire: Specific Health Problem (WPAI.SUP). The Work Productivity and Activity Impairment (WPAI) questionnaire is a well validated instrument to measure impairments in work and activities. Outcomes are expressed as impairment percentages, with higher numbers indicating greater impairment and less productivity, i.e., worse outcomes.

In some embodiments, treatment with a PPARδ agonist compound disclosed herein (e.g., Compound I), or a pharmaceutically acceptable salt thereof (e.g., Compound II) comprises a reduction of muscle symptoms of the disease or disorder being treated. In some embodiments, treatment comprises a reduction in muscle aches, muscle pain, muscle stiffness, muscle weakness, muscle cramping, or a combination thereof.

In some embodiments, treatment comprises improving a person's sense of feeling well, exercise tolerance, decreasing pain, decreasing fatigue, increasing strength, increasing survival or a combination thereof.

In some embodiments, an improvement in a person's sense of well-being, pain, and/or fatigue, is determined by asking the person treated to compare the aforementioned symptoms after treatment as compared to before treatment.

In some embodiments, improvements or changes in treatment outcomes are measured after about 2 weeks, about 4 weeks, about 6 weeks, about 8 weeks, about 10 weeks, about 12 weeks, about 14 weeks, about 16 weeks, about 18 weeks, about 20 weeks, about 24 weeks, about 26 weeks, about 52 weeks, or more than about 52 weeks of daily administration of Compound II. In some embodiments, improvements or changes in treatment outcomes are measured after about 12 weeks of daily administration of Compound II. In some embodiments, improvements or changes in treatment outcomes are measured after about 24 weeks of daily administration of Compound II. In some embodiments, improvements or changes in treatment outcomes are measured after about 52 weeks of daily administration of Compound II. In some embodiments, improvements or changes in treatment outcomes are measured after once daily administration of Compound II.

In some embodiments, treating the primary mitochondrial myopathy in a human comprises improving the human's exercise tolerance, improving muscle histology, decreasing pain, decreasing fatigue, improving cognition, improving overall well-being, a reduction in myoglobinuria, reducing tachycardia, a reduction in rhabdomyolysis, a reduction in muscle contracture, reducing the severity of PMM muscle symptoms, reducing impairments in work and activities, increasing survival, or a combination thereof. In some embodiments, treating the primary mitochondrial myopathy in a human comprises improving the human's exercise tolerance. In some embodiments, treating the primary mitochondrial myopathy in a human comprises improving muscle histology. In some embodiments, treating the primary mitochondrial myopathy in a human comprises decreasing pain. In some embodiments, treating the primary mitochondrial myopathy in a human comprises decreasing muscle pain. In some embodiments, treating the primary mitochondrial myopathy in a human comprises decreasing fatigue. In some embodiments, treating the primary mitochondrial myopathy in a human comprises improving cognition. In some embodiments, treating the primary mitochondrial myopathy in a human comprises improving overall well-being. In some embodiments, treating the primary mitochondrial myopathy in a human comprises a reduction in myoglobinuria. In some embodiments, treating the primary mitochondrial myopathy in a human comprises reducing tachycardia. In some embodiments, treating the primary mitochondrial myopathy in a human comprises a reduction in rhabdomyolysis. In some embodiments, treating the primary mitochondrial myopathy in a human comprises a reduction in muscle contracture. In some embodiments, treating the primary mitochondrial myopathy in a human comprises reducing the severity of PMM muscle symptoms. In some embodiments, treating the primary mitochondrial myopathy in a human comprises reducing impairments in work and activities. In some embodiments, treating the primary mitochondrial myopathy in a human comprises increasing survival.

In some embodiments, improving the human's exercise tolerance comprises increasing the distance walked during a 6-minute walk test, increasing the distance walked during a 12 minute walk test, increasing stair climbing capacity, increasing the number of stands in a 30 second sit to stand test, decreasing the feeling of exhaustion during exercise, or a combination thereof. In some embodiments, improving the human's exercise tolerance comprises increasing the distance walked during a 6-minute walk test. In some embodiments, improving the human's exercise tolerance comprises increasing the distance walked during a 12 minute walk test. In some embodiments, improving the human's exercise tolerance comprises increasing stair climbing capacity. In some embodiments, improving the human's exercise tolerance comprises increasing the number of stands in a 30 second sit to stand test. In some embodiments, improving the human's exercise tolerance comprises decreasing the feeling of exhaustion during exercise.

In some embodiments, increasing the distance walked during a 12 minute walk test comprises an increase of at least about 10 meters, at least about 20 meters, at least about 30 meters, at least about 40 meters, at least about 50 meters, at least about 60 meters, at least about 70 meters, at least about 80 meters, at least about 90 meters, at least about 100 meters, at least about 125 meters, or more than about 125 meters as measured after about 2 weeks, about 4 weeks, about 6 weeks, about 8 weeks, about 10 weeks, about 12 weeks, about 14 weeks, about 16 weeks, about 18 weeks, about 20 weeks, about 24 weeks, about 26 weeks, about 52 weeks, or more than about 52 weeks of daily administration of Compound II.

In some embodiments, decreasing fatigue in the human comprises decreases in the Modified Fatigue Impact Scale (MFIS) as measured after about 2 weeks, about 4 weeks, about 6 weeks, about 8 weeks, about 10 weeks, about 12 weeks, about 14 weeks, about 16 weeks, about 18 weeks, about 20 weeks, about 24 weeks, about 26 weeks, about 52 weeks, or more than about 52 weeks of daily administration of Compound II. In some embodiments, decreases in the Modified Fatigue Impact Scale (MFIS) comprises decreases in physical functioning subscores of the MFIS. In some embodiments, decreases in the Modified Fatigue Impact Scale (MFIS) comprises decreases in cognitive functioning subscores of the MFIS. In some embodiments, decreases in the Modified Fatigue Impact Scale (MFIS) comprises decreases psychosocial functioning subscores of the MFIS.

In some embodiments, decreasing pain comprises decreases in the brief pain inventory (BPI) scores by 1, 2, 3, 4, 5, or more than 5 as measured after about 2 weeks, about 4 weeks, about 6 weeks, about 8 weeks, about 10 weeks, about 12 weeks, about 14 weeks, about 16 weeks, about 18 weeks, about 20 weeks, about 24 weeks, about 26 weeks, about 52 weeks, or more than about 52 weeks of daily administration of Compound II.

In some embodiments, improving overall well-being comprises improving physical functioning, improving limitations due to physical health problems, improving limitations due to personal or emotional problems, improving emotional well-being, improving social functioning, or improving perceived change in health, or combinations thereof, as measured with the 36-Item Health Survey. In some embodiments, improving overall well-being comprises reductions in the 36-Item Health Survey scoring as measured as measured after about 2 weeks, about 4 weeks, about 6 weeks, about 8 weeks, about 10 weeks, about 12 weeks, about 14 weeks, about 16 weeks, about 18 weeks, about 20 weeks, about 24 weeks, about 26 weeks, about 52 weeks, or more than about 52 weeks of daily administration of Compound II.

In some embodiments, reducing the severity of PMM muscle symptoms comprises Patient Global Impression of Change (PGIC) scores by 1, 2, 3, 4, or more than 4 as measured after about 2 weeks, about 4 weeks, about 6 weeks, about 8 weeks, about 10 weeks, about 12 weeks, about 14 weeks, about 16 weeks, about 18 weeks, about 20 weeks, about 24 weeks, about 26 weeks, about 52 weeks, or more than about 52 weeks of daily administration of Compound II.

In some embodiments, reducing impairments in work and activities measure comprises reductions in Work Productivity and Activity Impairment Questionnaire: Specific Health Problem (WPAI.SHP) scores by at least 10% points, by at least 15% points, by at least 20% points, by at least 30% points, by at least 35% points, by at least 40% points, by at least 45% points, by at least 50% points, or more than 50% points as measured after about 2 weeks, about 4 weeks, about 6 weeks, about 8 weeks, about 10 weeks, about 12 weeks, about 14 weeks, about 16 weeks, about 18 weeks, about 20 weeks, about 24 weeks, about 26 weeks, about 52 weeks, or more than about 52 weeks of daily administration of Compound II.

Combination Treatments

In certain instances, it is appropriate to administer a PPARδ agonist compound disclosed herein (e.g., Compound I), or a pharmaceutically acceptable salt thereof (e.g., Compound II), in combination with one or more other therapeutic agents.

In one embodiment, the therapeutic effectiveness of a PPARδ agonist compound disclosed herein (e.g., Compound I), or a pharmaceutically acceptable salt thereof (e.g., Compound II), is enhanced by administration of an adjuvant (i.e., by itself the adjuvant has minimal therapeutic benefit, but in combination with another therapeutic agent, the overall therapeutic benefit to the patient is enhanced). Or, in some embodiments, the benefit experienced by a patient is increased by administering a PPARδ agonist compound disclosed herein (e.g., Compound I), or a pharmaceutically acceptable salt thereof (e.g., Compound II), with another agent (which also includes a therapeutic regimen) that also has therapeutic benefit.

In one specific embodiment, a PPARδ agonist compound disclosed herein (e.g., Compound I), or a pharmaceutically acceptable salt thereof (e.g., Compound II), is co-administered with a second therapeutic agent, wherein a PPARδ agonist compound disclosed herein (e.g., Compound I), or a pharmaceutically acceptable salt thereof (e.g., Compound II), and the second therapeutic agent modulate different aspects of the disease, disorder or condition being treated, thereby providing a greater overall benefit than administration of either therapeutic agent alone.

In any case, regardless of the disease, disorder or condition being treated, the overall benefit experienced by the patient is simply additive of the two therapeutic agents or the patient experiences a synergistic benefit.

For combination therapies described herein, dosages of the co-administered compounds vary depending on the type of co-drug employed, on the specific drug employed, on the disease or condition being treated and so forth. In additional embodiments, when co-administered with one or more other therapeutic agents, a PPARδ agonist compound disclosed herein (e.g., Compound I), or a pharmaceutically acceptable salt thereof (e.g., Compound II), is administered either simultaneously with the one or more other therapeutic agents, or sequentially.

In combination therapies, the multiple therapeutic agents (one of which is a PPARδ agonist compound disclosed herein (e.g., Compound I), or a pharmaceutically acceptable salt thereof (e.g., Compound II)) are administered in any order or even simultaneously. If administration is simultaneous, the multiple therapeutic agents are, by way of example only, provided in a single, unified form, or in multiple forms (e.g., as a single pill or as two separate pills).

Exemplary Agents for Use in Combination Therapy

In some embodiments, a PPARδ agonist compound disclosed herein (e.g., Compound I), or a pharmaceutically acceptable salt thereof (e.g., Compound II), is administered in combination with ubiquinol, ubiquinone, niacin, riboflavin, creatine, L-carnitine, acetyl-L-carnitine, biotin, thiamine, pantothenic acid, pyridoxine, alpha-lipoic acid, n-heptanoic acid, CoQ10, vitamin E, vitamin C, methylcobalamin, folinic acid, acid, resveratrol, N-acetyl-L-cysteine (NAC), zinc, folinic acid/leucovorin calcium, resveratrol, acipimox, elamipretide, cysteamine, succinate, NAD agonists, vatiquinone (EPI-743), omaveloxolone (RTA-408), nicotinic acid, nicotinamide, elamipretide, KL133, KH176, or a combination thereof.

In some embodiments, a PPARδ agonist compound disclosed herein (e.g., Compound I), or a pharmaceutically acceptable salt thereof (e.g., Compound II), is administered in combination with succinic acid, or salt thereof, or trisuccinylglycerol, or salt thereof. In some embodiments, a PPARδ agonist compound disclosed herein (e.g., Compound I), or a pharmaceutically acceptable salt thereof (e.g., Compound II), is administered in combination with a compound described in International PCT publication no. WO 2017/184583.

In some embodiments, Compound I, or a pharmaceutically acceptable salt thereof (e.g., Compound II), is co-administered with an antioxidant.

In some embodiments, a PPARδ agonist compound disclosed herein (e.g., Compound I), or a pharmaceutically acceptable salt thereof (e.g., Compound II), is co-administered with an odd-chain fatty acid, odd-chain fatty ketone, L-carnitine, or combinations thereof.

In some embodiments, a PPARδ agonist compound disclosed herein (e.g., Compound I), or a pharmaceutically acceptable salt thereof (e.g., Compound II), is co-administered with triheptanoin, n-heptanoic acid, a triglyceride, or a salt or thereof, or combinations thereof.

In some embodiments, a PPARδ agonist compound disclosed herein (e.g., Compound I), or a pharmaceutically acceptable salt thereof (e.g., Compound II), is administered in combination with a Nicotinamide Adenine Dinucleotide (NAD+) pathway modulator. NAD plays many important roles within cells, including serving as an oxidizing agent in oxidative phosphorylation which generates ATP from ADP. Increasing cellular concentrations of NAD will enhance the oxidative capacity within mitochondria, thereby increasing nutrient oxidation and boost energy supply, which is a primary role of mitochondria. In some embodiments, the NAD+ modulator targets Poly ADP Ribose Polymerase (PARP), Aminocarboxymuconate Semialdehyde Decarboxylase (ACMSD) and N'-Nicotinamide Methyltransferase (NNMT).

In some embodiments, a PPARδ agonist compound disclosed herein (e.g., Compound I), or a pharmaceutically acceptable salt thereof (e.g., Compound II), is administered in combination with a creatine supplement, a vitamin B-6 supplement, sucrose, or a combination thereof. In some embodiments, a PPARδ agonist compound disclosed herein (e.g., Compound I), or a pharmaceutically acceptable salt thereof (e.g., Compound II), is administered in combination with an ACE inhibitor. In some embodiments, the ACE inhibitor comprises benazepril (Lotensin), Captopril, Enalapril (Vasotec), Fosinopril, Lisinopril (Prinivil, Zestril), Moexipril, Perindopril, Quinapril (Accupril), Ramipril (Altace), Trandolapril. In some embodiments, the ACE inhibitor comprises ramipril.

EXAMPLES

The following examples are provided for illustrative purposes only and not to limit the scope of the claims provided herein.

Example 1: Preparation of (E)-2-(4-((3-(4-fluorophenyl)-3-(4-(3-morpholinoprop-1-yn-1-yl)phenyl) allyl)oxy)-2-methylphenoxy)acetic acid (Compound I)

The preparation of Compound I has been previously described (see, WO 2007/071766, U.S. Pat. Nos. 7,943,613, 8,362,016, 8,551,993, 9,663,481, 9,855,274, WO 2015/035171, U.S. Pat. Nos. 9,487,493, 9,968,613, each of which is incorporated by reference in its entirety).

Example 2: Preparation of sodium (E)-2-(4-((3-(4-fluorophenyl)-3-(4-(3-morpholinoprop-1-yn-1-yl) phenyl)allyl)oxy)-2-methylphenoxy)acetate (Compound II)

To a 72 L open head round bottom flask containing a solution of compound I (1089.4 g, 2.113 mol) in ethyl acetate (43 L) was added a solution of sodium hydroxide (82.0 g, 2.050 mol) in water (675 ml). The solution was heated to 40° C. and was filtered. The filtrates were concentrated under reduced pressure at 40° C. until 35 L of solvent were removed. The solution was stirred at 20° C. for 1 hr and was filtered. The filter cake was washed with ethyl acetate (4 L) and air-dried on the filter for 24 hrs followed by drying in a vacuum oven at 50° C. for 36 hrs to afford 1079.6 g of a beige solid. This solid was suspended in ethanol (22 L) in a 72L rbf. The solution was stirred 3 hrs at room temp and then was filtered. The filter cake was air-dried 2 hrs and then was slurried with ethanol (2×4 L) followed by filtration. The filter cake was air-dried 24 hrs and then transferred to a vacuum oven at 50° C. for 24 hrs to afford Compound II (937.2 g. 82.5%) as a beige solid. This reaction was run twice in this manner to yield: 905.7 g (Sample #1, HPLC=99.85%, KF=0.65%, Acetic acid=19 ppm) and 968.7 g (Sample #2, HPLC=99.87%, KF=0.53%, Acetic acid=44 ppm). Total=1874.4 g (82.5% yield).

The two samples above were blended in a rotovap flask at room temperature for 1 hr to yield 1859.0 g of Compound II. The XRPD analysis of the collected solid was consistent with Compound II, Form 1. $^1$H-NMR was consistent with the structure.

Example 2-1: Preparation of Form 1 of Compound II

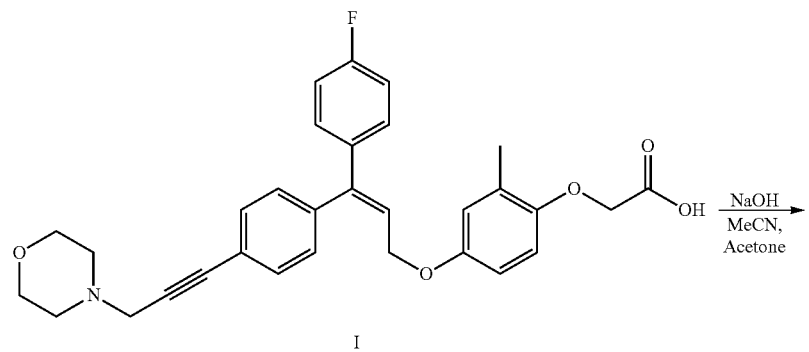

I

-continued

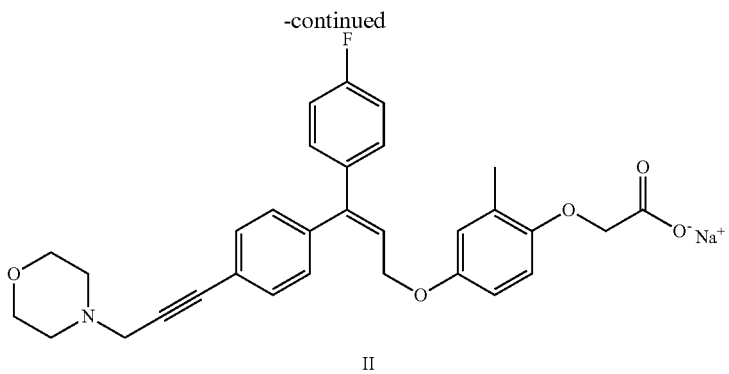

II

A solution of NaOH (1.1 eq) in water (1 ml/g) was added to Compound I in acetone (9 ml/g) at 50° C. and the mixture was stirred for 1-3 h to obtain a solution which was polish filtered. This solution was added to acetonitrile (12.5 ml/g), which was seeded with 4.2% w/w of Compound II (Form 1), at 35° C. over no less than 1.5 h. The resulting slurry was stirred at 35° C. for 1-3 h, cooled to 5° C., filtered under $N_2$, and twice washed with 2 ml/g cold acetone under a stream of $N_2$. The product was then dried at 45-55° C. for 15-20 h. $^1$H-NMR (30 MHz, 1:1 CDCl$_3$/DMSO-d6): δ 7.45 (d, 2H), 7.22 (m, 2H), 7.15 (d, 2H), 7.04 (m, 2H), 6.65 (d, 1H), 6.59 (d, 1H), 6.50 (dd, 1H), 6.24 (t, 1H), 4.44 (d, 2H), 4.18 (s, 2H), 3.67 (m, 4H), 3.50 (s, 2H), 2.57 (m, 4H), 2.16 (s, 3H). The XRPD analysis of the collected solid was consistent with Compound II, Form 1.

Example 3: Preparation of Amorphous Compound II from Crystalline Form 1 of Compound II Crystalline Form 1 of Compound II (500 mg) was dissolved in tBuOH/H$_2$O (1:1; 5.0 mL, 10 vol) at RT and filtered through a 0.45 m syringe tip filter and transferred to a clean 100 ml RBF. The solution was frozen in a cardice-acetone bath and dried under vacuum overnight. The resulting solid was analyzed by XRPD, $^1$H-NMR, DSC, TGA, KF and HPLC. Data was consistent with the amorphous material.

One sample was retained for analysis whilst additional samples were used as input to further polymorph screening.

Example 4: Preparation of Crystalline Hydrate Form 2 of Compound II from Crystalline Form 1 of Compound II Crystalline Form 1 of Compound II (4 g) was placed in a crystallization dish and stored in a stability chamber at 25° C./97% RH. XRPD analysis was regularly performed to verify the conversion to Form 2. Complete conversion was observed after 4 weeks at 25° C./97% RH.

The XRPD pattern was consistent with Form 2. The $^1$H-NMR spectrum was consistent with the proposed structure.

Example 5: Preparation of Crystalline Acetone Solvate Form 5 of Compound II from Crystalline Form 1 of Compound II Crystalline Form 1 of Compound II (25 mg) was weighed into HPLC vials and solvent was added (500p). The suspensions were stirred for 1 hr at 35° C. before being analyzed by XRPD. For XRPD analysis, two drops of suspension were pipetted onto the sample holder using the 4-minute method.

Results of the solvent screen are found in the following table:

| Solvent | XRPD |
| --- | --- |
| Acetone | initially Form 5; reverts to Form 1 |
| ACN | Form 1 |
| Acetone:ACN (1:1) | initially Form 5; reverts to Form 1 |
| Acetone:Water (99:1) | initially Form 5; reverts to Form 1 |
| ACN:Water (99:1) | Form 1 |
| Acetone:ACN:Water (49.5:49.5:1) | initially Form 5; reverts to Form 1 |

The XRPD performed on the aliquots recovered from the solvent mixtures showed that aliquots analyzed from acetone, acetone:acetonitrile, acetone:water and acetone:acetonitrile:water presented Form 5 initially but converted to Form 1 by the end of the run. The XRPD performed on the aliquots recovered from acetonitrile and acetonitrile:water showed the material remained as Form 1.

These additional experiments on Form 1 indicate that Form 5 is an acetone solvate as it was only observed from acetone and acetone solvent mixtures. Slurries in acetonitrile showed that Form 1 remained unchanged. Moreover, it was found that the conversion of Form 5 to Form 1 is reversible under these conditions and that Form 5 is the most stable form in acetone solvent systems. Form 5 proved difficult to isolate and fully characterize.

Example 6: Preparation of Crystalline Tetrahydrofuran Solvate Form 4 of Compound II from Crystalline Form 1 of Compound II Crystalline Form 1 of Compound II (499.3 mg) was weighed into a 100 ml RBF with stir bar and THE (5 mL, 10 vol) was added at 60° C. The sample was allowed to stir (500 rpm) for 24 h after which time an aliquot was taken and analyzed by XRPD, showing Form 4 to have been produced. The material was then isolated using a Buchner funnel and left to dry under suction vacuum for about 45 mins. The sample was produced with a 70.8% yield, showed Form 4 by XRPD, and the $^1$H-NMR spectrum was consistent with the structure, showing 1.1 mol eq of THF.

Example 7: Preparation of Crystalline Pattern 9 of Compound II from Crystalline Form 2 of Compound II Crystalline Hydrate Form 2 of Compound II was portioned into two and half was placed in the vacuum oven at RT. After 24 h the sample was analyzed by XRPD. Some small differences between the XRPD pattern and the Form 2 reference were noted. After 4 days in the vacuum oven complete conversion was observed. The material showed Pattern 9 by XRPD and a purity of 99.7%. The $^1$H-NMR spectrum was consistent with the proposed structure and showed no residual solvent to be present.

Example 8: Polymorph Screen 1: Solvent Screen; Preparation of Additional Solid State Forms of Compound II Crystalline Form 1 of Compound II (20 mg) was added into HPLC vials with a stir bar. Each sample was treated with increasing amounts of solvent (100-200 μL, 5-10 vol) at 25° C. After each addition the sample was stirred for 20 min and observations recorded before further solvent additions. If complete dissolution was observed, no further additions of solvent were made. If dissolution was not observed in 100 vol solvent (2 mL), the temperature was raised to 40° C. and held for 30 min to encourage dissolution. Clear solutions obtained were placed in the fridge (5° C.) and suspensions were matured (40° C./5° C., 8 h/cycle) for 24 h. After 24 hours an aliquot was taken (filtered and dried under suction) and analyzed by XRPD.

Maturation and subsequent XRPD analysis of the suspensions showed either poorly crystalline materials or XRPD patterns which matched or were similar to Form 1. A single sample, 2-methyltetrahydrofuran, showed significant enough differences to Form 1 for a new crystalline form to be acknowledged. This was denoted as Form 3 and displayed an absence of several Form 1 peaks at low 2θ values, as well as some peak shifts at higher 2θ angles.

All remaining material (suspensions or solutions) was placed for evaporation to encourage solid formation.

The evaporation of all the samples resulted in solids which displayed either Form 1, either with or without some small additional peaks, or predominantly amorphous samples by XRPD. Two samples, 1,4-dioxane and tetrahydrofuran, displayed a new pattern by XRPD, denoted as Form 4.

Example 9: Polymorph Screen 2: Low Temperature Slurry; Preparation of Additional Solid State Forms of Compound II Amorphous Compound II was slurried in a selection of solvents (5, 10 or 20 vol as appropriate to maintain adequate stirring) at 5° C. for 24 h. The slurries were then analyzed by XRPD.

After 24 h at 5° C. a number of samples showed differences by XRPD; five samples (methyl isobutyl ketone, 1,4-dioxane, chloroform, tetrahydrofuran, and dichloromethane) displayed Form 4, with varying levels of crystallinity and a single sample (diethyl ether) showed a new pattern, similar to a combination of Form 1 and Form 4 and was denoted as Form 5. A number of samples were poorly crystalline and a pattern not able to be identified, and the remainder of the samples displayed Form 1 with varying degrees of crystallinity.

The slurries were left stirring at 5° C. and analyzed again after 4 days.

After an extended period (4 days) at 5° C. the XPRD analysis results were similar, with a few samples displaying an increased level of crystallinity. Two samples showed a change relative to the 24 h data: 2-methyltetrahydrofuran showed a more crystalline pattern than seen after 24 h, which was denoted as Pattern 5, and EtOAc/H$_2$O (97.3:2.7) showed a poorly crystalline material with some differences with respect to the known patterns.

Example 10: Polymorph Screen 3: Liquid Assisted Grinding; Preparation of Additional Solid State Forms of Compound II To the Amorphous Compound II, two small ball bearings were added along with the appropriate solvent (5 μL). The samples were subjected to mechanical stress using a Fritsch Planetary Mill (500 rpm, 2 h) and N-Methyl-2-Pyrrolidone the recovered materials analyzed by XRPD.

A number of samples (total of 10) remained amorphous or predominantly amorphous with a single small peak between 2.8-3.0° 2θ, after the grinding. Two samples, sample 14 (1,4-dioxane) and sample 16 (chloroform) solvents respectively, displayed Form 4 by XRPD. A further four samples also displayed differences by XRPD: samples 15 (toluene), 4 (methyl isobutyl ketone), 19 (2-methyltetrahydrofuran) and 24 (N-methyl-2-pyrrolidone). The latter three were identified as Form 3. The XRPD pattern obtained from sample 15 was denoted as Form 3. The remainder of the samples converted to Form 1 during the grinding.

Example 11: Polymorph Screen 4: High Temperature Slurry; Additional Solid State Forms of Compound II Appropriate solvent was added to Amorphous Compound 11(300 μL, 10 vol/150 μL, 5 vol) and slurried for 24 h at 60° C. Where necessary the samples were left at either 50° C. or RT to slurry (solvent dependent).

The slurry samples were analyzed after 24 h and showed predominantly Form 1 by XRPD, with varying degrees of crystallinity. Five samples, however, showed differences by XRPD: sample obtained from methyl isobutyl ketone was assigned as Form 3, sample obtained from methyl ethyl ketone was assigned as Form 5, sample obtained from 1,4-dioxane was assigned as pattern 6, sample obtained from tetrahydrofuran was assigned as Form 4, and sample obtained from 2-methyltetrahydrofuran was assigned as pattern 5 (poorly crystalline).

Example 12: Preparation of Crystalline Ethyl Acetate Solvate Pattern 8 of Compound II from Amorphous Compound II EtOAc/H$_2$O (97.3:2.7; 300 μL, 10 vol) was added to amorphous Compound II and placed in the fridge under stirring. A portion was taken and analyzed by XRPD after 24 h, and the slurry left stirring at 4° C. The sample was further analyzed after 48 h and 6 days.

At all time-points analyzed, the same pattern was observed by XRPD, however this was different to that targeted in this experiment. The new pattern was denoted as Pattern 8.

Example 13: Preparation of Crystalline 2-Methyltetrahydrofuran Solvate Form 3 of Compound II from Crystalline Form 1 of Compound II Crystalline Form 1 of Compound II (506.8 mg) was weighed into a 100 ml RBF with stirrer bar and 2-methyltetrahydrofuran solvent (5 μL, 10 vol) added at 60° C. The sample was left to stir (500 rpm) for 3 days total, with an aliquot taken after 24 h and analyzed by XRPD. This showed that Pattern 5 had not been obtained and the sample was left for a prolonged duration.

After a further 2 days a second aliquot was taken and XPRD analysis indicated Form 3 to have formed. Additional 2-methyltetrahydrofuran (5 µL, 10 vol) was added and the sample cooled to 5° C. and left to stir over the weekend. The sample was filtered using a Büchner funnel and dried under suction vacuum for 15 min.

The aliquots of the attempted scale up of Pattern 5 analyzed by XRPD displayed Form 3 during the preparation at high temperature. Upon cooling, the sample also displayed From 3. This XRPD pattern persisted upon isolation. The sample was prepared with a yield of 84%. The $^1$H-NMR spectrum was consistent with the proposed structure and indicated 0.17 mol eq residual 2-methyltetrahydrofuran to be present.

Example 14: Thermodynamic Stability and Preparation of Crystalline Pattern 12 of Compound II Competitive slurries aiming to determine the order of stability between Form 1 and Form 2 were performed in a range of water activities (0.4-0.8).

Crystalline Form 1 (2 g) and Crystalline Hydrate Form 2 (2 g) were lightly ground together using a mortar and pestle and then mixed using a roller mixer for approximately 2 hours. An XRPD was collected on this sample.

Saturated solutions at 5° C./25° C. were prepared by suspending the mixed sample (200 mg) in 4 ml of the selected solvent and saturated solutions were prepared at 50° C. by suspending the mixed sample (100 mg) in 1 ml of the selected solvent. The saturated solutions were left stirring for 3 hrs at 25° C. and 50° C. The saturated solutions at 25° C. were filtered and split into solutions at 5° C. and 25° C. The mixed sample (50 mg) was added to the filtered solutions. Two control samples of Form 2 (50 mg) were prepared in 1 ml of acetone:water (99:1) and EtOH:water (95:5) and left stirring at 5° C., 25° C. and 50° C.

The samples were monitored at three different temperatures in a range of different water activities. Form 1 was present in most cases with no evidence of Form 2. From acetone and acetone:water (99:1) only Form 1 was observed. Form 5 peaks were observed in mixture with Form 1 for the slurry in EtOAc:Water (99:1). Form 4 was observed from the samples analyzed from THF:Water (98:2). Only Form 1 was observed from EtOH:Water (95:5) and IPA:Water (94:6).

Finally, a new pattern was identified from ACN:Water (93:7), denoted as Pattern 12. The material was later isolated by filtration and re-analyzed by XRPD. The sample maintained the same XRPD pattern, Pattern 12.

Example 15. X-Ray Powder Diffraction (XRPD)

Although the following diffractometers were used, other types of diffractometers could be used. Furthermore, other wavelengths could be used and converted to the Cu Kα. In some embodiments, Synchrotron Radiation X-Ray Powder Diffraction (SR-XRPD) can be used to characterize the crystalline forms.

"Characteristic peaks", to the extent they exist, are a subset of observed peaks and are used to differentiate one crystalline polymorph from another crystalline polymorph (polymorphs being crystalline forms having the same chemical composition). Characteristic peaks are determined by evaluating which observed peaks, if any, are present in one crystalline polymorph of a compound against all other known crystalline polymorphs of that compound to within ±0.2°2-Theta. The term "about" when used to describe an XRPD peak means±0.2°2-Theta.

XX.1 Bruker AXS C2 GADDS

XRPD diffractograms were collected on a Bruker AXS C2 GADDS diffractometer using Cu Kα radiation (40 kV, 40 mA), an automated XYZ stage, a laser video microscope for auto-sample positioning and a Våntec-500 2-dimensional area detector. X-ray optics consists of a single Göbel multilayer mirror coupled with a pinhole collimator of 0.3 mm.

The beam divergence, i.e. the effective size of the X-ray beam on the sample, was approximately 4 mm. A θ-θ continuous scan mode was employed with a sample-detector distance of 20 cm which gives an effective 2θ range of 1.5°-32.5°. Typically, the sample was exposed to the X-ray beam for 120 seconds. The software used for data collection and analysis was GADDS for Win7/XP and Diffrac Plus EVA respectively.

Samples run under ambient conditions (post VAC-XRPD) were analyzed as prepared for the vacuum experiment, using the sample retained within the Anton Parr metal recessed holder.

XX.2 Bruker AXS D8 Advance

XRPD diffractograms were collected on a Bruker D8 diffractometer using Cu Kα radiation (40 kV, 40 mA) and a θ-2θ goniometer fitted with a Ge monochromator. The incident beam passes through a 2.0 mm divergence slit followed by a 0.2 mm antiscatter slit and knife edge. The diffracted beam passes through an 8.0 mm receiving slit with 2.5° Soller slits followed by the Lynxeye Detector. The software used for data collection and analysis was Diffrac Plus XRD Commander and Diffrac Plus EVA respectively.

Samples were run under ambient conditions as flat plate specimens. The sample was prepared on a polished, zero-background (510) silicon wafer by gently pressing onto the flat surface or packed into a cut cavity. The sample was rotated in its own plane.

The details of the standard Pharmorphix data collection method are:
Angular range: 2 to 42° 2θ
Step size: 0.05° 2θ
Collection time: 0.5 s/step (total collection time: 6.40 min)

XX.3 PANalytical Empyrean

XRPD diffractograms were collected on a PANalytical Empyrean diffractometer using Cu Kα radiation (45 kV, 40 mA) in transmission geometry. A 0.5° slit, 4 mm mask and 0.04 rad Soller slits with a focusing mirror were used on the incident beam. A PIXcel3D detector, placed on the diffracted beam, was fitted with a receiving slit and 0.04 rad Soller slits. The software used for data collection was X'Pert Data Collector using X'Pert Operator Interface. The data were analyzed and presented using Diffrac Plus EVA or HighScore Plus.

Samples were prepared and analyzed in either a metal or Millipore 96 well-plate in transmission mode. X-ray transparent film was used between the metal sheets on the metal well-plate and powders (approximately 1-2 mg) were used as received. The Millipore plate was used to isolate and analyze solids from suspensions by adding a small amount of suspension directly to the plate before filtration under a light vacuum.

The scan mode for the metal plate used the gonio scan axis, whereas a 2θ scan was utilized for the Millipore plate.

The details of the standard screening data collection method are:
  Angular range: 2.5 to 32.0° 2θ
  Step size: 0.0130° 2θ
  Collection time: 12.75 s/step (total collection time of 2.07 min)

Non-Ambient Conditions

XRPD diffractograms were collected on a PANalytical Empyrean diffractometer using Cu Kα radiation (45 kV, 40 mA) in reflection geometry. The instrument is fitted with an Anton Paar CHC plus+ stage fitted with graphite/Kapton windows and equipped with air cooling/and coupled with a proUmid MHG32 Modular Humidity Generator, or a low vacuum pump system using an Edwards RV3 pump. A programmable divergence slit (in automatic mode), with a 10 mm fixed incident beam mask, Ni filter and 0.04 rad Soller slits were used on the incident beam. A PIXcel3D detector, placed on the diffracted beam, was fitted with a programmable antiscatter slit (in automatic mode) and 0.04 rad Soller slits.

The software used for data collection was X'Pert Data Collector and the data analyzed and presented using Diffrac Plus EVA or Highscore Plus.

For vacuum (VAC-XRPD) experiments the sample was prepared and analyzed in an Anton Paar chromed sample holder. A reference XPRD pattern was collected before applying the vacuum. Measurements were taken every 5 min for 1.5 h then at 20 min intervals for 2 h, followed by hourly sampling for 3 h. The sample was left under vacuum for 72 h, a final measurement taken and then the vacuum released. Further measurements (post vac) were collected every 10 mins for 3 h, exposing the sample to ambient conditions. The measurement parameters are as per the standard screening data collection method (detailed above).

For variable temperature (VT-XRPD) experiments the samples were prepared and analyzed in an Anton Paar chromed sample holder. A heating/cooling rate of 10° C./min was used with a 2 min isothermal hold before the measurement started. The measurement parameters are as per the standard screening data collection method (detailed above). Measurements were taken at the following temperatures:

| Target Temperature (° C.) |
| --- |
| 25 |
| 75 |
| 80 |
| 90 |
| 100 |
| 110 |
| 120 |
| 130 |
| 140 |
| 145 |
| 25 |

For variable humidity (VH-XRPD, Form 1) experiments the sample was prepared and analyzed in an Anton Paar chromed sample holder. The measurement parameters are as per the standard screening data collection method (detailed above). Measurements were taken at the following humidities:

| Target RH/% | Hold Duration |
| --- | --- |
| 40 | 1 h |
| 60 | 1 h |
| 80 | 1 h |
| 90 | 12.5 h |
| 80 | 2 h |
| 60 | 2 h |
| 40 | 2 h |
| 20 | 2 h |
| 10 | 12.5 h |
| 20 | 2 h |
| 40 | 2 h |

Data collection occurs at start and end of each section, with 1 h sampling interval.

Characterization of Solid State Forms and Patterns of Compound II

The X-Ray powder diffraction pattern for crystalline Form 1 of Compound II is displayed in FIG. 1. The X-Ray powder diffraction pattern for crystalline hydrate Form 2 of Compound II is displayed in FIG. 6. The X-Ray powder diffraction pattern for crystalline 2-methyltetrahydrofuran solvate Form 3 of Compound II is displayed in FIG. 9. The X-Ray powder diffraction pattern for crystalline tetrahydrofuran solvate Form 4 of Compound II is displayed in FIG. 12. The X-Ray powder diffraction pattern for crystalline acetone solvate Form 5 of Compound II is displayed in FIG. 15. The X-Ray powder diffraction pattern for crystalline hydrate Pattern 9 of Compound II is displayed in FIG. 18. The X-Ray powder diffraction pattern for amorphous Compound II is displayed in FIG. 21. The X-Ray powder diffraction pattern for pattern 12 of Compound II is displayed in FIG. 24.

Characterization of Crystalline Form 1 of Compound II

The X-Ray powder diffraction pattern for crystalline Form 1 of Compound II is displayed in FIG. 1. Characteristic peaks include the peaks listed in the following table:

| Angle 2-Theta (°) | Rel. Intensity (%) |
| --- | --- |
| 2.8 | 100.0 |
| 6.7 | 17.0 |
| 7.2 | 22.6 |
| 13.4 | 24.2 |
| 17.8 | 23.5 |
| 19.7 | 24.6 |
| 19.9 | 25.6 |
| 20.6 | 22.9 |
| 21.8 | 23.7 |

Characterization of Crystalline Hydrate Form 2 of Compound II

The X-Ray powder diffraction pattern for crystalline hydrate Form 2 of Compound II is displayed in FIG. 6. Characteristic peaks include the peaks listed in the following table:

| Angle 2-Theta (°) | Rel. Intensity (%) |
| --- | --- |
| 4.5 | 100.0 |
| 13.8 | 42.5 |
| 17.6 | 65.3 |
| 18.3 | 48.8 |
| 19.0 | 64.2 |
| 19.6 | 55.2 |
| 19.9 | 68.4 |
| 20.5 | 62.9 |
| 23.0 | 52.5 |

Characterization of the Crystalline Tetrahydrofuran Solvate Form 4 of Compound II The X-Ray powder diffraction pattern for crystalline tetrahydrofuran solvate Form 4 of Compound II is displayed in FIG. 12. Characteristic peaks include the peaks listed in the following table:

| Angle 2-Theta (°) | Rel. Intensity (%) |
| --- | --- |
| 3.3 | 100.0 |
| 5.7 | 16.3 |
| 11.9 | 14.4 |
| 19.8 | 15.2 |
| 20.1 | 42.4 |
| 20.7 | 23.2 |
| 22.9 | 17.1 |
| 23.1 | 15.6 |

Crystalline tetrahydrofuran solvate Form 4 of sodium (E)-2-(4-((3-(4-fluorophenyl)-3-(4-(3-morpholinoprop-1-yn-1-yl)phenyl)allyl)oxy)-2-methylphenoxy)acetate has an unchanged XRPD after heating to 110° C.

Characterization of Crystalline Acetone Solvate Form 5 of Compound II

The X-Ray powder diffraction pattern for crystalline acetone solvate Form 5 of Compound II is displayed in FIG. 15. Characteristic peaks include the peaks listed in the following table:

| Angle 2-Theta (°) | Rel. Intensity (%) |
| --- | --- |
| 2.8 | 100.0 |
| 8.3 | 15.4 |
| 8.7 | 11.3 |
| 13.1 | 16.1 |
| 19.4 | 21.9 |
| 20.2 | 12.2 |
| 21.3 | 16.6 |
| 24.6 | 14.6 |

Example 16: Differential Scanning Calorimetry (DSC)

XX.1 TA Instruments Q2000

DSC data were collected on a TA Instruments Q2000 equipped with a 50 position auto-sampler. Typically, 0.5-3 mg of each sample, in a pin-holed aluminum pan, was heated at 10° C./min from 25° C. to 275° C. A purge of dry nitrogen at 50 ml/min was maintained over the sample.

Modulated temperature DSC was carried out using an underlying heating rate of 2° C./min and temperature modulation parameters of 0.626° C. (amplitude) every 60 seconds (period).

The instrument control software was Advantage for Q Series and Thermal Advantage and the data were analyzed using Universal Analysis or TRIOS.

XX.2 TA Instruments Discovery DSC

DSC data were collected on a TA Instruments Discovery DSC equipped with a 50 position auto-sampler. Typically, 0.5-2 mg of each sample, in a pin-holed aluminum pan, was heated at 10° C./min from 25° C. to 280° C. A purge of dry nitrogen at 50 ml/min was maintained over the sample.

The instrument control software was TRIOS and the data were analyzed using TRIOS or Universal Analysis.

The DSC thermogram for crystalline Form 1 of Compound II is displayed in FIG. 2. The DSC thermogram for crystalline hydrate Form 2 of Compound II is displayed in FIG. 7. The DSC thermogram for crystalline 2-methyltetrahydrofuran solvate Form 3 of Compound II is displayed in FIG. 10. The DSC thermogram for crystalline tetrahydrofuran solvate Form 4 of Compound II is displayed in FIG. 13. The DSC thermogram for crystalline acetone solvate Form 5 of Compound II is displayed in FIG. 16. The DSC thermogram for crystalline hydrate Pattern 9 of Compound II is displayed in FIG. 19. The DSC thermogram for amorphous Compound II is displayed in FIG. 22. The DSC thermogram for crystalline Pattern 12 of Compound II is displayed in FIG. 25.

Differential Scanning Calorimetry (DSC) thermogram endotherms for selected forms and patterns are as described in the following table:

| Solid State Form | DSC Endotherms |
| --- | --- |
| amorphous | broad endotherm with onset at 43.1° C. and peak at about 60.3° C., broad exotherm with onset at 107.0° C. and peak at 112.9° C.; and endotherm with onset at 125.0° C. peak a 130.4° C. |
| Form 1 | onset at about 179.5° C. and peak at about 181.6° C. |
| Form 2 | six endothermic events: onset at about 44.1° C. and peak at about 72.4° C.; peak at about 92.4° C.; onset at about 107.0° C. and peak at about 118.5° C.; onset at about 127.6° C. and peak at about 130.0° C.; onset at about 146.9° C. and peak at about 149.9° C.; and onset at about 179.5° C. and peak at about 181.1° C. |
| Form 3 | three endothermic events: onset at about 58.7° C. and peak at about 73.2° C.; onset at about 114.5° C. and peak at about 136.2° C.; and onset at about 172.5° C. and peak at about 178.6° C. |
| Form 4 | two endothermic events: onset at about 111.7° C. and peak at about 114.5° C. with a broad shoulder starting at about 70° C.; and onset at about 142.5° C. and peak at about 147.2° C. with a broad shoulder starting at about 130.6° C. |
| Form 5 | two endothermic events having: an onset at 75.8° C. and two peaks at about 85.8° C. and 97.2° C.; and onset at 180.4° C. and a peak at 182.2 |
| Pattern 9 | three endothermic events: onset at about 38.5° C. and two peaks at about 71.5° C. and 94.1° C.; onset at about 107.1° C. and two peaks at about 118.0° C. and 130.0° C. and onset at about 146.8° C. and peak at about 150.0° C. |
| Pattern 5 | four endothermic events: onset at about 50.7° C. and two peaks at about 54.6° C. and 60.1° C.; onset at about 125.4° C. and peak at about 130.4° C.; onset at about 142.7° C. and peak at about 146.2° C.; and onset at about 172.4° C. and peak at about 181.0° C. |
| Pattern 6 | three endothermic events: onset at about 88.0° C. and two peaks at about 97.7° C. and 105.5° C.; onset at about 120.3° C. and four peaks at about 125.1° C., 132.4° C., 134.7° C., and 144.2° C.; and onset at about 176.5° C. and peak at about 180.3° C. |

| Solid State Form | DSC Endotherms |
|---|---|
| Pattern 12 | five endothermic events: onset at about 54.7° C. and peak at about 81.5° C.; onset at about 90.1° C. and peak at about 92.2° C.; onset at about 115.9° C. and peak at about 124.6° C.; onset at about 131.3° C. and peak at about 132.5° C.; and onset at about 146.8° C. and peak at about 150.6° C. |

Example 17: Thermogravimetric Analysis (TGA)

XX.1 TA Instruments Q500

TGA data were collected on a TA Instruments Q500 TGA, equipped with a 16 position auto-sampler. Typically, 5-10 mg of each sample was loaded onto a pre-tared aluminum DSC pan and heated at 10° C./min from ambient temperature to 350° C. A nitrogen purge at 60 ml/min was maintained over the sample.

The instrument control software was Advantage for Q Series and Thermal Advantage and the data were analyzed using Universal Analysis.

The TGA pattern for crystalline Form 1 of Compound II is displayed in FIG. 3. The TGA pattern for crystalline hydrate Form 2 of Compound II is displayed in FIG. 8. The TGA pattern for crystalline 2-methyltetrahydrofuran solvate Form 3 of Compound II is displayed in FIG. 11. The TGA pattern for crystalline tetrahydrofuran solvate Form 4 of Compound II is displayed in FIG. 14. The TGA pattern for crystalline hydrate Pattern 9 of Compound II is displayed in FIG. 20. The TGA pattern for amorphous Compound II is displayed in FIG. 23.

Thermogravimetric Analysis (TGA) patterns for selected forms and patterns are as described in the following table:

| Solid State Form | TGA Pattern |
|---|---|
| amorphous | 3.7 % w/w loss from 25 to 150° C., and a degradation onset at about 260° C. |
| Form 1 | 0.1% w/w loss from 25 to 60° C. and degradation onset at about 250° C. |
| Form 2 | 17.2% w/w loss from 25 to 145° C., and degradation onset at about 275° C. |
| Form 3 | 2.3% w/w loss from 25 to 82° C., a further 3.8% w/w loss from 82° C. to 155° C., and a degradation onset at about 275° C. |
| Form 4 | 14.3 % w/w loss from 25 to 175° C., and degradation onset at about 285° C. |
| Pattern 9 | 8.6% w/w loss from 25 to 105° C., and degradation onset at about 270° C. |
| Pattern 5 | 1.0% w/w loss from 25 to 51° C., a further 7.6% w/w loss from 51 to 91° C., a further 4.7% w/w loss from 91° C. to 156° C., and a degradation onset at about 275° C. |
| Pattern 6 | 15.6% w/w loss from 25 to 187° C., and a degradation onset at about 260° C. |

Example 18: Gravimetric Vapor Sorption (GVS)

Sorption isotherms were obtained using a SMS DVS Intrinsic moisture sorption analyzer, controlled by DVS Intrinsic Control software. The sample temperature was maintained at 25° C. by the instrument controls. The humidity was controlled by mixing streams of dry and wet nitrogen, with a total flow rate of 200 ml/min. The relative humidity was measured by a calibrated Rotronic probe (dynamic range of 1.0-100% RH), located near the sample. The weight change, (mass relaxation) of the sample as a function of % RH was constantly monitored by a microbalance (accuracy ±0.005 mg).

Typically, 5-30 mg of sample was placed in a tared mesh stainless steel basket under ambient conditions. The sample was loaded and unloaded at 40% RH and 25° C. (typical room conditions). A moisture sorption isotherm was performed as outlined below (2 scans per complete cycle). The standard isotherm was performed at 25° C. at 10% RH intervals over a 0-90% RH range. Typically, a double cycle (4 scans) was carried out. Data analysis was carried out within Microsoft Excel using the DVS Analysis Suite.

The method for SMS DVS Intrinsic experiments is outlined in the following table:

| Parameter | Value |
|---|---|
| Adsorption - Scan 1 (% RH) | 40-90 |
| Desorption, Adsorption - Scan 2 (% RH) | 90-0, 0-40 |
| Intervals (% RH) | 10 |
| Number of Scans | 4 |
| Flow rate (mL/min) | 200 |
| Temperature (° C.) | 25 |
| Stability (° C./min) | 0.2 |
| Sorption Time (hours) | 6 hour time out |
| Number of cycles | 2 |

Reversible water uptake for the crystalline forms and patterns as determined by Gravimetric Vapor Sorption (GVS) are as described in the following table:

| Solid State Form | Reversible Water Uptake between 0-90% RH |
|---|---|
| Form 1 | ~13.0% † |
| Form 2 | ~25% |
| Form 4 | ~23% |
| Form 5 | ~11% |
| Pattern 9 | ~27% |
| Form 3 | ~9.0% |

† GVS data for Form 1 can vary from batch to batch of synthesis

The samples were recovered after completion of the isotherm experiment at 90% RH and 25° C. and re-analyzed by XRPD. Results of the subsequent XRPD analysis are described in the following table:

| Solid State Form Before GVS | Solid State Form After GVS |
|---|---|
| Form 1 | Unchanged (Form 1) |
| Form 2 | Unchanged (Form 2) |
| Form 4 | Form 2 |
| Form 5 | Form 1 |
| Pattern 9 | Unchanged (Pattern 9) |
| Form 3 | Form 1 |

Example 19: Stability of Solid State Forms

Samples were assessed for stability under ambient or static storage conditions of 25° C./9700 RH and 40° C./75%

RH for 7 or 10 days. The samples were then re-analyzed by XRPD. Subsequent XRPD analysis results for the crystalline forms are described below:

| Solid State Form | 25° C./97% RH/7 days | 40° C./75% RH/7 days |
|---|---|---|
| Form 1 | Form 2 | Unchanged (Form 1) |
| Form 2 | Unchanged (Form 2) | Unchanged (Form 2) |
| Form 4 | Form 2 | Form 1 |
| Pattern 9 | some changes: similar to pattern 9 and Form 2 | some changes: similar to pattern 9 and Form 2 |
| Form 3 | — | Form 1 |

There was no change in the XRPD of the amorphous solid form under ambient storage conditions for 24 hours, 48 hours, 7 days, or 10 days. There was no change in the XRPD of the amorphous solid form under static storage of 40° C./75% RH for 10 days.

Example 20: High-Performance Liquid Chromatography (HPL) Methods

Purity analysis was performed on an Agilent UPl 100 series system (or equivalent) equipped with a diode array detector and using ChemStation software. Details of the methods used are provided below:

| 8 Minute Method | |
|---|---|
| Parameter | Value |
| Type of method | Reverse phase with gradient elution |
| Sample Preparation | 0.25 mg/mL in acetonitrile:water 1:1 |
| Column | Supelco Ascends Express C18, 100 × 4.6 mm, 2.7 µm |
| Column Temperature (° C.) | 25 |
| Injection (µL) | 5 |
| Wavelength, Bandwidth (nm) | 255, 90 |
| Flow Rate (mL/min) | 2 |
| Phase A | 0.1% TFA in water |
| Phase B | 0.085% TFA in acetonitrile |

| Timetable | Time (min) | % Phase A | % Phase B |
|---|---|---|---|
| | 0 | 95 | 5 |
| | 6 | 5 | 95 |
| | 6.2 | 95 | 5 |
| | 8 | 95 | 5 |

| 30 Minute Method | |
|---|---|
| Parameter | Value |
| Type of method | Reverse phase with gradient elution |
| Sample Preparation | 0.25 mg/mL in acetonitrile:water 1:1 |
| Column | Supelco Ascends Express C18, 100 × 4.6 mm, 2.7 µm |
| Column Temperature (° C.) | 25 |
| Injection (µL) | 5 |
| Wavelength, Bandwidth (nm) | 255, 90 |
| Flow Rate (mL/min) | 2 |
| Phase A | 0.1% TFA in water |
| Phase B | 0.085% TFA in acetonitrile |

| Timetable | Time (min) | % Phase A | % Phase B |
|---|---|---|---|
| | 0 | 95 | 5 |
| | 25 | 5 | 95 |
| | 25.2 | 95 | 5 |
| | 30 | 95 | 5 |

| 50 Minute Method | |
|---|---|
| Parameter | Value |
| Type of method | Reverse phase with gradient elution |
| Sample Preparation | 0.2 mg/mL in acetonitrile:water 1:1 |
| Column | Hichrom RPB C18, 250 × 4.6 mm, 5 µm |
| Column Temperature (° C.) | 35 |
| Injection (µL) | 20 |
| Wavelength, Bandwidth (nm): (detection) | 248 (4) |
| Wavelength, Bandwidth (nm): (reference) | 400 (100) |
| Flow Rate (mL/min) | 1.0 |
| Aqueous buffer | 0.1M Ammonium Dihydrogen Phosphate, pH 2.5 |
| Phase A | 60:40 (Aqueous buffer:ACN) |
| Phase B | 30:70 (Aqueous buffer:ACN) |

| Timetable | Time (min) | % Phase A | % Phase B |
|---|---|---|---|
| | 0.0 | 100.0 | 0.0 |
| | 10.0 | 100.0 | 0.0 |
| | 27.0 | 66.5 | 33.5 |

-continued

| | | |
|---|---|---|
| 39.0 | 0.0 | 100.0 |
| 40.0 | 100.0 | 0.0 |
| 50.0 | 100.0 | 0.0 |

Purity analysis of the different solid-state forms indicated >9900 purity of all forms. HPLC purity values are detailed in the table below:

| Solid State Form | HPLC Purity |
|---|---|
| amorphous | 99.5% (50 min method) |
| Form 1 | 99.6% (50 min method) |
| Form 2 | 99.3% (8 min method) |
| Form 3 | 99.5% (8 min method) |
| Form 4 | 99.6% (8 min method) |
| Pattern 9 | 99.7% (8 min method) |
| Pattern 5 | 99.6% (8 min method) |
| Pattern 6 | 99.1% (8 min method) |

Example 21: Karl Fisher (KF) Titration

The water content of each sample was measured on a Metrohm 874 Oven Sample Processor up to 150° C. with 851 Titrano Coulometer using Hydranal Coulomat AG oven reagent and nitrogen purge. Weighed solid samples were introduced into a sealed sample vial. Approximately 10 mg of sample was used per titration and duplicate determinations were made. An average of these results is presented unless otherwise stated. Data collection and analysis were performed using Tiamo software.

The KF analysis results for the crystalline forms are described in the following table:

| Solid State Form | KF |
|---|---|
| Form 1 | 0.7 wt % water (0.21 mol equiv) |
| Form 2 | 19.1 wt % water (150° C.) (7 mol equiv) |
| Pattern 9 | 1.7 wt %/2.3 wt % water (100° C.) (~0.6 mol equiv) |
| Form 3 | 0.5 wt % water (160° C.) (0.15 mol equiv) |
| amorphous | 3.0 wt % water (0.92 mol equiv) |

Example 22: Ion Chromatography

Data were collected on a Metrohm 930 Compact IC Flex with 858 Professional autosampler and 800 Dosino dosage unit monitor, using IC MagicNet software. Accurately weighed samples were prepared as stock solutions in a suitable solvent. Quantification was achieved by comparison with standard solutions of known concentration of the ion being analyzed. Analyzes were performed in duplicate and an average of the values is given unless otherwise stated.

| IC Method for Cation Chromatography | |
|---|---|
| Parameter | Value |
| Type of method | Cation exchange |
| Column | Metrosep C 4—250 (4.0 × 250 mm) |
| Column Temperature (° C.) | Ambient |
| Injection (μL) | Various |
| Detection | Conductivity detector |
| Flow Rate (mL/min) | 0.9 |
| Eluent | 1.7 mM Nitric Acid 0.7 mM Dipicolinic acid in a 5% acetone aqueous solution. |

| IC Method for Anion Chromatography | |
|---|---|
| Parameter | Value |
| Type of method | Anion exchange |
| Column | Metrosep A Supp 5—150 (4.0 × 150 mm) |
| Column Temperature (° C.) | Ambient |
| Injection (μL) | Various |
| Detection | Conductivity detector |
| Flow Rate (mL/min) | 0.7 |
| Eluent | 3.2 mM sodium carbonate, 1.0 mM sodium hydrogen carbonate in a 5% acetone aqueous solution. |

Ion chromatography of the crystalline Form 1 of Compound II indicated 1.1 mol equivalents of sodium (adjusted for water), with no other anions or cations present.

Ion chromatography of the crystalline 2-methyltetrahydrofuran solvate Form 3 of Compound II indicated 0.96 mol equivalents of sodium (adjusted for water), with no other anions or cations present.

Ion chromatography of the crystalline tetrahydrofuran solvate Form 4 of Compound II indicated 1.01 mol equivalents of sodium (adjusted for water), with no other anions or cations present.

Example 23: Fourier Transform Infrared (FTIR) Spectroscopy

Data were collected on a Perkin-Elmer Spectrum One fitted with a universal Attenuated Total Reflectance (ATR) sampling accessory from 4000-650 cm$^{-1}$ over 16 scans. The data were collected using Spectrum software and processed using ACD Spectrus Processor.

Characterization of Crystalline Form 1 of Compound II

The Fourier Transform Infrared (FTIR) spectrum for crystalline Form 1 of Compound II is shown in FIG. 4. Characteristic peaks include peaks at 810 cm$^{-1}$, 838 cm$^{-1}$, 1220 cm$^{-1}$, 1504 cm$^{-1}$, and 1612 cm$^{-1}$. Additional characteristic peaks are listed in the following table:

| Wavelength (cm$^{-1}$) | Rel. Intensity* |
|---|---|
| 798 | M |
| 810 | S |
| 838 | S |

-continued

| Wavelength (cm$^{-1}$) | Rel. Intensity* |
|---|---|
| 864 | M |
| 1009 | M |
| 1035 | M |
| 1043 | M |
| 1052 | M |
| 1115 | S |
| 1160 | M |
| 1220 | VS |
| 1236 | M |
| 1333 | M |
| 1413 | M |
| 1425 | M |
| 1504 | S |
| 1612 | VS |

*M = medium; S = strong; VS = very strong

Characterization of Crystalline Acetone Solvate Form 5 of Compound II

The Fourier Transform Infrared (FTIR) spectrum for crystalline acetone solvate Form 5 of Compound II is shown in FIG. 17. Characteristic peaks include peaks at 810 cm$^{-1}$, 838 cm$^{-1}$, 1220 cm$^{-1}$, 1504 cm$^{-1}$, and 1612 cm$^{-1}$. Additional characteristic peaks are listed below:

| Wavelength (cm$^{-1}$) | Rel. Intensity* |
|---|---|
| 798 | M |
| 810 | S |
| 838 | S |
| 864 | M |
| 1009 | M |
| 1042 | M |
| 1053 | M |
| 1116 | M |
| 1160 | M |
| 1220 | VS |
| 1236 | M |
| 1333 | M |
| 1412 | M |
| 1424 | M |
| 1504 | S |
| 1612 | VS |

*M = medium; S = strong; VS = very strong

Example 24: Raman Spectroscopy

Data were collected on a Renishaw inVia Qontor. Instrument control, data analysis and presentation software was WiRE.

Method: excitation source, $\lambda_{ex}$=785 nm laser, attenuated appropriately to avoid sample degradation
Raman shift range: 100-3200 cm$^{-1}$
Exposure time: 10 s
Accumulations: 1

Characterization of Crystalline Form 1 of Compound II

The Raman spectrum for crystalline Form 1 of Compound II is shown in FIG. 5. Characteristic peaks are listed in the following table:

| Wavelength (cm$^{-1}$) | Rel. Intensity* |
|---|---|
| 103 | M |
| 126 | M |
| 810 | M |
| 1158 | M |
| 1238 | M |
| 1604 | VS |
| 1629 | M |

*M = medium; S = strong; VS = very strong

Example 25: Single Crystal X-Ray Diffraction (SCXRD)

Preparation of Single Crystal

A crystal of Compound II (Form 1) was isolated from an aggregate of crystals obtained by evaporation from an EtOAc/H$_2$O (99:1 v/v %) solution. The approximate dimensions of the crystal were: 0.40×0.03×0.005 mm.

Collection and Characterization

Data were collected on a Rigaku Oxford Diffraction Supernova Dual Source, Cu at Zero, Atlas CCD diffractometer equipped with an Oxford Cryosystems Cobra cooling device. The data were collected using Cu Kα, radiation ($\lambda$=1.5418 Å) at a constant temperature with ω variable scan technique (2.807 to 50.989° θ). Additional collection and refinement parameters are outlined in Table 1, below.

Structures were solved and refined using the Bruker AXS SHELXTL suite or the OLEX$^2$ crystallographic software. Unless otherwise stated, hydrogen atoms attached to carbon were placed geometrically and allowed to refine with a riding isotropic displacement parameter. Hydrogen atoms attached to a heteroatom were located in a difference Fourier synthesis and were allowed to refine freely with an isotropic displacement parameter. A reference diffractogram for the crystal structure was generated in Mercury.

TABLE 1

Data collection and structure refinement for Compound II (Form 1)

| | |
|---|---|
| Diffractometer | SuperNova, Dual, Cu at zero, Atlas |
| Radiation source | SuperNova (Cu) X-ray Source, CuKα |
| Data collection method | omega scans |
| Theta range for data collection | 2.807 to 50.989° |
| Index ranges | −31 ≤ h ≤ 31, −6 ≤ k ≤ 5, −27 ≤ l ≤ 27 |
| Reflections collected | 28094 |
| Independent reflections | 5555 [R(int) = 0.1913] |
| Coverage of independent reflections | 58.4% |
| Variation in check reflections | n/a |
| Absorption correction | Multi-scan |
| Max. and min. transmission | 1.00000 and 0.42918 |
| Structure solution technique | Direct Methods |
| Structure solution program | SHELXTL (Sheldrick, 2013) |
| Refinement technique | Full-matrix least-squares on F$^2$ |
| Refinement program | SHELXL-2014/6 (Sheldrick, 2014) |
| Function minimised | Σ w(F$_o^2$ − F$_c^2$)$^2$ |

TABLE 1-continued

Data collection and structure refinement for Compound II (Form 1)

| | |
|---|---|
| Data/restraints/parameters | 5555/0/705 |
| Goodness-of-fit on $F^2$ | 1.007 |
| $\Delta/\sigma_{max}$ | 0.000 |
| Final R indices: | R1 = 0.0945, wR2 = 0.2099 |
| 2657 data; I > 2σ(I) | R1 = 0.1886, wR2 = 0.2771 |
| all data | |
| Weighting scheme | w = 1/[σ² ($F_o^2$) + 0.1224P)²] where P = ($F_o^2$ + 2$F_c^2$)/3 |
| Extinction coefficient | n/a |
| Largest diff peak and hole | 0.426 and −0.390 eÅ⁻³ |
| Refinement summary: | |
| Ordered Non-H atoms, XYZ | Freely refining |
| Ordered Non-H atoms, U | Anisotropic |
| H atoms (on carbon), XYZ | Idealized positions riding on attached atoms |
| H atoms (on carbon), U | Appropriate multiple of U(eq) for bonded atom |
| H atoms (on heteroatoms), XYZ | Freely refined |
| H atoms (on heteroatoms), U | Isotropic |
| Disordered atoms, OCC | No Disorder |
| Disordered atoms, XYZ | No Disorder |
| Disordered atoms, U | No Disorder |

The crystal structure of Compound II (Form 1) was determined at 100 K and a summary of the structural data can be found in Tables 2, 3, and 4. The X-ray data were collected up to 1.0 Å resolution, using exposures of 100 seconds per frame at the low θ-angle and 200 seconds per frame at the higher θ-angle. At certain crystal orientations, the diffraction pattern shows split and streaky reflections which reflects the overall crystal quality and could indicate potential twinning.

The crystals are monoclinic, space group P2/c and refined with a final R1 [I>2σ(I)] value of 9.45%. Platon ADDSYM analysis was performed and no additional space group was found. Moreover, the structure solution was also attempted in the more common P21/c space group, however, no satisfactory structure solution was found. Despite only low resolution data being collected for this crystal structure, the data was sufficient to successfully determine the crystal structure of Compound II (Form 1) in P2/c space group and confirm the atomic connectivity which is consistent with the molecular 2D representation. The asymmetric unit contains two fully ordered Compound I anions and two independent Na⁺ cations.

TABLE 2

Crystal Data of Compound II (Form 1) at 100 K

| Crystal System | Monoclinic |
|---|---|
| Space Group | P2/c |
| a (Å) | 31.581(3) |
| b (Å) | 6.1180(4) |
| c (Å) | 27.2046(18) |
| α | 90° |
| β | 94.447(7)° |
| γ | 90° |
| V (Å³) | 5240.4(7) |
| Z | 8 |
| Calculated Density (Mg/m³) | 1.363 |
| Absorption coefficient (mm⁻¹) | 0.937 |
| F(000) | 2256 |

TABLE 3

Fractional Atomic Coordinates for Compound II (Form 1) at 100 K

| | x/a | y/b | z/c |
|---|---|---|---|
| Na1A | 0.55177(12) | 0.7521(5) | 0.27685(13) |
| F1A | 0.11468(18) | 0.1067(9) | 0.5137(2) |
| O1A | 0.5084(2) | 1.6234(10) | 0.3364(2) |
| O2A | 0.4711(2) | 1.9101(10) | 0.3072(2) |
| O3A | 0.4420(2) | 1.4498(10) | 0.3786(2) |
| O4A | 0.3042(2) | 0.9658(10) | 0.4278(2) |
| O5A | −0.0492(2) | 0.8045(12) | 0.1069(3) |
| N1A | 0.0218(3) | 1.0358(13) | 0.1493(3) |
| C1A | 0.4750(3) | 1.7319(17) | 0.3316(3) |
| C2A | 0.4347(3) | 1.6488(15) | 0.3518(3) |
| C3A | 0.4054(3) | 1.3482(16) | 0.3910(3) |
| C4A | 0.3645(3) | 1.4107(15) | 0.3761(3) |
| C5A | 0.3295(3) | 1.2894(15) | 0.3868(3) |
| C6A | 0.3358(3) | 1.0998(17) | 0.4152(3) |
| C7A | 0.3763(3) | 1.0428(14) | 0.4321(3) |
| C8A | 0.4120(3) | 1.1565(16) | 0.4210(3) |
| C9A | 0.4557(3) | 1.0922(15) | 0.4400(3) |
| C10A | 0.2618(3) | 1.0346(15) | 0.4183(4) |
| C11A | 0.2352(3) | 0.8655(16) | 0.4405(3) |
| C12A | 0.1986(3) | 0.7796(15) | 0.4212(3) |
| C13A | 0.1766(3) | 0.6035(14) | 0.4464(3) |
| C14A | 0.1990(3) | 0.4644(16) | 0.4787(3) |
| C15A | 0.1781(3) | 0.2962(16) | 0.5027(3) |
| C16A | 0.1358(4) | 0.2724(16) | 0.4913(3) |
| C17A | 0.1116(3) | 0.4139(16) | 0.4608(3) |
| C18A | 0.1326(4) | 0.5764(16) | 0.4386(4) |
| C19A | 0.1763(3) | 0.8646(16) | 0.3748(3) |
| C20A | 0.1673(3) | 0.7262(15) | 0.3345(4) |
| C21A | 0.1426(3) | 0.7969(16) | 0.2942(4) |
| C22A | 0.1250(3) | 1.0087(18) | 0.2925(4) |
| C23A | 0.1354(3) | 1.1487(16) | 0.3320(4) |
| C24A | 0.1600(3) | 1.0762(16) | 0.3715(4) |
| C25A | 0.0966(4) | 1.0763(16) | 0.2511(4) |
| C26A | 0.0724(3) | 1.1350(17) | 0.2182(4) |
| C27A | 0.0403(3) | 1.2154(16) | 0.1803(4) |
| C28A | −0.0023(3) | 0.8873(15) | 0.1787(4) |
| C29A | −0.0221(4) | 0.7113(18) | 0.1459(4) |
| C30A | −0.0269(4) | 0.9488(18) | 0.0779(4) |
| C31A | −0.0076(3) | 1.1299(15) | 0.1108(4) |
| Na1B | 0.50100(12) | 1.2565(5) | 0.32498(12) |
| F1B | 0.94656(18) | 0.5969(8) | 0.4452(2) |
| O1B | 0.5610(2) | 1.1172(9) | 0.2949(2) |
| O2B | 0.5623(2) | 1.3963(11) | 0.2415(2) |
| O3B | 0.6224(2) | 0.9057(10) | 0.2598(2) |
| O4B | 0.7554(2) | 0.3890(10) | 0.2088(2) |
| O5B | 0.5490(2) | −0.7247(10) | 0.4023(2) |
| N1B | 0.6179(3) | −0.6391(12) | 0.4735(3) |

TABLE 3-continued

Fractional Atomic Coordinates for Compound II (Form 1) at 100 K

| | x/a | y/b | z/c |
|---|---|---|---|
| C1B | 0.5754(4) | 1.2146(19) | 0.2598(4) |
| C2B | 0.6129(3) | 1.1120(15) | 0.2360(4) |
| C3B | 0.6584(3) | 0.7925(15) | 0.2471(3) |
| C4B | 0.6805(3) | 0.8379(16) | 0.2073(4) |
| C5B | 0.7135(3) | 0.7053(15) | 0.1952(3) |
| C6B | 0.7243(3) | 0.5240(16) | 0.2248(4) |
| C7B | 0.7029(3) | 0.4838(14) | 0.2653(3) |
| C8B | 0.6697(3) | 0.6152(15) | 0.2783(3) |
| C9B | 0.6461(3) | 0.5722(13) | 0.3234(3) |
| C10B | 0.7719(3) | 0.2156(14) | 0.2414(3) |
| C11B | 0.8036(3) | 0.2993(14) | 0.2795(4) |
| C12B | 0.8085(3) | 0.2600(14) | 0.3285(3) |
| C13B | 0.8438(3) | 0.3582(15) | 0.3596(3) |
| C14B | 0.8624(3) | 0.2370(14) | 0.3989(3) |
| C15B | 0.8962(3) | 0.3143(16) | 0.4279(4) |
| C16B | 0.9127(3) | 0.5176(18) | 0.4166(4) |
| C17B | 0.8953(3) | 0.6460(15) | 0.3782(4) |
| C18B | 0.8614(3) | 0.5608(16) | 0.3505(4) |
| C19B | 0.7785(3) | 0.1160(17) | 0.3530(4) |
| C20B | 0.7610(3) | 0.1914(15) | 0.3965(4) |
| C21B | 0.7357(3) | 0.0582(15) | 0.4221(3) |
| C22B | 0.7278(3) | −0.1574(16) | 0.4069(4) |
| C23B | 0.7446(3) | −0.2323(13) | 0.3643(3) |
| C24B | 0.7692(3) | −0.0950(15) | 0.3375(3) |
| C25B | 0.7035(3) | −0.3033(16) | 0.4361(3) |
| C26B | 0.6837(3) | −0.4190(15) | 0.4608(3) |
| C27B | 0.6583(3) | −0.5563(14) | 0.4930(3) |
| C28B | 0.5892(3) | −0.4684(15) | 0.4538(3) |
| C29B | 0.5462(3) | −0.5614(16) | 0.4400(4) |
| C30B | 0.5779(3) | −0.8945(15) | 0.4192(4) |
| C31B | 0.6209(3) | −0.8071(14) | 0.4349(3) |

TABLE 4

Hydrogen Atom Coordinates for Compound II (Form 1) at 100 K

| | x/a | y/b | z/c |
|---|---|---|---|
| H2AA | 0.4236 | 1.7608 | 0.3738 |
| H2AB | 0.4129 | 1.6239 | 0.3242 |
| H4A | 0.3602 | 1.5421 | 0.3577 |
| H5A | 0.3017 | 1.3339 | 0.3751 |
| H | 0.3799 | 0.9176 | 0.4526 |
| H9AA | 0.467 | 1.2009 | 0.464 |
| H9AB | 0.474 | 1.0846 | 0.4125 |
| HA | 0.4548 | 0.9488 | 0.4559 |
| H10A | 0.2543 | 1.0456 | 0.3823 |
| H10B | 0.2574 | 1.1792 | 0.4334 |
| H11A | 0.2453 | 0.8126 | 0.4721 |
| H14A | 0.2288 | 0.482 | 0.4848 |
| H15A | 0.1931 | 0.2031 | 0.526 |
| H17A | 0.0817 | 0.398 | 0.4556 |
| H18A | 0.1169 | 0.6743 | 0.4171 |
| H20A | 0.1785 | 0.5819 | 0.3351 |
| H21A | 0.1372 | 0.7016 | 0.2668 |
| H23A | 0.1251 | 1.2947 | 0.3312 |
| H24A | 0.1664 | 1.1738 | 0.3982 |
| H27A | 0.0535 | 1.3232 | 0.1592 |
| H27B | 0.0174 | 1.2905 | 0.1966 |
| H28A | −0.0248 | 0.9694 | 0.1943 |
| HB | 0.0168 | 0.8208 | 0.2052 |
| HC | 0.0005 | 0.6246 | 0.1319 |
| H29B | −0.0388 | 0.6118 | 0.1656 |
| H30A | −0.0465 | 1.0122 | 0.0515 |
| H30B | −0.0042 | 0.8691 | 0.0622 |
| H31A | 0.0077 | 1.2344 | 0.0908 |
| H31B | −0.0305 | 1.2103 | 0.126 |
| H2BA | 0.6055 | 1.0894 | 0.2003 |
| H2BB | 0.6379 | 1.2097 | 0.24 |
| H4B | 0.6731 | 0.9624 | 0.1875 |
| H5B | 0.7286 | 0.7368 | 0.1672 |
| H7B | 0.711 | 0.3617 | 0.2855 |
| H9BA | 0.6446 | 0.7071 | 0.3426 |

TABLE 4-continued

Hydrogen Atom Coordinates for Compound II (Form 1) at 100 K

| | x/a | y/b | z/c |
|---|---|---|---|
| H9BB | 0.661 | 0.4595 | 0.3436 |
| H9BC | 0.6172 | 0.522 | 0.3133 |
| H10C | 0.7851 | 0.1016 | 0.2218 |
| H10D | 0.7481 | 0.1474 | 0.2576 |
| H11B | 0.824 | 0.3966 | 0.2677 |
| H14B | 0.8512 | 0.097 | 0.4057 |
| H15B | 0.9083 | 0.2316 | 0.455 |
| H17B | 0.9064 | 0.7862 | 0.3715 |
| H18B | 0.8491 | 0.6445 | 0.3236 |
| H20B | 0.7669 | 0.3358 | 0.4079 |
| H21B | 0.7235 | 0.1126 | 0.4505 |
| H23B | 0.7393 | −0.378 | 0.3535 |
| H24B | 0.7798 | −0.147 | 0.3079 |
| H27C | 0.6761 | −0.6831 | 0.5041 |
| H27D | 0.6535 | −0.4694 | 0.5228 |
| H28C | 0.6006 | −0.4018 | 0.4244 |
| H28D | 0.5869 | −0.3525 | 0.4788 |
| H29C | 0.5347 | −0.6278 | 0.4693 |
| H29D | 0.5267 | −0.4435 | 0.4277 |
| H30C | 0.5803 | −1.0023 | 0.3924 |
| H30D | 0.5664 | −0.9711 | 0.4473 |
| H31C | 0.6395 | −0.9277 | 0.4478 |
| H31D | 0.6337 | −0.7425 | 0.4062 |

Figure 26:
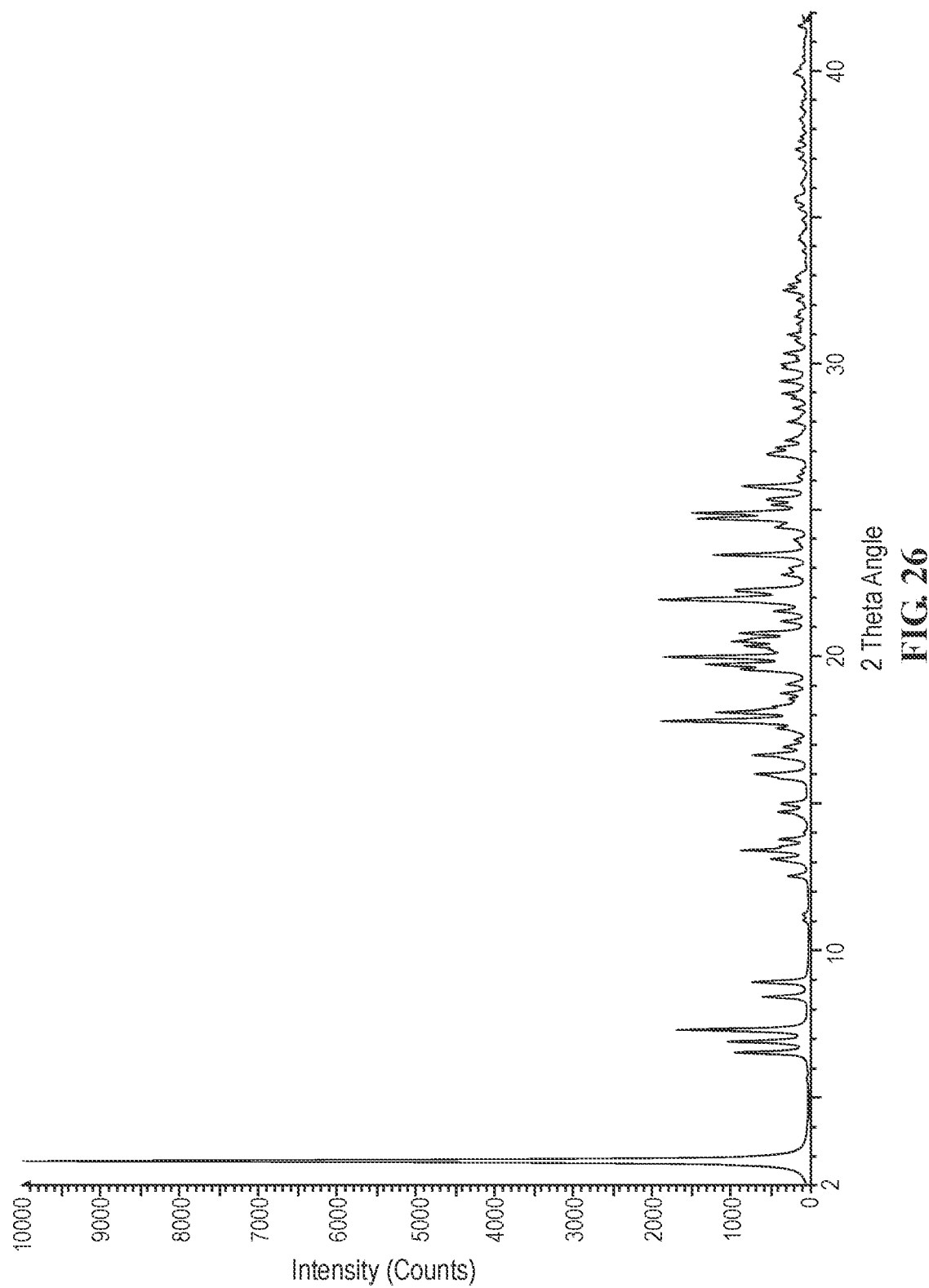
FIG. 26 illustrates a simulated XRPD pattern for Form 1 of Compound II.

The simulated XRPD pattern of Compound II (Form 1) at 100 K is shown in FIG. 26.

Figure 27:
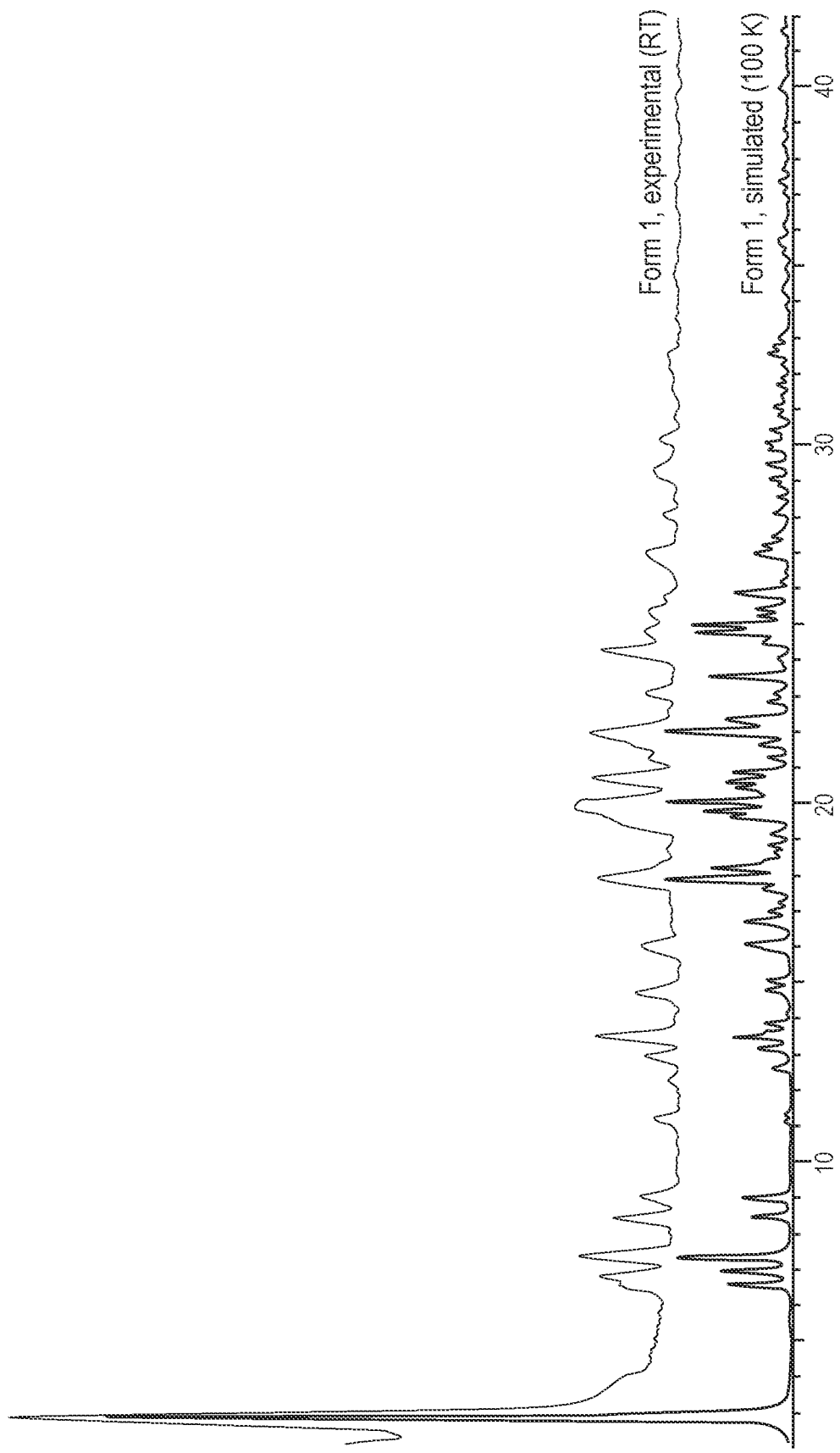
FIG. 27 illustrates the overlap of the simulated and experimental XRPD patterns for Form 1 of Compound II.

An overlay with the experimental diffractogram at RT confirms that the simulated diffractogram from the single crystal structure is consistent with the experimental Compound 11 (Form 1) diffractogram (FIG. 27).

Example A-1: Oral Solution

To prepare a pharmaceutical composition for oral delivery, a sufficient amount of a Compound I, or a pharmaceutically acceptable salt thereof (e.g., Compound II), is added to water (with optional solubilizer(s), optional buffer(s) and taste masking excipients) to provide a 1-20 mg/mL solution.

Example A-2: Oral Tablet

A tablet is prepared by mixing 20-50% by weight of Compound I, or a pharmaceutically acceptable salt thereof (e.g., Compound II), 20-50% by weight of microcrystalline cellulose, 1-10% by weight of low-substituted hydroxypropyl cellulose, and 1-10% by weight of magnesium stearate or other appropriate excipients. Tablets are prepared by direct compression. The total weight of the compressed tablets is maintained at 100-500 mg.

Example A-3: Oral Capsule

To prepare a pharmaceutical composition for oral delivery, 10-500 mg of Compound I, or a pharmaceutically acceptable salt thereof (e.g., Compound II), is optionally mixed with starch or other suitable powder blends. The mixture is incorporated into an oral dosage unit such as a hard gelatin capsule, which is suitable for oral administration.

In another embodiment, 10-500 mg of Compound I, or a pharmaceutically acceptable salt thereof (e.g., Compound II), is placed into Size 4 capsule, or size 1 capsule (hypromellose or hard gelatin) and the capsule is closed.

Example B-1: Determination of Binding Selectivity of Compound I to PPARα, PPARγ, and PPARδ

Compound I was tested on all three human PPAR subtypes (hPPAR): hPPARα, hPPARγ, and hPPARδ. The results of representative experiments in each human PPAR subtype are shown in Table 1. All assays were repeated at least three times for each subtype. Compound I is a potent and efficacious agonist of PPARδ, (EC50=31 nM), whereas the compound only shows minor activity on PPARα (EC50>10 μM) and PPARγ (EC50>10 μM).

The genes of interest were synthesized and cloned into an appropriate Jump-In™ retargeting vector following the User Guide of the Jump-in™ T-REx™ HEK293 Retargeting Kit (ThermoFisher Catalog No A15008). For example, the vector will be used to transfect and retarget the Jump-In™ HEK293 GripTite™ parental cell line. Stable pools will be antibiotic-selected for about 21 days and tested for target gene expression by functional assay.

Retargeting Methods:

Jump-In™ GripTite™ HEK293 parental cells were plated at 60-80% confluency in a T-75 flask in growth medium without antibiotics and transfected with a 1:1 ratio of expression construct and R4 integrase expression construct (20 μg DNA total) using Lipofectamine® LTX (50 μL) and PLUS™ Reagent (20 μL). Following a 48 hours incubation, cells were selected with 600 μg/mL Geneticin® and 10 μg/mL Blasticidin for ~21 days in growth medium.

BLA Assay Methods:

Jump-In™ GripTite™ HEK293 rPPAR Alpha, Delta or Gamma UAS-bla-Gal4 cell pools were plated in a 384-well plate format (20,000 cells per well) in OptiMeM without FBS in replicates (n=4). Cells were allowed to adhere for 8 hours before addition of Compound I (1 mM top concentration, 3-fold dilutions, 10-point titration). After 16 hours, the cells were loaded with LiveBLAzer®, a fluorescent BLA substrate that gives a blue/green readout of expressing/non-expressing cells, respectively. The blue/green readout was measured on a fluorescent plate reader (Tecan Safire II).

Example B-2: Cell Lines and Culture

Subjects. Skin biopsies for fibroblast culture are performed on a clinical basis with written informed consent from subjects and/or legal guardians.

Fibroblast cells with mutations in any one of the genes and/or proteins associated with a primary mitochondrial myopathy are obtained from patients' skin biopsies, while wild type (WT) fibroblast cells are obtained from healthy individuals. In some embodiments, fibroblast cells are obtained from subjects with a confirmed diagnosis of a primary mitochondrial myopathy (e.g., m.3243A>G mutation or mtDNA mutations) or they are purchased is available from commercial sources, e.g. from the Coriell Institute Coriell Institute for Medical Research (403 Haddon Avenue, Camden, New Jersey 08103).

Alternatively, fibroblast cells with mutations in any one of the genes and/or proteins associated with a fatty acid oxidation disorder (FAOD) ae obtained from patients' skin biopsies, while wild type (WT) fibroblast cells are obtained from healthy individuals. Fibroblast cells, in some cases, are obtained from subjects with a confirmed diagnosis of a fatty acid oxidation disorder (FAOD) (e.g. MCAD, VLCAD, CPT1, CACT, CPT2, LCHAD, and/or mitochondrial TFP deficiencies or mutations) or they, in some cases, are purchased is available from commercial sources, e.g. from the Coriell Institute for Medical Research (403 Haddon Avenue, Camden, New Jersey 08103).

Cell culture and treatments. Cells are grown in Dulbecco's Modified Eagle Medium (DMEM), Corning Life Sciences, Manassas, VA, containing high glucose levels or in DMEM devoid of glucose for 48-72 hr. Both media are supplemented with fetal bovine serum, glutamine, penicillin and/or streptomycin. In some experiments, fibroblasts are incubated with N-acetylcysteine, resveratrol, mitoQ, Trolox (a hydro-soluble analogue of vitamin E), or bezafibrate, prior to the analysis of parameters.

A PPARδ agonist compound is dissolved in phosphate buffer saline, PBS, as a stock solution. Amounts are added appropriately directly to cell culture media in flasks when the cultures are about 85-90 confluent. The cultures are allowed to grow for 48 h at 37° C., and then harvested. Harvested cell pellets are stored at −80° C. until immune and enzymatic assays analyses. 1 mL to 1.5 mL media samples are also stored at −80° C. for acylcarnitines.

Example B-3: Measurement of Mitochondrial Respiration

Oxygen consumption rate (OCR) is measured with a Seahorse XFe96 Extracellular Flux Analyzer (Sea horse Bioscience, Billerica, MA).

Briefly, the apparatus contains a fluorophore that is sensitive to changes in oxygen concentration, which enables it to accurately measure the rate at which cytochrome c oxidase (complex IV) reduces one $O_2$ molecule to two $H_2O$ molecules during OXPHOS. Cells are seeded in 96-well Seahorse tissue culture microplates in growth media at a density of 80,000 cells per well. To ensure equal cell numbers, cells are seeded in cell culture plates pre-coated with Cell-Tak, BD Biosciences, San Jose, CA All cell lines are measured with four to eight wells per cell line. Then, the entire set of experiments is repeated. Before running the Seahorse assay, cells are incubated for 1 hour without $CO_2$ in unbuffered DMEM. Initial OCR is measured to establish a baseline (basal respiration). Maximal respiration is also determined after the injection of 300 nM carbonyl cyanide 4-(trifluoromethoxy)phenylhydrazone (FCCP), Seahorse XF Cell Mito Stress Test Kit, Santa Clara, CA.

Example B-4: Clinical Trial for Primary Mitochondrial Myopathy (PMM)

A non-limiting example of a primary mitochondrial myopathy clinical trial in humans is described below.

Purpose: The purposes of this study was: to assess the safety and tolerability of 12 weeks treatment with Compound I, or a pharmaceutically acceptable salt or solvate thereof (e.g., Compound II), in patients with primary mitochondrial myopathy; to investigate pharmacokinetics of Compound I, or a pharmaceutically acceptable salt or solvate thereof, in patients with primary mitochondrial myopathy treated with Compound I, or a pharmaceutically acceptable salt or solvate thereof (e.g., Compound II); to investigate the pharmacodynamics effects of Compound I, or a pharmaceutically acceptable salt or solvate thereof (e.g., Compound II), in patients with primary mitochondrial myopathy treated with Compound I, or a pharmaceutically acceptable salt or solvate thereof (e.g., Compound II).

Intervention: Patients were administered 10-200 mg of Compound I, or a pharmaceutically acceptable salt or solvate thereof (e.g., Compound II), per day as single agent or in combination. For example, patients received 100 mg of Compound I, or a pharmaceutically acceptable salt or solvate thereof (e.g., Compound II), once daily for a total of 12 weeks. Other cohorts are contemplated.

Compound I, or a pharmaceutically acceptable salt or solvate thereof (e.g., Compound II), will be packed in bottles as capsules.

Detailed Description: Patients were given Compound I, or a pharmaceutically acceptable salt or solvate thereof (e.g., Compound II), orally once a day.

Inclusion Criteria: Primary mitochondrial myopathy (PMM) as defined by the International Workshop: Outcome measures and clinical trial readiness in primary mitochondrial myopathies in children and adults (Mancuso, M. et al. (2017, December). International Workshop: Outcome measures and clinical trial readiness in primary mitochondrial myopathies in children and adults. Consensus recommendations. 10-18 Nov. 2016, Rome, Italy. *Neuromuscul. Disord.*, 12, 1126-1137), and with a myopathy score of 2-4 on the Newcastle Mitochondrial Disease Adult Scale (NM-DAS) Section III Question 5. Approximately 12 patients have a confirmed m.3243A>G mutation and 12 patients have other mtDNA defects, with myopathy.

Currently following a stable dietary regimen with avoidance of fasting as documented by a 3-day dietary record obtained during the screening period.

A stable treatment regimen for at least 30 days prior to enrollment.

Expected and willing to remain on stable diet and medication through the study.

Ambulatory and able to perform the study exercise tests.

Adequate kidney function defined as an estimated glomerular filtration rate (eGFR)≥60 mL/min/1.73 m2 using the Cockcroft-Gault formula.

Able to swallow capsules.

Exclusion Criteria: Patients presenting with any of the following will not be included in the study:
  unstable or poorly controlled disease as determined by one or more of the following: echocardiogram with evidence of active or worsening cardiomyopathy at screening; presence of symptoms of acute rhabdomyolysis with elevations in serum CPK consistent with acute exacerbation of myopathy; evidence of acute crisis from their underlying disease.
  currently taking anticoagulants.
  have motor abnormalities other than those related to the mitochondrial disease that could interfere with the outcome measures.
  treatment with an investigational drug within 3 months prior to Day 1.
  evidence of significant concomitant clinical disease that in the opinion of the Investigator may need a change in management during the study or could interfere with the conduct or safety of this study. (Stable well-controlled chronic conditions such as controlled hypertension (BP<140/90 mmHg) thyroid disease, well-controlled Type 1 or Type 2 diabetes (HbA1c<8%), hypercholesterolemia, gastroesophageal reflux, or depression under control with medication (other than tricyclic antidepressants), are acceptable provided the symptoms and medications would not be predicted to compromise safety or interfere with the tests and interpretations of this study).
  history of cancer with the exception of in situ skin cancer.
  have been hospitalized within the 3 months prior to screening for any major medical condition (as deemed by the primary investigator).
  clinically significant cardiac disease or ECG abnormalities.
  any condition possibly reducing drug absorption (e.g., gastrectomy).
  history of clinically significant liver disease as evidenced by elevations in ALT, GGT or TB.
  positive hepatitis B surface antigen (HBsAg) or hepatitis C, or HIV at screening.
  evidence of clinically significant muscle damage tests (CPK>3×ULN)
  history of drug abuse or with a positive urine drug screen.
  history of regular alcohol consumption exceeding 14 drinks/week (1 drink=150 mL of wine or 360 mL of beer or 45 mL of spirits) within 6 months of screening.
  pregnant or nursing females.
  history of sensitivity to PPAR agonists.
  any other severe acute or chronic medical or psychiatric condition or laboratory abnormality that in the opinion of the Investigator may increase the risk associated with study participation or investigational product administration or may interfere with the interpretation of study results.

Outcome Measures: Safety Endpoints include: number and severity of adverse events. Absolute values, changes from baseline at Week 12 and incidence of clinically significant changes in: laboratory safety tests; electrocardiograms; supine vital signs.

Pharmacokinetic Endpoints include: Compound I plasma concentrations and identification of metabolites using pooled plasma.

Absolute values and changes from baseline to Week 12 in serum biomarkers: fibroblast growth factor 21 (FGF-21) and growth/differentiation factor 15 (GDF-15). Absolute values and changes from baseline to Week 12 in acylcarnitine panel. Changes from baseline to Week 12 in muscle histopathology.

Changes from baseline following 12 weeks of treatment with Compound I in: peak exercise test (including Borg scale); sub-maximal exercise test (including Borg scale); distance walked during a 12-minute walk test (including gait analysis); and 30 second sit to stand.

Change from baseline following 12 weeks of treatment with Compound I in muscle biopsy biomarkers (in order of importance if sample is sparse): mitochondrial DNA copy number; heteroplasmy level, respiratory chain enzyme activity (ATP-ADP levels, fatty acid oxidation gene expression or flux); messenger ribonucleic acid (mRNA) levels using transcriptomics; change from baseline in NMDAS; change from baseline in the SF-36; change from baseline in the Modified Fatigue Impact Scale score; change from baseline in Brief Pain Inventory (short form).

PMM Clinical Trial Results with Compound I

In general, Compound I was well tolerated among patients that participated in the study.

Figure 28:
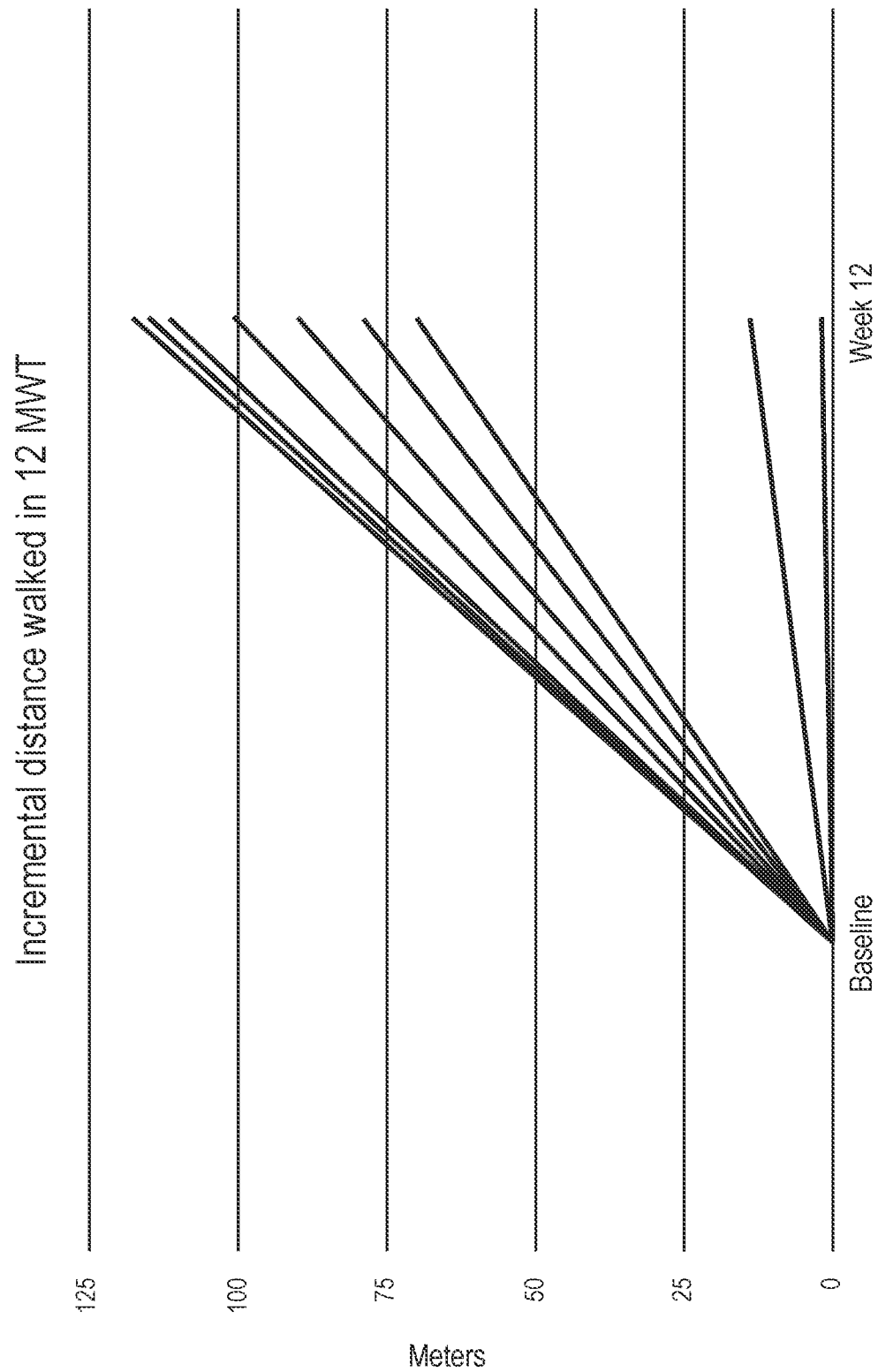
FIG. 28 shows the effect of administering Compound 1 (100 mg once a day for 12 weeks) to genetically diagnosed primary mitochondrial myopathy patients (mtDNA defects) with myopathy on the 12-minute walk test. Improvements in the 12-minute walk test over the course of the 12-week treatment regimen is shown for nine patients.

Improvements in exercise tolerance was observed in patients that received 100 mg of Compound I, or a pharmaceutically acceptable salt or solvate thereof (e.g., Compound II), once daily for a total of 12 weeks. Patients were able to increase the distance walked during a 12-minute walk test. Increases in the 12-minute walk test are displayed in FIG. 28. In this same group of patients, trends towards increases in peak VO$_2$ were observed for many patients that received 100 mg of Compound I, or a pharmaceutically acceptable salt or solvate thereof (e.g., Compound II), once daily for a total of 12 weeks.

Figure 29:
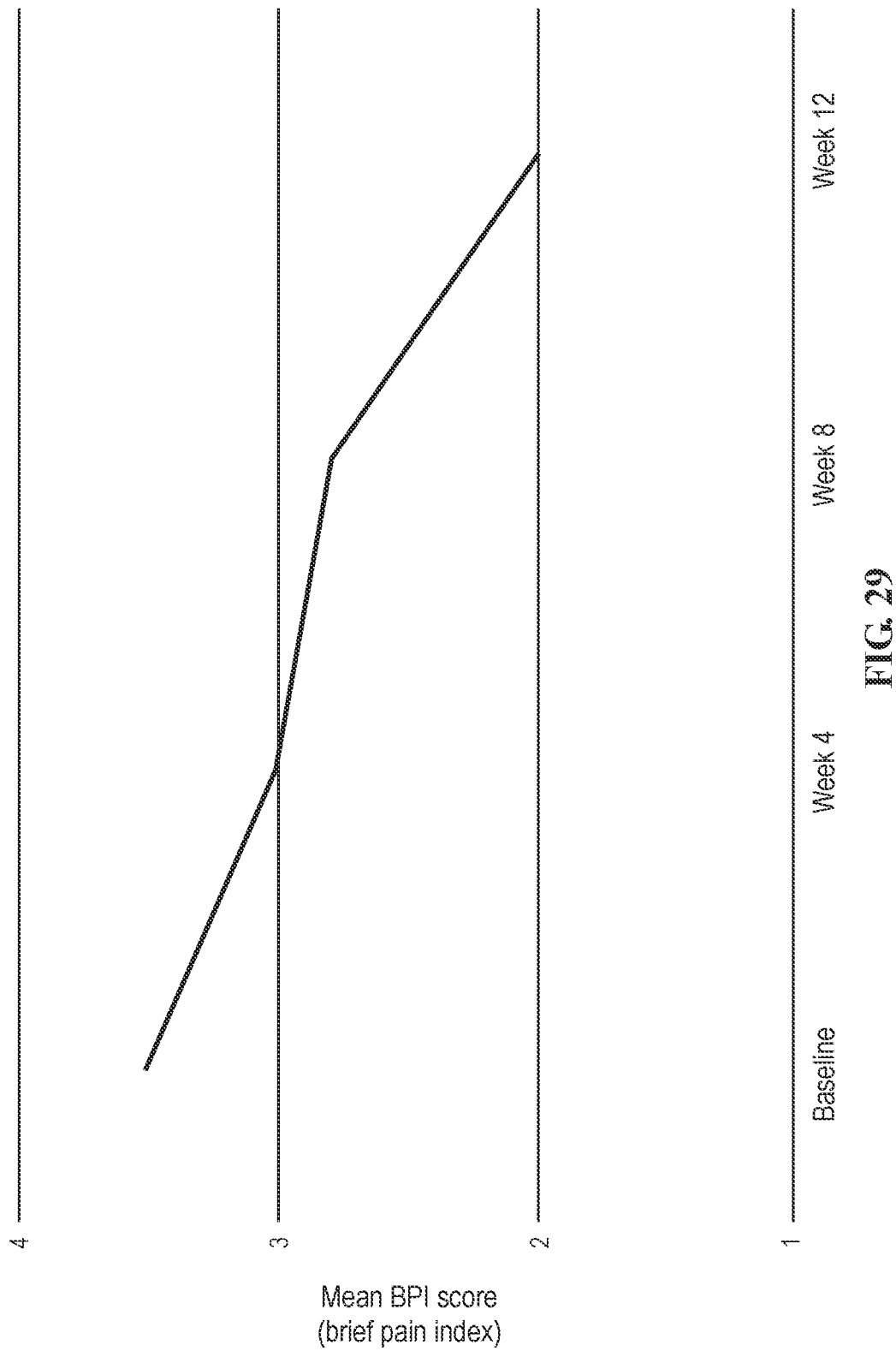
FIG. 29 shows the effect of administering Compound 1 (100 mg once a day for 12 weeks) to genetically diagnosed primary mitochondrial myopathy patients (mtDNA defects) with myopathy on pain scores. The mean brief pain inventory (BPI) score of nine patients administered Compound 1 decreased over the course of the 12-week treatment regimen.

Decreases in the brief pain inventory (BPI) was observed in patients that received 100 mg of Compound I, or a pharmaceutically acceptable salt or solvate thereof, once daily for a total of 12 weeks. FIG. 29 shows the decreases in the mean BPI scores resulting from administration of Compound 1, or a pharmaceutically acceptable salt or solvate thereof, to this group of patients. In this same group of patients, trends towards increases in Modified Fatigue Impact Scale scores were observed for many patients that received 100 mg of Compound I, or a pharmaceutically acceptable salt or solvate thereof, once daily for a total of 12 weeks.

Example B-5: A Phase 2b Clinical Trial for Primary Mitochondrial Myopathy (PMM)

Design: This is a randomized, double-blind, placebo-controlled, parallel group, multi-center, study designed to investigate the efficacy and safety of Compound I, or a pharmaceutically acceptable salt or solvate thereof (e.g., Compound II), administered once daily over a 24-week period to patients with PMM.

Patients are randomized (allocation 1:1) to the following two treatment groups: 100 mg/day of Compound I, or a pharmaceutically acceptable salt or solvate thereof (e.g., Compound II); or placebo.

Primary Objectives: To evaluate the efficacy of Compound I, or a pharmaceutically acceptable salt or solvate thereof (e.g., Compound II), in patients with PMM treated for 24 weeks, assessed by the effect on exercise endurance.

Secondary Objectives: To evaluate the efficacy of Compound I, or a pharmaceutically acceptable salt or solvate thereof (e.g., Compound II), in patients with PMM treated for 24 weeks, assessed by the effect on fatigue.

Safety Objectives: To evaluate the safety and tolerability of Compound I, or a pharmaceutically acceptable salt or solvate thereof (e.g., Compound II), in patients in subjects with PMM during 24 weeks of treatment.

Pharmacokinetic (PK) Objectives: To investigate the pharmacokinetics of Compound I, or a pharmaceutically acceptable salt or solvate thereof (e.g., Compound II), in patients with PMM.

Exploratory Objectives: To evaluate the efficacy of Compound I, or a pharmaceutically acceptable salt or solvate thereof (e.g., Compound II), in patients with PMM treated for 24 weeks, assessed by the effect on functional capacity. To evaluate the effect of Compound I, or a pharmaceutically acceptable salt or solvate thereof (e.g., Compound II), in patients on quality of life (QoL) of subjects with PMM after treatment for 24 weeks.

Primary Endpoints: Change from Baseline at Week 24 in distance walked during the 12-Minute Walk Test (12MWT).

Secondary Endpoints: Change from Baseline at Week 24 in the Modified Fatigue Impact Scale (MFIS) physical sub-scale score. Patient Global Impression of Change (PGIC) score at Week 24.

Safety Endpoints: Number and severity of adverse events (AE). Absolute values, changes from Baseline and incidence of potentially clinically significant changes in: laboratory safety tests, electrocardiograms (ECG), supine vital signs, slit lamp eye assessments.

Pharmacokinetic (PK) Endpoints: Compound I plasma concentrations.

Exploratory Endpoints: Change from Baseline at Week 24 in: number of sit to stands in the 30 second sit to stand (30STS) test, step count from pedometer, Patient Global Impression of Severity (PGIS) score, 36-Item Health Survey (SF-36) domain scores, MFIS total, cognitive and psychosocial sub-scale scores, Brief Pain Inventory (BPI) pain severity and pain interference scores, Work Productivity and Activity Impairment Questionnaire: Specific Health Problem (WPAI:SHP) scores.

Doses and Randomization: 100 mg of Compound I, or a pharmaceutically acceptable salt or solvate thereof (e.g., Compound II), orally administered once daily. Placebo orally once daily. The randomization is stratified by mutational genotype (m.3234A>G versus no more than 60% other mitochondrial DNA defects) and the screening 12-minute walk distance (12MWD) (≤500 meters or >500 meters).

Duration of Treatment: 24 weeks.

Inclusion Criteria: Patients must meet all of the following inclusion criteria:

age 18 years or older with PMM as defined by the International Workshop: Outcome measures and clinical trial readiness in primary mitochondrial myopathies in children and adults (Mancuso, M. et al. (2017, December). International Workshop: Outcome measures and clinical trial readiness in primary mitochondrial myopathies in children and adults. Consensus recommendations. 10-18 Nov. 2016, Rome, Italy. *Neuromuscul. Disord.*, 12, 1126-1137).

A confirmed PMM diagnosis due to known pathogenic gene mutation or deletion of the mitochondrial genome.

Documented PMM characterized by exercise intolerance or active muscle pain.

Ambulatory and able to perform the 12MWT independently.

Distance walked of ≤1000 meters at Screening in the 12MWT (must be obtained at least 4 weeks before randomization).

Have no changes to any therapeutic exercise regimen within 30 days prior to Day 1 and be willing to remain on the same therapeutic exercise regimen for the duration of the study.

Able to swallow doses.

Must agree to use highly effective methods of contraception from Screening through to 30 days after last dose in the study.

Concomitant medications (including supplements) must be stable for at least 1 month prior to enrolment and throughout participation in the study.

Exclusion Criteria: Patients with any of the following:

Participation in a prior Compound I, or a pharmaceutically acceptable salt or solvate thereof (e.g., Compound II), study.

Currently taking or anticipated to need a PPAR agonist during the study.

Patients with bone deformities or motor abnormalities other than related to the mitochondrial myopathy that may interfere with the outcome measures.

Clinically significant kidney disease or impairment calculated as estimated Glomerular Filtration Rate (eGFR) Grade 2 or above <60 ml/min/1.73 m$^2$ using the Chronic Kidney Disease Epidemiology Collaboration (CKD-EPI) creatinine equation.

Clinically significant liver disease or impairment of aspartate aminotransferase (AST) or alanine aminotransferase (ALT) Grade 2 or above >2.5×Upper limit of normal (ULN), or Total bilirubin >1.6×ULN or >ULN with other signs and symptoms of hepatotoxicity at Screening.

Uncontrolled diabetes and/or a Screening glycosylated hemoglobin (HbA1c) of >11%.

A history of cancer unless it is a history of in situ basal cell carcinoma in the skin.

Hospitalized within the 3 months prior to Screening for any major medical condition (as deemed by the Investigator).

Clinically significant cardiac disease and/or clinically significant ECG abnormalities that in the opinion of the Investigator should exclude the subject from completing exercise tests (i.e., study 12MWT and 30STS tests).

Any condition possibly reducing drug absorption.

Evidence of hospitalization for rhabdomyolysis within the year prior to enrolment.

Patients with positive hepatitis B surface antigen (HBsAg), hepatitis B core antibody (HBcAb) or hepatitis C or human immunodeficiency virus (HIV) at Screening.

Pregnant or nursing females.

History of sensitivity to PPAR agonists.

Patients with a history of drug dependency or a history of alcohol dependency.

Central or peripheral nervous system impairment that would interfere with the exercise tests.

Significant weakness not caused by the underlying primary muscle disease such as post stroke or neurogenic weakness.

Not eligible or have a contraindication for cataract surgery.

Any other medical or psychiatric condition or laboratory abnormality, history of an organ transplant, current or anticipated need for a prescription and/or non-prescription drug that would increase the risk associated with study participation or investigational product administration or interfere with the interpretation of study results and, in the judgment of the Investigator would make the subject inappropriate for entry into this study.

Study Visits: A total of 8 visits for each patient. The Screening Visit (Visit 1) must be completed no more than 6 weeks prior to the start of dosing. A minimum of 4 weeks between the Screening 12MWT and the Baseline 12MWT. Where possible patients should be pre-screened to assess the requirement for genotyping. Patients who are receiving prohibited medications must suspend the medications and have sufficient washout during the screening period prior to randomization.

Patients who successfully complete screening will undergo a Baseline Visit (Visit 2; Week 1). Once the Baseline assessments have been completed patients are randomized 1:1 to receive oral Compound I, or a pharmaceutically acceptable salt or solvate thereof (e.g., Compound II), 100 mg or placebo once daily for 24 weeks. In centers where the regulatory authority and the Ethics Committee or IRB allows, Visit 3 (Week 2), Visit 4 (Week 4), Visit 6 (Week 18) and Follow Up visit may be conducted either in the Study Center or at the subject's home using a home nursing service. Visit 5 (Week 12) and Visit 7 (Week 24) will be completed in the Study Center. A Follow Up Visit (Visit 8) will be performed, which can be carried out either in the Study Center or at the subject's home. Visit 8 will be completed 21-28 days after the last dose of study medication.

The planned maximum study duration for each patient in the study will be 34 weeks (6 weeks screening, 24 weeks treatment and 4 weeks follow up).

12-Minute Walk Test: The 12MWT is a practical test that requires simple equipment to execute. This test measures the distance a subject can walk on a flat, hard surface in a period of 12 minutes. There must be a minimum of 4 weeks between the Screening and Baseline 12MWT to minimize any training effect. Subjects who walk further than 1000 m at Screening will be excluded from the study. Subjects who walk ≤1000 m at Screening but subsequently walk greater than 1000 m at Baseline will be allowed to continue into the study but will be excluded from the per protocol analysis.

36 Item Health Survey V2.0@ (SF-36): The 36-Item Health Survey Version 2.0® asks questions which cover eight health concepts: physical functioning, bodily pain, role limitations due to physical health problems, role limitations due to personal or emotional problems, emotional well-being, social functioning, energy/fatigue, and general health perceptions. It also includes a single item that provides an indication of perceived change in health. A one-week recall period will be used.

Modified Fatigue Impact Scale (MFIS): The MFIS is a detailed tool, that is completed by the patient personally, rather than having an interview and thus, no training is required to deliver it. Scoring is simple, the score reflects functional limitation due to fatigue experienced within the previous month rather than a measure of the level of fatigue. It may be used in both the clinical and the research setting in people for whom fatigue is a predominant symptom.

There are 21 items, each of which is scored 0 (no problem) to 4 (extreme problem), providing a continuous scale of 0-84. It is composed of three subscales that describe the impact of fatigue on physical, cognitive and psychosocial functioning: a) Physical functioning (9 items) reflects motivation, effort, stamina, and coordination. The physical subscale can range from 0 to 36. b) Cognitive functioning (10 items) concerns concentration, memory, thinking and organization of thoughts. The cognitive subscale ranges from 0 to 40. c) Psychosocial functioning (2 items) describes the impact of fatigue upon isolation, emotions, workload, and coping. The psychosocial subscale can range from 0 to 8.

All items are scaled so that a higher score indicates a greater level of fatigue.

Brief Pain Inventory (BPI): The Brief Pain Inventory (Short Form) rapidly assesses the severity of pain and its impact on functioning. It is widely used in research and clinical settings. Four severity items will be investigated by the responses to the worst, least and average pain in last 24 hours and the pain right now (Questions 3, 4, 5 and 6). The higher score indicates worse pain. A pain severity score will be calculated as the mean of the non-missing 4 severity items. A higher score indicates greater pain severity. In addition, the average pain interference score will be derived as the average of the responses to the 7 components to Question 9. A higher score indicates the more pain interferes with daily functioning.

Patient Global Impression of Severity (PGIS): The patient is asked to rate the severity of their PMM muscle symptoms over the past 7 days: Overall, how would you rate the severity of your muscle symptoms related to your Primary Mitochondrial Myopathy over the past 7 days? Absent, mild, moderate, severe, or very severe Patient Global Impression of Change (PGIC): At the end of study treatment (Day 168) or Early Termination visit, the patient will be asked to rate their degree of improvement or worsening of PMM muscle symptoms compared to before the start of study drug, using a 7-point scale, standardized PGIC scale.

Overall, how would you rate the change in the severity of your muscle symptoms related to your Primary Mitochondrial Myopathy since starting the study? Very much improved, moderately improved, minimally improved, no change, minimally worse, moderately worse, or very much worse.

Work Productivity and Activity Impairment Questionnaire: Specific Health Problem (WPAI:SHP): The Work Productivity and Activity Impairment (WPAI) questionnaire is a well validated instrument to measure impairments in work and activities due to a specific disease. Outcomes are expressed as impairment percentages, with higher numbers indicating greater impairment and less productivity, i.e., worse outcomes.

30 Second Sit-To-Stand Test: The purpose of the 30 second sit-to-stand test is to assess leg strength and endurance. Patients are required to sit and rise to full standing position as many times as they can in 30 seconds. A patient can only conduct the test if they are able to stand without using their arms to assist them out of the chair. This test must be completed at least an hour after the 12MWT.

Pedometer Step Counts and eDiary: At the completion of the Screening visit each patient is given a pedometer (3DFitBud model A420S or equivalent). The site staff will set-up the pedometer with the eDiary (HMD Clinical Ltd) and train the patient on how and when to use it. Patients collect their daily step counts (from waking until bedtime) and enter the total step count each day in the eDiary.

PMM Phenotypic Description: To enable comparative descriptions of the phenotypic state of each patients' disease, 3 questions, taken from the Newcastle Mitochondrial Disease Adult Scale (NMDAS) will be completed by the physician. A physician will complete the questions at Baseline and Week 24 (or at the Early Termination Visit).

Rate function over the preceding 4 week period, according to patient and/or caregiver interview only. The clinician's subjective judgement of functional ability should not be taken into account.

Question 1—Exercise Tolerance: 0=Normal; 1=Unlimited on flat—symptomatic on inclines or stairs; 2=Able to walk <1000 m on the flat. Restricted on inclines or stairs—rest needed after 1 flight (12 steps); 3=Able to walk <500 m on the flat. Rest needed after 8 steps on stairs; 4=Able to walk <100 m on the flat. Rest needed after 4 steps on stairs; 5=Able to walk <25 m on the flat. Unable to do stairs alone.

Question 2—Gait Stability: 0=Normal; 1=Normal gait—occasional difficulties on turns, uneven ground, or if required to balance on narrow base; 2=Gait reasonably steady. Aware of impaired balance. Occasionally off balance when walking; 3=Unsteady gait. Always off balance when walking. Occasional falls. Gait steady with support of stick or person; 4=Gait grossly unsteady without support. High likelihood of falls. Can only walk short distances (<10 m) without support; 5=Unable to walk without support. Falls on standing.

Question 3—Myopathy: 0=Normal; 1=Minimal reduction in hip flexion and/or shoulder abduction only (e.g. MRC 4+/5); 2=Mild but clear proximal weakness in hip flexion and shoulder abduction (MRC 4/5). Minimal weakness in elbow flexion and knee extension (MRC 4+/5—both examined with joint at 90 degrees); 3=Moderate proximal weakness including elbow flexion and knee extension (MRC 4/5 or 4−/5) or difficulty rising from a 90 degree squat; 4=Waddling gait. Unable to rise from a 90 degree squat (=a chair) unaided; 5=Wheelchair dependent primarily due to proximal weakness.

Example B-6: Clinical Trial for Fatty Acid Oxidation Disorder

A non-limiting example of a fatty acid oxidation disorder (FAOD) clinical trial in humans is described below.

Purpose: The purposes of this study were: to assess the safety and tolerability of 12 weeks treatment with Compound I, or a pharmaceutically acceptable salt or solvate thereof (e.g., Compound II), in patients with FAOD; to investigate pharmacokinetics of Compound I, or a pharmaceutically acceptable salt or solvate thereof (e.g., Compound II), in patients with FAOD treated with Compound I, or a pharmaceutically acceptable salt or solvate thereof (e.g., Compound II); to investigate the pharmacodynamics effects of Compound I, or a pharmaceutically acceptable salt or solvate thereof (e.g., Compound II), in patients with FAOD treated with Compound I, or a pharmaceutically acceptable salt or solvate thereof (e.g., Compound II).

Intervention: Patients were administered 10-200 mg of Compound I, or a pharmaceutically acceptable salt or solvate thereof (e.g., Compound II), per day as single agent or in combination. In one cohort, patients received 50 mg of Compound I, or a pharmaceutically acceptable salt or solvate thereof (e.g., Compound II), once daily for a total of 12 weeks. In another cohort, patients received 100 mg of Compound I, or a pharmaceutically acceptable salt or solvate thereof (e.g., Compound II), once daily for a total of 12 weeks.

Compound I, or a pharmaceutically acceptable salt or solvate thereof, was packed in bottles as capsules.

Detailed Description: Patients were given Compound I, or a pharmaceutically acceptable salt or solvate thereof, orally once a day.

Eligibility: 18 years and older with FAOD.

Inclusion Criteria: Confirmed diagnosis of one of the following: carnitine palmitoyl transferase II deficiency (CPT2), very long-chain Acyl-CoA dehydrogenase deficiency (VLCAD), long-chain 3-hydroxyacyl-CoA dehydrogenase deficiency (LCHAD), or trifunctional protein deficiency (TFP).

A diagnostic acylcarnitine profile, in blood or cultured fibroblasts.

Genotyping with at least 1 allele that is not a stop codon or a frame shift.

Evidence of any one of the following clinical manifestations despite therapy: Chronic elevated Creatine Kinase (CPK) as evidenced by at least 2 blood CPK levels above the ULN obtained at least 3 months apart, history of cardiomyopathy, a clinical event of hypoglycemia, rhabdomyolysis, or exacerbation of cardiomyopathy within the 12 months preceding enrollment.

Followed a stable dietary regimen with avoidance of fasting as documented by a 3-day dietary record obtained during the screening period.

A stable treatment regimen for at least 30 days prior to enrollment.

Ambulatory and able to perform the study exercise tests.

Adequate kidney function defined as an estimated glomerular filtration rate (eGFR)>60 mL/min/1.73 m2 using the Cockcroft-Gault formula.

Able to swallow capsules.

Exclusion Criteria: Patients who presented with any of the following were not included in the study:
  unstable or poorly controlled disease as determined by one or more of the following: echocardiogram with evidence of active or worsening cardiomyopathy at screening; presence of symptoms of acute rhabdomyolysis with elevations in serum CPK consistent with acute exacerbation of myopathy; evidence of acute crisis from their underlying disease.

taking anticoagulants.

have motor abnormalities other than those related to the fatty acid oxidation disorder that could interfere with the outcome measures.

treatment with an investigational drug within 1 month or within 5 half-lives, whichever is longer.

evidence of significant concomitant clinical disease that in the opinion of the Investigator needed a change in management during the study or could interfere with the conduct or safety of this study. (Stable well-controlled chronic conditions such as controlled hypertension (BP<140/90 mmHg) thyroid disease, well-controlled Type 1 or Type 2 diabetes (HbA1c<8%), hypercholesterolemia, gastroesophageal reflux, or depression under control with medication (other than tricyclic antidepressants), were acceptable provided the symptoms and medications did not compromise safety or interfere with tests and interpretations of this study).

history of cancer with the exception of in situ skin cancer.

hospitalized within the 3 months prior to screening for any major medical condition.

any condition possibly reducing drug absorption (e.g., gastrectomy).

history of clinically significant liver disease as evidenced by elevations in ALT, GGT or TB.

positive hepatitis B surface antigen (HBsAg) or hepatitis C, or HIV at screening.

history of regular alcohol consumption exceeding 14 drinks/week (1 drink=150 mL of wine or 360 mL of beer or 45 mL of spirits) within 6 months of screening.

any other severe acute or chronic medical or psychiatric condition or laboratory abnormality that in the opinion of the Investigator would increase the risk associated with study participation or investigational product administration or would interfere with the interpretation of study results.

Primary Outcome Measures: Safety Endpoints included: number and severity of adverse events. Absolute values, changes from baseline at Week 12 and incidence of clinically significant changes in: laboratory safety tests; electrocardiograms; supine vital signs; evaluation of events of special interest (rhabdomyolysis) and clinically significant changes in laboratory parameters of muscle injury including total CPK, adolase, and cardiac specific troponin (cTn).

Pharmacokinetic Endpoints included: Compound I plasma concentrations and identification of metabolites using pooled plasma.

Pharmacodynamic Endpoints included: Absolute values and changes from baseline at Week 12 in: whole body fatty acid oxidation ($^{13}CO_2$ production) and blood acylcarnitines (UHPLC-MS/MS method).

Secondary Outcome Measures: Assessment of the change from baseline following 12 weeks of treatment with Compound I, or a pharmaceutically acceptable salt or solvate thereof (e.g., Compound II), in: submaximal treadmill exercise tolerance; distance walked during a 12 minute walk test; 36-Item Short Form Survey (SF-36) total score and subscales (questions 3-12). Change from baseline in Fatigue Impact Scale score (every visit). Change from baseline in Brief Pain Inventory (short form) (every visit). Blood inflammatory cytokines (Multiplex Immunoassay for sE-Selectin; GM-CSF; ICAM-1/CD54; IFN alpha; IFN gamma; IL-1 alpha; IL-1 beta; IL-4; IL-6; IL-8; IL-10; IL-12p70; IL-13; IL-17A/CTLA-8; IP-10/CXCL10; MCP-1/CCL2; MIP-1alpha/CCL3; MIP-1 beta/CCL4; sP-Selectin; TNF alpha).

FAOD Clinical Trial Results with Compound I

In general, Compound I was well tolerated among patients that participated in the study.

Figure 30:
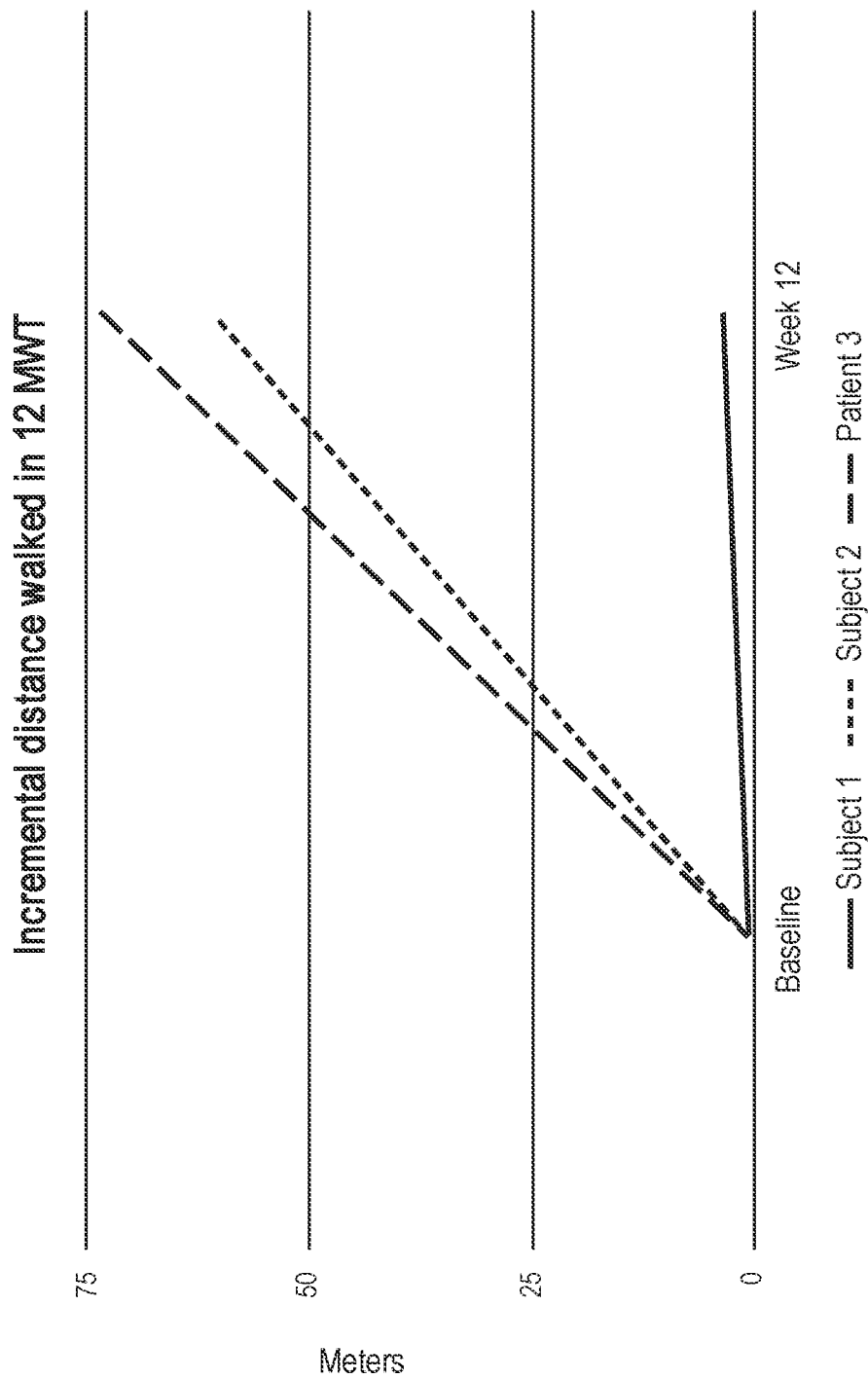
FIG. 30 shows the effect of Compound 1 (50 mg once a day for 12 weeks) on the 12-minute walk test in patients with genetically diagnosed long chain FAOD with symptoms of myopathy.

Improvements in exercise capacity was observed in patients that received 50 mg of Compound I, or a pharmaceutically acceptable salt, once daily for a total of 12 weeks. Patients were able to increase distance walked during a 12-minute walk test. FIG. 30 shows the results of the impact of Compound 1 on the 12-minute walk test in this group of patients. In this same group of patients, decreases in heart rate were observed during the last ten minutes of exercise.

A trend towards increases in exhaled $^{13}CO_2$ was observed in patients that received 50 mg of Compound I, or a pharmaceutically acceptable, once daily for a total of 12 weeks.

Another cohort of patients was administered 100 mg once-daily of Compound I, or a pharmaceutically acceptable salt or solvate thereof. Of the 24 patients that received study drug for 12 weeks, 3 patients received 50 mg/day and 21 patients received 100 mg/day. 8 patients (33.3%) had CPT2, 5 patients (20.8%) had LCHAD, 9 patients (37.5%) had VLCAD and 2 patients (8.3%) had TFP. Median age was 23 years, with 13 (54.2%) being male. Treatment-emergent adverse events (TEAEs) were reported by 18 (75%) patients, with 33 (30%) TEAEs reported as study drug related. The majority of study drug related TEAEs were mild or moderate in severity, with 3 (12.5%) patients discontinuing treatment. Rhabdomyolysis was the most common TEAE, reported by 4 (16.7%) patients. Baseline to Week 12 changes in 12MWT, SF-36 energy/fatigue domain, and MFIS are presented by genetic subgroup in Table 1. The LCHAD and CPT2 subgroups exhibited a 73.7 and 51.9 meter increase in 12MWT. The LCHAD and TFP subgroups exhibited a 19.5 and 25.0 point increase in SF-36 energy/fatigue domain, along with a 9.8 and 8.0 point decrease in MFIS.

TABLE 5

Baseline to Week 12 changes in endurance and fatigue by genetic subgroups[1]

| | 12 MWT (meters) | | SF-36 Energy/ Fatigue | | MFIS Total | |
|---|---|---|---|---|---|---|
| | Baseline Mean (±SE) | Mean Change (±SE) | Baseline Mean (±SE) | Mean Change (±SE) | Baseline Mean (±SE) | Mean Change (±SE) |
| LCHAD | 574.7 (133.4) | 73.7 (18.0) | 44.3 (10.4) | 19.5 (11.7) | 32.8 (6.5) | −9.8 (4.2) |
| CPT2 | 949.6 (119.1) | 51.9 (49.4) | 57.7 (3.2) | 0.8 (4.9) | 23.5 (6.7) | 1.0 (3.3) |
| VLCAD | 864.3 (65.1) | −36.7 (42.1) | 57.3 (9.3) | −17.8 (7.8) | 17.8 (6.8) | 15.6 (8.5) |

[1]Patients with baseline and Week 12 data; TFP not summarized as n = 2

Example B-7: A Prospective, Multicenter, Non-Interventional Study to Investigate the Disease Characteristics of Adult Patients with Long-Chain Fatty Acid Oxidation Disorders (the FORWARD Study)

In this study there was no drug intervention. The study included a Baseline visit and a follow up visit scheduled at Month 4. At these visits medical history, safety assessments, concomitant medications, exercise tests and quality of life questionnaire data were collected.

Patients (≥18 years): with a confirmed diagnosis of CPT2, VLCAD, TFP or LCHAD deficiencies; on stable management for at least 30 days prior to baseline Data collected at baseline and Month 4 (14-18 weeks) after the baseline visit: disease characteristics and symptoms; endurance measured by the 12-minute walk test (12MWT); blood and urine samples; Short Form Health Survey (SF-12)

Results 58 patients were enrolled, 52% diagnosed with CPT2. Gender split was relatively even (56.9% males).

12MWT: Compared with baseline, at Month 4 overall mean (SE) distance walked increased by 24.4 (10.0) meters. VLCAD patients exhibited the highest mean (SE) increase from baseline; 37.9 (17.4) meters. LCHAD patients exhibited the lowest mean (SE) change from baseline; 11.9 (26.7) meters, and the lowest mean distance walked compared with the other subgroups at both baseline and Month 4.

SF-12: Compared with baseline, at Month 4 overall mean (SE) score in the Physical Functioning component increased by 4.7 (2.9). All genetic subgroups exhibited an increase in the Physical Functioning score compared with baseline. The LCHAD subgroup exhibited the highest mean (SE) change with an 8.3 (7.1) point increase. The VLCAD subgroup exhibited the lowest mean (SE) change, with a 4.2 (8.6) point increase.

Conclusions

This study provided valuable information about disease characteristics, key safety events and the natural history of LC-FAOD in adults followed for 4 months.

The increases in distance walked from baseline in the 12MWT were consistent with a learning effect. Healthy individuals could walk 636 meters in 6 minutes, whereas individuals with LC-FAOD could only walk 835.5 meters in double the time (12 minutes).

The LCHAD population's low mean SF-12 physical component score at baseline (47.9) suggests that this population has more meaningful physical limitations than other LC-FAOD populations.

Both baseline values and changes from baseline observed at Month 4 in the 12MWT and SF-12 score support calculating performance of a placebo group in interventional trials.

Example B-8: Clinical Trial for McArdle Disease

A non-limiting example of a McArdle disease clinical trial in humans is described below.

Purpose: The purposes of this study was: to assess the safety and tolerability of 12 weeks treatment with Compound I, or a pharmaceutically acceptable salt thereof (e.g., Compound II), in patients with McArdle disease; to investigate pharmacokinetics of Compound I, or a pharmaceutically acceptable salt thereof (e.g., Compound II), in patients with McArdle disease treated with Compound I, or a pharmaceutically acceptable salt thereof, to investigate the pharmacodynamics effects of Compound I, or a pharmaceutically acceptable salt thereof (e.g., Compound II), in patients with McArdle disease treated with Compound I, or a pharmaceutically acceptable salt thereof (e.g., Compound II).

Intervention: Patients were administered 10-200 mg of Compound I, or a pharmaceutically acceptable salt thereof (e.g., Compound II), per day as single agent or in combination. For example, patients received 100 mg of Compound I, or a pharmaceutically acceptable salt thereof (e.g., Compound II), once daily for a total of 12 weeks. Other cohorts are contemplated. Compound I, or a pharmaceutically acceptable salt thereof (e.g., Compound II), was packed in bottles as capsules.

Detailed Description: Patients were given Compound I, or a pharmaceutically acceptable salt thereof (e.g., Compound II), orally once a day.

Inclusion Criteria: Patients were eligible for inclusion if they are male or female age 18 or older; have a genetically-established diagnosis of McArdle disease; have no changes to their exercise regimen within 30 days prior to Study Day 1 and were willing to remain on the same exercise regimen for the duration of the study; were ambulatory and able to perform the study exercise tests independently; able to remain on stable medication through the study and specifically must not commence or have changes to agents that affect metabolism such as medication for diabetes; followed a stable dietary regimen as documented by a 3-day dietary record obtained during the screening period; have adequate kidney function defined as an estimated glomerular filtration rate (eGFR)≥60 mL/min/1.73 m2 using the Modification of Diet in Renal Disease (MDRD) formula (Levey A S, Bosch J P, Lewis J B, Greene T, Rogers N, Roth D: A more accurate method to estimate glomerular filtration rate from serum creatinine: a new prediction equation. Modification of Diet in Renal Disease Study Group. Ann Intern Med 1999; 130:461-470) at Screening and Baseline; and able to swallow capsules.

Exclusion Criteria: Patients that were not eligible for participation include patients who participated in a prior Compound I study; have a history of hospital admission for a clinical event of rhabdomyolysis within the 3 months preceding enrollment (signed consent) or two hospitalization events within the preceding 12 months; have a documented history of ongoing rhabdomyolysis (last episode of rhabdomyolysis must have resolved 3 months prior to Baseline); were taking or anticipated to need a PPAR agonist during the study; were following or planning to start a ketogenic diet; have motor abnormalities other than related to McArdle disease that may interfere with the outcome measures; have received treatment with an investigational drug within 1 month or within 5 half-lives, whichever is longer; have a history of cancer (a history of in situ basal cell carcinoma in the skin is allowed); have been hospitalized within the 3 months prior to screening for any major medical condition; have cardiovascular disease; any condition possibly reducing drug absorption (e.g., gastrectomy, gastric bypass surgery or serious GI dysmotility); patients who have poor nutritional status as determined by the Investigator; patients with a history of clinically significant liver disease and/or liver function tests (e.g., Gamma-glutamyl transferase (GGT), alkaline phosphatase [AP], total Bilirubin >1.5× upper limit of normal (ULN); CK≥15,000 IU/L accompanied by significant clinical symptoms; pregnant or nursing females or planning a pregnancy during the study; patients with a history of sensitivity to PPAR agonists; patients with an inability to comprehend or unwilling to follow the study requirements including restrictions on treatments, attendance at clinic visits, completion of questionnaires and participation in laboratory testing as called for by the protocol; patients who are not eligible or have a contraindication for cataract surgery; and patients with any other severe acute or chronic medical or psychiatric condition or laboratory abnormality that may increase the risk associated with study participation or investigational product administration or may interfere with the interpretation of study results and, in the judgment of the Investigator in discussion with the Medical Monitor, would make the patient inappropriate for entry into this study.

It should be noted that routine blood testing of individuals with McArdle disease demonstrates elevated baseline CK levels in the range of 500-10,000 IU/L, with some patients having CK levels >10,000 IU/L. It is very rare for patients with McArdle disease to have normal CK levels. Patients may present for routine visits to the clinic with random CK levels of 10,000 IU/L to 20,000 IU/L and occasionally even higher levels. These patients appear well and have no evidence of a muscle contracture or myoglobinuria. Patients with McArdle disease experience dark urine when the CK level is around 39,000 IU/L.

The diagnosis of rhabdomyolysis in patients with McArdle disease is typically established with the presence of muscle pain, dark urine plus a marked acute elevation in serum CK and alterations in the urine analysis. No absolute cut-off value for CK elevation can be defined, and the CK should be considered in the clinical context of the history and examination findings. A stopping rule for raised CK levels is proposed which reflects the nature of the underlying disease and current clinical practice for evaluation and treatment of raised CK levels in these patients.

Given the profile of CK elevations in McArdle patients, an eligibility and monitoring threshold of 15,000 IU/L has been selected. In the event that a patient has a blood CK level >15,000 IU/L at the Screening Visit, they should be evaluated for the presence of clinical symptoms such as recent significant localized muscle pain, stiffness, cramping or presence of myoglobinuria. If no clinical symptoms and no urine color change is present, repeat blood CK level should be obtained. Screening may continue if CK level is reduced below 15,000 IU/L.

Outcome Measures: Pharmacokinetic endpoints measured included plasma concentrations of Compound I and identification of major metabolites. Other endpoints measured include changes from Baseline following 12 weeks of treatment with Compound I in Sub-maximal exercise test (e.g., change in Rating of Perceived Exertion (RPE) and Rating of Perceived Pain (RPP) and heart rate) and a 12-Minute Shuttle Walk test (12-MSW) (e.g., total distance walked, distance traveled per minute, number of pauses needed for rest, duration of time resting); change from Baseline in the McArdle Questionnaire score as recorded by the patient at Weeks 4, 8 and 12; change from Baseline in the Patient Global Impression of Severity (PGI-S) score, as measured at Weeks 4, 8 and 12; change from Baseline in the Patient Global Impression of Impact (PGI-I) score, as measured at Weeks 4, 8 and 12; change from Baseline in the 36-Item Short Form Survey (SF-36) scale scores (including the Physical Functioning scale) at Weeks 4, 8 and 12; change from Baseline in the Fatigue Assessment Scale total score, as measured at Weeks 4, 8 and 12; change from Baseline in the Work Productivity and Activity Impairment Questionnaire (WPAI) scores: as measured at Week 12; Patient Global Impression of Change (PGI-C)—patient rated change compared to Baseline, as measured at Week 12; and changes from Screening in acylcarnitine panel at Week 12.

A progressive exercise test was undertaken at screening to assess peak oxygen consumption (peak V02) using an electronically braked recumbent cycle ergometer.

Patients would have fasted for at least 2 hours prior to the test and would remain seated for at least 1 hour prior to the test to ensure they are fully rested.

Patients would be asked to cycle on a static bike for 15 minutes. During the first minute, workload would be increased and thereafter increased each minute. Heart rate and oxygen consumption would be monitored and recorded each minute together with Rating of Perceived Exertion (RPE) and Rating of Perceived Pain (RPP). The constant workload used in subsequent cycle tests would be derived from the oxidative capacity found in this screening test (corresponding work load to 60% V02 max).

12 Minute Shuttle Walk Test

The objective of the 12-minute shuttle walk test is to observe a second wind and measure the maximum distance walked in 12 minutes to assess exercise function. The test has been modified from the standard 12-minute walk test for cardiac, respiratory and cerebrovascular disease. Modification includes recording of RPP scale and heart rate each minute.

The patient would have fasted for at least 2 hours prior to the test and would remain seated for at least 1 hour prior to the test to ensure they are fully rested.

They would be asked to walk in a straight line the length of which is 10 meters turning at each end. The patient would be asked to walk as fast as they can in 12 minutes, but they must not let muscle pain exceed a Rating of Perceived Pain (RPP) level 4. If their muscle pain exceeds a level 4 on the RPP scale, they would be asked to stop or slow down until their pain is lower than level 4. This prevents contracture and together with the heart rate highlights a second wind. Any pauses for rest (frequency and, where possible, the time of pause and duration) would be recorded.

Sub-Maximal Exercise Test

Sub-maximal exercise ability is assessed during constant workload exercise. Patients would perform a cycling exercise using an electronically braked recumbent cycle ergometer at a workload corresponding to 60% (or as close as possible to 60%) of the peak exercise capacity as established by the peak cycle ergometer exercise test undertaken at Screening.

The patient would have fasted for at least 2 hours prior to the test and would remain seated for at least 1 hour prior to the test to ensure they are fully rested.

The patient would sit on the bicycle ergometer and be asked to cycle, aiming for a work rate as close as possible to 65 rpm. In the first minute, power would be increased gradually to reach the constant workload set during the screening test. At 15 minutes, the power would be incrementally increased each minute and the patient would stop exercising when they reach exhaustion, usually 4-6 minutes after the initial 15 minutes of cycling.

Heart rate, Rating of Perceived Exertion (RPE) and Rating of Perceived Pain (RPP) would be monitored every minute throughout the test. Vital signs including blood pressure would be measured before and after the cycle test.

Example B-9: Clinical Trial for Duchenne Muscular Dystrophy

A non-limiting example of a Duchenne muscular dystrophy (DMD) clinical trial in humans is described below.

Purpose: The purposes of this study are: to assess the tolerability of 24 weeks treatment with Compound I, or a pharmaceutically acceptable salt thereof (e.g., Compound II), in patients with DMD; to investigate pharmacokinetics of Compound I, or a pharmaceutically acceptable salt thereof, in patients with DMD treated with Compound I, or a pharmaceutically acceptable salt thereof (e.g., Compound II); to investigate the pharmacodynamics effects of Compound I, or a pharmaceutically acceptable salt thereof (e.g., Compound II), in patients with DMD treated with Compound I, or a pharmaceutically acceptable salt thereof (e.g., Compound II).

Intervention: Patients are administered 10-200 mg of Compound I, or a pharmaceutically acceptable salt thereof (e.g., Compound II), per day as single agent or in combination. For example, patients will receive 100 mg of Compound I, or a pharmaceutically acceptable salt thereof (e.g., Compound II), once daily for a total of 12 weeks. Other cohorts are contemplated.

Compound I, or a pharmaceutically acceptable salt thereof (e.g., Compound II), will be packed in bottles as capsules Patients are administered Compound I, or a pharmaceutically acceptable salt thereof (e.g., Compound II), at the low dose for 2 weeks and then at the high dose for 10 weeks with the total duration of 12 weeks in the double-blind (DB) part and open-label extension (OLE) part, respectively. Compound I, or a pharmaceutically acceptable salt thereof (e.g., Compound II), will be packed in bottles as capsules.

Detailed Description: Patients will be given Compound I, or a pharmaceutically acceptable salt thereof (e.g., Compound II), orally once a day.

Eligibility: 8 years to 16 years (child) male with DMD.

Inclusion Criteria: Confirmed diagnosis of one of the following: dystrophin immunofluorescence and/or Western blot showing severe dystrophin deficiency consistent with the diagnosis of DMD; identifiable mutation within the DMD gene (deletion/duplication of 1 or more exons), where reading frame can be predicted as "out-of-frame"; or complete dystrophin gene sequencing showing an alteration (point mutation, duplication or other) that is expected to preclude production of the functional dystrophin protein (i.e., nonsense mutation or deletion/duplication leading to a downstream stop codon). Able to perform the assisted 6-minute arm and leg cycling test (A6MCT) for muscular dystrophy.

Exclusion Criteria: Patients presenting with any of the following will not be included in the study: unstable or poorly controlled disease; currently taking anticoagulants; have motor abnormalities other than those related to DMD; treatment with an investigational drug within 1 month or within 5 half-lives, whichever is longer; evidence of significant concomitant clinical disease that in the opinion of the Investigator may need a change in management during the study or could interfere with the conduct or safety of this study; history of cancer with the exception of in situ skin cancer; have been hospitalized within the 3 months prior to screening for any major medical condition (as deemed by the primary investigator); any condition possibly reducing drug absorption (e.g., gastrectomy); history of clinically significant liver disease as evidenced by elevations in ALT, GGT or TB; any other severe acute or chronic medical or psychiatric condition or laboratory abnormality that in the opinion of the Investigator may increase the risk associated with study participation or investigational product administration or may interfere with the interpretation of study results; has had clinical signs and symptoms consistent with coronavirus (SARSCoV-2) infection or who has tested positive within 2 months prior to randomization at baseline; patient whose parent(s) and/or caregiver(s) have increased risk of coronavirus (SARS-CoV-2) exposure from work history (e.g., nursing home, meat processing facility and correctional facility) or recent travel history unless the patient's parent(s) and/or caregiver(s) have been appropriately vaccinated a COVID-19 vaccine.

Primary Outcome Measures: Safety Endpoints include: number and severity of adverse events. Absolute values, changes from baseline and incidence of clinically significant changes in: vital sign abnormalities; body weight change abnormalities; clinically significant body weight; electrocardiogram (ECG) abnormalities; echocardiography abnormalities; clinically significant echocardiography values; laboratory value abnormalities; suicidal ideation and/or behavior as assessed by Columbia-Suicide Severity Rating Scale (C-SSRS) Change from baseline in Columbia-Suicide Severity Rating Scale (C-SSRS); and digital span test.

Secondary Outcome Measures: To assess the change from baseline following 24 weeks of treatment with Compound I, or a pharmaceutically acceptable salt thereof, in: performance of Upper Limb Module (PUL), Pediatric Quality of Life (PedsQL) Multidimensional Fatigue Scale, distance walked in 2 minute assessed in meters, assisted 6 minute cycling test (a6MCT) maximal attained revolutions, and fat fraction by magnetic resonance spectroscopy (MRS).

Example B-10: Effects of Compound 1 in Individuals after Limb Immobilization

This phase 1, randomized, parallel group, placebo-controlled study was conducted at 2 centers in the United States. Fifty participants were planned for enrollment, 25 per group; participants could be replaced upon sponsor approval.

Screening was conducted 28 days before study start; eligibility was reviewed again at prespecified times during the study. Ambulatory, non-smoking, healthy male volunteers 30 to 55 years of age with a Body Mass Index (BMI) from 18 to 30 kg/m2 were recruited for the study. Key exclusion criteria included abnormal laboratory values at screening, a recent history of body weight fluctuations, positive urine drug screens, drug dependency or illicit drug use, professional sport participation within 30 days of screening, donation of whole blood within 90 days of dosing, and donation of plasma within 30 days of dosing. Concomitant medications within 14 days of dosing were not allowed unless approved by the sponsor. Those who had enrolled in another clinical trial within 90 days or had previously received Compound II were not allowed to participate.

Participants were randomly assigned 1:1 to receive either Compound II (100 mg BID) or matching placebo for 28 days using a computer generated randomization schedule provided by the sponsor. The principal investigator, study center staff, and participants were blinded to treatment; the protocol was amended so that sponsor personnel were not blinded. This change was made to allow investigation of observations concerning adherence to the protocol, discussed further in the pharmacodynamic results. Compound II and placebo were provided as capsules identical in appearance, taken orally with 240 ml of water prior to meals. Study drug was administered at the study site on Days 1 (PM dose), 6 (AM dose), 13 (PM dose), and 14, 15, 16, 29 (AM doses). At all other times study drug was self-administered just before breakfast and dinner. Dates and times were recorded in a diary, with compliance determined from the diaries and capsule counts. Study drug supplies were packaged according to the randomization codes by a contract research organization. Each dispensed bottle was labeled with the randomization number. Individual capsules were re-dispensed from these bottles by the study site staff, maintaining the blind. The total study duration for each subject was 42 days. Participants stayed overnight from Day 1 and Days 13 to 16.

Standardized meals, beverages and snacks were provided during the domicile periods. On Day 1, participants were leg-immobilized using a knee brace with 300 of flexion on the left leg to allow driving. Walking crutches were provided to prevent weight bearing on the immobilized leg. An accelerometer was issued at screening and was used to count the number of steps per day. Participants were to walk 4000 to 6000 steps each day for the duration of the leg immobilization period, and recorded accelerometer readings each evening before bedtime. The brace was removed on Day 14, and participants resumed normal physical activity gradually from Days 16 to 29. After stopping study drug on Day 29, participants were to resume regular daily activity gradually for another 2 weeks. Consumption of prescribed medications or over the counter products was prohibited from 14 days prior to dosing and throughout the study, with the exception of the treatment of an adverse event. Participants were not to consume alcohol or caffeine containing food and beverages 3 days before each study visit and domicile periods.

Participants were asked to fast for at least 8 hours prior to study visits on Days 1, 6, 14, 21, 29 and 42. The muscle strength test, physical performance test and punch biopsies from the quadriceps femoris (for biomarker assessment) occurred on Day 1 in the morning prior to dosing and on Days 14, 16, 21, 29, and 42.

Four participants (16.7%) prematurely discontinued from the study, 2 in each group. After the study began it was discovered that 2 men in the placebo group (16.7%) should have failed screening; both withdrew after 21 days of participation. In the Compound II group 1 participant (8.3%) was discontinued from the study due to an adverse event of elevated CK and another participant (8.3%) was withdrawn due to noncompliance.

TABLE 6

Change from baseline in muscle strength over time.

|   | Baseline | Day 14 | Day 21 | Day 29 | Day 42 |
|---|---|---|---|---|---|
| Number of Participants | | | | | |
| Compound II | 11 | 10 | 8 | 9 | 9 |
| Placebo | 11 | 11 | 11 | 10 | 10 |
| Change from baseline, mean (SD) | | | | | |
| Compound II | | −5.86 (28.818) | 32.82 (28.158) | 25.58 (40.598) | 37.96 (37.442) |
| Placebo | | −36.20 (34.339) | 2.72 (23.826) | 13.73 (25.712) | 30.00 (42.913) |

Compound II-treated individuals had up to 3.5-fold increases from baseline from Day 14 in pyruvate dehydrogenase lipoamide kinase isozyme 4, angiopoietin-like 4, and solute carrier family 25 member 34, important PPARδ-regulated genes involved in mitochondrial function and biogenesis.

The examples and embodiments described herein are for illustrative purposes only and various modifications or changes suggested to persons skilled in the art are to be included within the spirit and purview of this application and scope of the appended claims.

What is claimed is:

1. A method for treating a primary mitochondrial myopathy (PMM) in a human comprising orally administering to the human with PMM a solid form pharmaceutical composition comprising about 100 mg of crystalline sodium (E)-2-(4-((3-(4-fluorophenyl)-3-(4-(3-morpholinoprop-1-yn-1-yl)phenyl)allyl)oxy)-2-methylphenoxy)acetate (Compound II), wherein the human with PMM has at least one mutation or deletion in at least one mitochondrial DNA (mtDNA) gene; at least one mitochondrial DNA (mtDNA) defect; at least one mutation or deletion in at least one nuclear DNA (nDNA) gene involved in mitochondrial function; or a combination thereof; and wherein crystalline Compound II is characterized as having an XRPD pattern with peaks at 2.8±0.2° 2-Theta, 7.2±0.2° 2-Theta, 13.4±0.2° 2-Theta, 17.8±0.2° 2-Theta, 19.7±0.2° 2-Theta, 19.9±0.2° 2-Theta, and 20.6±0.2° 2-Theta as measured using Cu Kα radiation (crystalline Form 1).

2. The method of claim 1, wherein treating PMM in the human comprises improving the human's exercise tolerance, improving muscle histology, decreasing pain, decreasing fatigue, improving cognition, improving overall well-being, a reduction in myoglobinuria, reducing tachycardia, a reduction in rhabdomyolysis, a reduction in muscle contracture, reducing the severity of PMM muscle symptoms, reducing impairments in work and activities, increasing survival, or a combination thereof.

3. The method of claim 2, wherein improving the human's exercise tolerance comprises increasing the distance walked during a 6-minute walk test, increasing the distance walked during a 12 minute walk test, increasing stair climbing capacity, increasing the number of stands in a 30 second sit to stand test, decreasing the feeling of exhaustion during exercise, or a combination thereof.

4. The method of claim 2, wherein increasing the distance walked during a 12 minute walk test comprises an increase of at least about 10 meters, at least about 20 meters, at least about 30 meters, at least about 40 meters, at least about 50 meters, at least about 60 meters, at least about 70 meters, at least about 80 meters, at least about 90 meters, at least about 100 meters, at least about 125 meters, or more than about 125 meters as measured after about 2 weeks, about 4 weeks, about 6 weeks, about 8 weeks, about 10 weeks, about 12 weeks, about 14 weeks, about 16 weeks, about 18 weeks, about 20 weeks, about 24 weeks, about 26 weeks, about 52 weeks, or more than about 52 weeks of daily administration of Compound II.

5. The method of claim 2, wherein decreasing fatigue in the human comprises decreases in the Modified Fatigue Impact Scale (MIFS) as measured after about 2 weeks, about 4 weeks, about 6 weeks, about 8 weeks, about 10 weeks, about 12 weeks, about 14 weeks, about 16 weeks, about 18 weeks, about 20 weeks, about 24 weeks, about 26 weeks, about 52 weeks, or more than about 52 weeks of daily administration of Compound II.

6. The method of claim 5, wherein decreases in the Modified Fatigue Impact Scale (MIFS) comprises decreases in physical functioning subscores of the MFIS.

7. The method of claim 5, wherein decreases in the Modified Fatigue Impact Scale (MIFS) comprises decreases psychosocial functioning subscores of the MFIS.

8. The method of claim 5, wherein decreases in the Modified Fatigue Impact Scale (MIFS) comprises decreases in cognitive functioning subscores of the MFIS.

9. The method of claim 2, wherein decreasing pain comprises decreases in the brief pain inventory (BPI) scores by 1, 2, 3, 4, 5, or more than 5 as measured after about 2 weeks, about 4 weeks, about 6 weeks, about 8 weeks, about 10 weeks, about 12 weeks, about 14 weeks, about 16 weeks, about 18 weeks, about 20 weeks, about 24 weeks, about 26 weeks, about 52 weeks, or more than about 52 weeks of daily administration of Compound II.

10. The method of claim 2, wherein improving overall well-being comprises improving physical functioning, improving limitations due to physical health problems, improving limitations due to personal or emotional problems, improving emotional well-being, improving social functioning, or improving perceived change in health, or combinations thereof, as measured.

11. The method of claim 2, wherein improving overall well-being comprises reductions in the 36-Item Health Survey scoring as measured as measured after about 2 weeks, about 4 weeks, about 6 weeks, about 8 weeks, about 10 weeks, about 12 weeks, about 14 weeks, about 16 weeks, about 18 weeks, about 20 weeks, about 24 weeks, about 26 weeks, about 52 weeks, or more than about 52 weeks of daily administration of Compound II.

12. The method of claim 2, wherein reducing the severity of PMM muscle symptoms comprises Patient Global Impression of Change (PGIC) scores by 1, 2, 3, 4, or more than 4 as measured after about 2 weeks, about 4 weeks, about 6 weeks, about 8 weeks, about 10 weeks, about 12 weeks, about 14 weeks, about 16 weeks, about 18 weeks, about 20 weeks, about 24 weeks, about 26 weeks, about 52 weeks, or more than about 52 weeks of daily administration of Compound II.

13. The method of claim 2, wherein reducing impairments in work and activities measure comprises reductions in Work Productivity and Activity Impairment Questionnaire: Specific Health Problem (WPAI: SHP) scores by at least 10% points, by at least 15% points, by at least 20% points, by at least 30% points, by at least 35% points, by at least 40% points, by at least 45% points, by at least 50% points, or more than 50% points as measured after about 2 weeks, about 4 weeks, about 6 weeks, about 8 weeks, about 10 weeks, about 12 weeks, about 14 weeks, about 16 weeks, about 18 weeks, about 20 weeks, about 24 weeks, about 26 weeks, about 52 weeks, or more than about 52 weeks of daily administration of Compound II.

14. The method of claim 1, wherein Compound II is systemically administered to the human in the form of a powder, pill, tablet or capsule.

\* \* \* \* \*